United States Patent
Prakash et al.

(10) Patent No.: US 11,447,516 B2
(45) Date of Patent: *Sep. 20, 2022

(54) DITERPENE GLYCOSIDES CONTAINING AN ENT-ATISENE CORE, COMPOSITIONS AND METHODS

(71) Applicant: The Coca-Cola Company, Atlanta, GA (US)

(72) Inventors: Indra Prakash, Alpharetta, GA (US); Gil Ma, Atlanta, GA (US)

(73) Assignee: The Coca-Cola Company, Atlanta, GA (US)

( * ) Notice: Subject to any disclaimer, the term of this patent is extended or adjusted under 35 U.S.C. 154(b) by 360 days.

This patent is subject to a terminal disclaimer.

(21) Appl. No.: 16/338,626

(22) PCT Filed: Oct. 4, 2017

(86) PCT No.: PCT/US2017/055107
§ 371 (c)(1),
(2) Date: Apr. 1, 2019

(87) PCT Pub. No.: WO2018/067683
PCT Pub. Date: Apr. 12, 2018

(65) Prior Publication Data
US 2019/0241600 A1 Aug. 8, 2019

Related U.S. Application Data

(60) Provisional application No. 62/403,961, filed on Oct. 4, 2016.

(51) Int. Cl.
| | |
|---|---|
| *C07H 15/256* | (2006.01) |
| *A23L 2/60* | (2006.01) |
| *A23L 27/00* | (2016.01) |
| *A23L 27/30* | (2016.01) |
| *C07H 1/06* | (2006.01) |

(52) U.S. Cl.
CPC ............ *C07H 15/256* (2013.01); *A23L 2/60* (2013.01); *A23L 27/30* (2016.08); *A23L 27/36* (2016.08); *A23L 27/88* (2016.08); *C07H 1/06* (2013.01); *A23V 2002/00* (2013.01)

(58) Field of Classification Search
CPC ......... C07H 15/256; C07H 1/06; A23L 27/88; A23L 27/30; A23L 27/36; A23L 2/60; A23V 2002/00
USPC ............................... 426/534, 538, 548, 590
See application file for complete search history.

(56) References Cited

U.S. PATENT DOCUMENTS

| | | |
|---|---|---|
| 2004/0180930 A1 | 9/2004 | Akaike et al. |
| 2008/0206365 A1 | 8/2008 | Tachibana et al. |
| 2016/0039856 A1 | 2/2016 | Prakash et al. |

FOREIGN PATENT DOCUMENTS

WO WO 2016/120486 8/2016

OTHER PUBLICATIONS

European Search Report from EP 17859105.3, dated May 13, 2020.
Nobutoshi Tanaka et al: "Chemische und chemotaxonomische Untersuchungen van Filices. XXXIV. Chemische Untersuchungen der Inhaltsstoffe van Pteris purpureorachis COPEL.", Chemical and Pharmaceutical Bulletin, vol. 29, No. 3, 1981, pp. 663-666. (English abstract).
Mohamed A. Ibrahim et al: "Minor Diterpene Glycosides from the Leaves of Stevia rebaudi-ana", Journal of Natural Products, vol. 77, No. 5, 2014, pp. 1231-1235.
Ohtani Ket Al: "Minor diterpene glycosides from sweet leaves of *Rubus suavissimus*", Phytochemistry, vol. 31, No. 5, 1992, pp. 1553-1559.
Kuang Xinzhu et al: "ent-Atisane diterpenoids from Euphorbia fischeriana inhibit mammosphere formation in MCF-7 cells", Natural Medicines—Shoyakugaku Zasshi, Japanese Society of Pharmacognosy, vol. 70, No. 1, 2015, pp. 120-126.
International Search Report from PCT/US2017/055107, dated Dec. 11, 2017.

*Primary Examiner* — Leslie A Wong
(74) *Attorney, Agent, or Firm* — King & Spalding

(57) ABSTRACT

Novel diterpene glycosides containing ent-atisene cores are provided herein. Compositions and consumables comprising the novel diterpene glycosides are also provided herein. Methods of enhancing the sweetness and/or flavor of consumables using the novel diterpene glycosides, methods of preparing compositions and consumables comprising the novel diterpene glycosides and methods of purifying the novel diterpene glycosides are also provided.

18 Claims, 2 Drawing Sheets

DITERPENE GLYCOSIDES CONTAINING AN ENT-ATISENE CORE, COMPOSITIONS AND METHODS

CROSS REFERENCE TO RELATED APPLICATIONS

This application is a national phase application under 35 U.S.C. § 371 of International Application No. PCT/US2017/055107, filed on Oct. 4, 2017, which claims priority to U.S. Provisional Patent Application No. 62/403,961 filed Oct. 4, 2016. The contents of each of the above-identified applications is hereby fully incorporated herein by reference.

FIELD OF THE INVENTION

The present invention relates generally to novel diterpene glycosides, compositions (e.g., consumables) comprising said novel diterpene glycosides, and methods for their purification.

BACKGROUND OF THE INVENTION

Natural caloric sugars, such as sucrose, fructose and glucose, are utilized to provide a pleasant taste to beverages, foods, pharmaceuticals, and oral hygienic/cosmetic products. Sucrose, in particular, imparts a taste preferred by consumers. Although sucrose provides superior sweetness characteristics, it is disadvantageously caloric.

Non-caloric or low caloric sweeteners have been introduced to satisfy consumer demand. However, non- and low caloric sweeteners taste different from natural caloric sugars in ways that frustrate consumers. On a taste basis, non-caloric or low caloric sweeteners exhibit a temporal profile, maximal response, flavor profile, mouth feel, and/or adaptation behavior that differ from sugar. Specifically, non-caloric or low caloric sweeteners exhibit delayed sweetness onset, lingering sweet aftertaste, bitter taste, metallic taste, astringent taste, cooling taste and/or licorice-like taste. On a source basis, many non-caloric or low caloric sweeteners are synthetic sweeteners. Consumer desire for natural non-caloric or low caloric sweeteners that tastes like sucrose remains high.

*Stevia rebaudiana* Bertoni is a perennial shrub of the Asteraceae (Compositae) family native to certain regions of South America. Its leaves have been traditionally used for hundreds of years in Paraguay and Brazil to sweeten local teas and medicines. The plant is commercially cultivated in Japan, Singapore, Taiwan, Malaysia, South Korea, China, Israel, India, Brazil, Australia and Paraguay.

The leaves of the plant contain a mixture containing diterpene glycosides in an amount ranging from about 10% to 15% of the total dry weight. These diterpene glycosides are about 30 to 450 times sweeter than sugar. Structurally, the diterpene glycosides are characterized by a single base, steviol, and differ by the presence of carbohydrate residues at positions C13 and C19. Typically, on a dry weight basis, the four major steviol glycosides found in the leaves of Stevia are dulcoside A (0.3%), rebaudioside C (0.6-1.0%), rebaudioside A (3.8%) and stevioside (9.1%). Other glycosides identified in Stevia extract include rebaudioside B, D, E, and F, steviolbioside and rubusoside. Among these, only stevioside and rebaudioside A are available on a commercial scale.

The use of steviol glycosides has been limited to date by certain undesirable taste properties, including licorice taste, bitterness, astringency, sweet aftertaste, bitter aftertaste, licorice aftertaste, and become more prominent with increase of concentration. These undesirable taste attributes are particularly prominent in carbonated beverages, where full replacement of sugar requires concentrations of steviol glycosides that exceed 600 mg/L. Use of steviol glycosides in such high concentrations results in significant deterioration in the final product taste.

Accordingly, there remains a need to develop natural reduced or non-caloric sweeteners that provide a temporal and flavor profile similar to the temporal and flavor profile of sucrose.

There remains a further need for methods for purifying glycosides from stevia.

SUMMARY OF THE INVENTION

The present invention relates generally to novel diterpene glycosides that contain an ent-atisene core, and compositions and consumables comprising said novel diterpene glycosides, as well as methods for purifying said novel diterpene glycosides, methods for preparing compositions and consumables comprising said novel diterpene glycosides and methods for enhancing the flavor or sweetness of consumables using the novel diterpene glycosides. The novel diterpene glycosides of the present invention are isolated from Stevia plants.

In one aspect, the present invention provides a diterpene glycoside of Formula I:

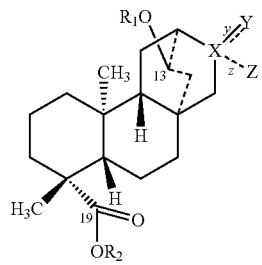

Formula I wherein when y is a double bond, X is C, Y is $CH_2$, z is absent and Z is absent;

when y is single bond, z is a single bond, X is C and Y and Z are each independently selected from methyl and hydroxyl; and $R_1$ and $R_2$ are each independently selected from a monosaccharide and an oligosaccharide.

In exemplary embodiments, each saccharide is selected from the group consisting of glucose, xylose, rhamnose, fructose, 6-deoxy-glucose and combinations thereof.

In one embodiment, $R_1$ is an oligosaccharide comprising glucose units.

In another embodiment, $R_2$ is an oligosaccharide comprising glucose units, and optionally, rhamnose units.

In a more particular embodiment, $R_1$ and $R_2$ are oligosaccharides comprising glucose units. In another more particular embodiment, $R_1$ and $R_2$ are oligosaccharides, wherein $R_1$ comprises glucose units and $R_2$ comprises a combination of glucose and rhamnose units.

The linkages between the saccharides can be α- or β-. In a particular embodiment, the linkages between the saccharides in the oligosaccharide of $R_1$ are all β. In another particular embodiment, the linkages between the saccharides in the oligosaccharides of $R_2$ are all β. In an alternative embodiment, the linkages between the saccharides in the oligosaccharide of $R_2$ are a mixture of α and β.
In one embodiment, the diterpene glycoside of formula I contains at least 5 saccharides, such as from about 4 to about 10 saccharides.
In a particular embodiment the diterpene glycoside is selected from the group consisting of:
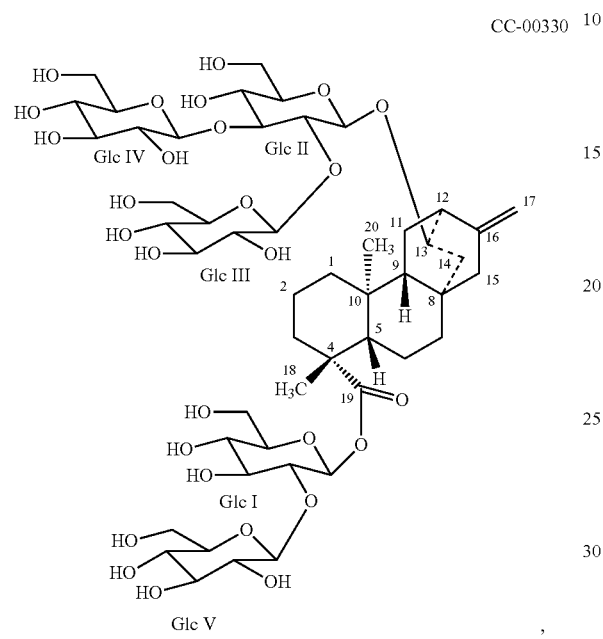
CC-00330
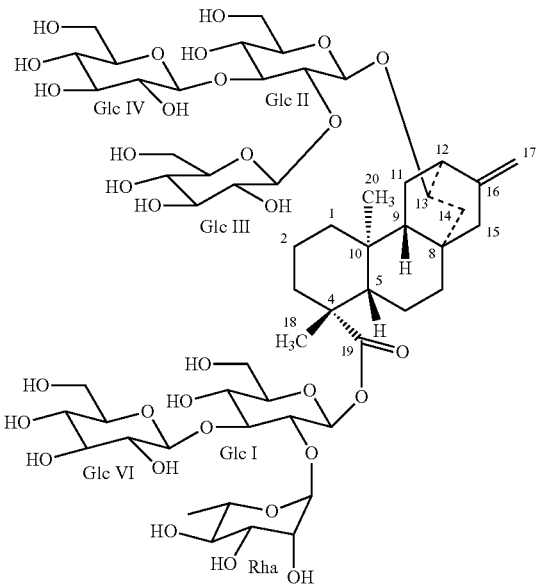
CC-00332
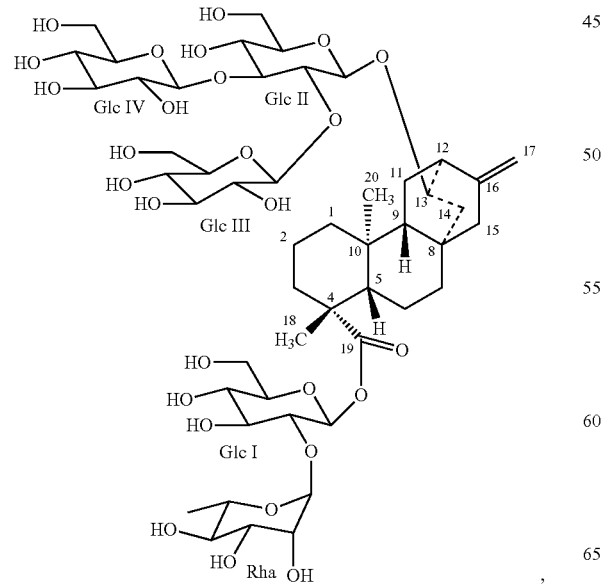
CC-00331
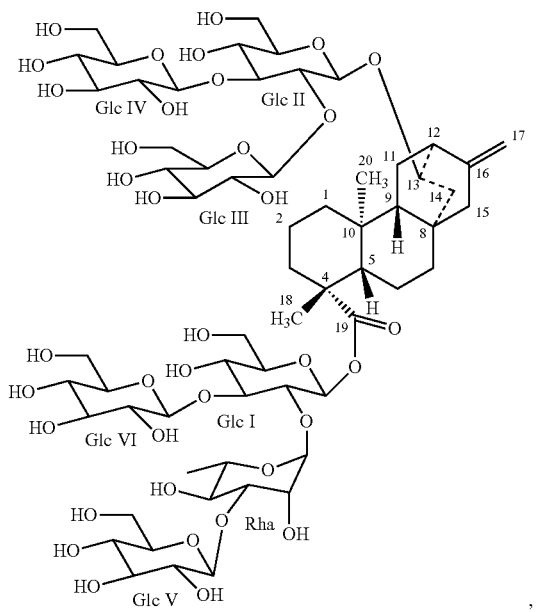
CC-00333

CC-00335
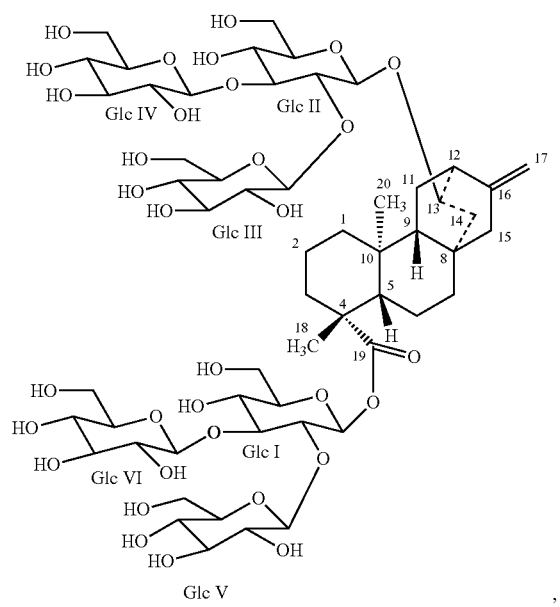
CC-00341
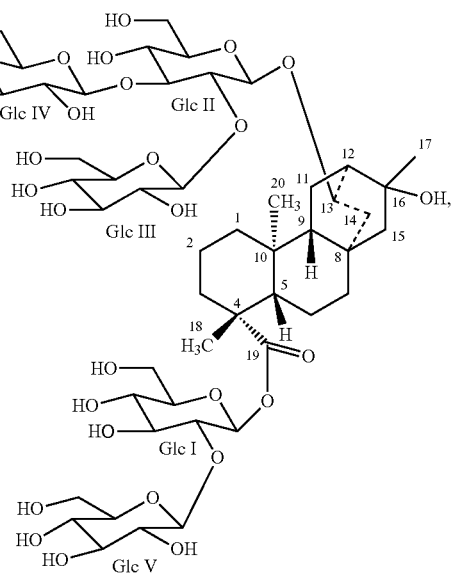
,
CC-00334
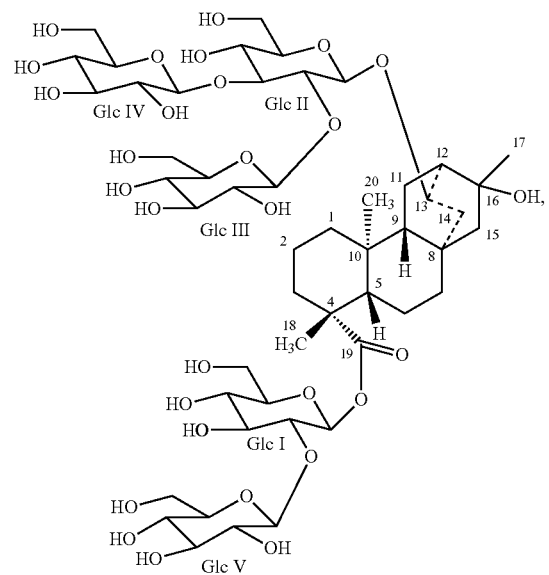
CC-00348
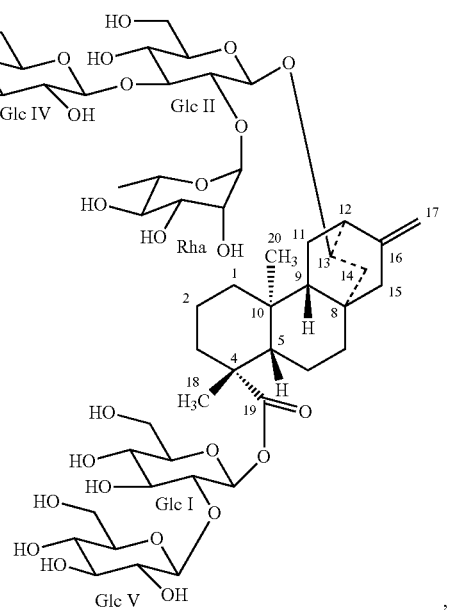
, and -continued

CC-00365

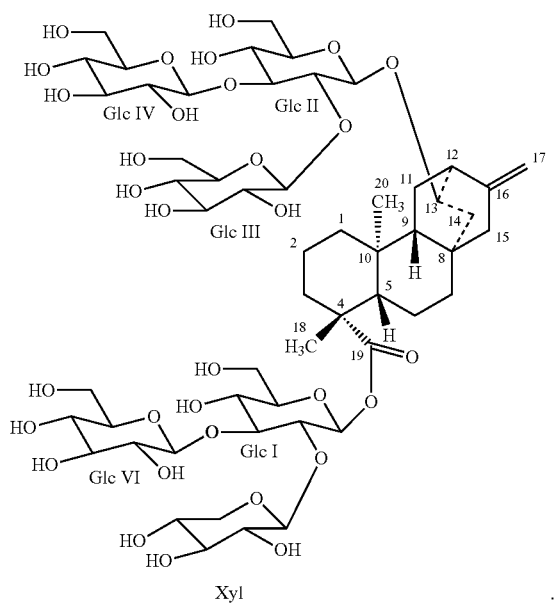

In a particular embodiment, the diterpene glycoside is isolated and purified.

In a further aspect, the present invention is a composition comprising at least one diterpene glycoside described herein.

In one embodiment, the present invention is a sweetener composition comprising at least one diterpene glycoside described herein.

In another embodiment, the present invention is a flavor enhancing composition comprising at least one diterpene glycoside described herein, wherein the diterpene glycoside is present in the composition in an amount effective to provide a concentration at or below the flavor recognition threshold of the diterpene glycoside when the flavor enhancing composition is added to a consumable.

In yet another embodiment, the present invention is a sweetness enhancing composition comprising at least one diterpene glycoside described herein, wherein the diterpene glycoside is present in the composition in an amount effective to provide a concentration at or below the sweetness recognition threshold of the diterpene glycoside when the sweetness enhancing composition is added to a consumable.

In yet another embodiment, the present invention is a consumable comprising at least one diterpene glycoside described herein. Suitable consumables include, but are not limited to, liquid-based or dry consumables, such as, for example, pharmaceutical compositions, edible gel mixes and compositions, dental compositions, foodstuffs, beverages and beverage products.

In a particular embodiment, the present invention is a beverage comprising at least one diterpene glycoside described herein. In a particular embodiment, the diterpene glycoside is present in the beverage at a concentration that is above, at or below the threshold sweetness recognition concentration of the diterpene glycoside.

In another particular embodiment, the present invention is a beverage product comprising a diterpene glycoside described herein. In a particular embodiment, the diterpene glycoside is present in the beverage product at a concentration that is above, at or below the threshold flavor recognition concentration of the diterpene glycoside.

In another aspect, the present invention is a method of preparing a consumable comprising (i) providing a consumable matrix and (ii) adding at least one diterpene glycoside described herein to the consumable matrix to provide a consumable.

In a particular embodiment, the present invention is a method of preparing a beverage comprising (i) providing a beverage matrix and (ii) adding at least one diterpene glycoside described herein to the beverage matrix to provide a beverage.

In another aspect, the present invention is a method of enhancing the sweetness of a consumable comprising (i) providing a consumable comprising at least one sweet ingredient and (ii) adding at least one diterpene glycoside described herein to the consumable to provide a consumable with enhanced sweetness, wherein the diterpene glycoside is present in the consumable with enhanced sweetness at a concentration at or below the sweetness recognition threshold of the diterpene glycoside. In a particular embodiment, the consumable is a beverage. In certain embodiments, the diterpene glycoside is added in the form of a composition, as described herein.

In a further aspect, the present invention is a method of enhancing the flavor of a consumable comprising (i) providing a consumable comprising at least one flavor ingredient and (ii) adding at least one diterpene glycoside described herein to the consumable to provide a consumable with enhanced flavor, wherein the diterpene glycoside is present in the consumable with enhanced flavor at a concentration at or below the flavor recognition threshold of the diterpene glycoside. In a particular embodiment, the consumable is a beverage. In certain embodiments, the diterpene glycoside is added in the form of a composition.

In some embodiments, the compositions of the present invention comprise one or more sweeteners, additives and/or functional ingredients In one embodiment, the present invention is a consumable comprising at least one diterpene glycoside of the present invention and one or more sweeteners, additives and/or functional ingredients. In another embodiment, the present invention is a beverage comprising at least one diterpene glycoside of formula of the present invention and one or more sweeteners, additives and/or functional ingredients In one aspect, the present invention is a method for purifying a diterpene glycoside of the present invention comprising (i) passing a solution comprising a source material comprising a diterpene glycoside of the formulae described herein through a HPLC column and (ii) eluting fractions comprising the diterpene glycoside of the formulae described herein to provide a purified diterpene glycoside of the formulae described herein. The method provides a purified diterpene glycoside of the formulae described herein in a purity greater than about 50% by weight on a dry basis.

The HPLC column can be preparative or semi-preparative. The fractions comprising the diterpene glycoside of interest may be eluted by adding an appropriate eluent. The method may optionally comprise additional steps, such as partial or substantially full removal of solvents and/or further purification steps, e.g. extraction, crystallization, chromatography and distillation.

In still other embodiments, the source material can be one fraction, or multiple fractions, containing unpurified diterpene glycoside of interest collected from a previous method or HPLC protocol. The material isolated can be subjected to further methods 2, 3, 4 or more times, each time providing a higher level of purity of the diterpene glycoside. The second and subsequent methods may have different HPLC protocols and different steps following elution.

DETAILED DESCRIPTION OF THE INVENTION

I. Compounds

Figure 1:
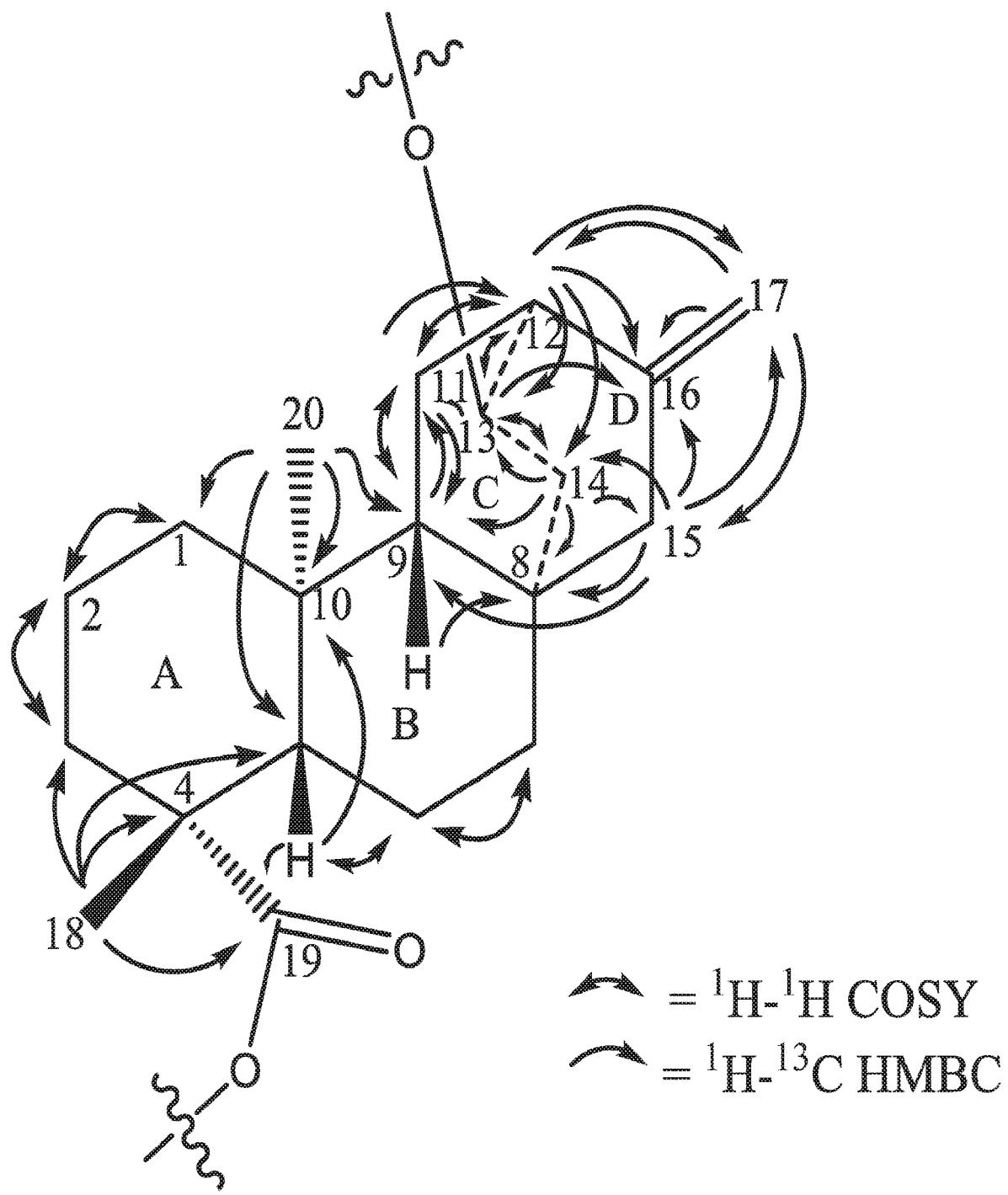
FIG. 1: Shows a summary of key HMBC and COSY correlations used to assign the aglycone region of diterpene glycosides CC-00330, CC-00331, CC-00332, CC-00333, CC-00335 and CC-00348.

In exemplary embodiments, the present invention provides a diterpene glycoside of Formula I:

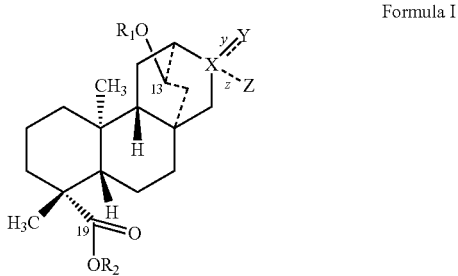

Formula I wherein when y is a double bond, X is C, Y is $CH_2$, z is absent and Z is absent;

when y is single bond, z is a single bond, X is C and Y and Z are each independently selected from methyl and hydroxyl; and $R_1$ and $R_2$ are each independently selected from a monosaccharide and an oligosaccharide.

In exemplary embodiments, saccharides of the monosaccharide and/or oligosaccharide are selected from the group consisting of glucose, xylose, rhamnose, fructose, 6-deoxy-glucose and combinations thereof. In one embodiment, each saccharide is selected from the group consisting of glucose, rhamnose and combinations thereof.

In one embodiment, $R_1$ and $R_2$ are both oligosaccharides. In a more particular embodiment, $R_1$ and $R_2$ are both oligosaccharides comprising glucose units. In an alternative embodiment, $R_1$ and $R_2$ are both oligosaccharides, wherein $R_1$ comprises glucose units and $R_2$ comprises a combination of glucose and rhamnose units.

The linkages between the saccharides can be α- or β. In a particular embodiment, the linkages between the saccharides in the oligosaccharide of $R_1$ are all β. In another particular embodiment, the linkages between the saccharides in the oligosaccharides of $R_2$ are all β. In an alternative embodiment, the linkages between the saccharides in the oligosaccharide of $R_2$ are a mixture of α and β.

In a more particular embodiment, $R_1$ is an oligosaccharide comprising glucose units having β linkages. In another more particular embodiment, $R_2$ is an oligosaccharide comprising glucose units having β linkages. In an alternative embodiment, $R_2$ is an oligosaccharide comprising glucose and rhamnose units, wherein the linkage with the rhamnose unit(s) is α.

In exemplary embodiments, the diterpene comprises at least 4 saccharides, preferably from 4 to 10 saccharides. In one embodiment, the diterpene comprises at least 5 saccharides, at least 6 saccharides, at least 7 saccharides, at least 8 saccharides, at least 9 saccharides or 10 saccharides.

In exemplary embodiments where $R_1$ is an oligosaccharide, the oligosaccharide may comprise from 2 to 8 saccharides, such as, for example, from 3 to 5 saccharides. In other embodiments, $R_1$ comprises at least 2 saccharides, at least 3 saccharides, at least 4 saccharides, at least 5 saccharides, at least six saccharides, at least seven saccharides or 8 saccharides.

In exemplary embodiments where $R_2$ is an oligosaccharide, the oligosaccharide may comprise from 2 to 8 saccharides, such as, for example, from 2 to 4 saccharides. In other embodiments, $R_2$ comprises at least 2 saccharides, at least 3 saccharides, at least 4 saccharides, at least 5 saccharides, at least 6 saccharides, at least 7 saccharides or 8 saccharides.

In a more particular embodiment wherein $R_1$ and $R_2$ are both oligosaccharides, $R_1$ comprises from 3 to 5 saccharides and $R_2$ comprises from 2 to 4 saccharides.

The compounds described herein have a plurality of stereocenters (R,S). Unless stereochemistry is specifically provided for, all stereochemical configurations are contemplated herein.

In exemplary embodiments, the present invention is a diterpene glycoside of Formula II:

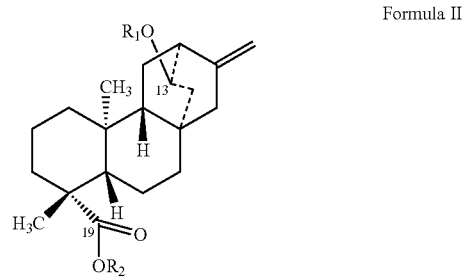

Formula II wherein $R_1$ and $R_2$ are each independently selected from a monosaccharide and an oligosaccharide, as discussed above.

In certain embodiments, the present invention is a diterpene glycoside selected from the group consisting of CC-00330
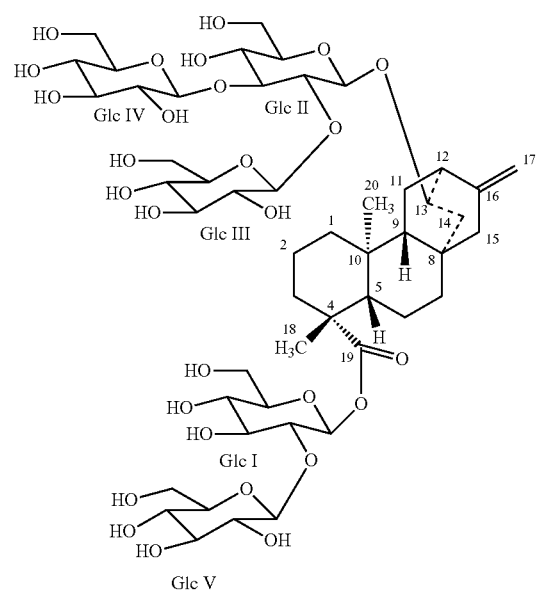
CC-00331
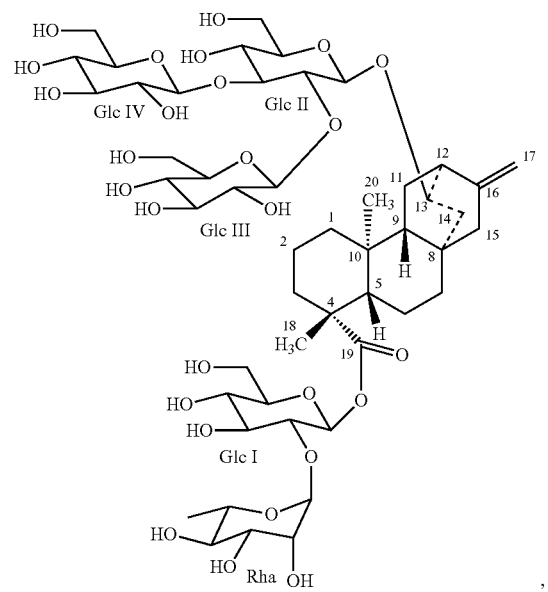
CC-00332
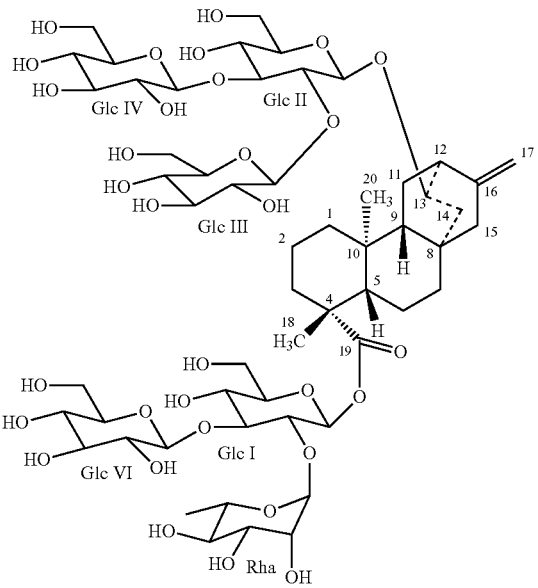
CC-00333
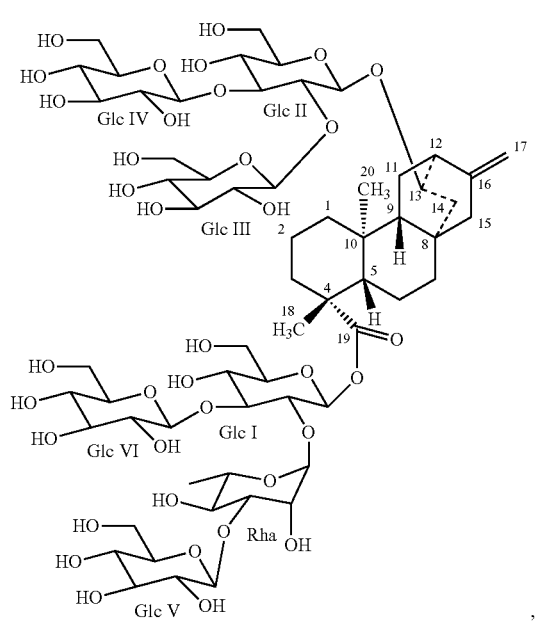

CC-00335, CC-00365, CC-00348 (chemical structures shown)

In exemplary embodiments, the present invention is a diterpene glycoside of Formula III:

Formula III (chemical structure shown)

wherein $R_1$ and $R_2$ are each independently selected from a monosaccharide and an oligosaccharide, as discussed above.

In certain embodiments, the present invention is a diterpene glycoside selected from the group consisting of

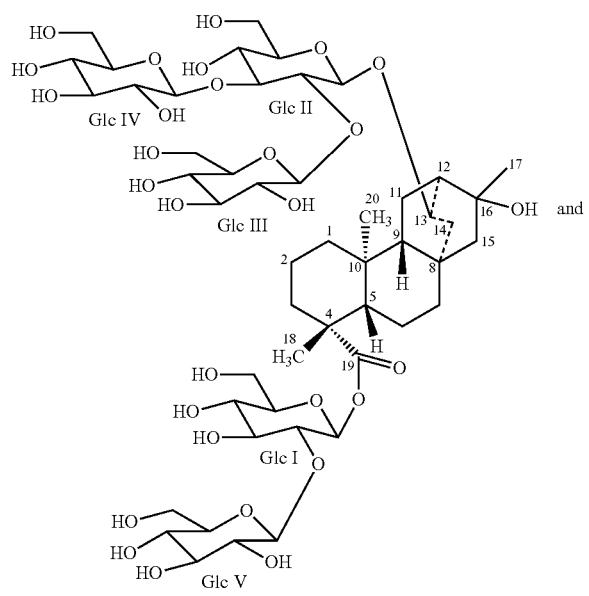

CC-00334

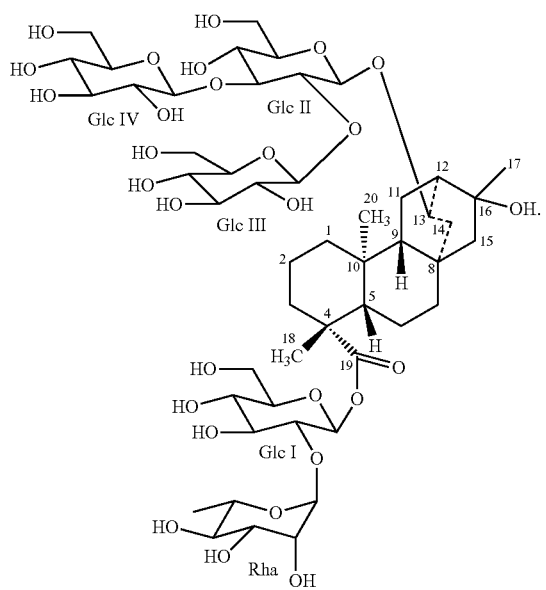

CC-00341

In exemplary embodiments, the diterpene glycoside of the present invention is isolated and purified. The term "isolated and purified", as used herein, means that the compound is about 95% by weight or greater on a dry basis, i.e. is greater than 95% pure. In more specific embodiments, the diterpene glycoside of the formulae described herein has a purity of about 96% or greater, about 97% or greater, about 98% or greater or about 99% or greater. In some embodiments, the compound is enzymatically produced and is in a purity of at least about 95% by weight or greater in a mixture.

In some embodiments, the diterpene glycoside of the present invention is sweet. The sweetness of a given composition is typically measured with reference to a solution of sucrose. See generally "A Systematic Study of Concentration-Response Relationships of Sweeteners," G. E. DuBois, D. E. Walters, S. S. Schiffman, Z. S. Warwick, B. J. Booth, S. D. Pecore, K. Gibes, B. T. Carr, and L. M. Brands, in *Sweeteners: Discovery, Molecular Design and Chemoreception*, D. E. Walters, F. T. Orthoefer, and G. E. DuBois, Eds., American Chemical Society, Washington, D.C. (1991), pp 261-276.

The sweetness of a non-sucrose sweetener can be measured against a sucrose reference by determining the non-sucrose sweetener's sucrose equivalence (SE). Typically, taste panelists are trained to detect sweetness of reference sucrose solutions containing between 1-15% sucrose (w/v). Other non-sucrose sweeteners are then tasted at a series of dilutions to determine the concentration of the non-sucrose sweetener that is as sweet as a given percent sucrose reference. For example, if a 1% solution of a sweetener is as sweet as a 10% sucrose solution, then the sweetener is said to be 10 times as potent as sucrose, and has 10% sucrose equivalence.

In one embodiment, the diterpene glycoside is present in an amount that, when added to a consumable, provides a sucrose equivalence of greater than about 2% (w/v), such as, for example, greater than about 3%, about 4%, about 5%, about 6%, about 7%, about 8%, about 9%, about 10%, about 11%, about 12%, about 13% or about 14%.

The amount of sucrose, and thus another measure of sweetness, in a reference solution may be described in degrees Brix (° Bx). One degree Brix is 1 gram of sucrose in 100 grams of solution and represents the strength of the solution as percentage by weight (% w/w) (strictly speaking, by mass). In one embodiment, the diterpene glycoside of the present invention is present in an amount that, when added to a consumable, provides a sweetness equivalent from about 0.50 to 14 degrees Brix, such as, for example, from about 5 to about 12 degrees Brix, about 7 to 10 degrees Brix, or above 10 degrees Brix.

In exemplary embodiments, an isolated and purified diterpene glycoside of the present invention has about 30% or more sweetness compared to the partially purified diterpene glycoside or Stevia leaf, such as, for example, about 40% or more, about 50% or more, about 60% or more, about 70% or more, about 80% or more or about 90% or more.

In other exemplary embodiments, an isolated and purified diterpene glycoside of the present invention has at least about 30% less bitterness (the taste stimulated by certain substances such as quinine, caffeine and sucrose octa-acetate) compared the partially purified diterpene glycoside or Stevia leaf, such as, for example, at least about 40%, at least about 50%, at least about 60%, at least about 70%, at least about 80% or at least about 90%. In a particular embodiment, the isolated and purified diterpene glycoside of the present invention has substantially no bitterness. Methods of measuring bitterness of a compound are known in the art.

In still other exemplary embodiments, an isolated and purified diterpene glycoside of the present invention has at least about 30% less sweet lingering aftertaste (the intensity of the sweet taste after expectoration) compared to the partially purified diterpene glycoside or Stevia leaf, such as, for example, at least about 50%, at least about 60%, at least about 70%, at least about 80% or at least about 90%. In a particular embodiment, the isolated and purified diterpene glycoside of the present invention has substantially no sweet lingering aftertaste. Methods of measuring sweet lingering aftertaste are known in the art.

In yet other exemplary embodiments, an isolated and purified diterpene glycoside of the present invention has at least about 30% less metallic taste (taste associated with metals, tinny or iron) compared to the partially purified diterpene glycoside or Stevia leaf, such as, for example, at least about 50%, at least about 60%, at least about 70%, at least about 80% or at least about 90%. In a particular embodiment, the isolated and purified diterpene glycoside of the present invention has substantially no metallic taste.

In exemplary embodiments, an isolated and purified diterepene glycoside of the present invention exhibits a maximal response (maximum sweetness (% SE) achieved with increasing concentration of compound) that is at least about 30% greater compared to the partially purified diterpene glycoside or Stevia leaf, such as, for example, at least about 40% greater, at least about 50% greater, at least about 60% greater, at least about 70% greater, at least about 80% greater or at least about 90% greater. Methods of measuring the maximal response of a compound are known in the art. In one embodiment, the method is an in vitro cell assay. In some embodiments, the cell is expressing a sweet taste receptor or a dimer of sweet taste receptor.

In other exemplary embodiments, an isolated and purified diterpene glycoside of the present invention exhibits a sweetness onset (the time until maximum sweetness is experienced) that is at least about 30% shorter than the partially purified diterpene glycoside or Stevia leaf, such as, for example, at least about 40% short, at least about 50% shorter, at least about 60% shorter, at least about 70% shorter, at least about 80% shorter or at least about 90% shorter. Methods of measuring sweetness onset are known in the art. In one embodiment, the method is an in vitro cell assay. In some embodiments, the cell is expressing a sweet taste receptor or a dimer of sweet taste receptor.

II. Compositions

The present invention includes compositions comprising at least one diterpene glycoside of the present invention. "Composition," as the term is used herein, refers to a mixture of at least one diterpene glycoside of the present invention and at least one other substance, wherein the diterpene glycoside is admixed with the at least one other substance. As used herein, "admix" means to mingle or add to something else, but in any case, requires an active step.

In a particular embodiment, the at least one other substance does not occur and/or is not admixed with the diterpene glycoside in nature, i.e. the Stevia leaf. As such, the compositions contemplated by the present invention do not occur in nature.

In one embodiment, the present invention is a composition comprising at least one diterpene glycoside of the present invention, provided as part of a mixture. In a particular embodiment, the mixture is selected from the group consisting of diterpene glycosides, stevia extract, by-products of other diterpene glycosides' isolation and purification processes, commercially available diterpene extracts or stevia extracts, by-products of biotransformation reactions of other diterpene glycosides, or any combination thereof.

In one embodiment, the mixture contains at least one diterpene glycoside of the present invention in an amount that ranges from about 1% to about 99% by weight on a dry basis, such as, for example, about 5% to about 99% by weight on a dry basis, from about 10% to about 99%, from about 20% to about 99%, from about 30% to about 99%, from about 40% to about 99%, from about 50% to about 99%, from about 60% to about 99%, from about 70% to about 99%, from about 80% to about 99% and from about 90% to about 99%. In a particular embodiment, the mixture contains at least one diterpene glycoside of the present invention in an amount greater than about 90% by weight on a dry basis, for example, greater than about 91%, greater than about 92%, greater than about 93%, greater than about 94%, greater than about 95%, greater than about 96%, greater than about 97%, greater than about 98% and greater than about 99%.

The term "purified diterpene glycoside", as used herein, refers to a diterpene glycoside present in at least about 50% by weight in a mixture, e.g. stevia extract, such as, for example, at least about 60%, at least about 70%, at least about 80%, at least about 90%, at least about 95% or at least about 97%.

In a particular embodiment, the mixture is an extract of a stevia plant variety. Suitable Stevia varieties include, but are not limited to *S. rebaudiana* Bertoni and *S. rebaudiana* Morita.

The stevia extract may contain one or more additional diterpene glycosides, i.e., diterpene glycosides that are not the diterpene glycosides of the present invention, including, but not limited to, stevioside, rebaudioside A, rebaudioside C, dulcoside A, rubusoside, steviolbioside, rebaudioside B, rebaudioside D, rebaudioside E, rebaudioside F, rebaudioside N, rebaudioside O and combinations thereof.

In one embodiment, the present invention is a composition comprising at least one diterpene glycoside described herein provided as a pure compound, i.e. >99% purity on a dry basis.

The diterpene glycosides of the present invention may be present in the composition in an amount effective to provide a concentration of diterpene glycoside of the present invention from about 1 ppm to about 10,000 ppm when the composition is added to a consumable, such as, for example, from about 1 ppm to about 4,000 ppm, from about 1 ppm to about 3,000 ppm, from about 1 ppm to about 2,000 ppm, from about 1 ppm to about 1,000 ppm.

In another embodiment, the diterpene glycoside of the present invention is present in the composition in an amount effective to provide a concentration of diterpene glycoside of the present invention from about 10 ppm to about 1,000 ppm when the composition is added to a consumable, such as, for example, from about 10 ppm to about 800 ppm, from about 50 ppm to about 800 ppm, or from about 50 ppm to about 600 ppm.

Sweetener Compositions

As noted above, in some embodiments, the diterpene glycoside of the present invention is sweet. Accordingly, the present invention also provides a sweetener composition comprising at least one diterpene glycoside of the present invention. "Sweetener composition," as the term is used herein, refers to a mixture of at least one diterpene of the present invention and at least one other substance, wherein the at least one diterpene glycoside is admixed with the at least one other substance.

In a particular embodiment, the at least one other substance does not occur and/or is not admixed with the diterpene glycoside in nature, i.e. the Stevia leaf. As such, the sweetener compositions contemplated by the present invention do not occur in nature. In one embodiment, the at least one other substance modulates the taste profile of the at least one diterpene glycoside to provide a composition with a more sucrose-like taste profile compared to the diterpene glycoside in nature and (if applicable) the at least one other substance in nature. For example, in certain embodiments the composition exhibits one or more of the following characteristics: improved sweetness potency, improved mouthfeel, decreased sweetness linger, decreased bitterness and/or decreased metallic taste.

In certain exemplary embodiments, the sweetener composition comprises at least one purified diterpene glycoside of this invention.

In one embodiment, the diterpene glycoside of the present invention is the sole sweetener in the sweetener composition, i.e. the diterpene glycoside is the only compound present in the sweetener composition that provides a detectable sweetness.

In further embodiments, the sweetener composition comprising at least one diterpene glycoside of the present invention in combination with at least one additional sweetener. In a particular embodiment, the at least one additional sweetener does not occur with the diterpene glycoside in nature, i.e. Stevia leaf. In a more particular embodiment, a sweetener composition comprises at least one purified diterpene glycoside at at least one additional sweetener that does not occur with the diterpene glycoside in nature.

The amount of diterpene glycoside of the present invention in the sweetener composition may vary. In one embodiment, the diterpene glycoside of the present invention is present in a sweetener composition in any amount to impart the desired sweetness when the sweetener composition is added to a sweetenable composition or sweetenable consumable. In a particular embodiment, the diterpene glycoside of the present invention is present in a concentration above its threshold sweetness recognition concentration.

In one embodiment, the diterpene glycoside of the present invention is present in the sweetener composition in an amount effective to provide a sucrose equivalence of greater than about 2% (w/v) when the sweetener composition is added to a sweetenable composition or sweetenable consumable, such as, for example, greater than about 3%, about 4%, about 5%, about 6%, about 7%, about 8%, about 9%, about 10%, about 11%, about 12%, about 13% or about 14%.

In some embodiments, a diterpene glycoside of the present invention is present in the sweetener composition in an amount that, when added to a consumable, will provide a concentration of the diterpene glycoside of the present invention from about 1 ppm to about 100 ppm, such as, for example, from about 1 ppm to about 90 ppm, from about 5 ppm to about 80 ppm, from about 5 ppm to about 70 ppm, from about 5 ppm to about 60 ppm, from about 5 ppm to about 50 ppm, from about 5 ppm to about 40 ppm, from about 5 ppm to about 30 ppm, from about 5 ppm to about 20 ppm, or 5 ppm to about 15 ppm.

In other embodiments, a diterpene glycoside of the present invention is present in the sweetener composition in an amount that, when added to a consumable, will provide a concentration of the diterpene glycoside of the present invention greater than about 10 ppm, such as, for example, greater than about 20 ppm, about 30 ppm, about 40 ppm, about 50 ppm, about 60 ppm, about 70 ppm, about 80 ppm, about 90 ppm, about 100 ppm, about 200 ppm, about 300 ppm, about 400 ppm, about 500 ppm, about 600 ppm, about 700 ppm, about 800 ppm or about 900 ppm.

In still other embodiments, a diterpene glycoside of the present invention is present in the sweetener composition in an amount that, when added to a consumable, will provide a concentration of the diterpene glycoside of the present invention from about 1 ppm to about 1,000 ppm, such as, for example, from about 10 ppm to about 1,000 ppm, from about 20 ppm to about 1,000 ppm, from about 30 ppm to about 1,000 ppm, from about 30 ppm to about 1,000 ppm, from about 40 ppm to about 1,000 ppm, from about 50 ppm to about 1,000 ppm, from about 60 ppm to about 1,000 ppm, from about 70 ppm to about 1,000 ppm, from about 80 ppm to about 1,000 ppm, from about 90 ppm to about 1,000 ppm, from about 100 ppm to about 1,000 ppm, from about 200 ppm to about 1,000 ppm, from about 300 ppm to about 1,000 ppm, from about 400 ppm to about 1,000 ppm, from about 500 ppm to about 1,000 ppm, from about 600 ppm to about 1,000 ppm, from about 700 ppm to about 1,000 ppm, from about 800 ppm to about 1,000 ppm or from about 900 ppm to about 1,000 ppm.

In one embodiment, the sweetener is at least one natural high-potency sweetener. As used herein, the phrase "natural high potency sweetener" refers to any sweetener found naturally in nature and characteristically has a sweetness potency greater than sucrose, fructose, or glucose, yet has less calories. The natural high potency sweetener can be provided as a pure compound or, alternatively, as part of an extract.

In another embodiment, the sweetener is at least one synthetic sweetener. As used herein, the phrase "synthetic sweetener" refers to any composition which is not found naturally in nature and characteristically has a sweetness potency greater than sucrose, fructose, or glucose, yet has less calories.

In still other embodiments, combinations of natural high potency sweeteners and synthetic sweeteners are contemplated.

In other embodiments, the sweetener is at least one carbohydrate sweetener. Suitable carbohydrate sweeteners are selected from, but not limited to, the group consisting of sucrose, glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheltulose, octolose, fucose, rhamnose, arabinose, turanose, sialose and combinations thereof.

Other suitable sweeteners include rebaudioside A, rebaudioside B, rebaudioside C, rebaudioside D, rebaudioside E, rebaudioside F, rebaudioside I, rebaudioside H, rebaudioside L, rebaudioside K, rebaudioside J, rebaudioside M, rebaudioside N, rebaudioside O, dulcoside A, dulcoside B, rubusoside, stevia, stevioside, mogroside IV, mogroside V, mogroside VI, Luo han guo, siamenoside, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, steviolbioside, hesperitin and cyclocarioside I, sugar alcohols such as erythritol, sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, glucosylated steviol glycosides (GSGs) and combinations thereof.

In a particular embodiment, the sweetener is at least one calorie-providing carbohydrate sweetener. Accordingly, incorporation of the sweetness enhancer reduces the quantity of the calorie-providing carbohydrate sweetener that must be used in a given consumable to achieve a particular SE, thereby allowing the preparation of reduced-calorie consumables.

In one embodiment, the sweetener is a caloric sweetener or mixture of caloric sweeteners. In another embodiment, the caloric sweetener is selected from sucrose, fructose, glucose, high fructose corn/starch syrup, a beet sugar, a cane sugar, and combinations thereof.

In another embodiment, the sweetener is a rare sugar selected from allulose, sorbose, lyxose, ribulose, xylose, xylulose D-allose, L-ribose, D-tagatose, L-glucose, L-fucose, L-arabinose, turanose, kojibiose and combinations thereof.

In still another embodiment, the sweetener is a mixture of at least one natural high potency sweeteners and at least one carbohydrate sweetener. In yet another embodiment, the sweetener is a mixture of at least one synthetic sweetener and at least one carbohydrate sweetener. In a further embodiment, the sweetener is at least one natural high potency sweetener, at least one synthetic sweetener and at least one carbohydrate sweetener.

In exemplary embodiments, a sweetener composition comprising at least one purified diterpene glycoside of the present invention has about 30% or more sweetness compared to a corresponding sweetener composition comprising partially purified diterpene glycoside or Stevia, such as, for example, about 40% or more, about 50% or more, about 60% or more, about 70% or more, about 80% or more or about 90% or more.

In other exemplary embodiments, a sweetener composition comprising at least one purified diterpene glycoside of the present invention has at least about 30% less bitterness (the taste stimulated by certain substances such as quinine, caffeine and sucrose octa-acetate) compared to a corresponding composition comprising partially purified diterpene glycoside or Stevia leaf, such as, for example, at least about 40%, at least about 50%, at least about 60%, at least about 70%, at least about 80% or at least about 90%. In a particular embodiment, a sweetener composition comprising at least one purified diterpene glycoside of the present invention has substantially no bitterness. Methods of measuring bitterness of a compound are known in the art.

In still other exemplary embodiments, a sweetener composition comprising at least one purified diterpene glycoside of the present invention has at least about 30% less sweet lingering aftertaste (the intensity of the sweet taste after expectoration) compared to a corresponding sweetener composition comprising partially purified diterpene glycoside or Stevia leaf, such as, for example, at least about 50%, at least about 60%, at least about 70%, at least about 80% or at least about 90%. In a particular embodiment, a sweetener composition comprising at least one purified diterpene glycoside of the present invention has substantially no sweet lingering aftertaste. Methods of measuring sweet lingering aftertaste are known in the art.

In yet other exemplary embodiments, a sweetener composition comprising at least one purified diterpene glycoside of the present invention has at least about 30% less metallic taste (taste associated with metals, tinny or iron) compared to a corresponding sweetener composition comprising partially purified diterpene glycoside or Stevia leaf, such as, for example, at least about 50%, at least about 60%, at least about 70%, at least about 80% or at least about 90%. In a particular embodiment, a sweetener composition comprising at least one purified diterpene glycoside of the present invention has substantially no metallic taste.

In exemplary embodiments, a sweetener composition comprising at least one purified diterepene glycoside of the present invention exhibits a maximal response (maximum sweetness (% SE) achieved with increasing concentration of compound) that is at least about 30% greater compared to a corresponding sweetener composition comprising partially purified diterpene glycoside or Stevia leaf, such as, for example, at least about 40% greater, at least about 50% greater, at least about 60% greater, at least about 70% greater, at least about 80% greater or at least about 90% greater. Methods of measuring the maximal response of a compound are known in the art.

In other exemplary embodiments, a sweetener composition comprising at least one purified diterpene glycoside of the present invention exhibits a sweetness onset (the time until maximum sweetness is experienced) that is at least about 30% shorter than a sweetener composition comprising partially purified diterpene glycoside or Stevia leaf, such as, for example, at least about 40% short, at least about 50% shorter, at least about 60% shorter, at least about 70% shorter, at least about 80% shorter or at least about 90% shorter. Methods of measuring sweetness onset are known in the art.

Sweetness Enhancers

In a particular embodiment, the diterpene glycoside of the present invention is a sweetness enhancer or modifier. "Sweetness enhancer", as the term is used herein, refers to a compound that enhances, amplifies or potentiates the perception of sweetness of a consumable (e.g. a beverage) when said compound is present in the consumable in a concentration at or below the compound's sweetener recognition threshold, i.e. in a concentration at which compound does not contribute any noticeable sweet taste in the absence of additional sweetener(s).

"Sweetness modifier", as the term is used herein, refers to a compound that changes the taste properties (such as linger, off-notes, or the like) of sweetness of a consumable (e.g. a beverage) when said compound is present in the consumable in a concentration at or below the compound's sweetener recognition threshold.

The term "sweetness enhancer" is synonymous with the terms "sweet taste potentiator," "sweetness potentiator," "sweetness amplifier," and "sweetness intensifier."

In a particular embodiment, the additional sweetener(s) does not naturally occur and/or is not admixed with the at least one diterpene glycoside sweetness enhancer in nature, i.e. Stevia leaf. As such, the sweetness-enhanced consumables contemplated by the present invention do not occur in nature.

In one embodiment, a diterpene glycoside of the present invention may be added directly to the consumable, i.e., not provided in the form of a composition but rather as compound, to enhance sweetness. In this embodiment, a diterpene glycoside of the present invention is added to the consumable at a concentration at or below its sweetness recognition threshold concentration, i.e., a sweetness enhancer. In a particular embodiment, a diterpene glycoside of the present invention is added to the consumable at a concentration below its sweetness recognition threshold concentration, i.e., a sweetness enhancer.

In certain embodiments, a diterpene glycoside of the present invention is a sweetness enhancer or modifier and is added to the consumable in an amount that will provide a concentration of the diterpene glycoside that is at least about 1%, at least about 5%, at least about 10%, at least about 15%, at least about 20%, at least about 25%, at least about 30%, at least about 35%, at least about 40%, at least about 45% or at least about 50% or more below its sweetness recognition threshold.

In still other embodiments, a diterpene glycoside of the present invention is a sweetness enhancer or modifier and is added to the consumable in an amount that will provide a concentration of the diterpene glycoside from about 1 ppm to about 1,000 ppm, such as, for example, from about 10 ppm to about 1,000 ppm, from about 20 ppm to about 1,000 ppm, from about 30 ppm to about 1,000 ppm, from about 30 ppm to about 1,000 ppm, from about 40 ppm to about 1,000 ppm, from about 50 ppm to about 1,000 ppm, from about 60 ppm to about 1,000 ppm, from about 70 ppm to about 1,000 ppm, from about 80 ppm to about 1,000 ppm, from about 90 ppm to about 1,000 ppm, from about 100 ppm to about 1,000 ppm, from about 200 ppm to about 1,000 ppm, from about 300 ppm to about 1,000 ppm, from about 400 ppm to about 1,000 ppm, from about 500 ppm to about 1,000 ppm, from about 600 ppm to about 1,000 ppm, from about 700 ppm to about 1,000 ppm, from about 800 ppm to about 1,000 ppm or from about 900 ppm to about 1,000 ppm.

In some embodiments, the diterpene glycosides of the present invention enhances the sucrose equivalence (SE) of the consumable by at least about 0.5%, about 0.6%, about 0.7%, about 0.8%, about 0.9%, about 1.0%, about 1.5%, about 2.0%, about 2.5%, about 3.0%, about 4.0% or about 5.0%, when compared to the SE of the consumable in the absence of the diterpene glycoside of the present invention.

In other embodiments, at least one diterpene glycoside of the present invention may be added to the consumable in the form of a sweetness enhancing composition. "Sweetness enhancing composition," as the term is used herein, refers to a composition of the present invention—as described above—wherein the composition enhances, amplifies or potentiates the perception of sweetness of a consumable (e.g. a beverage) when a diterpene glycoside of the present invention is present in the sweetness enhancer composition in an amount that will provide a concentration of the diterpene glycoside that is at or below its sweetness recognition threshold when added to the consumable. In a particular embodiment, the diterpene glycoside of the present invention in an amount that will provide a concentration of the diterpene glycoside of that is below its sweetness recognition threshold.

In certain embodiments, a diterpene glycoside of the present invention is present in the sweetness enhancing composition in an amount effective to provide a concentration of the diterpene glycoside that is at least about 1%, at least about 5%, at least about 10%, at least about 15%, at least about 20%, at least about 25%, at least about 30%, at least about 35%, at least about 40%, at least about 45% or at least about 50% or more below its sweetness recognition threshold when the sweetness enhancing composition is added to a consumable.

In still other embodiments, a diterpene glycoside of the present invention is present in the sweetness enhancing composition in an amount that, when added to the consumable, will provide a concentration of the diterpene glycoside from about 1 ppm to about 1,000 ppm, such as, for example, from about 10 ppm to about 1,000 ppm, from about 20 ppm to about 1,000 ppm, from about 30 ppm to about 1,000 ppm, from about 30 ppm to about 1,000 ppm, from about 40 ppm to about 1,000 ppm, from about 50 ppm to about 1,000 ppm, from about 60 ppm to about 1,000 ppm, from about 70 ppm to about 1,000 ppm, from about 80 ppm to about 1,000 ppm, from about 90 ppm to about 1,000 ppm, from about 100 ppm to about 1,000 ppm, from about 200 ppm to about 1,000 ppm, from about 300 ppm to about 1,000 ppm, from about 400 ppm to about 1,000 ppm, from about 500 ppm to about 1,000 ppm, from about 600 ppm to about 1,000 ppm, from about 700 ppm to about 1,000 ppm, from about 800 ppm to about 1,000 ppm or from about 900 ppm to about 1,000 ppm.

It is contemplated that the sweetness enhancing composition can include one or more sweetness enhancers or modifiers in addition to at least one diterpene glycoside of the present invention. In one embodiment, the sweetness enhancing composition can include one additional sweetness enhancer. In other embodiments, the composition can include two or more additional sweetness enhancers. In embodiments where two or more sweetness enhancers or modifiers are utilized, each one should be present at or below its respective sweetness recognition threshold concentration.

The one or more other sweetness enhancers or modifiers are selected from, but not limited to, the group consisting of 2-hydroxybenzoic acid, 3-hydroxybenzoic acid, 4-hydroxybenzoic acid, 2,4-dihydroxybenzoic acid, 3,4-dihydroxybenzoic acid, 2,5-dihydroxybenzoic acid, 2,6-dihydroxybenzoic acid, 2,3,4-trihydroxybenzoic acid, 2,4,6-trihydroxybenzoic acid, 3-aminobenzoic acid, 4-aminobenzoic acid, 4-O-β-D-glucosyl-hesperetin dihydrochalcone, MG isomogrosaide V, 4-hydroxycinnamic acid, 4-methoxycinnamic acid, 1-(2-hydroxyphenyl)-3-(4-pyridyl)-1-propanone, 4-ethoxybenzonitrile, 2-methoxy-5-(phenoxymethyl)-phenol, 1-(2,4-dihydroxyphenyl)-2-(3-methoxy-4-hydroxyphenyl)-ethanone, hesperetin, 2,3',6-trihydroxy-4'-methoxydihydrochalcone, N-(3'-methoxy-4'-hydroxybenzyl)-2,4,6-trihydroxybenzamide, 3'-7-dihydroxy-4'-methoxyflavan, FEMA GRAS flavor 4469, FEMA GRAS flavor 4701, FEMA GRAS flavor 4720, FEMA GRAS flavor 4774, FEMA GRAS flavor 4708, FEMA GRAS flavor 4728, FEMA GRAS flavor 4601, FEMA GRAS flavor 4802, 4-amino-5-(cyclohexyloxy)-2-methylquinoline-3-carboxylic acid, rebaudioside M, rebaudioside N, rebaudioside O, rebaudioside C and combinations thereof.

In one embodiment, addition of the sweetness enhancer or modifier increases the detected sucrose equivalence of the at least one sweetener in a consumable compared to the sucrose equivalence of the same consumable in the absence of the sweetness enhancer.

In a particular embodiment, the consumable is a beverage. According to this embodiment, a diterpene glycoside of the present invention and at least one sweetener is added to a beverage, wherein the diterpene glycoside is present in a concentration at or below its sweetness recognition threshold. In a particular embodiment, the detected sucrose equivalence is increased from about 0.2% to about 5.0%, such as, for example, about 1%, about 2%, about 3%, about 4% or about 5%.

Flavor Enhancers

In another particular embodiment, the diterpene glycoside of the present invention is a flavor enhancer. "Flavor enhancer", as the term is used herein, refers to a compound that enhances, amplifies or potentiates the perceptions of a flavor ingredient (i.e. any substance that provides sweetness, sourness, saltiness, savoriness, bitterness, metallic taste, etc.) when said compound is present in a consumable (e.g. a beverage) in a concentration at or below the compound's flavor recognition threshold, i.e. in a concentration at which compound does not contribute any noticeable flavor in the absence of any flavor ingredient(s). The term "flavor recognition threshold", as generally used herein, is the lowest known concentration of a compound that is perceivable by the human sense of taste as the particular flavor. The flavor recognition threshold concentration is specific for a particular compound, and can vary based on temperature, matrix, ingredients and/or flavor system.

The term "flavor enhancer" is synonymous with the terms "flavor potentiator," "flavor amplifier," and "flavor intensifier."

In a particular embodiment, the flavor ingredient(s) does not naturally occur and/or is not admixed with the at least one diterpene glycoside sweetness enhancer in nature, i.e. Stevia leaf. As such, the flavor-enhanced consumables contemplated by the present invention do not occur in nature.

In one embodiment, at least one diterpene glycoside of the present invention is added directly to the consumable, i.e., not provided in the form of a composition but rather as a compound, to enhance a flavor. In this embodiment, the diterpene glycoside of the present invention is added to the consumable at a concentration at or below its flavor recognition threshold concentration, i.e., a flavor enhancer. In a particular embodiment, the diterpene glycoside of the present invention is added to the consumable at a concentration below its flavor recognition threshold concentration, i.e., a flavor enhancer.

In certain embodiments, a diterpene glycoside of the present invention is a flavor enhancer and is added to the consumable in an amount that will provide a concentration of the diterpene glycoside that is at least about 1%, at least about 5%, at least about 10%, at least about 15%, at least about 20%, at least about 25%, at least about 30%, at least about 35%, at least about 40%, at least about 45% or at least about 50% or more below its flavor recognition threshold.

In still other embodiments, a diterpene glycoside of the present invention is a flavor enhancer and is added to the consumable in an amount that will provide a concentration of the diterpene glycoside from about 1 ppm to about 1,000 ppm, such as, for example, from about 10 ppm to about 1,000 ppm, from about 20 ppm to about 1,000 ppm, from about 30 ppm to about 1,000 ppm, from about 30 ppm to about 1,000 ppm, from about 40 ppm to about 1,000 ppm, from about 50 ppm to about 1,000 ppm, from about 60 ppm to about 1,000 ppm, from about 70 ppm to about 1,000 ppm, from about 80 ppm to about 1,000 ppm, from about 90 ppm to about 1,000 ppm, from about 100 ppm to about 1,000 ppm, from about 200 ppm to about 1,000 ppm, from about 300 ppm to about 1,000 ppm, from about 400 ppm to about 1,000 ppm, from about 500 ppm to about 1,000 ppm, from about 600 ppm to about 1,000 ppm, from about 700 ppm to about 1,000 ppm, from about 800 ppm to about 1,000 ppm or from about 900 ppm to about 1,000 ppm.

The diterpene glycosides of the present invention enhances the flavor of the consumable by at least about 0.5%, about 0.6%, about 0.7%, about 0.8%, about 0.9%, about 1.0%, about 1.5%, about 2.0%, about 2.5%, about 3.0%, about 4.0% or about 5.0%, when compared to the flavor of the consumable in the absence of the diterpene glycosides of the present invention.

In other embodiments, at least one diterpene glycoside of the present invention may be added to the consumable in the form of a flavor enhancing composition. "Flavor enhancing composition," as the term is used herein, refers to a mixture of at least one diterpene glycoside of the present invention and at least one flavor ingredient, wherein the at least one diterpene is admixed with the at least one flavor ingredient—wherein the composition enhances, amplifies or potentiates the perception of the flavor ingredient in a consumable (e.g. a beverage) when the at least one diterpene glycoside of the present invention is present in the flavor enhancer composition in an amount that will provide a concentration of the diterpene glycoside that is at or below its flavor recognition threshold when added to the consumable. Thus, the flavor enhancing compositions contemplated by the present invention do not occur in nature.

Addition of the flavor enhancing composition increases the detected flavor of the at least one flavor ingredient in the consumable compared to the detected flavor of the same ingredient in the consumable in the absence of the flavor enhancer. Without being bound by theory, the flavor enhancing composition likely does not contribute any noticeable taste to the consumable to which it is added because the flavor enhancer is present in the consumable in a concentration at or below the its flavor recognition threshold.

In one embodiment, the flavor enhancing composition comprises at least one diterpene glycoside of the present invention in an amount effective to provide a concentration of the at least one diterpene glycoside that is at or below its flavor recognition threshold when the flavor enhancing composition is added to a consumable.

In a particular embodiment, a diterpene glycoside of the present invention is present in the flavor enhancing composition in an amount effective to provide a concentration of the diterpene glycoside below its flavor recognition threshold when the flavor enhancing composition is added to a consumable.

In certain embodiment, a diterpene glycoside of the present invention is present in the flavor enhancing composition in an amount that, when added to a consumable, is effective to provide a concentration of the compound that is at least about 1%, at least about 5%, at least about 10%, at least about 15%, at least about 20%, at least about 25%, at least about 30%, at least about 35%, at least about 40%, at least about 45% or at least about 50% or more below its flavor recognition threshold.

In still other embodiments, a diterpene glycoside of the present invention is present in the flavor enhancing composition in an amount that, when added to the consumable, will provide a concentration of the diterpene glycoside from about 1 ppm to about 1,000 ppm, such as, for example, from about 10 ppm to about 1,000 ppm, from about 20 ppm to about 1,000 ppm, from about 30 ppm to about 1,000 ppm, from about 30 ppm to about 1,000 ppm, from about 40 ppm to about 1,000 ppm, from about 50 ppm to about 1,000 ppm, from about 60 ppm to about 1,000 ppm, from about 70 ppm to about 1,000 ppm, from about 80 ppm to about 1,000 ppm, from about 90 ppm to about 1,000 ppm, from about 100 ppm to about 1,000 ppm, from about 200 ppm to about 1,000 ppm, from about 300 ppm to about 1,000 ppm, from about 400 ppm to about 1,000 ppm, from about 500 ppm to about 1,000 ppm, from about 600 ppm to about 1,000 ppm, from about 700 ppm to about 1,000 ppm, from about 800 ppm to about 1,000 ppm or from about 900 ppm to about 1,000 ppm.

A person of skill in the art will be able to select the concentration of the diterpene glycoside of the present invention in the flavor enhancing composition so that it may impart an enhanced flavor to a consumable comprising at least one flavor ingredient.

Suitable flavor ingredients include, but are not limited to, vanillin, vanilla extract, mango extract, cinnamon, citrus, coconut, ginger, viridiflorol, almond, menthol (including menthol without mint), grape skin extract, and grape seed extract. "Flavorant" and "flavoring ingredient" are synonymous and can include natural or synthetic substances or combinations thereof. Flavorants also include any other substance which imparts flavor and may include natural or non-natural (synthetic) substances which are safe for human or animals when used in a generally accepted range. Non-limiting examples of proprietary flavorants include Döhler™ Natural Flavoring Sweetness Enhancer K14323 (Döhler™, Darmstadt, Germany), Symrise™ Natural Flavor Mask for Sweeteners 161453 and 164126 (Symrise™, Holzminden, Germany), Natural Advantage™ Bitterness Blockers 1, 2, 9 and 10 (Natural Advantage™, Freehold, N.J., U.S.A.), and Sucramask™ (Creative Research Management, Stockton, Calif., U.S.A.).

In another embodiment, the flavor enhancing composition comprising at least one diterpene glycoside of the present invention enhances flavors (either individual flavors or the overall flavor) when added to the consumable. These flavors include, but are not limited to, fruit flavors, including tropical fruit flavors, and vanilla-caramel type flavors.

The compositions described herein can be customized to provide the desired calorie content. For example, compositions can be "full-calorie", such that they impart the desired sweetness when added to a consumable (such as, for example, a beverage) and have about 120 calories per 8 oz serving. Alternatively, compositions can be "mid-calorie", such that they impart the desired sweetness when added to a consumable (such as, for example, as beverage) and have less than about 60 calories per 8 oz serving. In other embodiments, compositions can be "low-calorie", such that they impart the desired sweetness when added to a consumable (such as, for example, as beverage) and have less than 40 calories per 8 oz serving. In still other embodiments, the compositions can be "zero-calorie", such that they impart the desired sweetness when added to a consumable (such as, for example, a beverage) and have less than 5 calories per 8 oz. serving.

Additives

The compositions may comprise, in addition to at least one diterpene glycoside of the present invention, one or more additives and/or functional ingredients, detailed herein below.

Exemplary additives include, but are not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, caffeine, flavorants and flavoring ingredients, astringent compounds, proteins or protein hydrolysates, surfactants, emulsifiers, plant extracts, flavonoids, alcohols, polymers and combinations thereof.

In one embodiment, the composition further comprises one or more polyols. The term "polyol", as used herein, refers to a molecule that contains more than one hydroxyl group. A polyol may be a diol, triol, or a tetraol which contains 2, 3, and 4 hydroxyl groups respectively. A polyol also may contain more than 4 hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group.

Non-limiting examples of polyols in some embodiments include maltitol, mannitol, sorbitol, lactitol, xylitol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, reduced glucose syrup, and sugar alcohols or any other carbohydrates capable of being reduced which do not adversely affect taste.

Suitable amino acid additives include, but are not limited to, aspartic acid, arginine, glycine, glutamic acid, proline, threonine, theanine, cysteine, cystine, alanine, valine, tyrosine, leucine, arabinose, trans-4-hydroxyproline, isoleucine, asparagine, serine, lysine, histidine, ornithine, methionine, carnitine, aminobutyric acid (α-, β-, and/or δ-isomers), glutamine, hydroxyproline, taurine, norvaline, sarcosine, and their salt forms such as sodium or potassium salts or acid salts. The amino acid additives also may be in the D- or L-configuration and in the mono-, di-, or tri-form of the same or different amino acids. Additionally, the amino acids may be α-, β-, γ- and/or δ-isomers if appropriate. Combinations of the foregoing amino acids and their corresponding salts (e.g., sodium, potassium, calcium, magnesium salts or other alkali or alkaline earth metal salts thereof, or acid salts) also are suitable additives in some embodiments. The amino acids may be natural or synthetic. The amino acids also may be modified. Modified amino acids refers to any amino acid wherein at least one atom has been added, removed, substituted, or combinations thereof (e.g., N-alkyl amino acid, N-acyl amino acid, or N-methyl amino acid). Non-limiting examples of modified amino acids include amino acid derivatives such as trimethyl glycine, N-methyl-glycine, and N-methyl-alanine. As used herein, modified amino acids encompass both modified and unmodified amino acids. As used herein, amino acids also encompass both peptides and polypeptides (e.g., dipeptides, tripeptides, tetrapeptides, and pentapeptides) such as glutathione and L-alanyl-L-glutamine. Suitable polyamino acid additives include poly-L-aspartic acid, poly-L-lysine (e.g., poly-L-α-lysine or poly-L-ε-lysine), poly-L-ornithine (e.g., poly-L-α-ornithine or poly-L-ε-ornithine), poly-L-arginine, other polymeric forms of amino acids, and salt forms thereof (e.g., calcium, potassium, sodium, or magnesium salts such as L-glutamic acid mono sodium salt). The poly-amino acid additives also may be in the D- or L-configuration. Additionally, the poly-amino acids may be α-, β-, γ-, δ-, and ε-isomers if appropriate. Combinations of the foregoing poly-amino acids and their corresponding salts (e.g., sodium, potassium, calcium, magnesium salts or other alkali or alkaline earth metal salts thereof or acid salts) also are suitable additives in some embodiments. The poly-amino acids described herein also may comprise co-polymers of different amino acids. The poly-amino acids may be natural or synthetic. The poly-amino acids also may be modified, such that at least one atom has been added, removed, substituted, or combinations thereof (e.g., N-alkyl poly-amino acid or N-acyl poly-amino acid). As used herein, poly-amino acids encompass both modified and unmodified poly-amino acids. For example, modified poly-amino acids include, but are not limited to, poly-amino acids of various molecular weights (MW), such as poly-L-α-lysine with a MW of 1,500, MW of 6,000, MW of 25,200, MW of 63,000, MW of 83,000, or MW of 300,000.

Suitable sugar acid additives include, but are not limited to, aldonic, uronic, aldaric, alginic, gluconic, glucuronic, glucaric, galactaric, galacturonic, and salts thereof (e.g., sodium, potassium, calcium, magnesium salts or other physiologically acceptable salts), and combinations thereof.

Suitable nucleotide additives include, but are not limited to, inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, alkali or alkaline earth metal salts thereof, and combinations thereof. The nucleotides described herein also may comprise nucleotide-related additives, such as nucleosides or nucleic acid bases (e.g., guanine, cytosine, adenine, thymine, uracil).

Suitable organic acid additives include any compound which comprises a —COOH moiety, such as, for example, C2-C30 carboxylic acids, substituted hydroxyl C2-C30 carboxylic acids, butyric acid (ethyl esters), substituted butyric acid (ethyl esters), benzoic acid, substituted benzoic acids (e.g., 2,4-dihydroxybenzoic acid), substituted cinnamic acids, hydroxyacids, substituted hydroxybenzoic acids, anisic acid substituted cyclohexyl carboxylic acids, tannic acid, aconitic acid, lactic acid, tartaric acid, citric acid, isocitric acid, gluconic acid, glucoheptonic acids, adipic acid, hydroxycitric acid, malic acid, fruitaric acid (a blend of malic, fumaric, and tartaric acids), fumaric acid, maleic acid, succinic acid, chlorogenic acid, salicylic acid, creatine, caffeic acid, bile acids, acetic acid, ascorbic acid, alginic acid, erythorbic acid, polyglutamic acid, glucono delta lactone, and their alkali or alkaline earth metal salt derivatives thereof. In addition, the organic acid additives also may be in either the D- or L-configuration.

Suitable organic acid additive salts include, but are not limited to, sodium, calcium, potassium, and magnesium salts of all organic acids, such as salts of citric acid, malic acid, tartaric acid, fumaric acid, lactic acid (e.g., sodium lactate), alginic acid (e.g., sodium alginate), ascorbic acid (e.g., sodium ascorbate), benzoic acid (e.g., sodium benzoate or potassium benzoate), sorbic acid and adipic acid. The examples of the organic acid additives described optionally may be substituted with at least one group chosen from hydrogen, alkyl, alkenyl, alkynyl, halo, haloalkyl, carboxyl, acyl, acyloxy, amino, amido, carboxyl derivatives, alkylamino, dialkylamino, arylamino, alkoxy, aryloxy, nitro, cyano, sulfo, thiol, imine, sulfonyl, sulfenyl, sulfinyl, sulfamyl, carboxalkoxy, carboxamido, phosphonyl, phosphinyl, phosphoryl, phosphino, thioester, thioether, anhydride, oximino, hydrazino, carbamyl, phosphor or phosphonato.

Suitable inorganic acid additives include, but are not limited to, phosphoric acid, phosphorous acid, polyphosphoric acid, hydrochloric acid, sulfuric acid, carbonic acid, sodium dihydrogen phosphate, and alkali or alkaline earth metal salts thereof (e.g., inositol hexaphosphate Mg/Ca).

Suitable bitter compound additives include, but are not limited to, caffeine, quinine, urea, bitter orange oil, naringin, quassia, and salts thereof.

Suitable flavorants and flavoring ingredient additives include, but are not limited to, vanillin, vanilla extract, mango extract, cinnamon, citrus, coconut, ginger, viridiflorol, almond, menthol (including menthol without mint), grape skin extract, and grape seed extract. "Flavorant" and "flavoring ingredient" are synonymous and can include natural or synthetic substances or combinations thereof. Flavorants also include any other substance which imparts flavor and may include natural or non-natural (synthetic) substances which are safe for human or animals when used in a generally accepted range. Non-limiting examples of proprietary flavorants include Döhler™ Natural Flavoring Sweetness Enhancer K14323 (Döhler™ Darmstadt, Germany), Symrise™ Natural Flavor Mask for Sweeteners 161453 and 164126 (Symrise™, Holzminden, Germany), Natural Advantage™ Bitterness Blockers 1, 2, 9 and 10 (Natural Advantage™, Freehold, N.J., U.S.A.), and Sucramask™ (Creative Research Management, Stockton, Calif., U.S.A.).

Suitable polymer additives include, but are not limited to, chitosan, pectin, pectic, pectinic, polyuronic, polygalacturonic acid, starch, food hydrocolloid or crude extracts thereof (e.g., gum acacia senegal (Fibergum™), gum acacia seyal, carageenan), poly-L-lysine (e.g., poly-L-α-lysine or poly-L-ε-lysine), poly-L-ornithine (e.g., poly-L-α-ornithine or poly-L-ε-ornithine), polypropylene glycol, polyethylene glycol, poly(ethylene glycol methyl ether), polyarginine, polyaspartic acid, polyglutamic acid, polyethylene imine, alginic acid, sodium alginate, propylene glycol alginate, and sodium polyethyleneglycolalginate, sodium hexametaphosphate and its salts, and other cationic polymers and anionic polymers.

Suitable protein or protein hydrolysate additives include, but are not limited to, bovine serum albumin (BSA), whey protein (including fractions or concentrates thereof such as 90% instant whey protein isolate, 34% whey protein, 50% hydrolyzed whey protein, and 80% whey protein concentrate), soluble rice protein, soy protein, protein isolates, protein hydrolysates, reaction products of protein hydrolysates, glycoproteins, and/or proteoglycans containing amino acids (e.g., glycine, alanine, serine, threonine, asparagine, glutamine, arginine, valine, isoleucine, leucine, norvaline, methionine, proline, tyrosine, hydroxyproline, and the like), collagen (e.g., gelatin), partially hydrolyzed collagen (e.g., hydrolyzed fish collagen), and collagen hydrolysates (e.g., porcine collagen hydrolysate).

Suitable surfactant additives include, but are not limited to, polysorbates (e.g., polyoxyethylene sorbitan monooleate (polysorbate 80), polysorbate 20, polysorbate 60), sodium dodecylbenzenesulfonate, dioctyl sulfosuccinate or dioctyl sulfosuccinate sodium, sodium dodecyl sulfate, cetylpyridinium chloride (hexadecylpyridinium chloride), hexadecyltrimethylammonium bromide, sodium cholate, carbamoyl, choline chloride, sodium glycocholate, sodium taurodeoxycholate, lauric arginate, sodium stearoyl lactylate, sodium taurocholate, lecithins, sucrose oleate esters, sucrose stearate esters, sucrose palmitate esters, sucrose laurate esters, and other emulsifiers, and the like.

Suitable flavonoid additives are classified as flavonols, flavones, flavanones, flavan-3-ols, isoflavones, or anthocyanidins. Non-limiting examples of flavonoid additives include, but are not limited to, catechins (e.g., green tea extracts such as Polyphenon™ 60, Polyphenon™ 30, and Polyphenon™ 25 (Mitsui Norin Co., Ltd., Japan), polyphenols, rutins (e.g., enzyme modified rutin Sanmelin™ AO (San-fi Gen F.F.I., Inc., Osaka, Japan)), neohesperidin, naringin, neohesperidin dihydrochalcone, and the like.

Suitable alcohol additives include, but are not limited to, ethanol.

Suitable astringent compound additives include, but are not limited to, tannic acid, europium chloride ($EuCl_3$), gadolinium chloride ($GdCl_3$), terbium chloride ($TbCl_3$), alum, tannic acid, and polyphenols (e.g., tea polyphenols).

Exemplary functional ingredients include, but are not limited to, saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

Saponin

In certain embodiments, the functional ingredient is at least one saponin. As used herein, the at least one saponin may comprise a single saponin or a plurality of saponins as a functional ingredient for the composition provided herein. Generally, according to particular embodiments of this invention, the at least one saponin is present in the composition in an amount sufficient to promote health and wellness.

Saponins are glycosidic natural plant products comprising an aglycone ring structure and one or more sugar moieties. The combination of the nonpolar aglycone and the water soluble sugar moiety gives saponins surfactant properties, which allow them to form a foam when shaken in an aqueous solution.

Non-limiting examples of specific saponins for use in particular embodiments of the invention include group A acetyl saponin, group B acetyl saponin, and group E acetyl saponin.

Saponins can be found in a large variety of plants and plant products, and are especially prevalent in plant skins and barks where they form a waxy protective coating. Several common sources of saponins include soybeans, which have approximately 5% saponin content by dry weight, soapwort plants (*Saponaria*), the root of which was used historically as soap, as well as alfalfa, aloe, asparagus, grapes, chickpeas, yucca, and various other beans and weeds. Saponins may be obtained from these sources by using extraction techniques well known to those of ordinary skill in the art. A description of conventional extraction techniques can be found in U.S. Pat. Appl. No. 2005/0123662, the disclosure of which is expressly incorporated by reference.

Antioxidant

In certain embodiments, the functional ingredient is at least one antioxidant. As used herein, the at least one antioxidant may comprise a single antioxidant or a plurality of antioxidants. Generally, according to particular embodiments of this invention, the at least one antioxidant is present in the composition in an amount sufficient to promote health and wellness.

As used herein "antioxidant" refers to any substance which inhibits, suppresses, or reduces oxidative damage to cells and biomolecules. Without being bound by theory, it is believed that antioxidants inhibit, suppress, or reduce oxidative damage to cells or biomolecules by stabilizing free radicals before they can cause harmful reactions. As such, antioxidants may prevent or postpone the onset of some degenerative diseases.

Examples of suitable antioxidants for embodiments of this invention include, but are not limited to, vitamins, vitamin cofactors, minerals, hormones, carotenoids, carotenoid terpenoids, non-carotenoid terpenoids, flavonoids, flavonoid polyphenolics (e.g., bioflavonoids), flavonols, flavones, phenols, polyphenols, esters of phenols, esters of polyphenols, nonflavonoid phenolics, isothiocyanates, and combinations thereof. In some embodiments, the antioxidant is vitamin A, vitamin C, vitamin E, ubiquinone, mineral selenium, manganese, melatonin, α-carotene, β-carotene, lycopene, lutein, zeanthin, crypoxanthin, reservatol, eugenol, quercetin, catechin, gossypol, hesperetin, curcumin, ferulic acid, thymol, hydroxytyrosol, tumeric, thyme, olive oil, lipoic acid, glutathinone, gutamine, oxalic acid, tocopherol-derived compounds, butylated hydroxyanisole (BHA), butylated hydroxytoluene (BHT), ethyl enediaminetetraacetic acid (EDTA), tert-butylhydroquinone, acetic acid, pectin, tocotrienol, tocopherol, coenzyme Q10, zeaxanthin, astaxanthin, canthaxantin, saponins, limonoids, kaempfedrol, myricetin, isorhamnetin, proanthocyanidins, quercetin, rutin, luteolin, apigenin, tangeritin, hesperetin, naringenin, erodictyol, flavan-3-ols (e.g., anthocyanidins), gallocatechins, epicatechin and its gallate forms, epigallocatechin and its gallate forms (ECGC) theaflavin and its gallate forms, thearubigins, isoflavone, phytoestrogens, genistein, daidzein, glycitein, anythocyanins, cyaniding, delphinidin, malvidin, pelargonidin, peonidin, petunidin, ellagic acid, gallic acid, salicylic acid, rosmarinic acid, cinnamic acid and its derivatives (e.g., ferulic acid), chlorogenic acid, chicoric acid, gallotannins, ellagitannins, anthoxanthins, betacyanins and other plant pigments, silymarin, citric acid, lignan, antinutrients, bilirubin, uric acid, R-α-lipoic acid, N-acetylcysteine, emblicanin, apple extract, apple skin extract (applephenon), rooibos extract red, rooibos extract, green, hawthorn berry extract, red raspberry extract, green coffee antioxidant (GCA), aronia extract 20%, grape seed extract (VinOseed), cocoa extract, hops extract, mangosteen extract, mangosteen hull extract, cranberry extract, pomegranate extract, pomegranate hull extract, pomegranate seed extract, hawthorn berry extract, pomella pomegranate extract, cinnamon bark extract, grape skin extract, bilberry extract, pine bark extract, pycnogenol, elderberry extract, mulberry root extract, wolfberry (gogi) extract, blackberry extract, blueberry extract, blueberry leaf extract, raspberry extract, turmeric extract, citrus bioflavonoids, black currant, ginger, acai powder, green coffee bean extract, green tea extract, and phytic acid, or combinations thereof. In alternate embodiments, the antioxidant is a synthetic antioxidant such as butylated hydroxytolune or butylated hydroxyanisole, for example. Other sources of suitable antioxidants for embodiments of this invention include, but are not limited to, fruits, vegetables, tea, cocoa, chocolate, spices, herbs, rice, organ meats from livestock, yeast, whole grains, or cereal grains.

Particular antioxidants belong to the class of phytonutrients called polyphenols (also known as "polyphenolics"), which are a group of chemical substances found in plants, characterized by the presence of more than one phenol group per molecule. A variety of health benefits may be derived from polyphenols, including prevention of cancer, heart disease, and chronic inflammatory disease and improved mental strength and physical strength, for example. Suitable polyphenols for embodiments of this invention include catechins, proanthocyanidins, procyanidins, anthocyanins, quercerin, rutin, reservatrol, isoflavones, curcumin, punicalagin, ellagitannin, hesperidin, naringin, citrus flavonoids, chlorogenic acid, other similar materials, and combinations thereof.

In particular embodiments, the antioxidant is a catechin such as, for example, epigallocatechin gallate (EGCG). Suitable sources of catechins for embodiments of this invention include, but are not limited to, green tea, white tea, black tea, oolong tea, chocolate, cocoa, red wine, grape seed, red grape skin, purple grape skin, red grape juice, purple grape juice, berries, pycnogenol, and red apple peel.

In some embodiments, the antioxidant is chosen from proanthocyanidins, procyanidins or combinations thereof. Suitable sources of proanthocyanidins and procyanidins for embodiments of this invention include, but are not limited to, red grapes, purple grapes, cocoa, chocolate, grape seeds, red wine, cacao beans, cranberry, apple peel, plum, blueberry, black currants, choke berry, green tea, sorghum, cinnamon, barley, red kidney bean, pinto bean, hops, almonds, hazelnuts, pecans, pistachio, pycnogenol, and colorful berries.

In particular embodiments, the antioxidant is an anthocyanin. Suitable sources of anthocyanins for embodiments of this invention include, but are not limited to, red berries, blueberries, bilberry, cranberry, raspberry, cherry, pomegranate, strawberry, elderberry, choke berry, red grape skin, purple grape skin, grape seed, red wine, black currant, red currant, cocoa, plum, apple peel, peach, red pear, red cabbage, red onion, red orange, and blackberries.

In some embodiments, the antioxidant is chosen from quercetin, rutin or combinations thereof. Suitable sources of quercetin and rutin for embodiments of this invention include, but are not limited to, red apples, onions, kale, bog whortleberry, lingonberrys, chokeberry, cranberry, blackberry, blueberry, strawberry, raspberry, black currant, green tea, black tea, plum, apricot, parsley, leek, broccoli, chili pepper, berry wine, and ginkgo.

In some embodiments, the antioxidant is reservatrol. Suitable sources of reservatrol for embodiments of this invention include, but are not limited to, red grapes, peanuts, cranberry, blueberry, bilberry, mulberry, Japanese Itadori tea, and red wine.

In particular embodiments, the antioxidant is an isoflavone. Suitable sources of isoflavones for embodiments of this invention include, but are not limited to, soy beans, soy products, legumes, alfalfa sprouts, chickpeas, peanuts, and red clover.

In some embodiments, the antioxidant is curcumin. Suitable sources of curcumin for embodiments of this invention include, but are not limited to, turmeric and mustard.

In particular embodiments, the antioxidant is chosen from punicalagin, ellagitannin or combinations thereof. Suitable sources of punicalagin and ellagitannin for embodiments of this invention include, but are not limited to, pomegranate, raspberry, strawberry, walnut, and oak-aged red wine.

In particular embodiments, the antioxidant is chlorogenic acid. Suitable sources of chlorogenic acid for embodiments of this invention include, but are not limited to, green coffee, yerba mate, red wine, grape seed, red grape skin, purple grape skin, red grape juice, purple grape juice, apple juice, cranberry, pomegranate, blueberry, strawberry, sunflower, Echinacea, pycnogenol, and apple peel.

Dietary Fiber

In certain embodiments, the functional ingredient is at least one dietary fiber source. As used herein, the at least one dietary fiber source may comprise a single dietary fiber source or a plurality of dietary fiber sources as a functional ingredient for the compositions provided herein. Generally, according to particular embodiments of this invention, the at least one dietary fiber source is present in the composition in an amount sufficient to promote health and wellness.

Numerous polymeric carbohydrates having significantly different structures in both composition and linkages fall within the definition of dietary fiber. Such compounds are well known to those skilled in the art, non-limiting examples of which include non-starch polysaccharides, lignin, cellulose, methylcellulose, the hemicelluloses, β-glucans, pectins, gums, mucilage, waxes, inulins, oligosaccharides, fructooligosaccharides, cyclodextrins, chitins, and combinations thereof.

Food sources of dietary fiber include, but are not limited to, grains, legumes, fruits, and vegetables. Grains providing dietary fiber include, but are not limited to, oats, rye, barley, wheat, Legumes providing fiber include, but are not limited to, peas and beans such as soybeans. Fruits and vegetables providing a source of fiber include, but are not limited to, apples, oranges, pears, bananas, berries, tomatoes, green beans, broccoli, cauliflower, carrots, potatoes, celery. Plant foods such as bran, nuts, and seeds (such as flax seeds) are also sources of dietary fiber. Parts of plants providing dietary fiber include, but are not limited to, the stems, roots, leaves, seeds, pulp, and skin.

Although dietary fiber generally is derived from plant sources, indigestible animal products such as chitins are also classified as dietary fiber. Chitin is a polysaccharide composed of units of acetylglucosamine joined by β(1-4) linkages, similar to the linkages of cellulose.

Fatty Acid

In certain embodiments, the functional ingredient is at least one fatty acid. As used herein, the at least one fatty acid may be single fatty acid or a plurality of fatty acids. Generally, according to particular embodiments of this invention, the at least one fatty acid is present in the composition in an amount sufficient to promote health and wellness.

As used herein, "fatty acid" refers to any straight chain monocarboxylic acid and includes saturated fatty acids, unsaturated fatty acids, long chain fatty acids, medium chain fatty acids, short chain fatty acids, fatty acid precursors (including omega-9 fatty acid precursors), and esterified fatty acids. As used herein, "long chain polyunsaturated fatty acid" refers to any polyunsaturated carboxylic acid or acid" with a long aliphatic tail. As used herein, "omega-3 fatty acid" refers to any polyunsaturated fatty acid having a first double bond as the third carbon-carbon bond from the terminal methyl end of its carbon chain. In particular embodiments, the omega-3 fatty acid may comprise a long chain omega-3 fatty acid. As used herein, "omega-6 fatty acid" any polyunsaturated fatty acid having a first double bond as the sixth carbon-carbon bond from the terminal methyl end of its carbon chain.

Suitable omega-3 fatty acids for use in embodiments of the present invention can be derived from algae, fish, animals, plants, or combinations thereof, for example. Examples of suitable omega-3 fatty acids include, but are not limited to, linolenic acid, alpha-linolenic acid, eicosapentaenoic acid, docosahexaenoic acid, stearidonic acid, eicosatetraenoic acid and combinations thereof. In some embodiments, suitable omega-3 fatty acids can be provided in fish oils, (e.g., menhaden oil, tuna oil, salmon oil, bonito oil, and cod oil), microalgae omega-3 oils or combinations thereof. In particular embodiments, suitable omega-3 fatty acids may be derived from commercially available omega-3 fatty acid oils such as Microalgae DHA oil (from Martek, Columbia, Md.), OmegaPure (from Omega Protein, Houston, Tex.), Marinol C-38 (from Lipid Nutrition, Channahon, Ill.), Bonito oil and MEG-3 (from Ocean Nutrition, Dartmouth, NS), Evogel (from Symrise, Holzminden, Germany), Marine Oil, from tuna or salmon (from Arista Wilton, Conn.), OmegaSource 2000, Marine Oil, from menhaden and Marine Oil, from cod (from OmegaSource, RTP, NC).

Suitable omega-6 fatty acids include, but are not limited to, linoleic acid, gamma-linolenic acid, dihommo-gamma-linolenic acid, arachidonic acid, eicosadienoic acid, docosadienoic acid, adrenic acid, docosapentaenoic acid and combinations thereof.

Suitable esterified fatty acids for embodiments of the present invention may include, but are not limited to, monoacylglycerols containing omega-3 and/or omega-6 fatty acids, diacylglycerols containing omega-3 and/or omega-6 fatty acids, or triacylglycerols containing omega-3 and/or omega-6 fatty acids and combinations thereof.

Vitamin

In certain embodiments, the functional ingredient is at least one vitamin.

As used herein, the at least one vitamin may be single vitamin or a plurality of vitamins. Generally, according to particular embodiments of this invention, the at least one vitamin is present in the composition in an amount sufficient to promote health and wellness.

Vitamins are organic compounds that the human body needs in small quantities for normal functioning. The body uses vitamins without breaking them down, unlike other nutrients such as carbohydrates and proteins. To date, thirteen vitamins have been recognized, and one or more can be used in the compositions herein. Suitable vitamins include, vitamin A, vitamin D, vitamin E, vitamin K, vitamin B1, vitamin B2, vitamin B3, vitamin B5, vitamin B6, vitamin B7, vitamin B9, vitamin B12, and vitamin C.

Various other compounds have been classified as vitamins by some authorities. These compounds may be termed pseudo-vitamins and include, but are not limited to, compounds such as ubiquinone (coenzyme Q10), pangamic acid, dimethylglycine, taestrile, amygdaline, flavanoids, para-aminobenzoic acid, adenine, adenylic acid, and s-methyl-methionine. As used herein, the term vitamin includes pseudo-vitamins.

In some embodiments, the vitamin is a fat-soluble vitamin chosen from vitamin A, D, E, K and combinations thereof.

In other embodiments, the vitamin is a water-soluble vitamin chosen from vitamin B1, vitamin B2, vitamin B3, vitamin B6, vitamin B12, folic acid, biotin, pantothenic acid, vitamin C and combinations thereof.

Glucosamine

In certain embodiments, the functional ingredient is glucosamine. Generally, according to particular embodiments of this invention, glucosamine is present in the compositions in an amount sufficient to promote health and wellness. The compositions can further comprise chondroitin sulfate.

Mineral

In certain embodiments, the functional ingredient is at least one mineral. As used herein, the at least one mineral may be single mineral or a plurality of minerals. Generally, according to particular embodiments of this invention, the at least one mineral is present in an amount sufficient to promote health and wellness.

Minerals, in accordance with the teachings of this invention, comprise inorganic chemical elements required by living organisms. Minerals are comprised of a broad range of compositions (e.g., elements, simple salts, and complex silicates) and also vary broadly in crystalline structure. They may naturally occur in foods and beverages, may be added as a supplement, or may be consumed or administered separately from foods or beverages.

Minerals may be categorized as either bulk minerals, which are required in relatively large amounts, or trace minerals, which are required in relatively small amounts. Bulk minerals generally are required in amounts greater than or equal to about 100 mg per day and trace minerals are those that are required in amounts less than about 100 mg per day.

In particular embodiments of this invention, the mineral is chosen from bulk minerals, trace minerals or combinations thereof. Non-limiting examples of bulk minerals include calcium, chlorine, magnesium, phosphorous, potassium, sodium, and sulfur. Non-limiting examples of trace minerals include chromium, cobalt, copper, fluorine, iron, manganese, molybdenum, selenium, zinc, and iodine. Although iodine generally is classified as a trace mineral, it is required in larger quantities than other trace minerals and often is categorized as a bulk mineral.

In other particular embodiments of this invention, the mineral is a trace mineral, believed to be necessary for human nutrition, non-limiting examples of which include bismuth, boron, lithium, nickel, rubidium, silicon, strontium, tellurium, tin, titanium, tungsten, and vanadium.

The minerals embodied herein may be in any form known to those of ordinary skill in the art. For example, in a particular embodiment the minerals may be in their ionic form, having either a positive or negative charge. In another particular embodiment the minerals may be in their molecular form. For example, sulfur and phosphorous often are found naturally as sulfates, sulfides, and phosphates.

Preservative

In certain embodiments, the functional ingredient is at least one preservative. As used herein, the at least one preservative may be single preservative or a plurality of preservatives. Generally, according to particular embodiments of this invention, the at least one preservative is present in an amount sufficient to promote health and wellness.

In particular embodiments of this invention, the preservative is chosen from antimicrobials, antioxidants, antienzymatics or combinations thereof. Non-limiting examples of antimicrobials include sulfites, propionates, benzoates, sorbates, nitrates, nitrites, bacteriocins, salts, sugars, acetic acid, dimethyl dicarbonate (DMDC), ethanol, and ozone.

According to a particular embodiment, the preservative is a sulfite. Sulfites include, but are not limited to, sulfur dioxide, sodium bisulfite, and potassium hydrogen sulfite.

According to another particular embodiment, the preservative is a propionate. Propionates include, but are not limited to, propionic acid, calcium propionate, and sodium propionate.

According to yet another particular embodiment, the preservative is a benzoate. Benzoates include, but are not limited to, sodium benzoate and benzoic acid.

In another particular embodiment, the preservative is a sorbate. Sorbates include, but are not limited to, potassium sorbate, sodium sorbate, calcium sorbate, and sorbic acid.

In still another particular embodiment, the preservative is a nitrate and/or a nitrite. Nitrates and nitrites include, but are not limited to, sodium nitrate and sodium nitrite.

In yet another particular embodiment, the at least one preservative is a bacteriocin, such as, for example, nisin.

In another particular embodiment, the preservative is ethanol.

In still another particular embodiment, the preservative is ozone.

Non-limiting examples of antienzymatics suitable for use as preservatives in particular embodiments of the invention include ascorbic acid, citric acid, and metal chelating agents such as ethylenediaminetetraacetic acid (EDTA).

Hydration Agent

In certain embodiments, the functional ingredient is at least one hydration agent. As used herein, the at least one hydration agent may be single hydration agent or a plurality of hydration agents. Generally, according to particular embodiments of this invention, the at least one hydration agent is present in an amount sufficient to promote health and wellness.

Hydration agents help the body to replace fluids that are lost through excretion. For example, fluid is lost as sweat in order to regulate body temperature, as urine in order to excrete waste substances, and as water vapor in order to exchange gases in the lungs. Fluid loss can also occur due to a wide range of external causes, non-limiting examples of which include physical activity, exposure to dry air, diarrhea, vomiting, hyperthermia, shock, blood loss, and hypotension. Diseases causing fluid loss include diabetes, cholera, gastroenteritis, shigellosis, and yellow fever. Forms of malnutrition that cause fluid loss include the excessive consumption of alcohol, electrolyte imbalance, fasting, and rapid weight loss.

In a particular embodiment, the hydration agent is an electrolyte, non-limiting examples of which include sodium, potassium, calcium, magnesium, chloride, phosphate, bicarbonate, and combinations thereof. Suitable electrolytes for use in particular embodiments of this invention are also described in U.S. Pat. No. 5,681,569, the disclosure of which is expressly incorporated herein by reference. In particular embodiments, the electrolytes are obtained from their corresponding water-soluble salts. Non-limiting examples of salts for use in particular embodiments include chlorides, carbonates, sulfates, acetates, bicarbonates, citrates, phosphates, hydrogen phosphates, tartrates, sorbates, citrates, benzoates, or combinations thereof. In other embodiments, the electrolytes are provided by juice, fruit extracts, vegetable extracts, tea, or teas extracts.

In particular embodiments of this invention, the hydration agent is a carbohydrate to supplement energy stores burned by muscles. Suitable carbohydrates for use in particular embodiments of this invention are described in U.S. Pat. Nos. 4,312,856, 4,853,237, 5,681,569, and 6,989,171, the disclosures of which are expressly incorporated herein by reference. Non-limiting examples of suitable carbohydrates include monosaccharides, disaccharides, oligosaccharides, complex polysaccharides or combinations thereof. Non-limiting examples of suitable types of monosaccharides for use in particular embodiments include trioses, tetroses, pentoses, hexoses, heptoses, octoses, and nonoses. Non-limiting examples of specific types of suitable monosaccharides include glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheltulose, octolose, and sialose. Non-limiting examples of suitable disaccharides include sucrose, lactose, and maltose. Non-limiting examples of suitable oligosaccharides include saccharose, maltotriose, and maltodextrin. In other particular embodiments, the carbohydrates are provided by a corn syrup, a beet sugar, a cane sugar, a juice, or a tea.

In another particular embodiment, the hydration agent is a flavanol that provides cellular rehydration. Flavanols are a class of natural substances present in plants, and generally comprise a 2-phenylbenzopyrone molecular skeleton attached to one or more chemical moieties. Non-limiting examples of suitable flavanols for use in particular embodiments of this invention include catechin, epicatechin, gallocatechin, epigallocatechin, epicatechin gallate, epigallocatechin 3-gallate, theaflavin, theaflavin 3-gallate, theaflavin 3'-gallate, theaflavin 3,3' gallate, thearubigin or combinations thereof. Several common sources of flavanols include tea plants, fruits, vegetables, and flowers. In preferred embodiments, the flavanol is extracted from green tea.

In a particular embodiment, the hydration agent is a glycerol solution to enhance exercise endurance. The ingestion of a glycerol containing solution has been shown to provide beneficial physiological effects, such as expanded blood volume, lower heart rate, and lower rectal temperature.

Probiotics/Prebiotics

In certain embodiments, the functional ingredient is chosen from at least one probiotic, prebiotic and combination thereof. As used herein, the at least one probiotic or prebiotic may be single probiotic or prebiotic or a plurality of probiotics or prebiotics. Generally, according to particular embodiments of this invention, the at least one probiotic, prebiotic or combination thereof is present in an amount sufficient to promote health and wellness.

Probiotics, in accordance with the teachings of this invention, comprise microorganisms that benefit health when consumed in an effective amount. Desirably, probiotics beneficially affect the human body's naturally-occurring gastrointestinal microflora and impart health benefits apart from nutrition. Probiotics may include, without limitation, bacteria, yeasts, and fungi.

Prebiotics, in accordance with the teachings of this invention, are compositions that promote the growth of beneficial bacteria in the intestines. Prebiotic substances can be consumed by a relevant probiotic, or otherwise assist in keeping the relevant probiotic alive or stimulate its growth. When consumed in an effective amount, prebiotics also beneficially affect the human body's naturally-occurring gastrointestinal microflora and thereby impart health benefits apart from just nutrition. Prebiotic foods enter the colon and serve as substrate for the endogenous bacteria, thereby indirectly providing the host with energy, metabolic substrates, and essential micronutrients. The body's digestion and absorption of prebiotic foods is dependent upon bacterial metabolic activity, which salvages energy for the host from nutrients that escaped digestion and absorption in the small intestine.

According to particular embodiments, the probiotic is a beneficial microorganisms that beneficially affects the human body's naturally-occurring gastrointestinal microflora and imparts health benefits apart from nutrition. Examples of probiotics include, but are not limited to, bacteria of the genus *Lactobacilli, Bifidobacteria, Streptococci*, or combinations thereof, that confer beneficial effects to humans.

In particular embodiments of the invention, the at least one probiotic is chosen from the genus *Lactobacilli*. *Lactobacilli* (i.e., bacteria of the genus *Lactobacillus*, hereinafter "L.") have been used for several hundred years as a food preservative and for promoting human health. Non-limiting examples of species of *Lactobacilli* found in the human intestinal tract include *L. acidophilus, L. casei, L. fermentum, L. saliva roes, L. brevis, L. leichmannii, L. plantarum, L. cellobiosus, L. reuteri, L. rhamnosus, L. GG, L. bulgaricus*, and *L. thermophilus*.

According to other particular embodiments of this invention, the probiotic is chosen from the genus *Bifidobacteria*. *Bifidobacteria* also are known to exert a beneficial influence on human health by producing short chain fatty acids (e.g., acetic, propionic, and butyric acids), lactic, and formic acids as a result of carbohydrate metabolism. Non-limiting species of *Bifidobacteria* found in the human gastrointestinal tract include *B. angulatum, B. animalis, B. asteroides, B. bifidum, B. bourn, B. breve, B. catenulatum, B. choerinum, B. coryneforme, B. cuniculi, B. dentium, B. gallicum, B. gallinarum, B. indicum, B. longum, B. magnum, B. merycicum, B. minimum, B. pseudocatenulatum, B. pseudolongum, B. psychraerophilum, B. pullorum, B. ruminantium, B. saeculare, B. scardovii, B. simiae, B. subtile, B. thermacidophilum, B. thermophilum, B. urinalis*, and *B.* sp.

According to other particular embodiments of this invention, the probiotic is chosen from the genus *Streptococcus*. *Streptococcus thermophilus* is a gram-positive facultative anaerobe. It is classified as a lactic acid bacteria and commonly is found in milk and milk products, and is used in the production of yogurt. Other non-limiting probiotic species of this bacteria include *Streptococcus salivarus* and *Streptococcus cremoris*.

Probiotics that may be used in accordance with this invention are well-known to those of skill in the art. Non-limiting examples of foodstuffs comprising probiotics include yogurt, sauerkraut, kefir, kimchi, fermented vegetables, and other foodstuffs containing a microbial element that beneficially affects the host animal by improving the intestinal microbalance.

Prebiotics, in accordance with the embodiments of this invention, include, without limitation, mucopolysaccharides, oligosaccharides, polysaccharides, amino acids, vitamins, nutrient precursors, proteins and combinations thereof.

According to a particular embodiment of this invention, the prebiotic is chosen from dietary fibers, including, without limitation, polysaccharides and oligosaccharides. These compounds have the ability to increase the number of probiotics, which leads to the benefits conferred by the probiotics. Non-limiting examples of oligosaccharides that are categorized as prebiotics in accordance with particular embodiments of this invention include fructooligosaccharides, inulins, isomalto-oligosaccharides, lactilol, lactosucrose, lactulose, pyrodextrins, soy oligosaccharides, trans-galacto-oligosaccharides, and xylo-oligosaccharides.

According to other particular embodiments of the invention, the prebiotic is an amino acid. Although a number of known prebiotics break down to provide carbohydrates for probiotics, some probiotics also require amino acids for nourishment.

Prebiotics are found naturally in a variety of foods including, without limitation, bananas, berries, asparagus, garlic, wheat, oats, barley (and other whole grains), flaxseed, tomatoes, Jerusalem artichoke, onions and chicory, greens (e.g., dandelion greens, spinach, collard greens, chard, kale, mustard greens, turnip greens), and legumes (e.g., lentils, kidney beans, chickpeas, navy beans, white beans, black beans).

Weight Management Agent

In certain embodiments, the functional ingredient is at least one weight management agent. As used herein, the at least one weight management agent may be single weight management agent or a plurality of weight management agents. Generally, according to particular embodiments of this invention, the at least one weight management agent is present in an amount sufficient to promote health and wellness.

As used herein, "a weight management agent" includes an appetite suppressant and/or a thermogenesis agent. As used herein, the phrases "appetite suppressant", "appetite satiation compositions", "satiety agents", and "satiety ingredients" are synonymous. The phrase "appetite suppressant" describes macronutrients, herbal extracts, exogenous hormones, anorectics, anorexigenics, pharmaceutical drugs, and combinations thereof, that when delivered in an effective amount, suppress, inhibit, reduce, or otherwise curtail a person's appetite. The phrase "thermogenesis agent" describes macronutrients, herbal extracts, exogenous hormones, anorectics, anorexigenics, pharmaceutical drugs, and combinations thereof, that when delivered in an effective amount, activate or otherwise enhance a person's thermogenesis or metabolism.

Suitable weight management agents include macronutrient selected from the group consisting of proteins, carbohydrates, dietary fats, and combinations thereof. Consumption of proteins, carbohydrates, and dietary fats stimulates the release of peptides with appetite-suppressing effects. For example, consumption of proteins and dietary fats stimulates the release of the gut hormone cholecytokinin (CCK), while consumption of carbohydrates and dietary fats stimulates release of Glucagon-like peptide 1 (GLP-1).

Suitable macronutrient weight management agents also include carbohydrates. Carbohydrates generally comprise sugars, starches, cellulose and gums that the body converts into glucose for energy. Carbohydrates often are classified into two categories, digestible carbohydrates (e.g., monosaccharides, disaccharides, and starch) and non-digestible carbohydrates (e.g., dietary fiber). Studies have shown that non-digestible carbohydrates and complex polymeric carbohydrates having reduced absorption and digestibility in the small intestine stimulate physiologic responses that inhibit food intake. Accordingly, the carbohydrates embodied herein desirably comprise non-digestible carbohydrates or carbohydrates with reduced digestibility. Non-limiting examples of such carbohydrates include polydextrose; inulin; monosaccharide-derived polyols such as erythritol, mannitol, xylitol, and sorbitol; disaccharide-derived alcohols such as isomalt, lactitol, and maltitol; and hydrogenated starch hydrolysates. Carbohydrates are described in more detail herein below.

In another particular embodiment weight management agent is a dietary fat. Dietary fats are lipids comprising combinations of saturated and unsaturated fatty acids. Poly-unsaturated fatty acids have been shown to have a greater satiating power than mono-unsaturated fatty acids. Accordingly, the dietary fats embodied herein desirably comprise poly-unsaturated fatty acids, non-limiting examples of which include triacylglycerols.

In a particular embodiment, the weight management agent is an herbal extract. Extracts from numerous types of plants have been identified as possessing appetite suppressant properties. Non-limiting examples of plants whose extracts have appetite suppressant properties include plants of the genus *Hoodia, Trichocaulon, Caralluma, Stapelia, Orbea, Asclepias,* and *Camelia*. Other embodiments include extracts derived from Gymnema Sylvestre, Kola Nut, Citrus Auran tium, Yerba Mate, Griffonia Simplicifolia, Guarana, myrrh, guggul Lipid, and black current seed oil.

The herbal extracts may be prepared from any type of plant material or plant biomass. Non-limiting examples of plant material and biomass include the stems, roots, leaves, dried powder obtained from the plant material, and sap or dried sap. The herbal extracts generally are prepared by extracting sap from the plant and then spray-drying the sap. Alternatively, solvent extraction procedures may be employed. Following the initial extraction, it may be desirable to further fractionate the initial extract (e.g., by column chromatography) in order to obtain an herbal extract with enhanced activity. Such techniques are well known to those of ordinary skill in the art.

In a particular embodiment, the herbal extract is derived from a plant of the genus *Hoodia*, species of which include *H. alstonii, H. currorii, H. dregei, H. flava, H. gordonii, H. jutatae, H. mossamedensis, H. officinalis, H. parviflorai, H. pedicellata, H. pilifera, H. ruschii,* and *H. triebneri*. *Hoodia* plants are stem succulents native to southern Africa. A sterol glycoside of *Hoodia*, known as P57, is believed to be responsible for the appetite-suppressant effect of the *Hoodia* species.

In another particular embodiment, the herbal extract is derived from a plant of the genus *Caralluma*, species of which include *C. indica, C. fimbriata, C. attenuate, C. tuberculata, C. edulis, C. adscendens, C. stalagmifera, C. umbellate, C. penicillata, C. russeliana, C. retrospicens, C. Arabica,* and *C. lasiantha*. *Carralluma* plants belong to the same Subfamily as *Hoodia*, Asclepiadaceae. *Caralluma* are small, erect and fleshy plants native to India having medicinal properties, such as appetite suppression, that generally are attributed to glycosides belonging to the pregnane group of glycosides, non-limiting examples of which include caratuberside A, caratuberside B, bouceroside I, bouceroside II, bouceroside III, bouceroside IV, bouceroside V, bouceroside VI, bouceroside VII, bouceroside VIII, bouceroside IX, and bouceroside X.

In another particular embodiment, the at least one herbal extract is derived from a plant of the genus *Trichocaulon*. *Trichocaulon* plants are succulents that generally are native to southern Africa, similar to *Hoodia*, and include the species *T. piliferum* and *T. officinale*.

In another particular embodiment, the herbal extract is derived from a plant of the genus *Stapelia* or *Orbea*, species of which include *S. gigantean* and *O. variegate*, respectively. Both *Stapelia* and *Orbea* plants belong to the same Subfamily as *Hoodia*, Asclepiadaceae. Not wishing to be bound by any theory, it is believed that the compounds exhibiting appetite suppressant activity are saponins, such as pregnane glycosides, which include stavarosides A, B, C, D, E, F, G, H, I, J, and K.

In another particular embodiment, the herbal extract is derived from a plant of the genus *Asclepias*. *Asclepias* plants also belong to the Asclepiadaceae family of plants. Non-limiting examples of *Asclepias* plants include *A. incarnate*, *A. curassayica*, *A. syriaca*, and *A. tuberose*. Not wishing to be bound by any theory, it is believed that the extracts comprise steroidal compounds, such as pregnane glycosides and pregnane aglycone, having appetite suppressant effects.

In a particular embodiment, the weight management agent is an exogenous hormone having a weight management effect. Non-limiting examples of such hormones include CCK, peptide YY, ghrelin, bombesin and gastrin-releasing peptide (GRP), enterostatin, apolipoprotein A-IV, GLP-1, amylin, somastatin, and leptin.

In another embodiment, the weight management agent is a pharmaceutical drug. Non-limiting examples include phentenime, diethylpropion, phendimetrazine, sibutramine, rimonabant, oxyntomodulin, floxetine hydrochloride, ephedrine, phenethylamine, or other stimulants.

Osteoporosis Management Agent

In certain embodiments, the functional ingredient is at least one osteoporosis management agent. As used herein, the at least one osteoporosis management agent may be single osteoporosis management agent or a plurality of osteoporosis management agents. Generally, according to particular embodiments of this invention, the at least one osteoporosis management agent is present in an amount sufficient to promote health and wellness.

Osteoporosis is a skeletal disorder of compromised bone strength, resulting in an increased risk of bone fracture. Generally, osteoporosis is characterized by reduction of the bone mineral density (BMD), disruption of bone microarchitecture, and changes to the amount and variety of non-collagenous proteins in the bone.

In certain embodiments, the osteoporosis management agent is at least one calcium source. According to a particular embodiment, the calcium source is any compound containing calcium, including salt complexes, solubilized species, and other forms of calcium. Non-limiting examples of calcium sources include amino acid chelated calcium, calcium carbonate, calcium oxide, calcium hydroxide, calcium sulfate, calcium chloride, calcium phosphate, calcium hydrogen phosphate, calcium dihydrogen phosphate, calcium citrate, calcium malate, calcium citrate malate, calcium gluconate, calcium tartrate, calcium lactate, solubilized species thereof, and combinations thereof.

According to a particular embodiment, the osteoporosis management agent is a magnesium source. The magnesium source is any compound containing magnesium, including salt complexes, solubilized species, and other forms of magnesium. Non-limiting examples of magnesium sources include magnesium chloride, magnesium citrate, magnesium gluceptate, magnesium gluconate, magnesium lactate, magnesium hydroxide, magnesium picolate, magnesium sulfate, solubilized species thereof, and mixtures thereof. In another particular embodiment, the magnesium source comprises an amino acid chelated or creatine chelated magnesium.

In other embodiments, the osteoporosis agent is chosen from vitamins D, C, K, their precursors and/or beta-carotene and combinations thereof.

Numerous plants and plant extracts also have been identified as being effective in the prevention and treatment of osteoporosis. Non-limiting examples of suitable plants and plant extracts as osteoporosis management agents include species of the genus *Taraxacum* and *Amelanchier*, as disclosed in U.S. Patent Publication No. 2005/0106215, and species of the genus *Lindera, Artemisia, Acorus, Carthamus, Carum, Cnidium, Curcuma, Cyperus, Juniperus, Prunus, Iris, Cichorium, Dodonaea, Epimedium, Erigonoum, Soya, Mentha, Ocimum, thymus, Tanacetum, Plantago, Spearmint, Bixa, Vitis, Rosemarinus, Rhus*, and *Anethum*, as disclosed in U.S. Patent Publication No. 2005/0079232.

Phytoestrogen

In certain embodiments, the functional ingredient is at least one phytoestrogen. As used herein, the at least one phytoestrogen may be single phytoestrogen or a plurality of phytoestrogens. Generally, according to particular embodiments of this invention, the at least one phytoestrogen is present in an amount sufficient to promote health and wellness.

Phytoestrogens are compounds found in plants which can typically be delivered into human bodies by ingestion of the plants or the plant parts having the phytoestrogens. As used herein, "phytoestrogen" refers to any substance which, when introduced into a body causes an estrogen-like effect of any degree. For example, a phytoestrogen may bind to estrogen receptors within the body and have a small estrogen-like effect.

Examples of suitable phytoestrogens for embodiments of this invention include, but are not limited to, isoflavones, stilbenes, lignans, resorcyclic acid lactones, coumestans, coumestrol, equol, and combinations thereof. Sources of suitable phytoestrogens include, but are not limited to, whole grains, cereals, fibers, fruits, vegetables, black cohosh, agave root, black currant, black haw, chasteberries, cramp bark, dong quai root, devil's club root, false unicorn root, ginseng root, groundsel herb, licorice, liferoot herb, motherwort herb, peony root, raspberry leaves, rose family plants, sage leaves, sarsaparilla root, saw palmetto berried, wild yam root, yarrow blossoms, legumes, soybeans, soy products (e.g., miso, soy flour, soymilk, soy nuts, soy protein isolate, tempen, or tofu) chick peas, nuts, lentils, seeds, clover, red clover, dandelion leaves, dandelion roots, fenugreek seeds, green tea, hops, red wine, flaxseed, garlic, onions, linseed, borage, butterfly weed, caraway, chaste tree, vitex, dates, dill, fennel seed, gotu kola, milk thistle, pennyroyal, pomegranates, southernwood, soya flour, tansy, and root of the kudzu vine (pueraria root) and the like, and combinations thereof.

Isoflavones belong to the group of phytonutrients called polyphenols. In general, polyphenols (also known as "polyphenolics"), are a group of chemical substances found in plants, characterized by the presence of more than one phenol group per molecule.

Suitable phytoestrogen isoflavones in accordance with embodiments of this invention include genistein, daidzein, glycitein, biochanin A, formononetin, their respective naturally occurring glycosides and glycoside conjugates, matairesinol, secoisolariciresinol, enterolactone, enterodiol, textured vegetable protein, and combinations thereof.

Suitable sources of isoflavones for embodiments of this invention include, but are not limited to, soy beans, soy products, legumes, alfalfa sprouts, chickpeas, peanuts, and red clover.

Long-Chain Primary Aliphatic Saturated Alcohol

In certain embodiments, the functional ingredient is at least one long chain primary aliphatic saturated alcohol. As used herein, the at least one long chain primary aliphatic saturated alcohol may be single long chain primary aliphatic saturated alcohol or a plurality of long chain primary aliphatic saturated alcohols. Generally, according to particular embodiments of this invention, the at least one long chain primary aliphatic saturated alcohol is present in an amount sufficient to promote health and wellness.

Long-chain primary aliphatic saturated alcohols are a diverse group of organic compounds. The term alcohol refers to the fact these compounds feature a hydroxyl group (—OH) bound to a carbon atom. The term primary refers to the fact that in these compounds the carbon atom which is bound to the hydroxyl group is bound to only one other carbon atom. The term saturated refers to the fact that these compounds feature no carbon to carbon pi bonds. The term aliphatic refers to the fact that the carbon atoms in these compounds are joined together in straight or branched chains rather than in rings. The term long-chain refers to the fact that the number of carbon atoms in these compounds is at least 8 carbons).

Non-limiting examples of particular long-chain primary aliphatic saturated alcohols for use in particular embodiments of the invention include the 8 carbon atom 1-octanol, the 9 carbon 1-nonanol, the 10 carbon atom 1-decanol, the 12 carbon atom 1-dodecanol, the 14 carbon atom 1-tetradecanol, the 16 carbon atom 1-hexadecanol, the 18 carbon atom 1-octadecanol, the 20 carbon atom 1-eicosanol, the 22 carbon 1-docosanol, the 24 carbon 1-tetracosanol, the 26 carbon 1-hexacosanol, the 27 carbon 1-heptacosanol, the 28 carbon 1-octanosol, the 29 carbon 1-nonacosanol, the 30 carbon 1-triacontanol, the 32 carbon 1-dotriacontanol, and the 34 carbon 1-tetracontanol.

In a particularly desirable embodiment of the invention, the long-chain primary aliphatic saturated alcohols are policosanol. Policosanol is the term for a mixture of long-chain primary aliphatic saturated alcohols composed primarily of 28 carbon 1-octanosol and 30 carbon 1-triacontanol, as well as other alcohols in lower concentrations such as 22 carbon 1-docosanol, 24 carbon 1-tetracosanol, 26 carbon 1-hexacosanol, 27 carbon 1-heptacosanol, 29 carbon 1-nonacosanol, 32 carbon 1-dotriacontanol, and 34 carbon 1-tetracontanol.

Phytosterols

In certain embodiments, the functional ingredient is at least one phytosterol, phytostanol or combination thereof. Generally, according to particular embodiments of this invention, the at least one phytosterol, phytostanol or combination thereof is present in an amount sufficient to promote health and wellness.

As used herein, the phrases "stanol", "plant stanol" and "phytostanol" are synonymous.

Plant sterols and stanols are present naturally in small quantities in many fruits, vegetables, nuts, seeds, cereals, legumes, vegetable oils, bark of the trees and other plant sources. Although people normally consume plant sterols and stanols every day, the amounts consumed are insufficient to have significant cholesterol-lowering effects or other health benefits. Accordingly, it would be desirable to supplement food and beverages with plant sterols and stanols.

Sterols are a subgroup of steroids with a hydroxyl group at C-3. Generally, phytosterols have a double bond within the steroid nucleus, like cholesterol; however, phytosterols also may comprise a substituted side chain (R) at C-24, such as an ethyl or methyl group, or an additional double bond. The structures of phytosterols are well known to those of skill in the art.

At least 44 naturally-occurring phytosterols have been discovered, and generally are derived from plants, such as corn, soy, wheat, and wood oils; however, they also may be produced synthetically to form compositions identical to those in nature or having properties similar to those of naturally-occurring phytosterols. According to particular embodiments of this invention, non-limiting examples of phytosterols well known to those or ordinary skill in the art include 4-desmethylsterols (e.g., β-sitosterol, campesterol, stigmasterol, brassicasterol, 22-dehydrobrassicasterol, and Δ5-avenasterol), 4-monomethyl sterols, and 4,4-dimethyl sterols (triterpene alcohols) (e.g., cycloartenol, 24-methylenecycloartanol, and cyclobranol).

As used herein, the phrases "stanol", "plant stanol" and "phytostanol" are synonymous. Phytostanols are saturated sterol alcohols present in only trace amounts in nature and also may be synthetically produced, such as by hydrogenation of phytosterols. According to particular embodiments of this invention, non-limiting examples of phytostanols include β-sitostanol, campestanol, cycloartanol, and saturated forms of other triterpene alcohols.

Both phytosterols and phytostanols, as used herein, include the various isomers such as the α and β isomers (e.g., α-sitosterol and β-sitostanol, which comprise one of the most effective phytosterols and phytostanols, respectively, for lowering serum cholesterol in mammals).

The phytosterols and phytostanols of the present invention also may be in their ester form. Suitable methods for deriving the esters of phytosterols and phytostanols are well known to those of ordinary skill in the art, and are disclosed in U.S. Pat. Nos. 6,589,588, 6,635,774, 6,800,317, and U.S. Patent Publication Number 2003/0045473, the disclosures of which are incorporated herein by reference in their entirety. Non-limiting examples of suitable phytosterol and phytostanol esters include sitosterol acetate, sitosterol oleate, stigmasterol oleate, and their corresponding phytostanol esters. The phytosterols and phytostanols of the present invention also may include their derivatives.

Generally, the amount of functional ingredient in the composition varies widely depending on the particular composition and the desired functional ingredient. Those of ordinary skill in the art will readily ascertain the appropriate amount of functional ingredient for each composition.

In one embodiment, a method for preparing a composition comprises combining at least one diterpene glycoside of the present invention and at least one sweetener and/or additive and/or functional ingredient.

In a particular embodiment, a method for preparing a composition comprises combining at least one diterpene glycoside of the present invention and at least one sweetener and/or additive and/or functional ingredient, wherein the at least one sweetener and/or additive and/or functional ingredient does not exist with (is not admixed with) the at least one diterpene glycoside in nature, i.e. Stevia leaf, and the composition provides a more sucrose-like taste profile compared to the diterpene glycoside in nature and (if applicable) the at least one sweetener and/or additive and/or functional ingredient in nature. For example, in certain embodiments the composition exhibits one or more of the following characteristics: improved sweetness potency, improved mouthfeel, decreased sweetness linger, decreased bitterness and/or decreased metallic taste.

Consumables

In one embodiment, the present invention is a consumable comprising at least one diterpene glycoside of the present invention, or a composition comprising at least one diterpene glycoside of the present invention. In a particular embodiment, the at least one diterpene glycoside is purified.

The diterpene glycoside(s) of the present invention, or a composition comprising the same, can be admixed with any known edible or oral composition, referred to herein as a "consumable". Consumables, as used herein, mean substances which are contacted with the mouth of man or animal, including substances which are taken into and subsequently ejected from the mouth and substances which are drunk, eaten, swallowed or otherwise ingested, and are safe for human or animal consumption when used in a generally acceptable range.

Exemplary consumables include pharmaceutical compositions, edible gel mixes and compositions, dental compositions, foodstuffs (confections, condiments, chewing gum, cereal compositions baked goods dairy products, and tabletop sweetener compositions) beverages and beverage products. The consumables of the present invention require admixing and, as such, do not occur in nature.

For example, a beverage is a consumable. The beverage may be sweetened or unsweetened. The diterpene glycoside(s) of the present invention, or a composition comprising the same, may be added to a beverage or beverage matrix to sweeten the beverage or enhance its existing sweetness or flavor.

In one embodiment, the present invention is a consumable comprising at least one diterpene glycoside of the present invention. In particular embodiments, a diterpene glycoside of the present invention is present in the consumable in a concentration greater than about 1 ppm, such as, for example, from about 1 ppm to about 1,000 ppm, from about 25 ppm to about 1,000 ppm, from about 50 ppm to about 1,000 ppm, from about 75 ppm to about 1,000 ppm, from about 100 ppm to about 1,000 ppm, from about 200 ppm to about 1,000 ppm, from about 300 ppm to about 1,000 ppm, from about 400 ppm to about 1,000 ppm or from about 500 ppm to about 1,000 ppm.

In other particular embodiments, a diterpene glycoside of the present invention is present in the consumable in a purity of at least about 5% with respect to a mixture of diterpene glycosides or stevia extract, such as, for example, at least about 10%, at least about 20%, at least about 30%, at least about 40%, at least about 50%, at least about 60%, at least about 70%, at least about 80%, at least about 90%, at least about 95% or at least about 97%. In still other embodiments, a diterpene glycoside of the present invention is present in the consumable in >99% purity.

The consumable can optionally include additives, additional sweeteners, functional ingredients and combinations thereof, as described herein. Any of the additive, additional sweetener and functional ingredients described above can be present in the consumable.

In exemplary embodiments, a consumable comprising at least one purified diterpene glycoside of the present invention has about 30% or more sweetness compared to a corresponding consumable comprising partially purified diterpene glycoside or Stevia, such as, for example, about 40% or more, about 50% or more, about 60% or more, about 70% or more, about 80% or more or about 90% or more.

In other exemplary embodiments, a consumable comprising at least one purified diterpene glycoside of the present invention has at least about 30% less bitterness (the taste stimulated by certain substances such as quinine, caffeine and sucrose octa-acetate) compared to a corresponding consumable comprising partially purified diterpene glycoside or Stevia leaf, such as, for example, at least about 40%, at least about 50%, at least about 60%, at least about 70%, at least about 80% or at least about 90%. In a particular embodiment, a consumable comprising at least one purified diterpene glycoside of the present invention has substantially no bitterness. Methods of measuring bitterness of a compound are known in the art.

In still other exemplary embodiments, a consumable comprising at least one purified diterpene glycoside of the present invention has at least about 30% less sweet lingering aftertaste (the intensity of the sweet taste after expectoration) compared to a corresponding consumable comprising partially purified diterpene glycoside or Stevia leaf, such as, for example, at least about 50%, at least about 60%, at least about 70%, at least about 80% or at least about 90%. In a particular embodiment, a consumable comprising at least one purified diterpene glycoside of the present invention has substantially no sweet lingering aftertaste. Methods of measuring sweet lingering aftertaste are known in the art.

In yet other exemplary embodiments, a consumable comprising at least one purified diterpene glycoside of the present invention has at least about 30% less metallic taste (taste associated with metals, tinny or iron) compared to a corresponding consumable comprising partially purified diterpene glycoside or Stevia leaf, such as, for example, at least about 50%, at least about 60%, at least about 70%, at least about 80% or at least about 90%. In a particular embodiment, a consumable comprising at least one purified diterpene glycoside of the present invention has substantially no metallic taste.

In exemplary embodiments, a consumable comprising at least one purified diterepene glycoside of the present invention exhibits a maximal response (maximum sweetness (% SE) achieved with increasing concentration of compound) that is at least about 30% greater compared to a corresponding consumable comprising partially purified diterpene glycoside or Stevia leaf, such as, for example, at least about 40% greater, at least about 50% greater, at least about 60% greater, at least about 70% greater, at least about 80% greater or at least about 90% greater. Methods of measuring the maximal response of a compound are known in the art.

In other exemplary embodiments, a consumable comprising at least one purified diterpene glycoside of the present invention exhibits a sweetness onset (the time until maximum sweetness is experienced) that is at least about 30% shorter than a sweetener composition comprising partially purified diterpene glycoside or Stevia leaf, such as, for example, at least about 40% short, at least about 50% shorter, at least about 60% shorter, at least about 70% shorter, at least about 80% shorter or at least about 90% shorter. Methods of measuring sweetness onset are known in the art.

In another embodiment, the present invention is a beverage or beverage product comprising a composition that comprises at least one diterpene glycoside of the present invention. In a particular embodiment, the beverage or beverage product comprises a composition comprising at least one purified diterpene glycoside of the present invention.

As used herein a "beverage product" is a ready-to-drink beverage, a beverage concentrate, a beverage syrup, or a powdered beverage. Suitable ready-to-drink beverages include carbonated and non-carbonated beverages. Carbonated beverages include, but are not limited to, enhanced sparkling beverages, cola, lemon-lime flavored sparkling beverage, orange flavored sparkling beverage, grape flavored sparkling beverage, strawberry flavored sparkling beverage, pineapple flavored sparkling beverage, ginger-ale, soft drinks and root beer. Non-carbonated beverages include, but are not limited to fruit juice, fruit-flavored juice, juice drinks, nectars, vegetable juice, vegetable-flavored juice, sports drinks, energy drinks, enhanced water drinks, enhanced water with vitamins, near water drinks (e.g., water with natural or synthetic flavorants), coconut water, tea type drinks (e.g. black tea, green tea, red tea, oolong tea), coffee, cocoa drink, beverage containing milk components (e.g. milk beverages, coffee containing milk components, café au lait, milk tea, fruit milk beverages), beverages containing cereal extracts, smoothies and combinations thereof.

Beverage concentrates and beverage syrups are prepared with an initial volume of liquid matrix (e.g. water) and the desired beverage ingredients. Full strength beverages are then prepared by adding further volumes of water. Powdered beverages are prepared by dry-mixing all of the beverage ingredients in the absence of a liquid matrix. Full strength beverages are then prepared by adding the full volume of water.

Beverages comprise a matrix, i.e. the basic ingredient in which the ingredients—including the compositions of the present invention—are dissolved. In one embodiment, a beverage comprises water of beverage quality as the matrix, such as, for example deionized water, distilled water, reverse osmosis water, carbon-treated water, purified water, demineralized water and combinations thereof, can be used. Additional suitable matrices include, but are not limited to phosphoric acid, phosphate buffer, citric acid, citrate buffer and carbon-treated water.

In one embodiment, the present invention is a beverage comprising at least one diterpene glycoside of the present invention.

In a further embodiment, the present invention is a beverage product comprising at least one diterpene glycoside of the present invention.

The at least one diterpene glycoside can be provided as a single compound or as part of any composition described above. In an exemplary embodiment, the at least one diterpene glycoside is purified.

In a particular embodiment, a beverage or beverage product comprises at least one diterpene glycoside of the present invention in purified form and at least one other substance that does not occur with the diterpene glycoside in nature, i.e. Stevia leaf. In one embodiment, the at least other additional substance modulates the taste profile of the at least one diterpene glycoside to provide a beverage with a more sucrose-like taste profile compared to the diterpene glycoside in nature and (if applicable) the at least one other substance in nature. For example, in certain embodiments the beverage exhibits one or more of the following characteristics: improved sweetness potency, improved mouthfeel, decreased sweetness linger, decreased bitterness and/or decreased metallic taste.

The concentration of the diterpene glycoside of the present invention in the beverage may be above, at or below the threshold sweetness or flavor recognition concentration of the diterpene glycoside of the present invention.

In one embodiment, a diterpene glycoside of the present invention is present in the beverage in a concentration greater than about 1 ppm, such as, for example, from about 1 ppm to about 1,000 ppm, from about 25 ppm to about 1,000 ppm, from about 50 ppm to about 1,000 ppm, from about 75 ppm to about 1,000 ppm, from about 100 ppm to about 1,000 ppm, from about 200 ppm to about 1,000 ppm, from about 300 ppm to about 1,000 ppm, from about 400 ppm to about 1,000 ppm or from about 500 ppm to about 1,000 ppm.

In a more particular embodiment, a diterpene glycoside of the present invention is present in the beverage in a concentration from about 25 ppm to about 600 ppm, such as, for example, from about 25 ppm to about 500 ppm, from about 25 ppm to about 400 ppm, from about 25 ppm to about 300 ppm, from about 25 ppm to about 200 ppm, from about 25 ppm to about 100 ppm, from about 50 ppm to about 600 ppm, from about 50 ppm to about 500 ppm, from about 50 ppm to about 400 ppm, from about 50 ppm to about 300 ppm, from about 50 ppm to about 200 ppm, from about 50 ppm to about 100 ppm, from about 100 ppm to about 600 ppm, from about 100 ppm to about 500 ppm, from about 100 ppm to about 400 ppm, from about 100 ppm to about 300 ppm, from about 100 ppm to about 200 ppm, from about 200 ppm to about 600 ppm, from about 200 ppm to about 500 ppm, from about 200 ppm to about 400 ppm, from about 200 ppm to about 300 ppm, from about 300 ppm to about 600 ppm, from about 300 ppm to about 500 ppm, from about 300 ppm to about 400 ppm, from about 400 ppm to about 600 ppm, from about 400 ppm to about 500 ppm or from about 500 ppm to about 600 ppm.

In other particular embodiments, a diterpene glycoside of the present invention is present in the beverage in a purity of at least about 5% with respect to a mixture of diterpene glycosides or stevia extract, such as, for example, at least about 10%, at least about 20%, at least about 30%, at least about 40%, at least about 50%, at least about 60%, at least about 70%, at least about 80%, at least about 90%, at least about 95% or at least about 97%. In still other embodiments, a diterpene glycoside of the present invention is present in the beverage in >99% purity.

The beverage can include one or more sweeteners. Any of the sweeteners detailed herein can be used, including natural, non-natural, or synthetic sweeteners. These may be added to the beverage either before, contemporaneously with or after the diterpene glycoside(s) of the present invention. In a particular embodiment, the sweetener does not occur with the at least one diterpene glycoside in nature, i.e. Stevia leaf.

The consumable can optionally include additives, functional ingredients and combinations thereof, as described herein. Any of the additives and functional ingredients described above can be present in the consumable. In certain embodiments, the additive and/or functional ingredient modulates the taste profile of the at least one diterpene glycoside to provide a consumable with a more sucrose-like taste profile compared to the diterpene glycoside in nature and (if applicable) the additive and/or functional ingredient in nature. For example, in certain embodiments the consumable exhibits one or more of the following characteristics: improved sweetness potency, improved mouthfeel, decreased sweetness linger, decreased bitterness and/or decreased metallic taste.

It is contemplated that the pH of the consumable, such as, for example, a beverage, does not materially or adversely affect the taste of the sweetener. A non-limiting example of the pH range of the beverage may be from about 1.8 to about 10. A further example includes a pH range from about 2 to about 5. In a particular embodiment, the pH of beverage can be from about 2.5 to about 4.2. On of skill in the art will understand that the pH of the beverage can vary based on the type of beverage. Dairy beverages, for example, can have pHs greater than 4.2.

The titratable acidity of a beverage may, for example, range from about 0.01 to about 1.0% by weight of beverage.

In one embodiment, the sparkling beverage product has an acidity from about 0.01 to about 1.0% by weight of the beverage, such as, for example, from about 0.05% to about 0.25% by weight of beverage.

The carbonation of a sparkling beverage product has 0 to about 2% (w/w) of carbon dioxide or its equivalent, for example, from about 0.1 to about 1.0% (w/w).

The temperature of a beverage may, for example, range from about 4° C. to about 100° C., such as, for example, from about 4° C. to about 25° C.

The beverage can be a full-calorie beverage that has up to about 120 calories per 8 oz serving.

The beverage can be a mid-calorie beverage that has up to about 60 calories per 8 oz serving.

The beverage can be a low-calorie beverage that has up to about 40 calories per 8 oz serving.

The beverage can be a zero-calorie that has less than about 5 calories per 8 oz. serving.

In one embodiment, the beverage comprises natural sweetener(s) only, i.e. the only type of sweetener(s) are naturally-occurring.

In exemplary embodiments, a beverage comprising at least one purified diterpene glycoside of the present invention has about 30% or more sweetness compared to a corresponding beverage comprising partially purified diterpene glycoside or Stevia, such as, for example, about 40% or more, about 50% or more, about 60% or more, about 70% or more, about 80% or more or about 90% or more.

In other exemplary embodiments, a beverage comprising at least one purified diterpene glycoside of the present invention has at least about 30% less bitterness (the taste stimulated by certain substances such as quinine, caffeine and sucrose octa-acetate) compared to a corresponding beverage comprising partially purified diterpene glycoside or Stevia leaf, such as, for example, at least about 40%, at least about 50%, at least about 60%, at least about 70%, at least about 80% or at least about 90%. In a particular embodiment, a beverage comprising at least one purified diterpene glycoside of the present invention has substantially no bitterness.

In still other exemplary embodiments, a beverage comprising at least one purified diterpene glycoside of the present invention has at least about 30% less sweet lingering aftertaste (the intensity of the sweet taste after expectoration) compared to a corresponding beverage comprising partially purified diterpene glycoside or Stevia leaf, such as, for example, at least about 50%, at least about 60%, at least about 70%, at least about 80% or at least about 90%. In a particular embodiment, a beverage comprising at least one purified diterpene glycoside of the present invention has substantially no sweet lingering aftertaste.

In yet other exemplary embodiments, a beverage comprising at least one purified diterpene glycoside of the present invention has at least about 30% less metallic taste (taste associated with metals, tinny or iron) compared to a corresponding beverage comprising partially purified diterpene glycoside or Stevia leaf, such as, for example, at least about 50%, at least about 60%, at least about 70%, at least about 80% or at least about 90%. In a particular embodiment, a beverage comprising at least one purified diterpene glycoside of the present invention has substantially no metallic taste.

In exemplary embodiments, a beverage comprising at least one purified diterepene glycoside of the present invention exhibits a maximal response (maximum sweetness (% SE) achieved with increasing concentration of compound) that is at least about 30% greater compared to a corresponding beverage comprising partially purified diterpene glycoside or Stevia leaf, such as, for example, at least about 40% greater, at least about 50% greater, at least about 60% greater, at least about 70% greater, at least about 80% greater or at least about 90% greater.

In other exemplary embodiments, a beverage comprising at least one purified diterpene glycoside of the present invention exhibits a sweetness onset (the time until maximum sweetness is experienced) that is at least about 30% shorter than a beverage comprising partially purified diterpene glycoside or Stevia leaf, such as, for example, at least about 40% short, at least about 50% shorter, at least about 60% shorter, at least about 70% shorter, at least about 80% shorter or at least about 90% shorter.

III. Methods of Use

The compounds and compositions of the present invention can be used to impart sweetness or to enhance the flavor or sweetness of consumables or other compositions.

In one aspect, the present invention is a method of preparing a sweetened consumable comprising (i) providing a consumable and (ii) adding at least one diterpene glycoside of the present invention to the consumable to provide a sweetened consumable.

In a particular embodiment, a method of preparing a sweetened consumable comprises (i) providing an unsweetened consumable and (ii) adding at least one diterpene glycoside of the present invention to the unsweetened consumable to provide a sweetened consumable.

In a particular embodiment, the present invention is a method of preparing a sweetened beverage comprising (i) providing a beverage and (ii) adding at least one diterpene glycoside of the present invention to the beverage to provide a sweetened beverage.

In a particular embodiment, the present invention is a method of preparing a sweetened beverage comprising (i) providing an unsweetened beverage and (ii) adding at least one diterpene glycoside of the present invention to the unsweetened beverage to provide a sweetened beverage.

In the above methods, the diterpene glycoside(s) of the present invention may be provided as such, i.e., in the form of a compound, or in form of a composition. When provided as a composition, the amount of diterpene glycoside in the composition is effective to provide a concentration of the diterpene glycoside that is above, at or below its flavor or sweetness recognition threshold when the composition is added to the consumable (e.g., the beverage). When the diterpene glycoside(s) of the present invention is not provided as a composition, it may be added to the consumable at a concentration that is above, at or below its flavor or sweetness recognition threshold.

In one embodiment, the present invention is a method for enhancing the sweetness of a consumable comprising (i) providing a consumable comprising at least one sweet ingredient and (ii) adding at least one diterpene glycoside of the present invention, or a composition comprising the same, to the consumable to provide a consumable with enhanced sweetness, wherein the diterpene glycoside of the present invention is added to the consumable at a concentration at or below its sweetness recognition threshold. In a particular embodiment, a diterpene glycoside of the present invention is added to the consumable at a concentration below its sweetness recognition threshold.

In a particular embodiment, the present invention is a method for enhancing the sweetness of a beverage comprising (i) providing a beverage comprising at least one sweet ingredient and (ii) adding at least one diterpene glycoside of the present invention, or a composition comprising the same, to the beverage to provide a beverage with enhanced sweetness, wherein the diterpene glycoside is added to the beverage at a concentration at or below its sweetness recognition threshold. In a particular embodiment, the diterpene glycoside of the present invention is added to the consumable at a concentration below its sweetness recognition concentration threshold.

In another embodiment, the present invention is a method for enhancing the flavor of a consumable comprising (i) providing a consumable comprising at least one flavor ingredient and (ii) adding at least one diterpene glycoside of the present invention, or a composition comprising the same, to the consumable to provide a consumable with enhanced flavor, wherein the diterpene glycoside of the present invention is added to the consumable at a concentration at or below its flavor recognition threshold. In a particular embodiment, the diterpene glycoside of the present invention is added to the consumable at a concentration below its flavor recognition threshold.

In a particular embodiment, a method for enhancing the flavor of a beverage is provided that comprises (i) providing a beverage comprising at least one flavor ingredient and (ii) adding at least one diterpene glycoside of the present invention, or a composition comprising the same, to the beverage to provide a beverage with enhanced flavor, wherein the diterpene glycoside is added to the beverage at a concentration at or below the flavor recognition threshold of the diterpene glycoside. In a particular embodiment, the diterpene glycoside of the present invention is added to the consumable at a concentration below its flavor recognition threshold.

The present invention also includes methods of preparing sweetened compositions (e.g., sweetened consumables) and flavor enhanced compositions (e.g., flavored enhanced consumables) by adding at least one diterpene glycoside of the present invention or a composition comprising the same to such compositions/consumables.

IV. Methods of Purification

The present invention also extends to methods of purifying a diterpene glycoside of the present invention.

In one embodiment, the present invention is a method for purifying a diterpene glycoside of the present invention comprising (i) passing a solution comprising a source material comprising a diterpene glycoside of the present invention through a HPLC column and (ii) eluting fractions comprising a diterpene glycoside of the present invention to provide purified diterpene glycoside of the present invention. The HPLC column can be any suitable HPLC preparative or semi-preparative scale column.

As used herein, the term "preparative HPLC" refers to an HPLC system capable of producing high (500 or more) microgram, milligram, or gram sized product fractions. The term "preparative" includes both preparative and semi-preparative columns, but is not intended to include analytical columns, which provide fractions in the nanogram to low microgram range.

As used herein, an "HPLC compatible detector" is a detector suitable for use in an HPLC system which is capable of providing a detectable signal upon elution of a compound peak. For example, a detector capable of generating a signal when a compound elutes from the compound is an HPLC compatible detector. Where component absorbance varies widely, it may be necessary to utilize more than one detector. A detector capable of detecting a desired component is not an "incompatible" detector due to its inability to detect a non-desired peak.

An HPLC device typically includes at least the following components: a column, packed with a suitable stationary phase, a mobile phase, a pump for forcing the mobile phase through the column under pressure, and a detector for detecting the presence of compounds eluting off of the column. The devices can optionally include a means for providing for gradient elution, although such is not necessary using the methods described herein. Routine methods and apparatus for carrying out HPLC separations are well known in the art.

Suitable stationary phases are those in which the compound of interest elutes. Preferred columns can be, and are not limited to, normal phase columns (neutral, acidic or basic), reverse phase columns (of any length alkyl chain), a synthetic crosslinked polymer columns (e.g., styrene and divinylbenzene), size exclusion columns, ion exchange columns, bioaffinity columns, and any combination thereof. The particle size of the stationary phase is within the range from a few µm to several 100 µm.

Suitable detection devices include, but are not limited to, mass spectrometers, UV detectors, IR detectors and light scattering detectors. The methods described herein use any combination of these detectors. The most preferable embodiment uses mass spectrometers and UV detectors.

"Source material", as used herein, refers to the material being purified by the present method. The source material contains a diterpene glycoside of the present invention in a purity less than the purity provided by the present purification method. The source material can be liquid or solid. Exemplary source materials include, but are not limited to, mixtures of diterpene glycosides, stevia extract, Stevia plant leaves, by-products of other diterpene glycosides' isolation and purification processes, commercially available diterpene extracts or stevia extracts, by-products of biotransformation reactions of other diterpene glycosides, or any combination thereof.

As understood by persons skilled in the art, any solid source materials must be brought into solution prior to carrying out the HPLC method.

In one embodiment, a representative analytical HPLC protocol is correlated to a preparative or semi-preparative HPLC protocol used to purify a compound.

In another embodiment, appropriate conditions for purifying a diterpene glycoside of the present invention can be worked out by route scouting a representative sample for a given analytical HPLC column, solvent system and flow rate. In yet another embodiment, a correlated preparative or semipreparative HPLC method can be applied to purify a diterpene glycoside of the present invention with modifications to the purification parameters or without having to change the purification parameters.

In some embodiments, the eluent (mobile phase) is selected from the group consisting of water, acetonitrile, methanol, 2-propanol, ethyl acetate, dimethylformamide, dimethylsulfide, pyridine, triethylamine, formic acid, trifluoroacetic acid, acetic acid, an aqueous solution containing ammonium acetate, heptafluorobutyric acid, and any combination thereof.

In one embodiment, the HPLC method is isocratic. In another embodiment, the HPLC method is a gradient. In still another embodiment, the HPLC method is step-wise.

In one embodiment, impurities are eluted off of the HPLC column after eluting one or more fractions containing a diterpene glycoside of the present invention. In another embodiment, impurities are eluted off of the HPLC column before eluting one or more fractions containing a diterpene glycoside of the present invention.

The method can further include removal of solvent from the eluted solution, i.e. drying. In one embodiment, the method further comprises partial removal of solvents from the eluted solution to provide a concentrate comprising a diterpene glycoside of the present invention. In another embodiment, the method further comprises removing substantially all the solvent from the eluted solutions to provide substantially dry material comprising a diterpene glycoside of the present invention.

Removal of solvent can be performed by any known means to one of skill in the art including, but not limited to, evaporation, distillation, vacuum drying and spray drying.

The resulting purified fractions comprising a diterpene glycoside of the present invention can be further purified by other methods to increase purity. Suitable methods include, but are not limited to, crystallization, chromatography, extraction and distillation. Such methods are well-known to persons skilled in the art.

The source material can be one fraction, or multiple fractions, containing a diterpene glycoside of the present invention collected from at least one previous method or HPLC protocol. In one embodiment, multiple fractions from the same, previous methods or HPLC protocols are pooled and optionally, solvents are removed, prior to re-subjecting the source material to another method. In other embodiments, fractions from different, previous methods or HPLC protocol are pooled, and optionally, solvents are removed, prior to re-subjecting the source material to another method.

In one embodiment, the source material re-subjected to additional method(s) comprises liquid fractions obtained from one or more previous (and optionally, different) methods mixed with substantially dry material obtained via drying of fractions obtained from one or more previous (and optionally, different) methods. In another embodiment, the source material re-subjected to additional method(s) comprises substantially dry material obtained via drying of fractions obtained from one or more previous (and optionally, different) methods, where said source material is brought into solution prior to passing the solution through the next HPLC column.

The second and subsequent methods may have different HPLC protocols (e.g. solvent systems, columns, methods) and different steps following elution (e.g. partial removal of solvent, complete removal of solvent, elution of impurities, use of crystallization or extraction).

The material isolated can be subjected to further methods 2, 3, 4 or more times, each time providing a higher level of purity of purified diterpene glycoside of the present invention.

In one embodiment, the method provides a purified diterpene glycoside of the present invention in a purity of about 50% by weight or greater on a dry basis, such as, for example, about 60% or greater, about 65% or greater, about 70% or greater, about 75% or greater, about 80% or greater, about 85% or greater, about 90% or greater, about 95% or greater and about 97% or greater. In a particular embodiment, the method provides a diterpene glycoside of the present invention in a purity greater of about 99% or greater by weight on a dry basis.

EXAMPLES

Example 1

Isolation and Characterization of CC-00330

Materials

The material used for the isolation of all compounds herein was commercial Stevia extract, obtained from PureCircle.

HPLC Analysis

Preliminary HPLC analyses of samples were performed using a Waters 2695 Alliance System with the following method: Phenomenex Synergi Hydro-RP 80A, 4.6×250 mm, 4 µm (s/n 695639-21); Column Temp: 55° C.; Mobile Phase A: 0.00284% $NH_4OAc$ and 0.0116% HOAc in water; Mobile Phase B: Acetonitrile (MeCN); Flow Rate: 1.0 mL/min; Injection volume: 10 µL. Detection was by UV (210 nm) and CAD.

TABLE 1

| Gradient method | | |
|---|---|---|
| Time (min) | % A | % B |
| 0.0-8.5 | 75 | 25 |
| 10.0 | 71 | 29 |
| 16.5 | 70 | 30 |
| 18.5-24.5 | 66 | 34 |
| 26.5-29.0 | 48 | 52 |
| 31.0-37.0 | 30 | 70 |
| 38.0 | 75 | 25 |

HPLC Analysis—Secondary Process.

HPLC analyses of samples were performed using a Waters 2695 Alliance System with the following method: Waters XBridge Phenyl, 4.6×150 mm, 5 µm (PN 186003352 SN012634135129 03); Column Temp: ambient; Mobile Phase A: Water; Mobile Phase B: MeCN; Flow Rate: 1.0 mL/min; Injection volume: 10 µL. Detection was by UV (210 nm) and CAD.

TABLE 2

| Gradient method | | |
|---|---|---|
| Time (min) | % A | % B |
| 0.0 | 80 | 20 |
| 20.0 | 80 | 20 |
| 20.1 | 50 | 50 |
| 25.0 | 50 | 50 |
| 25.1 | 80 | 20 |

HPLC Analysis—Tertiary Process

HPLC analyses of samples were performed using a Waters 2695 Alliance System with the following method: Waters XBridge Amide, 4.6×150 mm, 3.5 µm (PN 186004869 SN 01253516613401); Column Temp: ambient; Mobile Phase A: Water; Mobile Phase B: MeCN; Flow Rate: 1.0 mL/min; Injection volume: 10 µL. Detection was by UV (210 nm) and CAD.

TABLE 3

| Gradient method | | |
|---|---|---|
| Time (min) | % A | % B |
| 0.0 | 15 | 85 |
| 20 | 30 | 70 |
| 20.1 | 50 | 50 |
| 25 | 50 | 50 |
| 25.1 | 15 | 85 |

Primary Preparative HPLC Method

Primary processing was performed using either a prepacked Waters XBridge RP18 column (50×250 mm, 7 µm)

or Phenomenex Luna C18 (2) column (50×250 mm, µm). The purification process was performed with a Waters Delta Prep LC Model 2000/4000 system coupled to a UV-Vis detector. Details of the preparative method are summarized in Table 4.

TABLE 4

Conditions for Primary Preparative HPLC Method.

Primary HPLC Parameters for the Isolation of CC-00330

| Column | Waters XBridge RP18 (50 × 250 mm, 7 µm) or Phenomenex Luna C18 (2) (50 × 250 mm, µm) at ambient temperature |
|---|---|
| Flow Rate (mL/min) | 100 |
| Detection | UV at 220 nm |
| Mobile Phases | (A) 65:35 water/methanol (MeOH) with 0.05% HOAc<br>(B) 40:60 water/methanol (MeOH) with 0.05% HOAc<br>(C) MeOH |
| Sample preparation | 4-10 g dissolved in 80 mL of MP-A |

| Gradient | | | |
|---|---|---|---|
| Time (min) | % MP-A | % MP-B | % MP-C |
| 0-35 | 100 | | |
| 50-63 | | 100 | |
| 63.1-68 | | | 100 |
| 68.1 | 100 | | |

Secondary Preparative HPLC Method

The secondary processing was performed using a Waters XBridge Phenyl (19×250 mm, 5 µm, PN 186004024, SN 12511306511I02) column. The purification process was performed with a Waters Delta Prep LC Model 2000/4000 system coupled to a UV-Vis detector. Details of the preparative method are summarized in Table 5.

TABLE 5

Conditions for Secondary Preparative HPLC Method.
Secondary HPLC Parameters for the Isolation of CC-00330

| Column | Waters XBridge Phenyl (19 × 250 mm, 5 µm) |
|---|---|
| Flow Rate (mL/min) | 20 |
| Detection | UV at 210 nm |
| Mobile Phases | (A) 20% MeCN in water<br>(B) MeCN |
| Sample preparation | 250 mg of sample, 20 mg/mL |
| Gradient | Isocratic 100% MP-A for 45 min for CC-00330, all others for 55 min |

Tertiary Processing Method

The tertiary processing was performed using a Waters XBridge Amide (19×250 mm, 5 µm, PN 186006606, SN 0107341600112 02)) column. The purification process was performed with a Waters Delta Prep LC Model 2000/4000 system coupled to a UV-Vis detector. Details of the preparative method are summarized in Table 6.

TABLE 6

Conditions for Tertiary HPLC Process.
Tertiary HPLC Parameters for the Isolation of CC-00330

| Column | Waters XBridge Amide (19 × 250 mm, 5 µm) |
|---|---|
| Flow Rate (mL/min) | 20 |

TABLE 6-continued

Conditions for Tertiary HPLC Process.
Tertiary HPLC Parameters for the Isolation of CC-00330

| Detection | UV at 210 nm |
|---|---|
| Mobile Phases | (A) 15% water in MeCN<br>(B) 30% water in MeCN |
| Sample preparation | dissolved in minimum volume of MP-A |
| Gradient: | 30-min linear ramp from 100% MP-A to 100% MP-B, Hold 100% MP-B 15 min |

Isolation Procedure

Fractions collected during the final pre-concentration step were filtered through a stainless steel sieve and concentrated in vacuo using a Buchi® Rotary Evaporator, Model R-114. The concentrated solution was dried for 48-72 h using the Kinetics Flexi-Dry Personal Freeze Dryer, followed by vacuum oven drying at 37° C. for 24 h to remove residual moisture.

MS and MS/MS

MS and MS/MS data were generated with a Waters QT of Micro mass spectrometer equipped with an electrospray ionization source. The sample was analyzed by negative ESI. The sample (~0.08 mg) was diluted with 50:50 $H_2O$:ACN+0.1% formic acid to a concentration of 20 µg/mL for HRMS and MS/MS and were introduced via direct infusion.

NMR

An attempt was made to dissolve 1.4 mg of the sample in 150 µL $CD_3OD$, however the sample did not dissolve readily—it turned cloudy. To this solution, another 50 µL $CD_3OD$ was added and the resulting solution was still cloudy. Addition of another 50 µL $CD_3OD$ turned it to faint cloudy. Sonication of this solution for ~5 min dissolved the sample and NMR data were acquired on a Bruker Avance 500 MHz instrument equipped with a 2.5 mm inverse probe. The $^{13}C$, HMBC and ROESY NMR data were acquired at the Rensselaer Polytechnic Institute, Troy, N.Y. using their Bruker Avance 600 MHz instrument equipped with a 5 mm cryo-probe. The $^1H$ NMR spectrum was referenced to the $CHD_2OD$ resonance at $\delta_H$ 3.30 ppm and $^{13}C$ NMR spectrum was referenced to the $CD_3OD$ resonance at $\delta_C$ 49.0 ppm.

Results and Discussion

Unless otherwise noted, all solvent ratios are listed as percent by volume (v/v).

Primary Purification

Approximately 300 g of Stevia extract was processed using the primary preparative HPLC method described above. Collected fractions were analyzed by HPLC-CAD and LC-MS using the analytical method summarized in Table 1.

Secondary Purification

Collected fractions from primary purification were reprocessed using the secondary preparative HPLC method described above. Fractions were analyzed using the analytical method summarized in Table 2.

Tertiary Purification

Collected fractions from secondary purification were reprocessed using the tertiary processing method described above.

Final Batch Preparation

The sample from tertiary purification was concentrated by rotary evaporation for final isolation. The concentrated solution was further dried via lyophilization for 48 h. The final yield of the batch was 1.4 mg. The purity was >99% based on direct infusion MS analysis.

Mass Spectrometry

The ESI-TOF mass spectrum acquired by infusion showed a [M-H]⁻ ion at m/z 1127.4760. The mass of the [M-H]⁻ ion was in agreement with the molecular formula $C_{50}H_{80}O_{28}$ (calcd for $C_{50}H_{79}O_{28}$: 1127.4758, error: 0.2 ppm) expected for CC-00330. The MS data confirmed that CC-00330 had a nominal mass of 1128 Daltons with the molecular formula, $C_{50}H_{80}O_{28}$. The ion observed at m/z 1241.4701 was due to [M+TFA-H]⁻.

The MS/MS spectrum of CC-00330, with the [M-H]⁻ ion at m/z 1127.0 selected for fragmentation, indicated sequential loss of five glucose units at m/z 965.4753, 803.4179, 641.3522, 479.2883 and 317.2303, which indicated the presence of five glucose units in the structure.

NMR Spectroscopy

A series of NMR experiments including $^1$H NMR, $^{13}$C NMR, $^1$H-$^1$H COSY, HSQC-DEPT, HMBC, ROESY and 1D TOCSY were acquired to allow assignment of CC-00330.

The 1D and 2D NMR data indicated the presence of a central diterpene core with an exocyclic double bond and five sugar units in the structure. In the HSQC-DEPT data, only eight methylene units were observed instead of nine methylene units that are commonly observed in the central diterpene core of related Stevia glycosides. Similarly in the HSQC-DEPT data, in addition to two methine units corresponding to C-5 and C-9 positions, two additional methine units at $\delta_H$ 2.50/$\delta_C$ 41.9 and $\delta_H$ 4.10/$\delta_C$ 78.1 were observed which is relatively rare in this class of compounds and thus indicated structural changes in the central diterpene core.

Complete analysis of 1D and 2D NMR data allowed assignment of the central core and confirmed the structural changes in rings C and D as discussed below. An HMBC correlation from the methyl protons at $\delta_H$ 1.23 to the carbonyl at $\delta_C$ 177.9 allowed assignment of one of the tertiary methyl groups (C-18) as well as C-19 and provided a starting point for the assignment of the rest of the aglycone. Additional HMBC correlations from the methyl protons (H-18) to carbons at $\delta_C$ 39.0 or 39.1, 45.2, and 58.4 allowed assignment of C-3, C-4, and C-5. Analysis of the $^1$H-$^{13}$C HSQC-DEPT data indicated that the carbon at $\delta_C$ 39.0 or 39.1 was a methylene and the carbon at $\delta_C$ 58.4 was a methine which were assigned as C-3 and C-5, respectively. This left the carbon at $\delta_C$ 45.2, which did not show a correlation in the HSQC-DEPT spectrum, to be assigned as the quaternary carbon, C-4. The $^1$H chemical shifts for C-3 ($\delta_H$ 1.04 and 2.27) and C-5 ($\delta_H$ 1.08) were assigned using the HSQC-DEPT data. COSY correlations between the H-3 protons ($\delta_H$ 1.04 and 2.27) and protons at $\delta_H$ 1.39 and 1.90 allowed assignment of the H-2 protons which in turn showed correlations with the protons at $\delta_H$ 0.89 and 1.57 which were assigned to H-1. The $^{13}$C chemical shifts for C-1 and C-2 were then assigned on the basis of HSQC-DEPT correlations.

The other tertiary methyl singlet, observed at $\delta_H$ 0.83 ($\delta_C$ 13.7 via HSQC-DEPT), showed HMBC correlations to C-1 and C-5 and was assigned as H-20. The methyl protons showed additional HMBC correlations to a quaternary carbon ($\delta_C$ 39.4) and a methine carbon ($\delta_C$ 52.4) which were assigned as C-10 and C-9, respectively. The $^1$H chemical shift for C-9 ($\delta_H$ 1.09) was assigned using the HSQC-DEPT data. COSY correlations between H-5 ($\delta_H$ 1.08) and the protons at $\delta_H$ 1.78 and 1.91 then allowed assignment of the H-6 protons which in turn showed correlations to protons at $\delta_H$ 1.14 and 1.57 which were assigned to H-7. The $^{13}$C chemical shifts for C-6 ($\delta_C$ 21.2) and C-7 ($\delta_C$ 40.3) were then determined from the HSQC-DEPT data. COSY correlations between H-9 ($\delta_H$ 1.09) and the protons at $\delta_H$ 1.41 and 1.61 allowed assignment of the H-11 protons. The HSQC-DEPT data was then used to assign C-11 ($\delta_C$ 27.6). The H-11 protons at $\delta_H$ 1.41 and 1.61 showed COSY correlation to a methine proton at $\delta_H$ 2.50 ($\delta_C$ 41.9 via HSQC-DEPT) instead of methylene protons in other Stevia glycosides. This data thus indicated that a methine group was present at position 12 instead of a methylene group. The H-12 proton ($\delta_H$ 2.50) also showed COSY correlations to a methine proton at $\delta_H$ 4.10 assigned to H-13 which in turn showed COSY correlations to protons at $\delta_H$ 1.11 and 2.45 (H-14). The HSQC-DEPT data was then used to assign C-13 ($\delta_C$ 78.1) and C-14 ($\delta_C$ 39.0 or 39.1). In this structure, a methine group was present at position 13 instead of a quaternary carbon commonly found in other Stevia glycosides further indicating structural changes in this part of the central core. The carbon chemical shift of C-13 ($\delta_C$ 78.1) indicated a hydroxyl or a substituted hydroxyl at C-13 similar to other Stevia glycosides. The above proton assignments for H-9 to H-14 spin system were further supported by 1D TOCSY experiments performed using selective irradiation of the H-12 and H-13 protons with several different mixing times. HMBC correlations from H-9 ($\delta_H$ 1.09) and H-14 ($\delta_H$ 1.11 and 2.45) to the carbon at $\delta_C$ 35.2 allowed the assignment of C-8 completing the assignment of ring C. The HSQC-DEPT data indicated that the exocyclic double bond was present in CC-00330 and was assigned based on the HMBC correlations. HMBC correlation from H-12 ($\delta_H$ 2.50) to a carbon at $\delta_C$ 109.6 allowed the assignment of the exocyclic methylene carbon (C-17). The HSQC-DEPT data was then used to assign the protons at C-17 ($\delta_H$ 4.68 and ~4.82 (obscured by water resonance)). The only remaining methylene group in the central core region at $\delta_H$ 1.86 and 2.10 ($\delta_C$ ~48.9 via HSQC-DEPT) was assigned to H-15 and supported by HMBC correlations from H-14 and H-17 to C-15 ($\delta_C$ ~48.9). The HMBC correlations from H-12 ($\delta_H$ 2.50), H-13 ($\delta_H$ 4.10), H-15 ($\delta_H$ 1.86 and 2.10) and H-17 ($\delta_H$ 4.68 and ~4.82) to a quaternary carbon at $\delta_C$ 148.0 allowed assignment of C-16 to complete the assignment of ring D and the central core. In addition, the data showed that instead of the commonly found ent-kaurene diterpenoid core in Stevia glycosides, CC-00330 contained ent-atisene diterpeniod core (FIG. 1). Additional HMBC correlations from H-9 to C-11; H-11 to C-12 and C-16; H-12 to C-9, C-13, and C-14; H-13 to C-11; H-14 to C-13; H-15 to C-8, C-9, C-14 and C-17 and H-17 to C-12 further confirmed the assignments made above.

A summary of the $^1$H and $^{13}$C chemical shifts for the aglycone are found in Table 7 and a summary of the key HMBC and COSY correlations used to assign the aglycone region are provided in FIG. 1.

TABLE 7

$^1$H and $^{13}$C NMR (500 and 150 MHz, CD$_3$OD), assignments of the aglycone.

| | CC-00330 | |
|---|---|---|
| Position | $^{13}$C | $^1$H |
| 1 | 40.8 | 0.89 m |
| | | 1.57 m |
| 2 | 19.9 | 1.39 m |
| | | 1.90 m |
| 3 | 39.0 or 39.1 | 1.04 m |
| | | 2.27 brd |
| | | (14.0) |

TABLE 7-continued $^1$H and $^{13}$C NMR (500 and 150 MHz,
CD$_3$OD), assignments of the aglycone.

| | CC-00330 | |
|---|---|---|
| Position | $^{13}$C | $^1$H |
| 4 | 45.2 | — |
| 5 | 58.4 | 1.08 m |
| 6 | 21.2 | 1.78 m |
| | | 1.91 m |
| 7 | 40.3 | 1.14 m |
| | | 1.57 m |
| 8 | 35.2 | — |
| 9 | 52.4 | 1.09 m |
| 10 | 39.4 | — |
| 11 | 27.6 | 1.41 m |
| | | 1.61 m |
| 12 | 41.9 | 2.50 brs |
| 13 | 78.1 | 4.10 m |
| 14 | 39.0 or 39.1 | 1.11 m |
| | | 2.45 m |
| 15 | ~48.9¥ | 1.86 m |
| | | 2.10 brd |
| | | (16.4) |
| 16 | 148.0 | — |
| 17 | 109.6 | 4.68 brs |
| | | ~4.82€ |
| 18 | 29.3 | 1.23 s |
| 19 | 177.9 | — |
| 20 | 13.7 | 0.83 s |

¥Resonance obscured by CD$_3$OD, assignment based on HSQC-DEPT data.
€Resonance obscured by H$_2$O, assignment based on HSQC-DEPT data.

Correlations observed in the ROESY spectrum were used to assign the relative stereochemistry of the central diterpene core. In the ROESY spectrum, NOE correlations were observed between H-20 one of the H-14 protons ($\delta_H$ 2.45) indicating that H-14 and H-20 are on the same face of the ring. This assignment was further supported by NOE correlations between H-20 and H-13. Similarly, NOE correlations were observed between H-18 and H-5/H-9 but no NOE correlations were observed with H-13, H-14 and H-20 indicating that H-5, H-9 and H-18 were on the opposite face of the ring compared to H-13, H-14 and H-20. The structure with central core relative stereochemistry is presented in FIG. 1.

Analysis of the $^1$H-$^{13}$C HSQC-DEPT data confirmed the presence of five anomeric protons all of which were well resolved at $\delta_H$ 5.54 ($\delta_C$ 94.2), 4.88 ($\delta_C$ 103.7), 4.79 ($\delta_C$ 103.5), 4.62 ($\delta_C$ 104.5), and 4.57 ($\delta_C$ 100.8) in the $^1$H NMR spectrum acquired at 300 K. All five anomeric protons had large couplings (7.5-8.0 Hz) indicating that they had δ-configurations. The anomeric proton observed at $\delta_H$ 5.54 showed an HMBC correlation to C-19 which indicated that it corresponded to the anomeric proton of Glc$_I$. Similarly, the anomeric proton observed at $\delta_H$ 4.57 showed an HMBC correlation to C-13 allowing it to be assigned as the anomeric proton of Glc$_{II}$. The reciprocal HMBC correlation from H-13 ($\delta_H$ 4.10) to the anomeric carbon of Glc$_{II}$ ($\delta_C$ 100.8) was also observed.

The Glc$_I$ anomeric proton ($\delta_H$ 5.54) showed a COSY correlation to a proton at $\delta_H$ 3.86 which was assigned as Glc$_I$ H-2 which in turn showed a COSY correlation to a proton at $\delta_H$ 3.67 (Glc$_I$ H-3). This latter proton showed an additional correlation with a proton at $\delta_H$ 3.42 (Glc$_I$ H-4). Due to data overlap the COSY spectrum did not allow assignment of the remaining protons. Therefore, a series of 1D TOCSY experiments were performed using selective irradiation of the Glc$_I$ anomeric proton with several different mixing times. In addition to confirming the assignments for Glc$_I$ H-2 through H-4, the TOCSY data allowed assignment of H-5 ($\delta_H$ 3.37) and H-6 ($\delta_H$ 3.69 and 3.81). The assignment of H-5 was further confirmed by COSY correlations between Glc$_I$ H-5/H-6. The $^{13}$C chemical shifts for Glc$_I$ C-2 ($\delta_C$ 78.5 or 78.6), C-3 ($\delta_C$ 78.9), C-4 ($\delta_C$ 71.1), C-5 ($\delta_C$ 77.5-78.6) and C-6 ($\delta_C$ 62.4) were assigned using the HSQC-DEPT data. The HMBC correlations observed from Glc$_I$ H-1 to C-2, H-2 to C-1 and C-3, H-3 to C-2 and C-4, H-4 to C-6 and H-6 to C-4 further confirmed the assignments made above to complete the assignment of Glc$_I$. In the $^1$H NMR spectrum a coupling value of 8.0 Hz for Glc$_I$ anomeric proton indicated β-configuration for Glc$_I$.

Of the four remaining unassigned sugar moieties one was assigned as a substituent at C-2 of Glc$_I$ on the basis of HMBC correlations. The anomeric proton observed at $\delta_H$ 4.88 showed an HMBC correlation to Glc$_I$ C-2 and was assigned as the anomeric proton of Glc$_V$. The reciprocal HMBC correlation from Glc$_I$ H-2 to the anomeric carbon of Glc$_V$ was also observed.

The Glc$_V$ anomeric proton ($\delta_H$ 4.88) showed a COSY correlation to a proton at $\delta_H$ 3.21 which was assigned as Glc$_V$ H-2 which in turn showed a COSY correlation to a proton at $\delta_H$ 3.34 (Glc$_V$ H-3). Due to data overlap the COSY spectrum did not allow assignment of the remaining protons. Therefore, a series of 1D TOCSY experiments were performed using selective irradiation of the Glc$_V$ anomeric proton with several different mixing times. In addition to confirming the assignments for Glc$_V$ H-2 and H-3, the TOCSY data allowed assignment of Glc$_V$ H-4 ($\delta_H$ 3.27), H-5 ($\delta_H$ 3.33) and H-6 ($\delta_H$ 3.68 and 3.89). The additional resonance at $\delta_H$ 4.83 ppm in the TOCSY spectra was due to water since Glc$_{II}$ H-1 at $\delta_H$ 4.88 is very close to the water resonance at $\delta_H$ 4.83 and was also was impacted by the TOCSY irradiation pulse. The assignment of H-5 was further confirmed by COSY correlations between Glc$_V$ H-5/H-6. The $^{13}$C chemical shifts for Glc$_V$ C-2 ($\delta_C$ 75.8 or 75.9), C-3 ($\delta_C$ 77.5-78.6), C-4 ($\delta_C$ 71.5 or 72.0 or 72.1), C-5 ($\delta_C$ 77.5-78.6) and C-6 ($\delta_C$ 63.3) were assigned using the HSQC-DEPT data. The HMBC correlations observed from Glc$_V$ H-1 to C-2 and C-3 and/or C-5, H-2 to C-1 and C-3, H-3 to C-4, H-4 to C-6 and H-6 ($\delta_H$ 3.68) to C-4 further confirmed the assignments made above to complete the assignment of Glc$_V$. In the $^1$H NMR spectrum a coupling value of 7.9 Hz for Glc$_V$ anomeric proton indicated β-configuration for Glc$_V$.

A summary of the $^1$H and $^{13}$C chemical shifts for the glycoside at C-19 are found in Table 8.

TABLE 8

$^1$H and $^{13}$C NMR (500 and 150 MHz,
CD$_3$OD), assignments of C-19 glycoside.

| | CC-00330 | |
|---|---|---|
| Position | $^{13}$C | $^1$H |
| Glc$_I$-1 | 94.2 | 5.54 d |
| | | (8.0) |
| Glc$_I$-2 | 78.5 or 78.6 | 3.86 m |
| Glc$_I$-3 | 78.9 | 3.67 m |
| Glc$_I$-4 | 71.1 | 3.42 m |
| Glc$_I$-5 | 77.5-78.6¥ | 3.37 m |
| Glc$_I$-6 | 62.4 | 3.69 m, 3.81 m |
| Glc$_V$-1 | 103.7 | 4.88 d |
| | | (7.9) |
| Glc$_V$-2 | 75.8 or 75.9 | 3.21 m |
| Glc$_V$-3 | 77.5-78.6¥ | 3.34 m |
| Glc$_V$-4 | 71.5 or 72.0 or 72.1 | 3.27 m |

TABLE 8-continued $^1$H and $^{13}$C NMR (500 and 150 MHz, CD$_3$OD), assignments of C-19 glycoside.

| | CC-00330 | |
|---|---|---|
| Position | $^{13}$C | $^1$H |
| Glc$_{IV}$-5 | 77.5-78.6* | 3.33 m |
| Glc$_{IV}$-6 | 62.5 or 62.6 | 3.68 m, 3.89 m |

*Nine carbon resonances in the range of 77.5-78.6 (77.53, 77.91, 78.08, 78.21, 78.38, 78.54, and 78.64), hence chemical shifts could not be unequivocally assigned. Two carbon resonances expected in this range are apparently not resolved.

Assignment of Glc$_{II}$ was carried out in a similar manner. The Glc$_{II}$ anomeric proton ($\delta_H$ 4.57) showed a COSY correlation to a proton at $\delta_H$ 3.65 which was assigned as Glc$_{II}$ H-2 and in turn showed a COSY correlation to a proton at $\delta_H$ 3.71 (Glc$_{II}$ H-3). This latter proton showed an additional correlation with a proton at $\delta_H$ 3.38 (Glc$_{II}$ H-4). Due to data overlap the COSY spectrum did not allow assignment of the remaining protons. Therefore, a series of 1D TOCSY experiments were performed using selective irradiation of the Glc$_{II}$ anomeric proton with several different mixing times. In addition to confirming the assignments for Glc$_{II}$ H-2 through H-4, the TOCSY data allowed assignment of H-5 ($\delta_H$ 3.37) and H-6 ($\delta_H$ 3.66 and 3.87). The assignment of H-5 was further confirmed by COSY correlations between Glc$_{II}$ H-5/H-6. The $^{13}$C chemical shifts for Glc$_{II}$ C-2 ($\delta_C$ 80.0), C-3 ($\delta_C$ 87.4), C-4 ($\delta_C$ 70.0), C-5 ($\delta_C$ 77.5-78.6), and C-6 ($\delta_C$ 62.5 or 62.6) were assigned using the HSQC-DEPT data. The HMBC correlations observed from Glc$_{II}$ H-1 to C-5, H-2 to C-1 and C-3, H-3 to C-2 and C-4, H-4 to C-3, C-5 and H-6 ($\delta_H$ 3.87) to C-4 and C-5 further confirmed the assignments made above to complete the assignment of Glc$_{II}$. In the $^1$H NMR spectrum a coupling value of 7.5 Hz for Glc$_{II}$ anomeric proton indicated β-configuration for Glc$_{II}$.

The remaining two unassigned glucose moieties were assigned as substituents at C-2 and C-3 of Glc$_{II}$ on the basis of HMBC correlations. The anomeric proton observed at $\delta_H$ 4.79 showed an HMBC correlation to Glc$_{II}$ C-2 and was assigned as the anomeric proton of Glc$_{III}$. The anomeric proton observed at $\delta_H$ 4.62 showed an HMBC correlation to Glc$_{II}$ C-3 and was assigned as the anomeric proton of Glc$_{IV}$. The reciprocal HMBC correlations from Glc$_{II}$ H-2 to the anomeric carbon of Glc$_{III}$ and from Glc$_{II}$ H-3 to the anomeric carbon of Glc$_{IV}$ were also observed.

The anomeric proton of Glc$_{III}$ ($\delta_H$ 4.79) showed a COSY correlation with a proton at $\delta_H$ 3.18 which was assigned as Glc$_{III}$ H-2. Glc$_{III}$ C-2 ($\delta_C$ 75.8 or 75.9) was then assigned using the HSQC-DEPT data. Due to data overlap the COSY spectrum did not allow assignment of the remaining protons. Therefore, a series of 1D TOCSY experiments were performed using selective irradiation of the Glc$_{III}$ anomeric proton with several different mixing times. In addition to confirming the assignments for Glc$_{III}$ H-2, the TOCSY data allowed assignment of Glc$_{III}$ H-3 ($\delta_H$ 3.33), H-4 ($\delta_H$ 3.20), H-5 ($\delta_H$ 3.28) and H-6 ($\delta_H$ 3.63 and 3.85). The additional resonance at $\delta_H$ 4.68 ppm in the TOCSY spectra is due one of the H-17 protons since Glc$_{III}$ H-1 at $\delta_H$ 4.79 is very close to one of the H-17 protons at $\delta_H$ ~4.82 (obscured by water resonance), hence $\delta_H$ ~4.82 was impacted by the TOCSY irradiation pulse which showed correlation to its germinal pair at $\delta_H$ 4.68. The second additional resonance at $\delta_H$ 4.83 ppm in the TOCSY spectra is due to water since Glc$_{III}$ H-1 at $\delta_H$ 4.79 is very close to the water resonance at $\delta_H$ 4.83 which was also was impacted by the TOCSY irradiation pulse. The assignment of H-5 was further confirmed by COSY correlations between Glc$_{III}$ H-5/H-6. The $^{13}$C chemical shifts for Glc$_{III}$ C-3 ($\delta_C$ 77.5-78.6), C-4 ($\delta_C$ 72.0 or 72.1), C-5 ($\delta_C$ 77.5-78.6), and C-6 ($\delta_C$ 63.3) were assigned using the HSQC-DEPT data. HMBC correlations observed from Glc$_{III}$ H-1 to C-3 and/or C-5, H-2 to C-1 and C-3, H-4 to C-3 and C-6 and H-6 ($\delta_H$ 3.85) to C-4 further confirmed the assignments made above to complete the assignment of Glc$_{III}$. In the $^1$H NMR spectrum a coupling value of 8.0 Hz for Glc$_{III}$ anomeric proton indicated β-configuration for Glc$_{III}$.

The anomeric proton of Glc$_{IV}$ ($\delta_H$ 4.62) showed a COSY correlation with a proton at $\delta_H$ 3.25 which was assigned as Glc$_{IV}$ H-2. Due to data overlap the COSY spectrum did not allow assignment of the remaining protons. Therefore, a series of 1D TOCSY experiments were performed using selective irradiation of the Glc$_{IV}$ anomeric proton with several different mixing times. In addition to confirming the assignments for Glc$_{IV}$ H-2, the TOCSY data allowed assignment of Glc$_{IV}$ H-3 ($\delta_H$ 3.35), H-4 ($\delta_H$ 3.28) and H-5 ($\delta_H$ 3.33). The protons observed at $\delta_H$ 3.63 and 3.88 in the TOCSY spectrum were assigned as the Glc$_{IV}$ H-6 protons. The assignment of H-5 was further confirmed by COSY correlations between Glc$_{IV}$ H-5/H-6. The $^{13}$C chemical shifts for Glc$_{IV}$ C-2 ($\delta_C$ 75.3), C-3 ($\delta_C$ 77.5-78.6), C-4 ($\delta_C$ 71.5 or 72.0 or 72.1), C-5 ($\delta_C$ 77.5-78.6), and C-6 ($\delta_C$ 62.5 or 62.6) were assigned using the HSQC-DEPT data. The HMBC correlations observed from Glc$_{IV}$ H-1 to C-3 and/or C-5, H-2 to C-1 and C-3, H-3 to C-1, C-2 and C-4, H-4 to C-6 and H-6 ($\delta_H$ 3.88) to C-4 further confirmed the assignments made above to complete the assignment of Glc$_{IV}$. In the $^1$H NMR spectrum a coupling value of 7.8 Hz for Glc$_{IV}$ anomeric proton indicated β-configuration for Glc$_{IV}$.

A summary of the $^1$H and $^{13}$C chemical shifts for the glycoside at C-13 are found in Table 9.

TABLE 9

$^1$H and $^{13}$C NMR (500 and 150 MHz, CD$_3$OD), assignments of C-13 glycoside.

| | CC-00330 | |
|---|---|---|
| Position | $^{13}$C | $^1$H |
| Glc$_{II}$-1 | 100.8 | 4.57 d (7.5) |
| Glc$_{II}$-2 | 80.0 | 3.65 m |
| Glc$_{II}$-3 | 87.4 | 3.71 m |
| Glc$_{II}$-4 | 70.0 | 3.38 m |
| Glc$_{II}$-5 | 77.5-78.6* | 3.37 m |
| Glc$_{II}$-6 | 62.5 or 62.6 | 3.66 m, 3.87 m |
| Glc$_{III}$-1 | 103.5 | 4.79 d (8.0) |
| Glc$_{III}$-2 | 75.8 or 75.9 | 3.18 m |
| Glc$_{III}$-3 | 77.5-78.6* | 3.33 m |
| Glc$_{III}$-4 | 72.0 or 72.1 | 3.20 m |
| Glc$_{III}$-5 | 77.5-78.6* | 3.28 m |
| Glc$_{III}$-6 | 63.3 | 3.63 m, 3.85 m |
| Glc$_{IV}$-1 | 104.5 | 4.62 d (7.8) |
| Glc$_{IV}$-2 | 75.3 | 3.25 m |
| Glc$_{IV}$-3 | 77.5-78.6* | 3.35 m |
| Glc$_{IV}$-4 | 71.5 or 72.0 or 72.1 | 3.28 m |
| Glc$_{IV}$-5 | 77.5-78.6* | 3.33 m |
| Glc$_{IV}$-6 | 63.3 | 3.63 m, 3.88 m |

*Nine carbon resonances in the range of 77.5-78.6 (77.53, 77.91, 78.08, 78.21, 78.38, 78.54, and 78.64), hence chemical shifts could not be unequivocally assigned. Two carbon resonances expected in this range are apparently not resolved.

The structure was determined to be 13-[(2-O-β-D-glucopyranosyl-3-O-β-D-glucopyranosyl-β-D-glucopyranosyl)oxy]ent-atis-16-en-19-oic acid-[(2-O-β-D-glucopyranosyl-β-D-glucopyranosyl) ester].

Example 2

Isolation and Characterization of CC-00331

Materials

The material used for the isolation of CC-00331 was Stevia extract. HPLC Analysis, isolation procedure, was performed as described for Example 1.

MS and MS/MS

MS and MS/MS data were generated with a Waters QT of Micro mass spectrometer equipped with an electrospray ionization source. The sample was analyzed by negative ESI. The sample (~0.1 mg) was diluted with 50:50 $H_2O$:ACN+0.1% formic acid to a concentration of 100 μg/mL for HRMS and MS/MS and were introduced via direct infusion.

NMR

The sample was prepared by dissolving 2.6 mg in 150 μL of $CD_3OD$ and NMR data were acquired on a Bruker Avance 500 MHz instrument equipped with a 2.5 mm inverse probe and a 5 mm broad band probe. The HMBC data were acquired at the Rensselaer Polytechnic Institute, Troy, N.Y. using their Bruker Avance 600 MHz instrument equipped with a 5 mm cryo-probe. The $^1H$ NMR spectrum was referenced to the $CHD_2OD$ resonance at $\delta_H$ 3.30 ppm and $^{13}C$ NMR spectrum was referenced to the $CD_3OD$ resonance at $\delta_C$ 49.0 ppm.

Results and Discussion

Unless otherwise noted, all solvent ratios are listed as percent by volume (v/v).

Primary Purification

Approximately 300 g of Stevia extract was processed using the primary preparative HPLC method described above. Collected fractions were analyzed by HPLC-CAD and LC-MS using the analytical method summarized in Table 1.

Secondary Purification

Collected fractions from primary purification were reprocessed using the secondary preparative HPLC method described above. Fractions were analyzed using the analytical method summarized in Table 2.

Tertiary Purification

Collected fractions from secondary purification were reprocessed using the tertiary processing method described above.

Final Batch Preparation

The sample from tertiary preparation was concentrated by rotary evaporation for final isolation. The concentrated solution was further dried via lyophilization for 48 h. The final yield of the batch was 4.5 mg. The purity was >99% based on direct infusion MS analysis.

Mass Spectrometry

The ESI-TOF mass spectrum acquired by infusion showed a [M-H]⁻ ion at m/z 1111.4830. The mass of the [M-H]⁻ ion was in agreement with the molecular formula $C_{50}H_{80}O_{27}$ (calcd for $C_{50}H_{79}O_{27}$: 1111.4809, error: 1.9 ppm) expected for CC-00331. The MS data confirmed that CC-00331 had a nominal mass of 1112 Daltons with the molecular formula, $C_{50}H_{80}O_{27}$. The ion observed at m/z 1225.4783 was due to [M+TFA-H]⁻.

The MS/MS spectrum of CC-00331, with the [M-H]⁻ ion at m/z 1111.4 selected for fragmentation, indicated loss of one glucose unit at m/z 947.4371 followed by loss of one rhamnose unit at m/z 803.3752 and sequential loss of three sugar units at m/z 641.3210, 479.2636 and 317.1950 indicating the presence of four glucose and one rhamnose units in the structure.

NMR Spectroscopy

A series of NMR experiments including $^1H$ NMR, $^{13}C$ NMR, $^1H$-$^1H$ COSY, HSQC-DEPT, HMBC, ROESY and 1D TOCSY were acquired to allow assignment of CC-00331.

The 1D and 2D NMR data indicated the presence of a central diterpene core with an exocyclic double bond and five sugar units in the structure. In the HSQC-DEPT data, only eight methylene units were observed instead of nine methylene units that are commonly observed in the central diterpene core of related Stevia glycosides. Similarly in the HSQC-DEPT data, in addition to two methine units corresponding to C-5 and C-9 positions, two additional methine units at $\delta_H$ 2.48/$\delta_C$ 42.3 and $\delta_H$ 4.04/$\delta_C$ 79.0 were observed which is relatively rare in this class of compounds and thus indicated structural changes in the central diterpene core.

Complete analysis of 1D and 2D NMR data allowed assignment of the central core and confirmed the structural changes in rings C and D as discussed below. An HMBC correlation from the methyl protons at $\delta_H$ 1.25 to the carbonyl at $\delta_C$ 177.2 allowed assignment of one of the tertiary methyl groups (C-18) as well as C-19 and provided a starting point for the assignment of the rest of the aglycone. Additional HMBC correlations from the methyl protons (H-18) to carbons at $\delta_C$ 38.5, 45.1, and 59.1 allowed assignment of C-3, C-4, and C-5. Analysis of the $^1H$-$^{13}C$ HSQC-DEPT data indicated that the carbon at $\delta_C$ 38.5 was a methylene and the carbon at $\delta_C$ 59.1 was a methine which were assigned as C-3 and C-5, respectively. This left the carbon at $\delta_C$ 45.1, which did not show a correlation in the HSQC-DEPT spectrum, to be assigned as the quaternary carbon, C-4. The $^1H$ chemical shifts for C-3 ($\delta_H$ 1.07 and 2.27) and C-5 ($\delta_H$ 1.07) were assigned using the HSQC-DEPT data. COSY correlations between the H-3 protons ($\delta_H$ 1.07 and 2.27) and protons at $\delta_H$ 1.38 and 1.90 allowed assignment of the H-2 protons which in turn showed correlations with the protons at $\delta_H$ 0.89 and 1.58 which were assigned to H-1. The $^{13}C$ chemical shifts for C-1 and C-2 were then assigned on the basis of HSQC-DEPT correlations.

The other tertiary methyl singlet, observed at $\delta_H$ 0.84 ($\delta_C$ 14.0 via HSQC-DEPT), showed HMBC correlations to C-1 and C-5 and was assigned as H-20. The methyl protons showed additional HMBC correlations to a quaternary carbon ($\delta_C$ 39.4) and a methine carbon ($\delta_C$ 52.2) which were assigned as C-10 and C-9, respectively. The $^1H$ chemical shift for C-9 ($\delta_H$ 1.09) was assigned using the HSQC-DEPT data. COSY correlations between H-5 ($\delta_H$ 1.07) and the protons at $\delta_H$ 1.79 and 1.88 then allowed assignment of the H-6 protons which in turn showed correlations to protons at $\delta_H$ 1.15 and 1.55 which were assigned to H-7. The $^{13}C$ chemical shifts for C-6 ($\delta_C$ 21.1) and C-7 ($\delta_C$ 40.2) were then determined from the HSQC-DEPT data. COSY correlations between H-9 ($\delta_H$ 1.09) and the protons at $\delta_H$ 1.43 and 1.60 allowed assignment of the H-11 protons. The HSQC-DEPT data was then used to assign C-11 ($\delta_C$ 27.6). The H-11 protons at $\delta_H$ 1.43 and 1.60 showed COSY correlation to a methine proton at $\delta_H$ 2.48 ($\delta_C$ 42.3 via HSQC-DEPT) instead of methylene protons in other Stevia glycosides. This data thus indicated that a methine group was present at position 12 instead of a methylene group. The H-12 proton ($\delta_H$ 2.48) also showed COSY correlations to a methine proton at $\delta_H$ 4.04 assigned to H-13 which in turn showed COSY correlations to protons at $\delta_H$ 1.15 and 2.43 (H-14). The HSQC-DEPT data was then used to assign C-13 ($\delta_C$ 79.0) and C-14 ($\delta_C$ 39.0). In this structure, a methine group was present at position 13 instead of a quaternary carbon commonly found in other Stevia glycosides further indicating structural changes in this part of the central core. The carbon chemical shift of C-13 ($\delta_C$ 79.0) indicated a hydroxyl or a substituted hydroxyl at C-13 similar to other Stevia glycosides. The above proton assignments for H-9 to H-14 spin system were further supported by 1D TOCSY experiments performed using selective irradiation of the H-12 and H-13 protons with several different mixing times. HMBC correlations from H-9 ($\delta_H$ 1.09) and H-14 ($\delta_H$ 1.15 and 2.43) to the carbon at $\delta_C$ 35.2 allowed the assignment of C-8 completing the assignment of ring C. The HSQC-DEPT data indicated that the exocyclic double bond was present in 2 and was assigned based on the HMBC correlations. Thus, HMBC correlation from H-12 ($\delta_H$ 2.48) to a carbon at $\delta_C$ 109.5 allowed the assignment of the exocyclic methylene carbon (C-17). The HSQC-DEPT data was then used to assign the protons at C-17 ($\delta_H$ 4.68 and ~4.82 (obscured by water resonance). The only remaining methylene group in the central core region at $\delta_H$ 1.87 and 2.09 ($\delta_C$ ~49.0 via HSQC-DEPT) was assigned to H-15 and supported by HMBC correlations from H-14 and H-17 to C-15 ($\delta_C$ ~49.0). The HMBC correlations from H-12 ($\delta_H$ 2.48), H-13 ($\delta_H$ 4.04), H-15 ($\delta_H$ 1.87 and 2.09) and H-17 ($\delta_H$ 4.68 and ~4.82) to a quaternary carbon at $\delta_C$ 148.0 allowed assignment of C-16 to complete the assignment of ring D and the central core. In addition, the data showed that instead of the commonly found ent-kaurene diterpenoid core in Stevia glycosides, CC-00331 contained an ent-atisene diterpeniod core (FIG. 1). Additional HMBC correlations from H-9 to C-11; H-11 to C-12 and C-16; H-12 to C-9, C-13, and C-14; H-13 to C-11; H-14 to C-13; H-15 to C-8, C-9, C-14 and C-17 and H-17 to C-12 further confirmed the assignments made above.

A summary of the $^1$H and $^{13}$C chemical shifts for the aglycone are found in Table 7.

TABLE 7

$^1$H and $^{13}$C NMR (500 and 125 MHz, CD$_3$OD), assignments of aglycone.

| | CC-00331 | |
|---|---|---|
| Position | $^{13}$C | $^1$H |
| 1 | 40.8 | 0.89 m |
| | | 1.58 m |
| 2 | 20.0 | 1.38 m |
| | | 1.90 m |
| 3 | 38.5 | 1.07 m |
| | | 2.27 brd |
| | | (13.5) |
| 4 | 45.1 | — |
| 5 | 59.1 | 1.07 m |
| 6 | 21.1 | 1.79 m |
| | | 1.88 m |
| 7 | 40.2 | 1.15 m |
| | | 1.55 m |
| 8 | 35.2 | — |
| 9 | 52.2 | 1.09 m |
| 10 | 39.4 | — |
| 11 | 27.6 | 1.43 m |
| | | 1.60 m |
| 12 | 42.3 | 2.48 brs |
| 13 | 79.0 | 4.04 m |
| 14 | 39.0 | 1.15 m |
| | | 2.43 m |

TABLE 7-continued $^1$H and $^{13}$C NMR (500 and 125 MHz, CD$_3$OD), assignments of aglycone.

| | CC-00331 | |
|---|---|---|
| Position | $^{13}$C | $^1$H |
| 15 | ~49.0$^¥$ | 1.87 m |
| | | 2.09 brd |
| | | (16.7) |
| 16 | 148.0 | — |
| 17 | 109.5 | 4.68 brd |
| | | (1.5) |
| | | ~4.82$^€$ |
| 18 | 29.7 | 1.25 s |
| 19 | 177.2 | — |
| 20 | 14.0 | 0.84 s |

$^¥$Resonance obscured by CD$_3$OD, assignment based on HSQC-DEPT data.
$^€$Resonance obscured by H$_2$O, assignment based on HSQC-DEPT data.

Correlations observed in the ROESY spectrum were used to assign the relative stereochemistry of the central diterpene core. In the ROESY spectrum, NOE correlations were observed between H-20 one of the H-14 protons ($\delta_H$ 2.43) indicating that H-14 and H-20 are on the same face of the ring. This assignment was further supported by NOE correlations between H-20 and H-13. Similarly, NOE correlations were observed between H-18 and H-5/H-9 but no NOE correlations were observed with H-13, H-14 and H-20 indicating that H-5, H-9 and H-18 were on the opposite face of the ring compared to H-13, H-14 and H-20. The structure with central core relative stereochemistry is shown in FIG. 1.

Analysis of the $^1$H-$^{13}$C HSQC-DEPT data confirmed the presence of five anomeric protons all of which were well resolved at $\delta_H$ 5.57 ($\delta_C$ 94.2), 5.28 ($\delta_C$ 101.8), 4.79 ($\delta_C$ 103.5), 4.63 ($\delta_C$ 104.5), and 4.53 ($\delta_C$ 101.7) in the $^1$H NMR spectrum acquired at 300 K. Four of the anomeric protons had large couplings (7.9-7.4 Hz) indicating that they had β-configurations and one anomeric proton observed as a broad doublet at $\delta_H$ 5.28 had a small coupling of 1.4 Hz indicating that this had α-configuration. The anomeric proton observed at $\delta_H$ 5.57 showed an HMBC correlation to C-19 which indicated that it corresponded to the anomeric proton of Glc$_I$. Similarly, the anomeric proton observed at $\delta_H$ 4.53 showed an HMBC correlation to C-13 allowing it to be assigned as the anomeric proton of Glc$_{II}$. The reciprocal HMBC correlation from H-13 ($\delta_H$ 4.04) to the anomeric carbon of Glc$_{II}$ ($\delta_C$ 101.7) was also observed.

The Glc$_I$ anomeric proton ($\delta_H$ 5.57) showed a COSY correlation to a proton at $\delta_H$ 3.60 which was assigned as Glc$_I$ H-2. Due to data overlap the COSY spectrum did not allow assignment of the remaining protons. Therefore, a series of 1D TOCSY experiments were performed using selective irradiation of the Glc$_I$ anomeric proton with several different mixing times. In addition to confirming the assignments for Glc$_I$ H-2, the TOCSY data allowed assignment of H-3 ($\delta_H$ 3.57), H-4 ($\delta_H$ 3.42), H-5 ($\delta_H$ 3.36) and H-6 ($\delta_H$ 3.69 and 3.80). The assignment of H-4 and H-5 were further confirmed by COSY correlations between Glc$_I$ H-3/H-4 and H-5/H-6. The $^{13}$C chemical shifts for Glc$_I$ C-2 ($\delta_C$ 78.1 or 78.2 or 78.3), C-3 ($\delta_C$ 79.1), C-4 ($\delta_C$ 71.4), C-5 ($\delta_C$ 78.1 or 78.2 or 78.3) and C-6 ($\delta_C$ 62.5 or 62.6 or 62.7) were assigned using the HSQC-DEPT data. The HMBC correlations observed from Glc$_I$ H-1 to C-2 and C-3, H-2 to C-1 and C-3, H-3 to C-2 and C-4, H-4 to C-6 and H-6 ($\delta_H$ 3.80) to C-4 further confirmed the assignments made above to complete the assignment of Glc$_I$. In the $^1$H NMR spectrum a coupling value of 7.4 Hz for Glc$_I$ anomeric proton indicated β-configuration for Glc$_I$.

Of the four remaining unassigned sugar moieties one was assigned as substituent at C-2 of Glc$_I$ on the basis of HMBC correlations. The anomeric proton observed at δ$_H$ 5.28 showed an HMBC correlation to Glc$_I$ C-2 and was assigned as the anomeric proton of Rha. The reciprocal HMBC correlation from Glc$_I$ H-2 to the anomeric carbon of Rha was also observed.

The anomeric proton of Rha (δ$_H$ 5.28) showed a COSY correlation to a proton at δ$_H$ 3.91 which was assigned as Rha H-2. Rha C-2 (δ$_C$ 72.0 or 72.1 or 72.2) was then assigned using HSQC-DEPT data supporting a rhamnose unit. The Rha H-2 in turn showed a COSY correlation to a proton at δ$_H$ 3.62 (Rha H-3). The later proton showed an additional correlation with a proton at δ$_H$ 3.37 (Rha H-4) which in turn showed a COSY correlation to a proton at δ$_H$ 3.75 (Rha H-5). Rha H-5 showed additional correlations to the methyl protons at δ$_H$ 1.24 (Rha H-6), thus completing $^1$H assignments of Rha spin system. This spin system was further confirmed by a series of 1D TOCSY experiments which were performed using selective irradiation of the Rha anomeric proton with several different mixing times. The $^{13}$C chemical shifts for Rha C-3 (δ$_C$ 72.0 or 72.1 or 72.2), C-4 (δ$_C$ 73.8), C-5 (δ$_C$ 70.3), and C-6 (δ$_C$ 18.3) were assigned using the HSQC-DEPT data. The HMBC correlations observed from Rha H-1 to C-2 and/or C-3 and C-5, H-2 to C-3, H-3 to C-4, H-4 to C-6, and H-6 to C-4 and C-5 further confirmed the assignments made above to complete the assignment of Rha. In the $^1$H NMR spectrum, Rha anomeric proton is observed as a broad doublet having a coupling value of 1.4 Hz which indicated α-configuration for Rha.

A summary of the $^1$H and $^{13}$C chemical shifts for the glycoside at C-19 are found in Table 8.

TABLE 8

$^1$H and $^{13}$C NMR (500 and 125 MHz, CD$_3$OD), assignments of C-19 glycoside.

| | CC-00331 | |
|---|---|---|
| Position | $^{13}$C | $^1$H |
| Glc$_I$-1 | 94.2 | 5.57 d (7.4) |
| Glc$_I$-2 | 78.1 or 78.2 or 78.3 | 3.60 m |
| Glc$_I$-3 | 79.1 | 3.57 m |
| Glc$_I$-4 | 71.4 | 3.42 m |
| Glc$_I$-5 | 78.1 or 78.2 or 78.3 | 3.36 m |
| Glc$_I$-6 | 62.5 or 62.6 or 62.7 | 3.69 m, 3.80 m |
| Rha-1 | 101.8 | 5.28 brd (1.4) |
| Rha-2 | 72.0 or 72.1 or 72.2 | 3.91 m |
| Rha-3 | 72.0 or 72.1 or 72.2 | 3.62 m |
| Rha-4 | 73.8 | 3.37 m |
| Rha-5 | 70.3 | 3.75 m |
| Rha-6 | 18.3 | 1.24, d (6.2) |

Assignment of Glc$_{II}$ was carried out in a similar manner. The Glc$_{II}$ anomeric proton (δ$_H$ 4.53) showed a COSY correlation to a proton at δ$_H$ 3.62 which was assigned as Glc$_{II}$ H-2 and in turn showed a COSY correlation to a proton at δ$_H$ 3.69 (Glc$_{II}$ H-3). This latter proton showed an additional correlation with a proton at δ$_H$ 3.38 (Glc$_{II}$ H-4). Due to data overlap the COSY spectrum did not allow assignment of the remaining protons. Therefore, a series of 1D TOCSY experiments were performed using selective irradiation of the Glc$_{II}$ anomeric proton with several different mixing times. In addition to confirming the assignments for Glc$_{II}$ H-2 through H-4, the TOCSY data allowed assignment of H-5 (δ$_H$ 3.30) and H-6 (δ$_H$ 3.66 and 3.86). The additional resonances at δ$_H$ 3.51-3.58 and 3.78 ppm in the TOCSY spectra were due impurities peaks since some impurities are close to Glc$_{II}$ H-1 at δ$_H$ 4.53, which were impacted by the TOCSY irradiation pulse. The assignment of H-5 was further confirmed by COSY correlations between Glc$_{II}$ H-5/H-6. The $^{13}$C chemical shifts for Glc$_{II}$ C-2 (δ$_C$ 80.3), C-3 (δ$_C$ 87.3), C-4 (δ$_C$ 70.0), C-5 (δ$_C$ 77.5), and C-6 (δ$_C$ 62.5 or 62.6 or 62.7) were assigned using the HSQC-DEPT data. The HMBC correlations observed from Glc$_{II}$ H-1 to C-2 and C-5, H-2 to C-1 and C-3, H-3 to C-2 and C-4, H-4 to C-5 and C-6 and H-6 (δ$_H$ 3.86) to C-4 further confirmed the assignments made above to complete the assignment of Glc$_{II}$. In the $^1$H NMR spectrum a coupling value of 7.6 Hz for Glc$_{II}$ anomeric proton indicated β-configuration for Glc$_{II}$.

The remaining two unassigned glucose moieties were assigned as substituents at C-2 and C-3 of Glc$_{II}$ on the basis of HMBC correlations. The anomeric proton observed at δ$_H$ 4.79 showed an HMBC correlation to Glc$_{II}$ C-2 and was assigned as the anomeric proton of Glc$_{III}$. The anomeric proton observed at δ$_H$ 4.63 showed an HMBC correlation to Glc$_{II}$ C-3 and was assigned as the anomeric proton of Glc$_{IV}$. The reciprocal HMBC correlations from Glc$_{II}$ H-2 to the anomeric carbon of Glc$_{III}$ and from Glc$_{II}$ H-3 to the anomeric carbon of Glc$_{IV}$ were also observed.

The anomeric proton of Glc$_{III}$ (δ$_H$ 4.79) showed a COSY correlation with a proton at δ$_H$ 3.16 which was assigned as Glc$_{III}$ H-2. Glc$_{III}$ C-2 (δ$_C$ 75.9) was then assigned using the HSQC-DEPT data. Due to data overlap the COSY spectrum did not allow assignment of the remaining protons. Therefore, a series of 1D TOCSY experiments were performed using selective irradiation of the Glc$_{III}$ anomeric proton with several different mixing times. In addition to confirming the assignments for Glc$_{III}$ H-2, the TOCSY data allowed assignment of Glc$_{III}$ H-3 (δ$_H$ 3.32), H-4 (δ$_H$ 3.18), H-5 (δ$_H$ 3.28) and H-6 (δ$_H$ 3.63 and 3.84). The additional resonance at δ$_H$ 4.68 ppm in the TOCSY spectra is due one of the H-17 protons since Glc$_{III}$ H-1 at δ$_H$ 4.79 is very close to one of the H-17 protons at δ$_H$ ~4.82 (obscured by water resonance), hence δ$_H$ ~4.82 was impacted by the TOCSY irradiation pulse and hence showed correlation to its germinal pair at δ$_H$ 4.68. The second additional resonance at δ$_H$ 4.84 ppm in the TOCSY spectra is due to water since Glc$_{III}$ H-1 at δ$_H$ 4.79 is very close to the water resonance at δ$_H$ 4.84 and thus was also was impacted by the TOCSY irradiation pulse. The assignment of H-5 was further confirmed by COSY correlations between Glc$_{III}$ H-5/H-6. The $^{13}$C chemical shifts for Glc$_{III}$ C-3 (δ$_C$ 77.9-78.3), C-4 (δ$_C$ 72.0 or 72.1 or 72.2), C-5 (δ$_C$ 77.9-78.3), and C-6 (δ$_C$ 63.3) were assigned using the HSQC-DEPT data. HMBC correlations observed from Glc$_{III}$ H-1 to C-3 and/or C-5, H-2 to C-1 and C-3, H-3 to C-4, H-4 to C-3 and/or C-5 and C-6 and H-6 (δ$_H$ 3.84) to C-4 further confirmed the assignments made above to complete the assignment of Glc$_{III}$. In the $^1$H NMR spectrum a coupling value of 7.9 Hz for Glc$_{III}$ anomeric proton indicated β-configuration for Glc$_{III}$.

The anomeric proton of Glc$_{IV}$ (δ$_H$ 4.63) showed COSY correlation with a proton at δ$_H$ 3.26 which was assigned as Glc$_{IV}$ H-2. Due to data overlap the COSY spectrum did not allow assignment of the remaining protons. Therefore, a series of 1D TOCSY experiments were performed using selective irradiation of the Glc$_{IV}$ anomeric proton with several different mixing times. In addition to confirming the assignments for Glc$_{IV}$ H-2, the TOCSY data allowed assignment of Glc$_{IV}$ H-3 ($\delta_H$ 3.36), H-4 ($\delta_H$ 3.29) and H-5 ($\delta_H$ 3.34). The protons observed at $\delta_H$ 3.63 and 3.88 in the TOCSY spectrum were assigned as the Glc$_{IV}$ H-6 protons. The additional resonances at $\delta_H$ 4.68 and ~4.82 ppm in the TOCSY spectra were due H-17 protons since Glc$_{IV}$ H-1 at $\delta_H$ 4.63 is very close to one of the H-17 protons at $\delta_H$ 4.68, hence $\delta_H$ 4.68 was also impacted by the TOCSY irradiation pulse and hence showed correlation to its germinal pair at $\delta_H$ ~4.82. The assignment of H-5 was further confirmed by COSY correlations between Glc$_{IV}$ H-5/H-6. The $^{13}$C chemical shifts for Glc$_{IV}$ C-2 ($\delta_C$ 75.3), C-3 ($\delta_C$ 77.9-78.3), C-4 ($\delta_C$ 71.5), C-5 ($\delta_C$ 77.9-78.3), and C-6 ($\delta_C$ 62.5 or 62.6 or 62.7) were assigned using the HSQC-DEPT data. The HMBC correlations observed from Glc$_{IV}$ H-1 to C-3 and/or C-5, H-2 to C-1 and C-3, H-3 to C-2 and C-4, H-4 to C-3 and/or C-5 and C-6 and H-6 ($\delta_H$ 3.88) to C-4 further confirmed the assignments made above to complete the assignment of Glc$_{IV}$. In the $^1$H NMR spectrum a coupling value of 7.8 Hz for Glc$_{IV}$ anomeric proton indicated β-configuration for Glc$_{IV}$.

A summary of the $^1$H and $^{13}$C chemical shifts for the glycoside at C-13 are found in Table 9.

TABLE 9

$^1$H and $^{13}$C NMR (500 and 125 MHz, CD$_3$OD), assignments of C-13 glycoside.

| Position | CC-00331 | |
|---|---|---|
| | $^{13}$C | $^1$H |
| Glc$_{II}$-1 | 100.7 | 4.53 d (7.6) |
| Glc$_{II}$-2 | 80.3 | 3.62 m |
| Glc$_{II}$-3 | 87.3 | 3.69 m |
| Glc$_{II}$-4 | 70.0 | 3.38 m |
| Glc$_{II}$-5 | 77.5 | 3.30 m |
| Glc$_{II}$-6 | 62.5 or 62.6 or 62.7 | 3.66 m, 3.86 m |
| Glc$_{III}$-1 | 103.5 | 4.79 d (7.9) |
| Glc$_{III}$-2 | 75.9 | 3.16 m |
| Glc$_{III}$-3 | 77.9-78.3§ | 3.32 m |
| Glc$_{III}$-4 | 72.0 or 72.1 or 72.2 | 3.18 m |
| Glc$_{III}$-5 | 77.9-78.3§ | 3.28 m |
| Glc$_{III}$-6 | 63.3 | 3.63 m, 3.84 m |
| Glc$_{IV}$-1 | 104.5 | 4.63 d (7.8) |
| Glc$_{IV}$-2 | 75.3 | 3.26 m |
| Glc$_{IV}$-3 | 77.9-78.3§ | 3.36 m |
| Glc$_{IV}$-4 | 71.5 | 3.29 m |
| Glc$_{IV}$-5 | 77.9-78.3§ | 3.34 m |
| Glc$_{IV}$-6 | 62.5 or 62.6 or 62.7 | 3.63 m, 3.88 m |

§Six carbon resonances in the range of 77.9-78.3 (77.88, 78.02, 78.14, 78.20, 78.22, and 78.32), hence chemical shifts could not be unequivocally assigned.

The structure was determined to be 13-[(2-O-β-D-glucopyranosyl-3-O-β-D-glucopyranosyl-β-D-glucopyranosyl)oxy] ent-atis-16-en-19-oic acid-[(2-O-α-L-rhamnopyranosyl-β-D-glucopyranosyl) ester].

Example 3

Isolation and Characterization of CC-00332

Materials

The material used for the isolation of CC-00332 was a Stevia extract. HPLC Analysis, isolation procedure, were performed as described for Example 1 with the deviations described below.

MS and MS/MS

MS and MS/MS data were generated with a Waters QT of Micro mass spectrometer equipped with an electrospray ionization source. The sample was analyzed by negative ESI. The sample (~0.2 mg) was diluted with 50:50 H$_2$O:ACN+0.1% formic acid to a concentration of 100 μg/mL for HRMS and MS/MS and were introduced via direct infusion.

NMR

An attempt was made to dissolve 2.7 mg of the sample in 150 μL CD$_3$OD, however the sample did not dissolve readily—it turned faint cloudy. To this solution, another 50 μL CD$_3$OD was added which dissolved the sample and NMR data were acquired on a Bruker Avance 500 MHz instrument equipped with a 2.5 mm inverse probe and a 5 mm broad band probe. The HMBC data was acquired at the Rensselaer Polytechnic Institute, Troy, N.Y. using their Bruker Avance 600 MHz instrument equipped with a 5 mm cryo-probe. The $^1$H NMR spectrum was referenced to the CHD$_2$OD resonance at $\delta_H$ 3.30 ppm and $^{13}$C NMR spectrum was referenced to the CD$_3$OD resonance at $\delta_C$ 49.0 ppm.

Results and Discussion

Unless otherwise noted, all solvent ratios are listed as percent by volume (v/v).

Primary Purification

Approximately 300 g of Stevia extract was processed using the primary preparative HPLC method described above. Collected fractions were analyzed by HPLC-CAD and LC-MS using the analytical method summarized in Table 1.

Secondary Purification

Collected fractions from primary processing were reprocessed using the secondary preparative HPLC method described above, using 18% MeCN in water as mobile phase A. Fractions were analyzed using the analytical method summarized in Table 2.

Tertiary Purification

Collected fractions from secondary processing were reprocessed using the tertiary processing method described above.

Final Batch Preparation

The sample from tertiary purification was concentrated by rotary evaporation for final isolation. The concentrated solution was further dried via lyophilization for 48 h. The final yield of the batch was 7.9 mg. The purity was >99% based on direct infusion MS analysis.

Mass Spectrometry.

The ESI-TOF mass spectrum acquired by infusion showed a [M-H]$^-$ ion at m/z 1273.5353. The mass of the [M-H]$^-$ ion was in agreement with the molecular formula C$_{56}$H$_{90}$O$_{32}$ (calcd for C$_{56}$H$_{89}$O$_{32}$: 1273.5337, error: 1.3 ppm) expected for CC-00332. The MS data confirmed that CC-00332 has a nominal mass of 1274 Daltons with the molecular formula, C$_{56}$H$_{90}$O$_{32}$. The ion observed at m/z 1388.5381 was due to [M+TFA]$^-$.

The MS/MS spectrum of CC-00332, with the [M-H]$^-$ ion at m/z 1273.5 selected for fragmentation, indicated loss of two glucose units at m/z 1111.4684 and 949.4500 followed by loss of one rhamnose unit at m/z 803.3704 and sequential loss of three sugar units at m/z 641.3172, 479.2629 and 317.1921 indicating the presence of five glucose and one rhamnose units in the structure.

NMR Spectroscopy.

A series of NMR experiments including $^1$H NMR, $^{13}$C NMR, $^1$H-$^1$H COSY, HSQC-DEPT, HMBC, ROESY and 1D TOCSY were acquired to allow assignment of CC-00332.

The 1D and 2D NMR data indicated the presence of a central diterpene core with an exocyclic double bond and six sugar units in the structure. In the HSQC-DEPT data, only eight methylene units were observed instead of nine methylene units that are commonly observed in the central diterpene core of related Stevia glycosides. Similarly in the HSQC-DEPT data, in addition to two methine units corresponding to C-5 and C-9 positions, two additional methine units at $\delta_H$ 2.48/$\delta_C$ 42.3 and $\delta_H$ 4.05/$\delta_C$ 78.8 were observed which is relatively rare in this class of compounds and thus indicated structural changes in the central diterpene core.

Complete analysis of 1D and 2D NMR data allowed assignment of the central core and confirmed the structural changes in rings C and D as discussed below. An HMBC correlation from the methyl protons at $\delta_H$ 1.26 to the carbonyl at $\delta_C$ 177.0 allowed assignment of one of the tertiary methyl groups (C-18) as well as C-19 and provided a starting point for the assignment of the rest of the aglycone. Additional HMBC correlations from the methyl protons (H-18) to carbons at $\delta_C$ 38.5, 45.1, and 59.1 allowed assignment of C-3, C-4, and C-5. Analysis of the $^1$H-$^{13}$C HSQC-DEPT data indicated that the carbon at $\delta_C$ 38.5 was a methylene and the carbon at $\delta_C$ 59.1 was a methine which were assigned as C-3 and C-5, respectively. This left the carbon at $\delta_C$ 45.1, which did not show a correlation in the HSQC-DEPT spectrum, to be assigned as the quaternary carbon, C-4. The $^1$H chemical shifts for C-3 ($\delta_H$ 1.06 and 2.25) and C-5 ($\delta_H$ 1.06) were assigned using the HSQC-DEPT data. COSY correlations between the H-3 protons ($\delta_H$ 1.06 and 2.25) and protons at $\delta_H$ 1.38 and 1.91 allowed assignment of the H-2 protons which in turn showed correlations with the protons at $\delta_H$ 0.88 and 1.57 which were assigned to H-1. The $^{13}$C chemical shifts for C-1 and C-2 were then assigned on the basis of HSQC-DEPT correlations.

The other tertiary methyl singlet, observed at $\delta_H$ 0.84 ($\delta_C$ 13.9 via HSQC-DEPT), showed HMBC correlations to C-1 and C-5 and was assigned as H-20. The methyl protons showed additional HMBC correlations to a quaternary carbon ($\delta_C$ 39.4) and a methine carbon ($\delta_C$ 52.3) which were assigned as C-10 and C-9, respectively. The $^1$H chemical shift for C-9 ($\delta_H$ 1.08) was assigned using the HSQC-DEPT data. COSY correlations between H-5 ($\delta_H$ 1.06) and the protons at $\delta_H$ 1.79 and 1.88 then allowed assignment of the H-6 protons which in turn showed correlations to protons at $\delta_H$ 1.14 and 1.55 which were assigned to H-7. The $^{13}$C chemical shifts for C-6 ($\delta_C$ 21.1) and C-7 ($\delta_C$ 40.3) were then determined from the HSQC-DEPT data. COSY correlations between H-9 ($\delta_H$ 1.08) and the protons at $\delta_H$ 1.42 and 1.60 allowed assignment of the H-11 protons. The HSQC-DEPT data was then used to assign C-11 ($\delta_C$ 27.6). The H-11 protons at $\delta_H$ 1.42 and 1.60 showed COSY correlation to a methine proton at $\delta_H$ 2.48 ($\delta_C$ 42.3 via HSQC-DEPT) instead of methylene protons in other Stevia glycosides. This data thus indicated that a methine group was present at position 12 instead of a methylene group. The H-12 proton ($\delta_H$ 2.48) also showed COSY correlations to a methine proton at $\delta_H$ 4.05 assigned to H-13 which in turn showed COSY correlations to protons at $\delta_H$ 1.14 and 2.44 (H-14).

The HSQC-DEPT data was then used to assign C-13 ($\delta_C$ 78.8) and C-14 ($\delta_C$ 39.0). In this structure, a methine group was present at position 13 instead of a quaternary carbon commonly found in other Stevia glycosides further indicating structural changes in this part of the central core. The carbon chemical shift of C-13 ($\delta_C$ 78.8) indicated a hydroxyl or a substituted hydroxyl at C-13 similar to other Stevia glycosides. The above proton assignments for H-9 to H-14 spin system were further supported by 1D TOCSY experiments performed using selective irradiation of the H-12 and H-13 protons with several different mixing times. HMBC correlations from H-9 ($\delta_H$ 1.08) and H-14 ($\delta_H$ 1.14 and 2.44) to the carbon at $\delta_C$ 35.2 allowed the assignment of C-8 completing the assignment of ring C. The HSQC-DEPT data indicated that the exocyclic double bond was present in CC-00332 and was assigned based on the HMBC correlations. Thus, HMBC correlation from H-12 ($\delta_H$ 2.48) to a carbon at $\delta_C$ 109.5 allowed the assignment of the exocyclic methylene carbon (C-17). The HSQC-DEPT data was then used to assign the protons at C-17 ($\delta_H$ 4.68 and 4.81 (obscured by water resonance). The only remaining methylene group corresponding to the central core region at $\delta_H$ 1.86 and 2.09 ($\delta_C$ ~49.0 via HSQC-DEPT) was assigned to H-15 and supported by HMBC correlations from H-14 and H-17 to C-15 ($\delta_C$ ~49.0). The HMBC correlations from H-12 ($\delta_H$ 2.48), H-13 ($\delta_H$ 4.05), H-15 ($\delta_H$ 1.86 and 2.09) and H-17 ($\delta_H$ 4.68 and ~4.81) to a quaternary carbon at $\delta_C$ 148.0 allowed assignment of C-16 to complete the assignment of ring D and the central core. In addition, the data showed that instead of the commonly found ent-kaurene diterpenoid core in Stevia glycosides, CC-00332 contained ent-atisene diterpeniod core (as shown in FIG. 1). Additional HMBC correlations from H-9 to C-11; H-11 to C-9, C-12 and C-16; H-12 to C-9, C-13, and C-14; H-13 to C-11; H-14 to C-13; H-15 to C-8, C-9, C-14 and C-17 and H-17 to C-12 further confirmed the assignments made above.

A summary of the $^1$H and $^{13}$C chemical shifts for the aglycone are found in Table 7.

TABLE 7

$^1$H and $^{13}$C NMR (500 and 125 MHz, CD$_3$OD), assignments of aglycone.

| | CC-00332 | |
|---|---|---|
| Position | $^{13}$C | $^1$H |
| 1 | 40.8 | 0.88 m |
| | | 1.57 m |
| 2 | 20.0 | 1.38 m |
| | | 1.91 m |
| 3 | 38.5 | 1.06 m |
| | | 2.25 brd |
| | | (13.6) |
| 4 | 45.1 | — |
| 5 | 59.1 | 1.06 m |
| 6 | 21.1 | 1.79 m |
| | | 1.88 m |
| 7 | 40.3 | 1.14 m |
| | | 1.55 m |
| 8 | 35.2 | — |
| 9 | 52.3 | 1.08 m |
| 10 | 39.4 | — |
| 11 | 27.6 | 1.42 m |
| | | 1.60 m |
| 12 | 42.3 | 2.48 brs |
| 13 | 78.8 | 4.05 m |
| 14 | 39.0 | 1.14 m |
| | | 2.44 m |

TABLE 7-continued $^1$H and $^{13}$C NMR (500 and 125 MHz,
CD$_3$OD), assignments of aglycone.

| | CC-00332 | |
|---|---|---|
| Position | $^{13}$C | $^1$H |
| 15 | ~49.0$^¥$ | 1.86 m |
| | | 2.09 brd |
| | | (16.7) |
| 16 | 148.0 | — |
| 17 | 109.5 | 4.68 brd |
| | | (1.7) |
| | | ~4.81$^€$ |
| 18 | 29.7 | 1.26 s |
| 19 | 177.0 | — |
| 20 | 13.9 | 0.84 s |

$^¥$Resonance obscured by CD$_3$OD, assignment based on HSQC-DEPT data.
$^€$Resonance obscured by H$_2$O, assignment based on HSQC-DEPT data.

Correlations observed in the ROESY spectrum were used to assign the relative stereochemistry of the central diterpene core. In the ROESY spectrum, NOE correlations were observed between H-20 one of the H-14 protons ($\delta_H$ 2.44) indicating that H-14 and H-20 are on the same face of the ring. This assignment was further supported by NOE correlations between H-20 and H-13. Similarly, NOE correlations were observed between H-18 and H-5/H-9 but no NOE correlations were observed with H-13, H-14 and H-20 indicating that H-5, H-9 and H-18 were on the opposite face of the ring compared to H-13, H-14 and H-20.

Analysis of the $^1$H-$^{13}$C HSQC-DEPT data for CC-00332 confirmed the presence of six anomeric protons, of which four were well resolved at $\delta_H$ 5.65 ($\delta_C$ 94.4), 5.21 ($\delta_C$ 102.2), 4.79 ($\delta_C$ 103.5) and 4.63 ($\delta_C$ 104.4 or 104.5) and two were overlapped at 4.54 ($\delta_C$ 104.4 or 104.5 and 101.6) in the $^1$H NMR spectrum acquired at 300 K. Five of the anomeric protons had large couplings (7.9-6.9 Hz) indicating that they had β-configurations and one anomeric proton observed as a broad doublet at $\delta_H$ 5.21 had a small coupling of 1.7 Hz indicating that this had α-configuration. The anomeric proton observed at $\delta_H$ 5.65 showed an HMBC correlation to C-19 which indicated that it corresponded to the anomeric proton of Glc$_I$. Similarly, the anomeric proton observed at $\delta_H$ 4.54 showed an HMBC correlation to C-13 allowing it to be assigned as the anomeric proton of Glc$_{II}$. The reciprocal HMBC correlation from H-13 ($\delta_H$ 4.05) to the anomeric carbon of Glc$_{II}$ ($\delta_C$ 100.6) was also observed.

The Glc$_I$ anomeric proton ($\delta_H$ 5.65) showed a COSY correlation to a proton at $\delta_H$ 3.81 which was assigned as Glc$_I$ H-2. Due to data overlap the COSY spectrum did not allow assignment of the remaining protons. Therefore, a series of 1D TOCSY experiments were performed using selective irradiation of the Glc$_I$ anomeric proton with several different mixing times. In addition to confirming the assignments for Glc$_I$ H-2, the TOCSY data allowed assignment of H-3 ($\delta_H$ 3.79), H-4 ($\delta_H$ 3.62), H-5 ($\delta_H$ 3.43) and H-6 ($\delta_H$ 3.71 and 3.81). These assignments were further confirmed by COSY correlations between Glc$_I$ H-3/H-4, H-4/H-5 and H-5/H-6. The $^{13}$C chemical shifts for Glc$_I$ C-2 ($\delta_C$ 78.8), C-3 ($\delta_C$ 87.0), C-4 ($\delta_C$ 69.4), C-5 ($\delta_C$ 77.8) and C-6 ($\delta_C$ 62.5-62.7) were assigned using the HSQC-DEPT data. The HMBC correlations observed from Glc$_I$ H-1 to C-2, C-3 and C-5, H-2 to C-1 and C-3, H-3 to C-2 and C-4, H-4 to C-6 and H-6 ($\delta_H$ 3.81) to C-4 further confirmed the assignment of Glc$_I$. In the $^1$H NMR spectrum a coupling value of 6.9 Hz for Glc$_I$ anomeric proton indicated β-configuration for Glc$_I$.

Of the five remaining unassigned sugar moieties two were assigned as substituents at C-2 and C-3 of Glc$_I$ on the basis of HMBC correlations. The anomeric proton observed at $\delta_H$ 5.21 showed an HMBC correlation to Glc$_I$ C-2 and was assigned as the anomeric proton of Rha. The reciprocal HMBC correlation from Glc$_I$ H-2 to the anomeric carbon of Rha was also observed. Similarly, anomeric proton observed at $\delta_H$ 4.54 showed an HMBC correlation to Glc$_I$ C-3 and was assigned as the anomeric proton of Glc$_{VI}$. The reciprocal HMBC correlation from Glc$_I$ H-2 to the anomeric carbon of Glc$_{VI}$ was also observed.

The anomeric proton of Rha ($\delta_H$ 5.21) showed a COSY correlation to a proton at $\delta_H$ 3.98 which was assigned as Rha H-2. Rha C-2 ($\delta_C$ 72.0 or 72.1) was then assigned using HSQC-DEPT data supporting a rhamnose unit. The Rha H-2 in turn showed a COSY correlation to a proton at $\delta_H$ 3.63 (Rha H-3). This latter proton showed an additional correlation with a proton at $\delta_H$ 3.37 (Rha H-4) which in turn showed a COSY correlation to a proton at $\delta_H$ 3.72 (Rha H-5). Rha H-5 showed additional correlations to the methyl protons at $\delta_H$ 1.22 (Rha H-6), thus completing $^1$H assignments of Rha spin system. This spin system was further confirmed by a series of 1D TOCSY experiments which were performed using selective irradiation of the Rha anomeric proton with several different mixing times. The $^{13}$C chemical shifts for Rha C-3 ($\delta_C$ 72.0 or 72.1), C-4 ($\delta_C$ 73.8), C-5 ($\delta_C$ 70.6), and C-6 ($\delta_C$ 18.4) were assigned using the HSQC-DEPT data. The HMBC correlations observed from the Rha H-1 to C-2 and/or C-3 and C-5, H-2 to C-3, H-3 to C-4, H-4 to C-6, and H-6 to C-4 and C-5 further confirmed the assignments made above to complete the assignment of Rha. In the $^1$H NMR spectrum, Rha anomeric proton is observed as a broad doublet having a coupling value of 1.7 Hz which indicated α-configuration for Rha.

Since the anomeric protons observed at $\delta_H$ 4.54 corresponded to two glucose units, assignments for those glucose units were made by combined analysis of COSY, HSQC-DEPT, HMBC and 1D-TOCSY NMR data. As discussed above, on the basis of HMBC correlations, one of the anomeric protons at $\delta_H$ 4.54 was assigned to Glc$_{VI}$, which showed a COSY correlation with a proton at $\delta_H$ 3.27 which was assigned as Glc$_{VI}$ H-2 and in turn showed a COSY correlation to a proton at $\delta_H$ 3.39 (Glc$_{VI}$ H-3). This latter proton showed an additional correlation with a proton at $\delta_H$ 3.29 (Glc$_{VI}$ H-4). Due to data overlap the COSY spectrum did not allow assignment of the remaining protons. Therefore, a series of 1D TOCSY experiments were performed using selective irradiation of the Glc$_{VI}$ anomeric proton with several different mixing times. Since the anomeric proton of Glc$_{VI}$ at $\delta_H$ 4.54 overlapped exactly with Glc$_{II}$ anomeric proton (discussed below), TOCSY irradiation pulse at $\delta_H$ 4.54 showed protons of both Glc$_{II}$ and Glc$_{VI}$ spin systems. From this 1D TOCSY data it was evident that the partially resolved methylene resonance at $\delta_H$ 3.90 (H-6) belonged to either Glc$_{VI}$ or Glc$_{II}$ spin system. Therefore this proton was utilized for 1D TOCSY experiment with several different mixing times. The 1D TOCSY spectra showed resonances at $\delta_H$ 3.64 (corresponding to its germinal pair, also confirmed by COSY spectrum) and at $\delta_H$ 3.27, 3.39 and 3.29 (methine protons via HSQC-DEPT) confirming that $\delta_H$ 3.90 belongs to Glc$_{VI}$ H-6. Hence, in addition to confirming the assignments for Glc$_{VI}$ H-2, H-3, H-4, and H-6 (geminal pair), the TOCSY data allowed assignment of Glc$_{VI}$ H-5 ($\delta_H$ 3.34). The additional resonances at $\delta_H$ 4.63, 3.88, and 3.63 ppm observed in the TOCSY spectra are due to Glc$_{IV}$ protons (discussed below) since one of the Glc$_{IV}$ H-6 protons at $\delta_H$ 3.88 being very close to Glc$_{VI}$ H-6 ($\delta_H$ 3.90) was also impacted by the TOCSY irradiation pulse. The $^{13}$C chemical shifts for C-2 ($\delta_C$ 75.1), C-3 ($\delta_C$ 77.5-78.3), C-4 ($\delta_C$ 71.5 or 71.6), C-5 ($\delta_C$ 77.5-78.3), and C-6 ($\delta_C$ 62.5-62.7) were assigned using the HSQC-DEPT data. The HMBC correlations observed from Glc$_{VI}$ H-1 to C-2, H-2 to C-1 and C-3, H-3 to C-2 and C-4, H-4 to C-3, C-5 and C-6 and H-6 to C-4 further confirmed the assignments made above to complete the assignment of Glc$_{VI}$. In the $^1$H NMR spectrum a coupling value of 7.9 Hz for Glc$_{VI}$ anomeric proton indicated β-configuration for Glc$_{VI}$.

A summary of the $^1$H and $^{13}$C chemical shifts for the glycoside at C-19 are found in Table 8.

TABLE 8

$^1$H and $^{13}$C NMR (500 and 125 MHz, CD$_3$OD), assignments of C-19 glycoside.

| Position | CC-00332 | |
|---|---|---|
| | $^{13}$C | $^1$H |
| Glc$_I$-1 | 94.4 | 5.65 d (6.9) |
| Glc$_I$-2 | 78.8 | 3.81 m |
| Glc$_I$-3 | 87.0 | 3.79 m |
| Glc$_I$-4 | 69.4 | 3.62 m |
| Glc$_I$-5 | 77.8 | 3.43 m |
| Glc$_I$-6 | 62.5-62.7¶ | 3.71 m, 3.81 m |
| Rha-1 | 102.0 | 5.21 brd (1.7) |
| Rha-2 | 72.0 or 72.1 | 3.98 m |
| Rha-3 | 72.0 or 72.1 | 3.63 m |
| Rha-4 | 73.8 | 3.37 m |
| Rha-5 | 70.6 | 3.72 m |
| Rha-6 | 18.4 | 1.22, d (6.2) |
| Glc$_{VI}$-1 | 104.4 or 104.5 | 5.54 d (7.9) |
| Glc$_{VI}$-2 | 75.1 | 3.27 m |
| Glc$_{VI}$-3 | 77.5-78.3§ | 3.39 m |
| Glc$_{VI}$-4 | 71.5 or 71.6 | 3.29 m |
| Glc$_{VI}$-5 | 77.5-78.3§ | 3.34 m |
| Glc$_{VI}$-6 | 62.5-62.7¶ | 3.64 m, 3.90 m |

¶Four carbon resonances in the range of 62.5-62.7 (62.53, 62.55, 62.62, and 62.70), hence chemical shifts could not be unequivocally assigned.
§Eight carbon resonances in the range of 77.5-78.3 (77.51, 77.76, 77.88, 78.00, 78.06, 78.22, 78.20, and 78.27), hence chemical shifts could not be unequivocally assigned.

As discussed above, the anomeric protons at $\delta_H$ 4.54 assigned to Glc$_{II}$ and Glc$_{VI}$ on the basis of HMBC correlations. The complete assignment of Glc$_{II}$ spin system was done by combined analysis of COSY, HSQC-DEPT, HMBC and 1D-TOCSY NMR data. The Glc$_{II}$ anomeric proton ($\delta_H$ 4.54) showed a COSY correlation to a proton at $\delta_H$ 3.63 which was assigned as Glc$_{II}$ H-2 and in turn showed a COSY correlation to a proton at $\delta_H$ 3.69 (Glc$_{II}$ H-3). This latter proton showed an additional correlation with a proton at $\delta_H$ 3.39 (Glc$_{II}$ H-4). Due to data overlap the COSY spectrum did not allow assignment of the remaining protons. Therefore, a series of 1D TOCSY experiments were performed using selective irradiation of the Glc$_{II}$/Glc$_{VI}$ anomeric protons with several different mixing times. Since anomeric proton at $\delta_H$ 4.54 also correspond to the anomeric proton of Glc$_{VI}$, TOCSY irradiation pulse at $\delta_H$ 4.54 showed resonances for the protons of both sugar units, Glc$_{II}$ and Glc$_{VI}$. The proton assignments for Glc$_{VI}$ were made as discussed above and thus the remaining resonances in the TOCSY spectra were due to the protons of Glc$_{II}$. Hence, in addition to providing supporting evidence for the assignments for Glc$_{II}$ H-2 through H-4, the TOCSY data allowed assignment of H-5 ($\delta_H$ 3.31) and H-6 ($\delta_H$ 3.66 and 3.86). The $^{13}$C chemical shifts for Glc$_{II}$ C-2 ($\delta_C$ 80.3), C-3 ($\delta_C$ 87.4), C-4 ($\delta_C$ 70.0), C-5 ($\delta_C$ 77.5-78.3), and C-6 ($\delta_C$ 62.5-62.7) were assigned using the HSQC-DEPT data. The HMBC correlations observed from Glc$_{II}$ H-1 to C-2 and C-5, H-2 to C-1 and C-3, H-3 to C-2 and C-4, H-4 to C-5 and C-6 and H-6 ($\delta_H$ 3.86) to C-4 further confirmed the assignments made above to complete the assignment of Glc$_{II}$. In the $^1$H NMR spectrum a coupling value of 7.9 Hz for Glc$_{II}$ anomeric proton indicated β-configuration for Glc$_{II}$.

The remaining two unassigned glucose moieties were assigned as substituents at C-2 and C-3 of Glc$_{II}$ on the basis of HMBC correlations. The anomeric proton observed at $\delta_H$ 4.79 showed an HMBC correlation to Glc$_{II}$ C-2 and was assigned as the anomeric proton of Glc$_{III}$. The anomeric proton observed at $\delta_H$ 4.63 showed an HMBC correlation to Glc$_{II}$ C-3 and was assigned as the anomeric proton of Glc$_{IV}$. The reciprocal HMBC correlations from Glc$_{II}$ H-2 to the anomeric carbon of Glc$_{III}$ and from Glc$_{II}$ H-3 to the anomeric carbon of Glc$_{IV}$ were also observed.

The anomeric proton of Glc$_{III}$ ($\delta_H$ 4.79) showed a COSY correlation with a proton at $\delta_H$ 3.16 which was assigned as Glc$_{III}$ H-2 and in turn showed a COSY correlation to a proton at $\delta_H$ 3.32 (Glc$_{III}$ H-3). Glc$_{III}$ C-2 ($\delta_C$ 75.9) and C-3 ($\delta_C$ 77.5-78.3) were then assigned using the HSQC-DEPT data. Due to data overlap the COSY spectrum did not allow assignment of the remaining protons. Therefore, a series of 1D TOCSY experiments were performed using selective irradiation of the Glc$_{III}$ anomeric proton with several different mixing times. In addition to confirming the assignments for Glc$_{III}$ H-2 and H-3, the TOCSY data allowed assignment of Glc$_{III}$ H-4 ($\delta_H$ 3.18), H-5 ($\delta_H$ 3.28) and H-6 ($\delta_H$ 3.63 and 3.84). The assignment of H-5 was further confirmed by COSY correlations between Glc$_{III}$ H-5/H-6. The additional resonance at $\delta_H$ 4.68 ppm in the TOCSY spectra is due one of the H-17 protons since Glc$_{III}$ H-1 at $\delta_H$ 4.79 is very close to one of the H-17 protons at $\delta_H$ ~4.81 (obscured by water resonance), hence $\delta_H$ ~4.81 was impacted by the TOCSY irradiation pulse which showed correlation to its germinal pair at $\delta_H$ 4.68. The second additional resonance at $\delta_H$ 4.83 ppm in the TOCSY spectra is due to water since Glc$_{III}$ H-1 at $\delta_H$ 4.79 is very close to the water resonance at $\delta_H$ 4.83 and was also was impacted by the TOCSY irradiation pulse. The $^{13}$C chemical shifts for Glc$_{III}$ C-4 ($\delta_C$ 72.0 or 72.1), C-5 ($\delta_C$ 77.5-78.3), and C-6 ($\delta_C$ 63.3) were assigned using the HSQC-DEPT data. HMBC correlations observed from Glc$_{III}$ H-1 to C-3 and/or C-5, H-2 to C-1 and C-3, H-3 to C-4, H-4 to C-5 and C-6 and H-6 ($\delta_H$ 3.63) to C-4 further confirmed the assignments made above to complete the assignment of Glc$_{III}$. In the $^1$H NMR spectrum a coupling value of 7.9 Hz for Glc$_{III}$ anomeric proton indicated β-configuration for Glc$_{III}$.

The anomeric proton of Glc$_{IV}$ ($\delta_H$ 4.63) showed a COSY correlation with a proton at $\delta_H$ 3.25 which was assigned as Glc$_{IV}$ H-2. Due to data overlap the COSY spectrum did not allow assignment of the remaining protons. Therefore, a series of 1D TOCSY experiments were performed using selective irradiation of the Glc$_{IV}$ anomeric proton with several different mixing times. In addition to confirming the assignments for Glc$_{IV}$ H-2, the TOCSY data allowed assignment of Glc$_{IV}$ H-3 ($\delta_H$ 3.35), H-4 ($\delta_H$ 3.28) and H-5 ($\delta_H$ 3.33). The protons observed at $\delta_H$ 3.63 and 3.88 in the TOCSY spectrum were assigned as the Glc$_{IV}$ H-6 protons. The additional minor resonances at $\delta_H$ 4.68 and ~4.81 ppm in the TOCSY spectra were H-17 protons since Glc$_{IV}$ H-1 at $\delta_H$ 4.63 is close to one of the H-17 protons at $\delta_H$ 4.68, hence $\delta_H$ 4.68 was also impacted by the TOCSY irradiation pulse which showed correlation to its germinal pair at $\delta_H$ ~4.81. The assignment for H-5 was further confirmed by COSY correlations between Glc$_{IV}$ H-5/H-6. The $^{13}$C chemical shifts for Glc$_{IV}$ C-2 ($\delta_C$ 75.3), C-3 ($\delta_C$ 77.5-78.3), C-4 ($\delta_C$ 71.5 or 71.6), C-5 ($\delta_C$ 77.5-78.3), and C-6 ($\delta_C$ 62.5-62.7) were assigned using the HSQC-DEPT data. The HMBC correlations observed from Glc$_{IV}$ H-1 to C-3 and/or C-5, H-2 to C-1 and C-3, H-3 to C-2 and C-4, H-4 to C-3, C-5 and C-6 and H-6 ($\delta_H$ 3.88) to C-4 further confirmed the assignments made above to complete the assignment of Glc$_{IV}$. In the $^1$H NMR spectrum a coupling value of 7.8 Hz for Glc$_{IV}$ anomeric proton indicated β-configuration for Glc$_{IV}$.

Some impurity resonances were observed in $^1$H NMR spectrum at $\delta_H$ 5.35, 4.71, 4.65, 4.36, 4.12, and 3.54 ppm.

A summary of the $^1$H and $^{13}$C chemical shifts for the glycoside at C-13 are found in Table 9.

TABLE 9

$^1$H and $^{13}$C NMR (500 and 125 MHz, CD$_3$OD), assignments of C-13 glycoside.

| Position | CC-00332 $^{13}$C | $^1$H |
|---|---|---|
| Glc$_{II}$-1 | 101.6 | 4.54 d (7.9) |
| Glc$_{II}$-2 | 80.3 | 3.63 m |
| Glc$_{II}$-3 | 87.4 | 3.69 m |
| Glc$_{II}$-4 | 70.0 | 3.39 m |
| Glc$_{II}$-5 | 77.5-78.3§ | 3.31 m |
| Glc$_{II}$-6 | 62.5-62.7¶ | 3.66 m, 3.86 m |
| Glc$_{III}$-1 | 103.5 | 4.79 d (7.9) |
| Glc$_{III}$-2 | 75.9 | 3.16 m |
| Glc$_{III}$-3 | 77.5-78.3§ | 3.32 m |
| Glc$_{III}$-4 | 72.0 or 72.1 | 3.18 m |
| Glc$_{III}$-5 | 77.5-78.3§ | 3.28 m |
| Glc$_{III}$-6 | 63.3 | 3.63 m, 3.84 m |
| Glc$_{IV}$-1 | 104.4 or 104.5 | 4.63 d (7.8) |
| Glc$_{IV}$-2 | 75.3 | 3.25 m |
| Glc$_{IV}$-3 | 77.5-78.3§ | 3.35 m |
| Glc$_{IV}$-4 | 71.5 or 71.6 | 3.28 m |
| Glc$_{IV}$-5 | 77.5-78.3§ | 3.33 m |
| Glc$_{IV}$-6 | 62.5-62.7¶ | 3.63 m, 3.88 m |

§Eight carbon resonances in the range of 77.5-78.3 (77.51, 77.76, 77.88, 78.00, 78.06, 78.22, 78.20, and 78.27), hence chemical shifts could not be unequivocally assigned.
¶Four carbon resonances in the range of 62.5-62.7 (62.53, 62.55, 62.62, and 62.70), hence chemical shifts could not be unequivocally assigned.

The structure was determined to be 13-[(2-O-β-D-glucopyranosyl-3-O-β-D-glucopyranosyl-β-D-glucopyranosyl)oxy] ent-atis-16-en-19-oic acid-[(2-O-α-L-rhamnopyranosyl-3-O-β-D-glucopyranosyl-β-D-glucopyranosyl) ester].

Example 4

Isolation and Characterization of CC-00333

Materials.

The material used for the isolation of CC-00333 was a Stevia extract. HPLC Analysis, isolation procedure, were performed as in Example 1 with the deviations described below.

MS and MS/MS.

MS and MS/MS data were generated with a Waters QT of Micro mass spectrometer equipped with an electrospray ionization source. The sample was analyzed by negative ESI. The sample (~0.2 mg) was diluted with 50:50 H$_2$O: ACN+0.1% formic acid to a concentration of 100 μg/mL for HRMS and MS/MS and were introduced via direct infusion.

NMR.

An attempt was made to dissolve 2.6 mg of the sample in 150 μL CD$_3$OD, however the sample did not dissolve readily. To this solution, another 50 μL CD$_3$OD was added and the resulting solution was still cloudy. Addition of another 50 μL CD$_3$OD turned it to faint cloudy. This sample was transferred in NMR tube where the undissolved sample dissolved while keeping it for ~30 min and NMR data were acquired on a Bruker Avance 500 MHz instrument equipped with a 2.5 mm inverse probe and a 5 mm broad band probe. The HMBC data were acquired at the Rensselaer Polytechnic Institute, Troy, N.Y. using their Bruker Avance 600 MHz instrument equipped with a 5 mm cryo-probe. The $^1$H NMR spectrum was referenced to the CHD$_2$OD resonance at $\delta_H$ 3.30 ppm and $^{13}$C NMR spectrum was referenced to the CD$_3$OD resonance at $\delta_C$ 49.0 ppm.

Results and Discussion

Unless otherwise noted, all solvent ratios are listed as percent by volume (v/v).

Primary Purification.

Approximately 300 g of Stevia extract was processed using the primary preparative HPLC method described above. Collected fractions were analyzed by LC-MS using the analytical method summarized in Table 1.

Secondary Purification.

Collected fractions from the primary purification were reprocessed with conditions summarized above. Fractions were analyzed using the analytical method summarized in Table 2.

Tertiary Purification.

Collected fractions were reprocessed with conditions summarized above—where the gradient was a 30-min linear ramp from 100% MP-A to 100% MP-B with 5-min isocratic holds at 87%, 47% and 30% MP-A composition.

Final Batch Preparation.

Pure fractions from tertiary processing were concentrated by rotary evaporation for final isolation. The concentrated solution was further dried via lyophilization for 48 h. The final yield was 3.8 mg. The purity was >99% based on direct infusion MS analysis.

Mass Spectrometry.

The ESI-TOF mass spectrum acquired by infusing a sample of CC-00333 showed a [M-H]$^-$ ion at m/z 1435.5844. The mass of the [M-H]$^-$ ion was in good agreement with the molecular formula C$_{62}$H$_{100}$O$_{37}$ (calcd for C$_{62}$H$_{99}$O$_{37}$: 1435.5865, error: −1.5 ppm) expected for CC-00333. The MS data confirmed that CC-00333 has a nominal mass of 1436 Daltons with the molecular formula, C$_{62}$H$_{100}$O$_{37}$.

The MS/MS spectrum of CC-00333, selecting the [M-H]$^-$ ion at m/z 1435.5 for fragmentation, indicated loss of three glucose units at m/z 1273.5428, 1111.4835 and 949.4512 followed by loss of one rhamnose unit at m/z 803.3798 and sequential loss of three sugar units at m/z 641.3209, 479.2545 and 317.1973 and thus indicated the presence of six glucose and one rhamnose units in the structure.

NMR Spectroscopy.

A series of NMR experiments including $^1$H NMR, $^{13}$C NMR, $^1$H-$^1$H COSY, HSQC-DEPT, HMBC, ROESY and 1D TOCSY were acquired to assign CC-00333.

The 1D and 2D NMR data indicated the presence of a central diterpene core with an exocyclic double bond and six sugar units in the structure. In the HSQC-DEPT data, only eight methylene units were observed instead of nine methylene units that are commonly observed in the central diterpene core of related Stevia glycosides. Similarly in the HSQC-DEPT data, in addition to two methine units corresponding to C-5 and C-9 positions, two additional methine units at $\delta_H$ 2.48/$\delta_C$ 42.3 and $\delta_H$ 4.05/$\delta_C$ 78.9 were observed which is relatively rare in this class of compounds and thus indicated structural changes in the central diterpene core.

Complete analysis of 1D and 2D NMR data allowed assignment of the central core and confirmed the structural changes in rings C and D as discussed below. An HMBC correlation from the methyl protons at $\delta_H$ 1.26 to the carbonyl at $\delta_C$ 176.9 allowed assignment of one of the tertiary methyl groups (C-18) as well as C-19 and provided a starting point for the assignment of the rest of the aglycone. Additional HMBC correlations from the methyl protons (H-18) to carbons at $\delta_C$ 39.0, 45.1, and 59.2 allowed assignment of C-3, C-4, and C-5. Analysis of the $^1$H-$^{13}$C HSQC-DEPT data indicated that the carbon at $\delta_C$ 39.0 was a methylene and the carbon at $\delta_C$ 59.2 was a methine which were assigned as C-3 and C-5, respectively. This left the carbon at $\delta_C$ 45.1, which did not show a correlation in the HSQC-DEPT spectrum, to be assigned as the quaternary carbon, C-4. The $^1$H chemical shifts for C-3 ($\delta_H$ 1.06 and 2.23) and C-5 ($\delta_H$ 1.06) were assigned using the HSQC-DEPT data. COSY correlations between the H-3 protons ($\delta_H$ 1.06 and 2.23) and protons at $\delta_H$ 1.37 and 1.93 allowed assignment of the H-2 protons which in turn showed correlations with the protons at $\delta_H$ 0.88 and 1.57 which were assigned to H-1. The $^{13}$C chemical shifts for C-1 and C-2 were then assigned on the basis of HSQC-DEPT correlations.

The other tertiary methyl singlet, observed at $\delta_H$ 0.85 ($\delta_C$ 13.9 via HSQC-DEPT), showed HMBC correlations to C-1 and C-5 and was assigned as H-20. The methyl protons showed additional HMBC correlations to a quaternary carbon ($\delta_C$ 39.4) and a methine carbon ($\delta_C$ 52.3) which were assigned as C-10 and C-9, respectively. The $^1$H chemical shift for C-9 ($\delta_H$ 1.08) was assigned using the HSQC-DEPT data. COSY correlations between H-5 ($\delta_H$ 1.06) and the protons at $\delta_H$ 1.79 and 1.85 then allowed assignment of the H-6 protons which in turn showed correlations to protons at $\delta_H$ 1.14 and 1.55 which were assigned to H-7. The $^{13}$C chemical shifts for C-6 ($\delta_C$ 21.1) and C-7 ($\delta_C$ 40.2) were then determined from the HSQC-DEPT data. COSY correlations between H-9 ($\delta_H$ 1.08) and the protons at $\delta_H$ 1.42 and 1.59 allowed assignment of the H-11 protons. The HSQC-DEPT data was then used to assign C-11 ($\delta_C$ 27.7). The H-11 protons at $\delta_H$ 1.42 and 1.59 showed COSY correlation to a methine proton at $\delta_H$ 2.48 ($\delta_C$ 42.3 via HSQC-DEPT) instead of methylene protons in other Stevia glycosides. This data thus indicated that a methine group was present at position 12 instead of a methylene group. The H-12 proton ($\delta_H$ 2.48) also showed COSY correlations to a methine proton at $\delta_H$ 4.05 assigned to H-13 which in turn showed COSY correlations to protons at $\delta_H$ 1.14 and 2.44 (H-14). The HSQC-DEPT data was then used to assign C-13 ($\delta_C$ 78.9) and C-14 ($\delta_C$ 39.0). In this structure, a methine group was present at position 13 instead of a quaternary carbon commonly found in other Stevia glycosides further indicating structural changes in this part of the central core. The carbon chemical shift of C-13 ($\delta_C$ 78.9) indicated a hydroxyl or a substituted hydroxyl at C-13 similar to other Stevia glycosides. The above proton assignments for H-9 to H-14 spin system were further supported by 1D TOCSY experiments performed using selective irradiation of the H-12 and H-13 protons with several different mixing times. HMBC correlations from H-9 ($\delta_H$ 1.08) and H-14 ($\delta_H$ 1.14 and 2.44) to the carbon at $\delta_C$ 35.2 allowed the assignment of C-8 completing the assignment of ring C. The HSQC-DEPT data indicated that the exocyclic double bond was present in CC-00333 and was assigned based on the HMBC correlations. Thus, HMBC correlation from H-12 ($\delta_H$ 2.48) to a carbon at $\delta_C$ 109.4 allowed the assignment of the exocyclic methylene carbon (C-17). The HSQC-DEPT data was then used to assign the protons at C-17 ($\delta_H$ 4.68 and ~4.81 (obscured by water resonance)). The only remaining methylene group in the central core region at $\delta_H$ 1.86 and 2.09 ($\delta_C$ ~49.0 via HSQC-DEPT) was assigned to H-15 and supported by HMBC correlations from H-14 and H-17 to C-15 ($\delta_C$ ~49.0). The HMBC correlations from H-12 ($\delta_H$ 2.48), H-13 ($\delta_H$ 4.05), H-15 ($\delta_H$ 1.86 and 2.09) and H-17 ($\delta_H$ 4.68 and ~4.81) to a quaternary carbon at $\delta_C$ 148.1 allowed assignment of C-16 to complete the assignment of ring D and the central core. In addition, the data show that instead of the commonly found ent-kaurene diterpenoid core in Stevia glycosides, CC-00333 contained an ent-atisene diterpeniod core (as shown in FIG. 1). Additional HMBC correlations from H-9 to C-11; H-11 to C-9, C-12 and C-16; H-12 to C-9, C-13, and C-14; H-13 to C-11; H-14 to C-13; H-15 to C-8, C-9, C-14 and C-17 and H-17 to C-12 further confirmed the assignments made above.

A summary of the $^1$H and $^{13}$C chemical shifts for the aglycone are found in Table 7.

TABLE 7

$^1$H and $^{13}$C NMR (500 and 125 MHz, CD$_3$OD), assignments of aglycone

| | CC-00333 | |
| --- | --- | --- |
| Position | $^{13}$C | $^1$H |
| 1 | 40.8 | 0.88 m |
| | | 1.57 m |
| 2 | 20.1 | 1.37 m |
| | | 1.93 m |
| 3 | 39.0 | 1.06 m |
| | | 2.23 brd |
| | | (13.2) |
| 4 | 45.1 | — |
| 5 | 59.2 | 1.06 m |
| 6 | 21.1 | 1.79 m |
| | | 1.85 m |
| 7 | 40.2 | 1.14 m |
| | | 1.55 m |
| 8 | 35.2 | — |
| 9 | 52.3 | 1.08 m |
| 10 | 39.4 | — |
| 11 | 27.7 | 1.42 m |
| | | 1.59 m |
| 12 | 42.3 | 2.48 brs |
| 13 | 78.9 | 4.05 m |
| 14 | 39.0 | 1.14 m |
| | | 2.44 m |
| 15 | ~49.0$^¥$ | 1.86 m |
| | | 2.09 brd |
| | | (16.9) |
| 16 | 148.1 | — |
| 17 | 109.4 | 4.68 brs |
| | | ~4.81$^ε$ |
| 18 | 29.8 | 1.26 s |
| 19 | 176.9 | — |
| 20 | 13.9 | 0.85 s |

$^¥$Resonance obscured by CD$_3$OD, assignment based on HSQC-DEPT data.
$^ε$Resonance obscured by H$_2$O, assignment based on HSQC-DEPT data.

Correlations observed in the ROESY spectrum were used to assign the relative stereochemistry of the central diterpene core. In the ROESY spectrum, NOE correlations were observed between H-20 one of the H-14 protons ($\delta_H$ 2.44) indicating that H-14 and H-20 are on the same face of the ring. This assignment was further supported by NOE correlations between H-20 and H-13. Similarly, NOE correlations were observed between H-18 and H-5/H-9 but no NOE correlations were observed with H-13, H-14 and H-20 indicating that H-5, H-9 and H-18 were on the opposite face of the ring compared to H-13, H-14 and H-20.

Analysis of the $^1$H-$^{13}$C HSQC-DEPT data for CC-00333 confirmed the presence of seven anomeric protons which were well resolved at $\delta_H$ 5.64 ($\delta_C$ 94.5), 5.16 ($\delta_C$ 101.7), 4.79 ($\delta_C$ 103.5), 4.63 ($\delta_C$ 104.5), 4.58 ($\delta_C$ 105.1), 4.54 ($\delta_C$ 101.6), and 4.50 ($\delta_C$ 105.0) in the $^1$H NMR spectrum acquired at 300 K. Six of the anomeric protons had large couplings (7.3-7.9 Hz) indicating that they had β-configurations and remaining one anomeric proton observed as a broad doublet at $\delta_H$ 5.16 had a small coupling of 1.4 Hz indicating that this had α-configuration. The anomeric proton observed at $\delta_H$ 5.64 showed an HMBC correlation to C-19 which indicated that it corresponded to the anomeric proton of Glc$_I$. Similarly, the anomeric proton observed at $\delta_H$ 4.54 showed an HMBC correlation to C-13 allowing it to be assigned as the anomeric proton of Glc$_{II}$. The reciprocal HMBC correlation from H-13 ($\delta_H$ 4.05) to the anomeric carbon of Glc$_{II}$ ($\delta_C$ 101.6) was also observed.

The Glc$_I$ anomeric proton ($\delta_H$ 5.64) showed a COSY correlation to a proton at $\delta_H$ 3.81 which was assigned as Glc$_I$ H-2. Due to data overlap the COSY spectrum did not allow assignment of the remaining protons. Therefore, a series of 1D TOCSY experiments were performed using selective irradiation of the Glc$_I$ anomeric proton with several different mixing times. In addition to confirming the assignments for Glc$_I$ H-2, the TOCSY data allowed assignment of H-3 ($\delta_H$ 3.76), H-4 ($\delta_H$ 3.59), H-5 ($\delta_H$ 3.41) and H-6 ($\delta_H$ 3.71 and 3.80). These assignments were further confirmed by COSY correlations between Glc$_I$ H-3/H-4, H-4/H-5 and H-5/H-6. The $^{13}$C chemical shifts for Glc$_I$ C-2 ($\delta_C$ 79.7), C-3 ($\delta_C$ 86.6), C-4 ($\delta_C$ 69.4), C-5 ($\delta_C$ 77.4-78.2) and C-6 ($\delta_C$ 62.5-62.7) were assigned using the HSQC-DEPT data. The HMBC correlations observed from Glc$_I$ H-1 to C-3 and C-5, H-2 to C-1 and C-3, H-3 to C-2 and C-4, H-4 to C-6 and H-6 ($\delta_H$ 3.80) to C-4 further confirmed the assignments made above to complete the assignment of Glc$_I$. In the $^1$H NMR spectrum a coupling value of 7.3 Hz for Glc$_I$ anomeric proton indicated β-configuration for Glc$_I$.

Of the six remaining unassigned sugar moieties two were assigned as substituents at C-2 and C-3 of Glc$_I$ on the basis of HMBC correlations. The anomeric proton observed at $\delta_H$ 5.16 showed an HMBC correlation to Glc$_I$ C-2 and was assigned as the anomeric proton of Rha. The reciprocal HMBC correlation from Glc$_I$ H-2 to the anomeric carbon of Rha was also observed. Similarly, anomeric proton observed at $\delta_H$ 4.50 showed an HMBC correlation to Glc$_I$ C-3 and was assigned as the anomeric proton of Glc$_{VI}$. The reciprocal HMBC correlation from Glc$_I$ H-3 to the anomeric carbon of Glc$_{VI}$ was also observed.

The anomeric proton of Rha ($\delta_H$ 5.16) showed a COSY correlation to a proton at $\delta_H$ 4.25 which was assigned as Rha H-2. Rha C-2 ($\delta_C$ 70.9) was then assigned using HSQC-DEPT data supporting a rhamnose unit. The Rha H-2 in turn showed a COSY correlation to a proton at $\delta_H$ 3.73 (Rha H-3). This latter proton showed an additional correlation with a proton at $\delta_H$ 3.52 (Rha H-4) which in turn showed a COSY correlation to a proton at $\delta_H$ 3.78 (Rha H-5). Rha H-5 showed additional correlations to the methyl protons at $\delta_H$ 1.22 (Rha H-6), thus completing $^1$H assignments of Rha spin system. This spin system was further confirmed by a series of 1D TOCSY experiments which were performed using selective irradiation of the Rha anomeric proton with several different mixing times. The $^{13}$C chemical shifts for Rha C-2 ($\delta_C$ 70.9), C-3 ($\delta_C$ 83.0), C-4 ($\delta_C$ 72.6), C-5 ($\delta_C$ 70.2), and C-6 ($\delta_C$ 18.4) were assigned using the HSQC-DEPT data. The HMBC correlations observed from Rha H-1 to C-2, C-3 and C-5, H-2 to C-3, H-3 to C-4, H-4 to C-6, and H-6 to C-4 and C-5 further confirmed the assignments made above to complete the assignment of Rha. In the $^1$H NMR spectrum, Rha anomeric proton is observed as a broad doublet having a coupling value of 1.4 Hz which indicated α-configuration for Rha. The relatively downfield carbon chemical shift of Rha C-3 ($\delta_C$ 83.0) indicated an attachment of a sugar unit at this position and confirmed as discussed below.

The anomeric proton observed at $\delta_H$ 4.58 showed an HMBC correlation to Rha C-3 and was assigned as the anomeric proton of Glc$_V$. The reciprocal HMBC correlation from Rha H-3 to the anomeric carbon of Glc$_V$ ($\delta_C$ 105.1) was also observed.

The Glc$_V$ anomeric proton ($\delta_H$ 4.58) showed a COSY correlation to a proton at $\delta_H$ 3.28 which was assigned as Glc$_V$ H-2 which in turn showed a COSY correlation to a proton at $\delta_H$ 3.41 (Glc$_V$ H-3). Due to data overlap the COSY spectrum did not allow assignment of the remaining protons. Therefore, a series of 1D TOCSY experiments were performed using selective irradiation of the Glc$_V$ anomeric proton with several different mixing times. In addition to confirming the assignments for Glc$_V$ H-2 and H-3, the TOCSY data allowed assignment of Glc$_V$ H-4 ($\delta_H$ 3.33), H-5 ($\delta_H$ 3.46) and H-6 ($\delta_H$ 3.69 and 3.87). The additional resonances at $\delta_H$ 4.63 and 4.54 ppm in the TOCSY spectra were due to Glc$_{IV}$ and Glc$_{II}$, respectively, since Glc$_V$ H-1 at $\delta_H$ 4.58 is very close to the anomeric protons of Glc$_{IV}$ and Glc$_{II}$, which were also impacted by the TOCSY irradiation pulse. Consequently, an additional resonance at $\delta_H$ 3.62 ppm in the TOCSY spectra was due to Glc$_{II}$ H-2. The assignment of H-5 was further confirmed by COSY correlations between Glc$_V$ H-5/H-6. The $^{13}$C chemical shifts for Glc$_V$ C-2 ($\delta_C$ 75.3 or 75.4), C-3 ($\delta_C$ 77.4-78.2), C-4 ($\delta_C$ 71.3), C-5 ($\delta_C$ 77.4 or 77.5 or 77.6) and C-6 ($\delta_C$ 62.5-62.7) were assigned using the HSQC-DEPT data. The HMBC correlations observed from Glc$_V$ H-1 to C-2, C-3 and/or C-5, H-2 to C-1 and C-3, H-3 to C-4, H-4 to C-6 and H-6 ($\delta_H$ 3.87) to C-4 further confirmed the assignments made above to complete the assignment of Glc$_V$. In the $^1$H NMR spectrum a coupling value of 7.7 Hz for Glc$_V$ anomeric proton indicated β-configuration for Glc$_V$.

Assignment of Glc$_{VI}$ was carried out in a similar manner. The anomeric proton of Glc$_{VI}$ ($\delta_H$ 4.50) showed a COSY correlation with a proton at $\delta_H$ 3.27 which was assigned as Glc$_{VI}$ H-2. Due to data overlap the COSY spectrum did not allow assignment of the remaining protons. Therefore, a series of 1D TOCSY experiments were performed using selective irradiation of the Glc$_{VI}$ anomeric proton with several different mixing times. In addition to confirming the assignments for Glc$_{VI}$ H-2, the TOCSY data allowed assignment of Glc$_{VI}$ H-3 ($\delta_H$ 3.41), H-4 ($\delta_H$ 3.29), H-5 ($\delta_H$ 3.36) and H-6 ($\delta_H$ 3.64 and 3.90). The additional resonance at $\delta_H$ 4.54 ppm in the TOCSY spectra was due to Glc$_{II}$ since Glc$_{VI}$ H-1 at $\delta_H$ 4.50 is very close to the anomeric protons of Glc$_{II}$ ($\delta_H$ 4.54), which was also impacted by the TOCSY irradiation pulse and showed correlations to the resonances at $\delta_H$ 3.62, 3.69 and 3.86 ppm in the TOCSY spectra. The assignment of H-5 was further confirmed by COSY correlations between Glc$_{VI}$ H-5/H-6. The $^{13}$C chemical shifts for Glc$_{VI}$ C-2 ($\delta_C$ 75.1), C-3 ($\delta_C$ 77.4-78.2), C-4 ($\delta_C$ 71.5 or 71.6), C-5 ($\delta_C$ 77.4-78.2) and C-6 ($\delta_C$ 62.5-62.7) were assigned using the HSQC-DEPT data. The HMBC correlations observed from Glc$_{VI}$ H-1 to C-2, C-3 and/or C-5, H-2 to C-1 and C-3, H-3 to C-2 and C-4, H-4 to C-6 and H-6 to C-4 further confirmed the assignments made above to complete the assignment of Glc$_{VI}$. In the $^1$H NMR spectrum a coupling value of 7.8 Hz for Glc$_{VI}$ anomeric proton indicated β-configuration for Glc$_{VI}$.

A summary of the $^1H$ and $^{13}C$ chemical shifts for the glycoside at C-19 are found in Table 8.

TABLE 8

$^1H$ and $^{13}C$ NMR (500 and 125 MHz, CD$_3$OD), assignments of C-19 glycoside.

| Position | CC-00333 $^{13}C$ | $^1H$ |
|---|---|---|
| Glc$_I$-1 | 94.5 | 5.64 d (7.3) |
| Glc$_I$-2 | 79.7 | 3.81 m |
| Glc$_I$-3 | 86.8 | 3.76 m |
| Glc$_I$-4 | 69.4 | 3.59 m |
| Glc$_I$-5 | 77.4-78.2$^§$ | 3.41 m |
| Glc$_I$-6 | 62.5-62.7$^€$ | 3.71 m, 3.80 m |
| Rha-1 | 101.7 | 5.16 brd (1.4) |
| Rha-2 | 70.9 | 4.25 m |
| Rha-3 | 83.0 | 3.73 m |
| Rha-4 | 72.6 | 3..52 t (9.4) |
| Rha-5 | 70.2 | 3.78 m |
| Rha-6 | 18.4 | 1.22, d (6.2) |
| Glc$_V$-1 | 105.1 | 4.58 d (7.7) |
| Glc$_V$-2 | 75.3 or 75.4 | 3.28 m |
| Glc$_V$-3 | 77.4-78.2$^§$ | 3.41 m |
| Glc$_V$-4 | 71.3 | 3.33 m |
| Glc$_V$-5 | 77.4 or 77.5 or 77.6 | 3.46 m |
| Glc$_V$-6 | 62.5-62.7$^€$ | 3.69 m, 3.87 m |
| Glc$_{VI}$-1 | 105.0 | 4.50 d (7.8) |
| Glc$_{VI}$-2 | 75.1 | 3.27 m |
| Glc$_{VI}$-3 | 77.4-78.2$^§$ | 3.41 m |
| Glc$_{VI}$-4 | 71.5 or 71.6 | 3.29 m |
| Glc$_{VI}$-5 | 77.4-78.2$^§$ | 3.36 m |
| Glc$_{VI}$-6 | 62.5-62.7$^€$ | 3.64 m, 3.90 m |

$^§$Ten carbon resonances in the range of 77.4-78.2 (77.39, 77.52, 77.58, 77.78, 77.90, 78.00, 78.02, 78.16, 78.21, and 78.23), hence chemical shifts could not be unequivocally assigned.
$^€$Five carbon resonances in the range of 62.5-62.7 (62.45, 62.52, 62.53, 62.61, and 62.72), hence chemical shifts could not be unequivocally assigned.

Assignment of Glc$_{II}$ was carried out in a similar manner. The Glc$_{II}$ anomeric proton ($δ_H$ 4.54) showed a COSY correlation to a proton at $δ_H$ 3.62 which was assigned as Glc$_{II}$ H-2 and in turn showed a COSY correlation to a proton at $δ_H$ 3.69 (Glc$_{II}$ H-3). This latter proton showed an additional correlation with a proton at $δ_H$ 3.38 (Glc$_{II}$ H-4) which in turn showed a COSY correlation to a proton at $δ_H$ 3.30 (Glc$_{II}$ H-5). Glc$_{II}$ H-5 showed additional correlations to the protons at $δ_H$ 3.64 and 3.86 (Glc$_{II}$ H-6), thus completing $^1H$ assignments of Glc$_{II}$ spin system. This spin system was further confirmed by a series of 1D TOCSY experiments which were performed using selective irradiation of the Glc$_{II}$ anomeric proton with several different mixing times. The additional resonances at $δ_H$ 4.58 and 4.50 ppm in the TOCSY spectra were due to Glc$_V$ and Glc$_{VI}$, respectively, since Glc$_{II}$ H-1 at $δ_H$ 4.54 is very close to the anomeric protons of Glc$_V$ ($δ_H$ 4.58) and Glc$_{VI}$ ($δ_H$ 4.50), and were also impacted by the TOCSY irradiation pulse. Consequently, the additional resonances at $δ_H$ 3.90, 3.46, 3.41, 3.28 and 3.27 ppm in the TOCSY spectra were due to Glc$_V$ and Glc$_{VI}$ protons. The $^{13}C$ chemical shifts for Glc$_{II}$ C-2 ($δ_C$ 80.3), C-3 ($δ_C$ 87.4), C-4 ($δ_C$ 70.0), C-5 ($δ_C$ 77.4-78.2), and C-6 ($δ_C$ 62.5-62.7) were assigned using the HSQC-DEPT data. The HMBC correlations observed from Glc$_{II}$ H-1 to C-5, H-2 to C-1 and C-3, H-3 to C-2 and C-4, H-4 to C-6 and H-6 ($δ_H$ 3.86) to C-4 further confirmed the assignments made above to complete the assignment of Glc$_{II}$. In the $^1H$ NMR spectrum a coupling value of 7.6 Hz for Glc$_{II}$ anomeric proton indicated β-configuration for Glc$_{II}$.

The remaining two unassigned glucose moieties were assigned as substituents at C-2 and C-3 of Glc$_{II}$ on the basis of HMBC correlations. The anomeric proton observed at $δ_H$ 4.79 showed an HMBC correlation to Glc$_{II}$ C-2 and was assigned as the anomeric proton of Glc$_{III}$. The anomeric proton observed at $δ_H$ 4.63 showed an HMBC correlation to Glc$_{II}$ C-3 and was assigned as the anomeric proton of Glc$_{IV}$. The reciprocal HMBC correlations from Glc$_{II}$ H-2 to the anomeric carbon of Glc$_{III}$ and from Glc$_{II}$ H-3 to the anomeric carbon of Glc$_{IV}$ were also observed.

The anomeric proton of Glc$_{III}$ ($δ_H$ 4.79) showed a COSY correlation with a proton at $δ_H$ 3.16 which was assigned as Glc$_{III}$ H-2 and in turn showed a COSY correlation to a proton at $δ_H$ 3.32 (Glc$_{III}$ H-3). This latter proton showed an additional correlation with a proton at $δ_H$ 3.18 (Glc$_{III}$ H-4). Glc$_{III}$ C-2 ($δ_C$ 75.9), C-3 ($δ_C$ 77.4-78.2), and C-4 ($δ_C$ 72.0) were then assigned using the HSQC-DEPT data. Due to data overlap the COSY spectrum did not allow assignment of the remaining protons. Therefore, a series of 1D TOCSY experiments were performed using selective irradiation of the Glc$_{III}$ anomeric proton with several different mixing times. In addition to confirming the assignments for Glc$_{III}$ H-2 through H-4, the TOCSY data allowed assignment of Glc$_{III}$ H-5 ($δ_H$ 3.28) and H-6 ($δ_H$ 3.63 and 3.84). The additional resonance at $δ_H$ 4.68 ppm in the TOCSY spectra is due one of the H-17 protons since Glc$_{III}$ H-1 at $δ_H$ 4.79 is very close to one of the H-17 protons at $δ_H$ ~4.81 (obscured by water resonance), hence $δ_H$ ~4.81 was impacted by the TOCSY irradiation pulse and hence showed correlation to its germinal pair at $δ_H$ 4.68. The second additional resonance at $δ_H$ 4.83 ppm in the TOCSY spectra is due to water since Glc$_{III}$ H-1 at $δ_H$ 4.79 is very close to the water resonance at $δ_H$ 4.83 which was also was impacted by the TOCSY irradiation pulse. The assignment of H-5 was further confirmed by COSY correlations between Glc$_{III}$ H-5/H-6. The $^{13}C$ chemical shifts for C-5 ($δ_C$ 77.4-78.2), and C-6 ($δ_C$ 63.3) were assigned using the HSQC-DEPT data. HMBC correlations observed from Glc$_{III}$ H-1 to C-3 and/or C-5, H-2 to C-1 and C-3, H-4 to C-3 and C-6 and H-6 ($δ_H$ 3.84) to C-4 further confirmed the assignments made above to complete the assignment of Glc$_{III}$. In the $^1H$ NMR spectrum a coupling value of 7.9 Hz for Glc$_{III}$ anomeric proton indicated β-configuration for Glc$_{III}$.

The anomeric proton of Glc$_{IV}$ ($δ_H$ 4.63) showed COSY correlation with a proton at $δ_H$ 3.25 which was assigned as Glc$_{IV}$ H-2 and in turn showed a COSY correlation to a proton at $δ_H$ 3.35 (Glc$_{IV}$ H-3). Due to data overlap the COSY spectrum did not allow assignment of the remaining protons. Therefore, a series of 1D TOCSY experiments were performed using selective irradiation of the Glc$_{IV}$ anomeric proton with several different mixing times. In addition to confirming the assignments for Glc$_{IV}$ H-2 and H-3 the TOCSY data allowed assignment of Glc$_{IV}$ H-4 ($δ_H$ 3.28) and H-5 ($δ_H$ 3.33). The protons observed at $δ_H$ 3.63 and 3.88 in the TOCSY spectrum were assigned as the Glc$_{IV}$ H-6 protons. The additional resonances at $δ_H$ 4.68 and ~4.81 ppm in the TOCSY spectra were due H-17 protons since Glc$_{IV}$ H-1 at $δ_H$ 4.63 is very close to one of the H-17 protons at $δ_H$ 4.68, hence $δ_H$ 4.68 was also impacted by the TOCSY irradiation pulse which showed correlation to its germinal pair at $δ_H$ ~4.81. The assignment for H-5 was further confirmed by COSY correlations between Glc$_{IV}$ H-5/H-6. The $^{13}C$ chemical shifts for Glc$_{IV}$ C-2 ($δ_C$ 75.3 or 75.4), C-3 ($δ_C$ 77.4-78.2), C-4 ($δ_C$ 71.5 or 71.6), C-5 ($δ_C$ 77.4-78.2), and C-6 ($δ_C$ 62.5-62.7) were assigned using the HSQC-DEPT data. The HMBC correlations observed from Glc$_{IV}$ H-1 to C-3 and/or C-5, H-2 to C-1, H-3 to C-2 and C-4, H-4 to C-3, C-5 and C-6 and H-6 to C-4 further confirmed the assignments made above to complete the assignment of Glc$_{IV}$. In the $^1$H NMR spectrum a coupling value of 7.8 Hz for Glc$_{IV}$ anomeric proton indicated β-configuration for Glc$_{IV}$.

A summary of the $^1$H and $^{13}$C chemical shifts for the glycoside at C-13 are found in Table 9.

TABLE 9

$^1$H and $^{13}$C NMR (500 and 125 MHz, CD$_3$OD), assignments of C-13 glycoside.

| Position | CC-00333 | |
|---|---|---|
| | $^{13}$C | $^1$H |
| Glc$_{II}$-1 | 101.6 | 4.54 d (7.6) |
| Glc$_{II}$-2 | 80.3 | 3.62 m |
| Glc$_{II}$-3 | 87.4 | 3.69 m |
| Glc$_{II}$-4 | 70.0 | 3.38 m |
| Glc$_{II}$-5 | 77.4-78.2$^§$ | 3.30 m |
| Glc$_{II}$-6 | 62.5-62.7$^€$ | 3.64 m, 3.86 m |
| Glc$_{III}$-1 | 103.5 | 4.79 d (7.9) |
| Glc$_{III}$-2 | 75.9 | 3.16 m |
| Glc$_{III}$-3 | 77.4-78.2$^§$ | 3.32 m |
| Glc$_{III}$-4 | 72.0 | 3.18 m |
| Glc$_{III}$-5 | 77.4-78.2$^§$ | 3.28 m |
| Glc$_{III}$-6 | 63.3 | 3.63 m, 3.84 m |
| Glc$_{IV}$-1 | 104.5 | 4.63 d (7.8) |
| Glc$_{IV}$-2 | 75.3 or 75.4 | 3.25 m |
| Glc$_{IV}$-3 | 77.4-78.2$^§$ | 3.35 m |
| Glc$_{IV}$-4 | 71.5 or 71.6 | 3.28 m |
| Glc$_{IV}$-5 | 77.4-78.2$^§$ | 3.33 m |
| Glc$_{IV}$-6 | 62.5-62.7$^€$ | 3.63 m, 3.88 m |

$^§$Ten carbon resonances in the range of 77.4-78.2 (77.39, 77.52, 77.58, 77.78, 77.90, 78.00, 78.02, 78.16, 78.21, and 78.23), hence chemical shifts could not be unequivocally assigned.
$^€$Five carbon resonances in the range of 62.5-62.7 (62.45, 62.52, 62.53, 62.61, and 62.72), hence chemical shifts could not be unequivocally assigned.

The structure was determined to be (13-[(2-O-β-D-glucopyranosyl-3-O-β-D-glucopyranosyl-β-D-glucopyranosyl) oxy] ent-atis-16-en-19-oic acid-[(2-O-α-L-rhamnopyranosyl-(3-O-β-D-glucopyranosyl)-3-O-β-D-glucopyranosyl-β-D-glucopyranosyl) ester]).

Example 5

Isolation and Characterization of CC-00335

Materials.

The material used for the isolation of CC-00335 was Stevia extract. HPLC Analysis, isolation procedure, were performed as described for Example 1 with the deviations described below.

MS and MS/MS.

MS and MS/MS data were generated with a Waters QT of Micro mass spectrometer equipped with an electrospray ionization source. The sample was analyzed by negative ESI. About 20 μL aliquot of the NMR sample was blown dry under nitrogen and used for the analyses. The sample was diluted with 50:50 H$_2$O:ACN+0.1% formic acid and introduced via direct infusion for HRMS and MS/MS.

NMR.

An attempt was made to dissolve 4.8 mg of the sample in 100 μL CD$_3$OD, however the sample did not dissolve readily. To this sample, another 50 μL CD$_3$OD was added and the sample was sonicated for ~2 mins. The sample did not dissolve completely. Using the soluble portion, NMR data was acquired on a Bruker Avance 500 MHz instrument equipped with a 2.5 mm inverse probe. The HMBC NMR data was acquired at the Rensselaer Polytechnic Institute, Troy, N.Y. using their Bruker Avance 600 MHz instrument equipped with a 5 mm cryo-probe. The $^1$H NMR spectrum was referenced to the CHD$_2$OD resonance at δ$_H$ 3.30 ppm and $^{13}$C NMR spectrum was referenced to the CD$_3$OD resonance at δ$_C$ 49.0 ppm.

Results and Discussion

Unless otherwise noted, all solvent ratios are listed as percent by volume (v/v).

Primary Purification.

Approximately 300 g of Stevia extract was processed using the primary preparative HPLC method described above. Collected fractions were analyzed by LC-MS using the analytical method summarized in Table 1.

Secondary Purification.

Collected fractions from primary purification were reprocessed with conditions summarized above, but where the mobile phase (A) was 18% MeCN in water. Fractions were analyzed using the analytical method summarized in Table 2.

Tertiary Purification.

Collected fractions from secondary purification were reprocessed with conditions summarized above.

Final Batch Preparation.

Collected fractions from tertiary purification were concentrated by rotary evaporation for final isolation. The concentrated solution was further dried via lyophilization for 48 h. The final yield of the batch was 4.8 mg. The purity was >99% based on direct infusion MS analysis.

Mass Spectrometry.

The ESI-TOF mass spectrum acquired by infusing a sample of CC-00335 showed a [M-H]$^-$ ion at m/z 1289.5219. The mass of the [M-H]$^-$ ion was in good agreement with the molecular formula C$_{56}$H$_{90}$O$_{33}$ (calcd for C$_{56}$H$_{89}$O$_{33}$: 1289.5286, error: −5.2 ppm) expected for CC-00335. The MS data confirmed that CC-00335 has a nominal mass of 1290 Daltons with the molecular formula, C$_{56}$H$_{90}$O$_{33}$. The ion observed at m/z 1403.5231 was due to [M+TFA−H]$^-$.

The MS/MS spectrum, selecting the [M-H]$^-$ ion at m/z 1289.5 for fragmentation, indicated sequential loss of six glucose units at m/z 1127.4094, 965.3893, 803.3491, 641.2938, 479.2516 and 317.1835 indicated the presence of six glucose units in the structure.

NMR Spectroscopy.

A series of NMR experiments including $^1$H NMR, $^{13}$C NMR, $^1$H-$^1$H COSY, HSQC-DEPT, HMBC, ROESY and 1D TOCSY were acquired to allow assignment of CC-00335.

The 1D and 2D NMR data indicated the presence of a central diterpene core with an exocyclic double bond and six sugar units in the structure. In the $^1$H NMR spectrum acquired at 300 K, five anomeric protons were clearly observed while one was completely obscured by the water resonance which was partially resolved in the $^1$H NMR spectrum acquired at 294 K. Therefore all NMR data were acquired at 294 K. In the HSQC-DEPT data, only eight methylene units were observed instead of nine methylene units that are commonly observed in the central diterpene core of related Stevia glycosides. Similarly in the HSQC-DEPT data, in addition to two methine units corresponding to C-5 and C-9 positions, two additional methine units at δ$_H$ 2.46/δ$_C$ 42.4 and δ$_H$ 4.18/δ$_C$ 78.2 were observed which is relatively rare in this class of compounds and thus indicated structural changes in the central diterpene core.

Complete analysis of the 1D and 2D NMR data allowed assignment of the central core and confirmed the structural changes in rings C and D as discussed below. An HMBC correlation from the methyl protons at $\delta_H$ 1.23 to the carbonyl at $\delta_C$ 177.9 allowed assignment of one of the tertiary methyl groups (C-18) as well as C-19 and provided a starting point for the assignment of the rest of the aglycone. Additional HMBC correlations from the methyl protons (H-18) to carbons at $\delta_C$ 39.0, 45.1, and 58.4 allowed assignment of C-3, C-4, and C-5. Analysis of the $^1$H-$^{13}$C HSQC-DEPT data indicated that the carbon at $\delta_C$ 39.0 was a methylene and the carbon at $\delta_C$ 58.4 was a methine which were assigned as C-3 and C-5, respectively. This left the carbon at $\delta_C$ 45.1, which did not show a correlation in the HSQC-DEPT spectrum, to be assigned as the quaternary carbon, C-4. The $^1$H chemical shifts for C-3 ($\delta_H$ 1.02 and 2.30) and C-5 ($\delta_H$ 1.07) were assigned using the HSQC-DEPT data. COSY correlations between the H-3 protons ($\delta_H$ 1.02 and 2.30) and protons at $\delta_H$ 1.37 and 1.92 allowed assignment of the H-2 protons which in turn showed correlations with the protons at $\delta_H$ 0.88 and 1.56 which were assigned to H-1. The $^{13}$C chemical shifts for C-1 and C-2 were then assigned on the basis of HSQC-DEPT correlations and are summarized in Table 7.

TABLE 7

$^1$H and $^{13}$C NMR (500 and 150 MHz, CD$_3$OD, 294K), assignments of aglycone.

| | CC-00335 | |
|---|---|---|
| Position | $^{13}$C | $^1$H |
| 1 | 40.7 | 0.88 m |
| | | 1.56 m |
| 2 | 19.9 | 1.37 m |
| | | 1.92 m |
| 3 | 39.0 | 1.02 m |
| | | 2.30 brd |
| | | (13.6) |
| 4 | 45.1 | — |
| 5 | 58.4 | 1.07 m |
| 6 | 21.3 | 1.78 m |
| | | 1.92 m |
| 7 | 40.2 | 1.14 m |
| | | 1.55 m |
| 8 | 35.2 | — |
| 9 | 52.5 | 1.07 m |
| 10 | 39.4 | — |
| 11 | 27.7 | 1.42 m |
| | | 1.59 m |
| 12 | 42.4 | 2.46 brs |
| 13 | 78.2 | 4.18 m |
| 14 | 38.8 | 1.12 m |
| | | 2.42 m |
| 15 | ~48.8[¥] | 1.87 m |
| | | 2.08 brd |
| | | (16.7) |
| 16 | 148.0 | — |
| 17 | 109.6 | 4.68 brs |
| | | ~4.81[ϵ] |
| 18 | 29.0 | 1.23 s |
| 19 | 177.9 | — |
| 20 | 13.7 | 0.82 s |

[¥]Resonance obscured by CD$_3$OD, assignment based on HSQC-DEPT data.
[ϵ]Resonance obscured by H$_2$O, assignment based on HSQC-DEPT data.

The other tertiary methyl singlet, observed at $\delta_H$ 0.82 ($\delta_C$ 13.7 via HSQC-DEPT), showed HMBC correlations to C-1 and C-5 and was assigned as H-20. The methyl protons showed additional HMBC correlations to a quaternary carbon ($\delta_C$ 39.4) and a methine carbon ($\delta_C$ 52.5) which were assigned as C-10 and C-9, respectively. The $^1$H chemical shift for C-9 ($\delta_H$ 1.07) was assigned using the HSQC-DEPT data. COSY correlations between H-5 ($\delta_H$ 1.07) and the protons at $\delta_H$ 1.78 and 1.92 then allowed assignment of the H-6 protons which in turn showed correlations to protons at $\delta_H$ 1.14 and 1.55 which were assigned to H-7. The $^{13}$C chemical shifts for C-6 ($\delta_C$ 21.3) and C-7 ($\delta_C$ 40.2) were then determined from the HSQC-DEPT data. COSY correlations between H-9 ($\delta_H$ 1.07) and the protons at $\delta_H$ 1.42 and 1.59 allowed assignment of the H-11 protons. The HSQC-DEPT data was then used to assign C-11 ($\delta_C$ 27.7). The H-11 protons at $\delta_H$ 1.42 and 1.59 showed COSY correlation to a methine proton at $\delta_H$ 2.46 ($\delta_C$ 42.4 via HSQC-DEPT) instead of methylene protons in other Stevia glycosides. This data thus indicated that a methine group was present at position 12 instead of a methylene group. The H-12 proton ($\delta_H$ 2.46) also showed COSY correlations to a methine proton at $\delta_H$ 4.18 assigned to H-13 which in turn showed COSY correlations to protons at $\delta_H$ 1.12 and 2.42 (H-14). The HSQC-DEPT data was then used to assign C-13 ($\delta_C$ 78.2) and C-14 ($\delta_C$ 38.8). In this structure, a methine group was present at position 13 instead of a quaternary carbon commonly found in other Stevia glycosides further indicating structural changes in this part of the central core. The carbon chemical shift of C-13 ($\delta_C$ 78.2) indicated a hydroxyl or a substituted hydroxyl group at C-13 similar to other Stevia glycosides. The above proton assignments for H-9 to H-14 spin system were further supported by 1D TOCSY experiments performed using selective irradiation of the H-12 and H-13 protons with several different mixing times. HMBC correlations from H-9 ($\delta_H$ 1.07) and H-14 ($\delta_H$ 1.12 and 2.42) to the carbon at $\delta_C$ 35.2 allowed the assignment of C-8 completing the assignment of ring C. The HSQC-DEPT data indicated that the exocyclic double bond was present in CC-00335 and was assigned based on the HMBC correlations. HMBC correlation from H-12 ($\delta_H$ 2.46) to a carbon at $\delta_C$ 109.6 allowed the assignment of the exocyclic methylene carbon (C-17). The HSQC-DEPT data was then used to assign the protons at C-17 ($\delta_H$ 4.68 and ~4.81 (obscured by water resonance)). The only remaining methylene group in the central core region at $\delta_H$ 1.87 and 2.08 ($\delta_C$ ~48.8 via HSQC-DEPT) was assigned to H-15 and supported by HMBC correlations from H-14 and H-17 to C-15 ($\delta_C$ ~48.8). The HMBC correlations from H-13 ($\delta_H$ 4.18), H-15 ($\delta_H$ 1.87 and 2.08) and H-17 ($\delta_H$ 4.68 and ~4.81) to a quaternary carbon at $\delta_C$ 148.0 allowed assignment of C-16 to complete the assignment of ring D and the central core. In addition, the data showed that instead of the commonly found ent-kaurene diterpenoid core in Stevia glycosides, CC-00335 contained an ent-atisene diterpeniod core (as shown in FIG. 1). Additional HMBC correlations from H-9 to C-11; H-11 to C-12 and C-16; H-12 to C-9, C-13 and C-14; H-13 to C-11; H-14 to C-12 and C-13; H-15 to C-8, C-9, C-14 and C-17 and H-17 to C-12 further confirmed the assignments made above.

Correlations observed in the ROESY spectrum were used to assign the relative stereochemistry of the central diterpene core. In the ROESY spectrum, NOE correlations were observed between H-20 and one of the H-14 protons ($\delta_H$ 2.42). indicating that H-14 and H-20 are on the same face of the ring. This assignment was further supported by NOE correlations between H-20 and H-13. Similarly, NOE correlations were observed between H-18 and H-5/H-9 but no NOE correlations were observed with H-13, H-14 and H-20 indicating that H-5, H-9 and H-18 were on the opposite face of the ring compared to H-13, H-14 and H-20.

As mentioned above, in the $^1$H NMR spectrum acquired at 300 K, five anomeric protons were clearly observed while one was completely obscured by the water resonance which was partially resolved in the $^1$H NMR spectrum acquired at 294 K. Therefore all NMR data was acquired at 294 K. Analysis of the $^1$H-$^{13}$C HSQC-DEPT data for CC-00335 confirmed the presence of six anomeric protons which were well resolved or at $\delta_H$ 5.57 ($\delta_C$ 94.2), 5.04 ($\delta_C$ 103.1), 4.64 ($\delta_C$ 104.4), 4.61 ($\delta_C$ 100.5) and sufficiently resolved at 4.70 ($\delta_C$ 104.2), 4.83 ($\delta_C$ 103.5) in the $^1$H NMR spectrum acquired at 294 K. All six anomeric protons had large couplings (7.7-8.1 Hz) indicating that they had β-configurations. The anomeric proton observed at $\delta_H$ 5.57 showed an HMBC correlation to C-19 which indicated that it corresponded to the anomeric proton of Glc$_I$. Similarly, the anomeric proton observed at $\delta_H$ 4.61 showed an HMBC correlation to C-13 allowing it to be assigned as the anomeric proton of Glc$_{II}$. The reciprocal HMBC correlation from H-13 ($\delta_H$ 4.18) to the anomeric carbon of Glc$_{II}$ ($\delta_C$ 100.5) was also observed.

The Glc$_I$ anomeric proton ($\delta_H$ 5.57) showed a COSY correlation to a proton at $\delta_H$ 4.04 which was assigned as Glc$_I$ H-2 which in turn showed a COSY correlation to a proton at $\delta_H$ 3.92 (Glc$_I$ H-3). This latter proton showed an additional correlation with a proton at $\delta_H$ 3.55 (Glc$_I$ H-4). Due to data overlap the COSY spectrum did not allow assignment of the remaining protons. Therefore, a series of 1D TOCSY experiments were performed using selective irradiation of the Glc$_I$ anomeric proton with several different mixing times. In addition to confirming the assignments for Glc$_I$ H-2 through H-4, the TOCSY data allowed assignment of H-5 ($\delta_H$ 3.42) and H-6 ($\delta_H$ 3.71 and 3.82). The assignments were further confirmed by 1D TOCSY data of Glc$_I$ H-2 ($\delta_H$ 4.04). The $^{13}$C chemical shifts for Glc$_I$ C-2 ($\delta_C$ 76.9), C-3 ($\delta_C$ 88.1), C-4 ($\delta_C$ 69.7), C-5 ($\delta_C$ 78.5) and C-6 ($\delta_C$ 62.2) were assigned using the HSQC-DEPT data. The HMBC correlations observed from Glc$_I$ H-1 to C-2, C-3 and C-5, H-2 to C-1 and C-3, H-3 to C-2 and C-4, H-4 to C-3, C-5 and C-6 and H-6 to C-4 and C-5 further confirmed the assignments made above to complete the assignment of Glc$_I$. In the $^1$H NMR spectrum a coupling value of 8.1 Hz for Glc$_I$ anomeric proton indicated β-configuration for Glc$_I$.

Of the five remaining unassigned sugar moieties two were assigned as substituents at C-2 and C-3 of Glc$_I$ on the basis of HMBC correlations. The anomeric proton observed at $\delta_H$ 5.04 showed an HMBC correlation to Glc$_I$ C-2 and was assigned as the anomeric proton of Glc$_V$. The reciprocal HMBC correlation from Glc$_I$ H-2 to the anomeric carbon of Glc$_V$ was also observed. Similarly, the anomeric proton observed at $\delta_H$ 4.70 showed an HMBC correlation to Glc$_I$ C-3 and was assigned as the anomeric proton of Glc$_{VI}$. The reciprocal HMBC correlation from Glc$_I$ H-3 to the anomeric carbon of Glc$_{VI}$ was also observed.

The Glc$_V$ anomeric proton ($\delta_H$ 5.04) showed a COSY correlation to a proton at $\delta_H$ 3.18 which was assigned as Glc$_V$ H-2. Due to data overlap the COSY spectrum did not allow assignment of the remaining protons. Therefore, a series of 1D TOCSY experiments were performed using selective irradiation of the Glc$_V$ anomeric proton with several different mixing times. In addition to confirming the assignments for Glc$_V$ H-2, the TOCSY data allowed assignment of Glc$_V$ H-3 ($\delta_H$ 3.37), Glc$_V$ H-4 ($\delta_H$ 3.18), H-5 ($\delta$ 3.33) and H-6 ($\delta_H$ 3.64 and 3.90). The $^{13}$C chemical shifts for Glc$_V$ C-2 ($\delta_C$ 75.8), C-3 ($\delta_C$ 77.5-78.5), C-4 ($\delta_C$ 72.7), C-5 ($\delta_C$ 77.5-78.5) and C-6 ($\delta_C$ 63.6) were assigned using the HSQC-DEPT data. The HMBC correlations observed from Glc$_V$ H-1 to C-3 and/or C-5, H-2 to C-1 and C-3, H-3 to C-2 and C-4, H-4 to C-3 and/or C-5 and C-6 and H-6 ($\delta_H$ 3.64 and 3.90) to C-4 and C-5 further confirmed the assignments made above to complete the assignment of Glc$_V$. In the $^1$H NMR spectrum a coupling value of 8.0 Hz for Glc$_V$ anomeric proton indicated β-configuration for Glc$_V$.

The Glc$_{VI}$ anomeric proton ($\delta_H$ 4.70) showed a COSY correlation to a proton at $\delta_H$ 3.29 which was assigned as Glc$_{VI}$ H-2. Due to data overlap the COSY spectrum did not allow assignment of the remaining protons. Therefore, a series of 1D TOCSY experiments were performed using selective irradiation of the Glc$_V$ anomeric proton with several different mixing times. In addition to confirming the assignments for Glc$_{VI}$ H-2, the TOCSY data allowed assignment of Glc$_{VI}$ H-3 ($\delta_H$ 3.41), H-4 ($\delta_H$ 3.29), H-5 ($\delta_H$ 3.37) and H-6 ($\delta_H$ 3.63 and 3.90). The resonance at $\delta_H$ 4.68 in the TOCSY spectra is due one of the H-17 protons since Glc$_{VI}$ H-1 at $\delta_H$ 4.70 is very close to the proton at $\delta_H$ 4.68 and hence it was impacted by the TOCSY irradiation pulse and consequently showed correlation to its germinal pair at $\delta_H$ 4.81. The $^{13}$C chemical shifts for Glc$_{VI}$ C-2 ($\delta_C$ 75.3 or 75.4), C-3 ($\delta_C$ 77.5-78.5), C-4 ($\delta_C$ 71.5 or 71.6), C-5 ($\delta_C$ 77.5-78.5) and C-6 ($\delta_C$ 62.5-62.6) were assigned using the HSQC-DEPT data. The HMBC correlations observed from Glc$_{VI}$ H-1 to C-2 and C-3 and/or C-5, H-2 to C-1 and C-3, H-3 to C-2 and C-4, H-4 to C-3 and/or C-5 and C-6, H-5 to C-4 and H-6 ($\delta_H$ 3.90) to C-4 further confirmed the assignments made above to complete the assignment of Glc$_{VI}$. In the $^1$H NMR spectrum a coupling value of 8.0 Hz for Glc$_{VI}$ anomeric proton indicated β-configuration for Glc$_{VI}$.

A summary of the $^1$H and $^{13}$C chemical shifts for the glycoside at C-19 are found in Table 8.

TABLE 8

$^1$H and $^{13}$C NMR (500 and 150 MHz, CD$_3$OD, 294K), assignments of C-19 glycoside.

| | CC-00335 | |
|---|---|---|
| Position | $^{13}$C | $^1$H |
| Glc$_I$-1 | 94.2 | 5.57 d (8.1) |
| Glc$_I$-2 | 76.9 | 4.04 t (8.5) |
| Glc$_I$-3 | 88.1 | 3.92 m |
| Glc$_I$-4 | 69.7 | 3.55 m |
| Glc$_I$-5 | 78.5 | 3.42 m |
| Glc$_I$-6 | 62.2 | 3.71 m, 3.82 m |
| Glc$_V$-1 | 103.1 | 5.04 d (8.0) |
| Glc$_V$-2 | 75.8† | 3.18 m |
| Glc$_V$-3 | 77.5-78.5¥ | 3.37 m |
| Glc$_V$-4 | 72.7 | 3.18 m |
| Glc$_V$-5 | 77.5-78.5¥ | 3.33 m |
| Glc$_V$-6 | 63.6 | 3.64 m, 3.90 m |
| Glc$_{VI}$-1 | 104.2 | 4.70 d (8.0) |
| Glc$_{VI}$-2 | 75.3 or 75.4 | 3.29 m |
| Glc$_{VI}$-3 | 77.5-78.5¥ | 3.41 m |
| Glc$_{VI}$-4 | 71.5 or 71.6 | 3.29 m |
| Glc$_{VI}$-5 | 77.5-78.5¥ | 3.37 m |
| Glc$_{VI}$-6 | 62.5 or 62.6 | 3.63 m, 3.90 m |

†75.78 or 75.83 ppm
¥Ten carbon resonances in the range of 77.5-78.2 (77.48, 77.84, 77.98, 78.15, 78.16, 78.20, 78.24 and 78.49), hence chemical shifts could not be unequivocally assigned. Two carbon resonances expected in this range are apparently not resolved.

Assignment of Glc$_{II}$ was carried out in a similar manner. The Glc$_{II}$ anomeric proton ($\delta_H$ 4.61) showed a COSY correlation to a proton at $\delta_H$ 3.64 which was assigned as Glc$_{II}$ H-2. Due to data overlap the COSY spectrum did not allow assignment of the remaining protons. Therefore, a series of 1D TOCSY experiments were performed using selective irradiation of the Glc$_{II}$ anomeric proton with several different mixing times. In addition to confirming the assignments for Glc$_{II}$ H-2, the TOCSY data allowed assignment of H-3 ($\delta_H$ 3.80), H-4 ($\delta_H$ 3.37), H-5 ($\delta_H$ 3.37) and H-6 ($\delta_H$ 3.66 and 3.86). The resonances at $\delta_H$ 4.64, $\delta_H$ 3.28 and $\delta_H$ 3.26 in the TOCSY spectra are due to Glc$_{IV}$ protons since Glc$_{IV}$ H-1 at $\delta_H$ 4.64 is very close to Glc$_{II}$ H-1 at $\delta_H$ 4.61 and hence it was also impacted by the TOCSY irradiation pulse and consequently showed TOCSY correlation to protons in its spin system. The $^{13}$C chemical shifts for Glc$_{II}$ C-2 ($\delta_C$ 80.3), C-3 ($\delta_C$ 87.4), C-4 ($\delta_C$ 70.0), C-5 ($\delta_C$ 77.5-78.5), and C-6 ($\delta_C$ 62.5 or 62.6) were assigned using the HSQC-DEPT data. The HMBC correlations observed from Glc$_{II}$ H-1 to C-2 and C-5, H-2 to C-1 and C-3, H-3 to C-2 and C-4, H-4 to C-3, C-5 and C-6 and H-6 to C-4 and C-5 further confirmed the assignments made above to complete the assignment of Glc$_{II}$. In the $^1$H NMR spectrum a coupling value of 7.7 Hz for Glc$_{II}$ anomeric proton indicated β-configuration for Glc$_{II}$.

The remaining two unassigned glucose moieties were assigned as substituents at C-2 and C-3 of Glc$_{II}$ on the basis of HMBC correlations. The anomeric proton observed at $\delta_H$ 4.83 showed an HMBC correlation to Glc$_{II}$ C-2 and was assigned as the anomeric proton of Glc$_{III}$. The anomeric proton observed at $\delta_H$ 4.64 showed an HMBC correlation to Glc$_{II}$ C-3 and was assigned as the anomeric proton of Glc$_{IV}$. The reciprocal HMBC correlations from Glc$_{II}$ H-2 to the anomeric carbon of Glc$_{III}$ and from Glc$_{II}$ H-3 to the anomeric carbon of Glc$_{IV}$ were also observed.

The anomeric proton of Glc$_{III}$ ($\delta_H$ 4.83) showed a COSY correlation with a proton at $\delta_H$ 3.18 which was assigned as Glc$_{III}$ H-2. Glc$_{III}$ C-2 ($\delta_C$ 75.8) was then assigned using the HSQC-DEPT data. Due to data overlap the COSY spectrum did not allow assignment of the remaining protons. Therefore, a series of 1D TOCSY experiments were performed using selective irradiation of the Glc$_{III}$ anomeric proton with several different mixing times. In addition to confirming the assignments for Glc$_{III}$ H-2, the TOCSY data allowed assignment of Glc$_{III}$ H-3 ($\delta_H$ 3.33), H-4 ($\delta_H$ 3.18), H-5 ($\delta_H$ 3.28) and H-6 ($\delta_H$ 3.62 and 3.85). The resonances at $\delta_H$ 4.81 and $\delta_H$ 4.68 in the TOCSY spectra were due H-17 protons since Glc$_{III}$ H-1 at $\delta_H$ 4.83 were very close to one of the H-17 protons at $\delta_H$ 4.81 which was impacted by the TOCSY irradiation pulse and consequently showed correlation to its germinal pair at $\delta_H$ 4.68. The resonance at $\delta_H$ 4.91 in the TOCSY spectra was due to water and since Glc$_{III}$ H-1 at $\delta_H$ 4.83 overlapped with the broad water resonance centered at $\delta_H$ 4.91 which was also was impacted by the TOCSY irradiation pulse. The other additional resonances at $\delta_H$ 4.87 in the TOCSY spectra were likely due to hydroxyl proton of the solvent (methanol) since Glc$_{III}$ H-1 at $\delta_H$ 4.83 overlapped with this broad resonance which was also was impacted by the TOCSY irradiation pulse. The $^{13}$C chemical shifts for Glc$_{III}$ C-3 ($\delta_C$ 77.5-78.5), C-4 ($\delta_C$ 72.0), C-5 ($\delta_C$ 77.5-78.5), and C-6 ($\delta_C$ 63.3) were assigned using the HSQC-DEPT data. HMBC correlations observed from Glc$_{III}$ H-1 to C-2, C-3 and/or C-5, H-2 to C-1 and C-3, H-3 to C-2 and C-4, H-4 to C-3 and/or C-5 and C-6 and H-6 ($\delta_H$ 3.85) to C-4 further confirmed the assignments made above to complete the assignment of Glc$_{III}$. In the $^1$H NMR spectrum a coupling value of 8.0 Hz for Glc$_{III}$ anomeric proton indicated β-configuration for Glc$_{III}$.

The anomeric proton of Glc$_{IV}$ ($\delta_H$ 4.64) showed a COSY correlation with a proton at $\delta_H$ 3.26 which was assigned as Glc$_{IV}$ H-2. Due to data overlap the COSY spectrum did not allow assignment of the remaining protons. Therefore, a series of 1D TOCSY experiments were performed using selective irradiation of the Glc$_{IV}$ anomeric proton with several different mixing times. In addition to confirming the assignments for Glc$_{IV}$ H-2, the TOCSY data allowed assignment of Glc$_{IV}$ H-3 ($\delta_H$ 3.39), H-4 ($\delta_H$ 3.28) and H-5 ($\delta_H$ 3.36). The protons observed at $\delta_H$ 3.62 and 3.88 in the TOCSY spectrum were assigned as the Glc$_{IV}$ H-6 protons. The resonances at $\delta_H$ 4.68, and $\delta_H$ 4.81 in the TOCSY spectra were due to H-17 protons since Glc$_{IV}$ H-1 at $\delta_H$ 4.64 is very close to one of the H-17 protons at $\delta_H$ 4.68 and hence it was also impacted by the TOCSY irradiation pulse and consequently showed TOCSY correlation to its germinal pair at $\delta_H$ 4.81. Similarly the proton at $\delta_H$ 4.61 (Glc$_{II}$ H-1) is also observed since it is very close to Glc$_{IV}$ H-1 at $\delta_H$ 4.64 and was impacted by the TOCSY irradiation pulse. The $^{13}$C chemical shifts for Glc$_{IV}$ C-2 ($\delta_C$ 75.3 or 75.4), C-3 ($\delta_C$ 77.5-78.5), C-4 ($\delta_C$ 71.5 or 71.6), C-5 ($\delta_C$ 77.5-78.5), and C-6 ($\delta_C$ 62.5 or 62.6) were assigned using the HSQC-DEPT data. The HMBC correlations observed from Glc$_{IV}$ H-1 to C-2, C-3 and/or C-5, H-2 to C-1 and C-3, H-3 to C-1, C-2 and C-4, H-4 to C-3 and/or C-5, C-6 and H-6 ($\delta_H$ 3.88) to C-4 further confirmed the assignments made above to complete the assignment of Glc$_{IV}$. In the $^1$H NMR spectrum a coupling value of 7.8 Hz for Glc$_{IV}$ anomeric proton indicated β-configuration for Glc$_{IV}$.

A summary of the $^1$H and $^{13}$C chemical shifts for the glycoside at C-13 are found in Table 9.

TABLE 9

$^1$H and $^{13}$C NMR (500 and 150 MHz, CD$_3$OD, 294K), assignments of C-13 glycoside.

| | CC-00335 | |
|---|---|---|
| Position | $^{13}$C | $^1$H |
| Glc$_{II}$-1 | 100.5 | 4.61 d (7.7) |
| Glc$_{II}$-2 | 80.3 | 3.64 m |
| Glc$_{II}$-3 | 87.4 | 3.80 m |
| Glc$_{II}$-4 | 70.0 | 3.37 m |
| Glc$_{II}$-5 | 77.5-78.5$^¥$ | 3.37 m |
| Glc$_{II}$-6 | 62.5 or 62.6 | 3.66 m, 3.86 m |
| Glc$_{III}$-1 | 103.5 | 4.83 d (8.0) |
| Glc$_{III}$-2 | 75.8† | 3.18 m |
| Glc$_{III}$-3 | 77.5-78.5$^¥$ | 3.33 m |
| Glc$_{III}$-4 | 72.0 | 3.18 m |
| Glc$_{III}$-5 | 77.5-78.5$^¥$ | 3.28 m |
| Glc$_{III}$-6 | 63.3 | 3.62 m, 3.85 m |
| Glc$_{IV}$-1 | 104.4 | 4.64 d (7.8) |
| Glc$_{IV}$-2 | 75.3 or 75.4 | 3.26 m |
| Glc$_{IV}$-3 | 77.5-78.5$^¥$ | 3.39 m |
| Glc$_{IV}$-4 | 71.5 or 71.6 | 3.28 m |
| Glc$_{IV}$-5 | 77.5-78.5$^¥$ | 3.36 m |
| Glc$_{IV}$-6 | 62.5 or 62.6 | 3.62 m, 3.88 m |

†75.78 or 75.83 ppm
$^¥$Ten carbon resonances in the range of 77.5-78.5 (77.48, 77.84, 77.98, 78.15, 78.16, 78.20, 78.24 and 78.49), hence chemical shifts could not be unequivocally assigned. Two carbon resonances expected in this range are apparently not resolved.

The structure was determined to be (13-[(2-O-β-D-glucopyranosyl-3-O-β-D-glucopyranosyl-β-D-glucopyranosyl)oxy] ent-atis-16-en-19-oic acid-[(2-O-β-D-glucopyranosyl-3-O-β-D-glucopyranosyl-β-D-glucopyranosyl) ester]).

Example 6

Isolation and Characterization of CC-00334

Materials.

The material used for the isolation of CC-00334 was Stevia extract. HPLC Analysis, isolation procedure, were performed as in Example 1 with the deviations described below.

MS and MS/MS.

MS and MS/MS data were generated with a Waters QT of Micro mass spectrometer equipped with an electrospray ionization source. The sample was analyzed by negative ESI. The sample (~0.1 mg) was diluted with 50:50 $H_2O$: ACN+0.1% formic acid to a concentration of 100 μg/mL for HRMS and MS/MS and were introduced via direct infusion.

NMR.

The sample was prepared by dissolving 2.3 mg in 150 μL of $CD_3OD$ and NMR data were acquired on a Bruker Avance 500 MHz instrument equipped with a 2.5 mm inverse probe and a 5 mm broad band probe. The HMBC data were acquired at the Rensselaer Polytechnic Institute, Troy, N.Y. using their Bruker Avance 600 MHz instrument equipped with a 5 mm cryo-probe. The $^1H$ NMR spectrum was referenced to the $CHD_2OD$ resonance at $\delta_H$ 3.30 ppm and $^{13}C$ NMR spectrum was referenced to the $CD_3OD$ resonance at $\delta_C$ 49.0 ppm.

Results and Discussion

Unless otherwise noted, all solvent ratios are listed as percent by volume (v/v).

Primary Purification.

Approximately 300 g of Stevia extract was processed using the primary preparative HPLC method described above. Collected fractions were analyzed by LC-MS using the analytical method summarized in Table 1.

Secondary Purification.

Collected fractions from primary purification were reprocessed with conditions summarized above, but with 18% MeCN in water as mobile phase A. Fractions were analyzed using the analytical method summarized in Table 2.

Tertiary Purification.

Collected fractions from secondary purification were reprocessed with conditions summarized above.

Final Batch Preparation.

Collected fractions from tertiary purification were concentrated by rotary evaporation for final isolation. The concentrated solution was further dried via lyophilization for 48 h. The final yield of the batch was 5.5 mg. The purity was >99% based on direct infusion MS analysis.

Mass Spectrometry.

The ESI-TOF mass spectrum acquired by infusing a sample of CC-00334 showed a [M-H]$^-$ ion at m/z 1145.4865. The mass of the [M-H]$^-$ ion was in good agreement with the molecular formula $C_{50}H_{82}O_{29}$ (calcd for $C_{50}H_{81}O_{29}$: 1145.4864, error: 0.1 ppm) expected. The MS data confirmed that CC-00334 has a nominal mass of 1146 Daltons with the molecular formula, $C_{50}H_{82}O_{29}$.

The MS/MS spectrum of CC-00334, selecting the [M-H]$^-$ ion at m/z 1145.5 for fragmentation, indicated loss of five glucose units at m/z 983.4330, 821.3828, 659.3322, 497.2747 and 335.2058 indicating the presence of five glucose units in the structure.

NMR Spectroscopy.

A series of NMR experiments including $^1H$ NMR, $^{13}C$ NMR, $^1H$-$^1H$ COSY, HSQC-DEPT, HMBC, ROESY and 1D TOCSY were acquired to allow assignment of CC-00334.

The 1D and 2D NMR data indicated the presence of a central diterpene core with five sugar units in the structure. $^1H$ NMR and HSQC-DEPT data indicated the presence of three methyl groups instead of two commonly observed in other Stevia glycosides. In addition, the NMR data indicated that the exocyclic double bond is absent in CC-00334. In the HSQC-DEPT data, only eight methylene units were observed instead of nine methylene units that are commonly observed in the central diterpene core of related Stevia glycosides. Similarly in the HSQC-DEPT data, in addition to two methine units corresponding to C-5 and C-9 positions, two additional methine units at $\delta_H$ 1.89/$\delta_C$ 42.1 and $\delta_H$ 4.15/$\delta_C$ 77.9 were observed which is relatively rare in this class of compounds and thus indicated structural changes in the central diterpene core. In addition, the HSQC-DEPT data indicated absence of the exocyclic double bond from the central core which is commonly found in Stevia glycosides.

Complete analysis of 1D and 2D NMR data allowed assignment of the central core and confirmed the structural changes in rings C and D as discussed below. An HMBC correlation from the methyl protons at $\delta_H$ 1.23 to the carbonyl carbon at $\delta_C$ 177.9 allowed assignment of one of the tertiary methyl groups (C-18) as well as C-19 and provided a starting point for the assignment of the rest of the aglycone. Additional HMBC correlations from the methyl protons (H-18) to carbons at $\delta_C$ 39.0, 45.2, and 58.7 allowed assignment of C-3, C-4, and C-5. Analysis of the $^1H$-$^{13}C$ HSQC-DEPT data indicated that the carbon at $\delta_C$ 39.0 was a methylene and the carbon at $\delta_C$ 58.7 was a methine which were assigned as C-3 and C-5, respectively. This left the carbon at $\delta_C$ 45.2, which did not show a correlation in the HSQC-DEPT spectrum, to be assigned as the quaternary carbon, C-4. The $^1H$ chemical shifts for C-3 ($\delta_H$ 1.04 and 2.28) and C-5 ($\delta_H$ 1.07) were assigned using the HSQC-DEPT data. COSY correlations between the H-3 protons ($\delta_H$ 1.04 and 2.28) and protons at $\delta_H$ 1.38 and 1.89 allowed assignment of the H-2 protons which in turn showed correlations with the protons at $\delta_H$ 0.90 and 1.57 which were assigned to H-1. The $^{13}C$ chemical shifts for C-1 and C-2 were then assigned on the basis of HSQC-DEPT correlations and are summarized in Table 7.

TABLE 7

$^1H$ and $^{13}C$ NMR (500 and 150 MHz, $CD_3OD$), assignments of aglycone.

| | CC-00334 | |
|---|---|---|
| Position | $^{13}C$ | $^1H$ |
| 1 | 40.7 | 0.90 brt (11.8) |
| | | 1.57 brd (12.5) |
| 2 | 20.0 | 1.38 m |
| | | 1.89 m |
| 3 | 39.0 | 1.04 m |
| | | 2.28 brd (13.4) |
| 4 | 45.2 | — |
| 5 | 58.7 | 1.07 m |
| 6 | 21.1 | 1.76 brd (14.3) |
| | | 1.91 m |
| 7 | 40.2 | 1.10 m |
| | | 1.48 m |
| 8 | 35.4 | — |
| 9 | 51.3 | 1.13 m |
| 10 | 39.3 | — |
| 11 | 23.7 | 1.05 m |
| | | 2.08 m |
| 12 | 42.1 | 1.89 brs |
| 13 | 77.9 | 4.15 brt (8.2) |
| 14 | 38.4 | 1.02 m |
| | | 2.37 brt (12.4) |
| 15 | 58.6 | 1.19 brd (14.0) |
| | | 1.37 brd (13.6) |

TABLE 7-continued $^1$H and $^{13}$C NMR (500 and 150 MHz, CD$_3$OD), assignments of aglycone.

| | CC-00334 | |
|---|---|---|
| Position | $^{13}$C | $^1$H |
| 16 | 71.8 | — |
| 17 | 33.6 | 1.41 s |
| 18 | 29.3 | 1.23 s |
| 19 | 177.9 | — |
| 20 | 13.6 | 0.83 s |

The other tertiary methyl singlet, observed at $\delta_H$ 0.83 ($\delta_C$ 13.6 via HSQC-DEPT), showed HMBC correlations to C-1 and C-5 and was assigned as H-20. The methyl protons showed additional HMBC correlations to a quaternary carbon ($\delta_C$ 39.3) and a methine carbon ($\delta_C$ 51.3) which were assigned as C-10 and C-9, respectively. The $^1$H chemical shift for C-9 ($\delta_H$ 1.13) was assigned using the HSQC-DEPT data. COSY correlations between H-5 ($\delta_H$ 1.07) and the protons at $\delta_H$ 1.76 and 1.91 then allowed assignment of the H-6 protons which in turn showed correlations to protons at $\delta_H$ 1.10 and 1.48 which were assigned to H-7. The $^{13}$C chemical shifts for C-6 ($\delta_C$ 21.1) and C-7 ($\delta_C$ 40.2) were then determined from the HSQC-DEPT data. COSY correlations between H-9 ($\delta_H$ 1.13) and the protons at $\delta_H$ 1.05 and 2.08 allowed assignment of the H-11 protons. The HSQC-DEPT data was then used to assign C-11 ($\delta_C$ 23.7). The H-11 protons at $\delta_H$ 1.05 and 2.08 showed COSY correlation to a methine proton at $\delta_H$ 1.89 ($\delta_C$ 42.1 via HSQC-DEPT) instead of methylene protons in other Stevia glycosides. This data thus indicated that a methine group was present at position 12 instead of a methylene group. The H-12 proton ($\delta_H$ 1.89) also showed COSY correlations to a methine proton at $\delta_H$ 4.15 assigned to H-13 which in turn showed COSY correlations to protons at $\delta_H$ 1.02 and 2.37 (H-14). The HSQC-DEPT data was then used to assign C-13 ($\delta_C$ 77.9) and C-14 ($\delta_C$ 38.4). In this structure, a methine group was present at position 13 instead of a quaternary carbon commonly found in other Stevia glycosides further indicating structural changes in this part of the central core. The carbon chemical shift of C-13 ($\delta_C$ 77.9) indicated a hydroxyl or a substituted hydroxyl at C-13 similar to other Stevia glycosides. The above proton assignments for H-9 to H-14 spin system were further supported by 1D TOCSY experiments performed using selective irradiation of H-13 proton with several different mixing times. HMBC correlations from H-9 ($\delta_H$ 1.13) and H-14 ($\delta_H$ 1.02 and 2.37) to the carbon at $\delta_C$ 35.4 allowed the assignment of C-8 completing the assignment of ring C. H-14 ($\delta_H$ 1.02 and 2.37) also showed HMBC correlations to a carbon at $\delta_C$ 58.6 which was assigned as C-15. The $^1$H chemical shifts at C-15 ($\delta_H$ 1.19 and 1.37) were assigned using the HSQC-DEPT data. The third tertiary methyl singlet, observed at $\delta_H$ 1.41, showed HMBC correlations to the carbons at $\delta_C$ 42.1 (C-12) and $\delta_C$ 58.6 (C-15) thus was assigned to H-17 ($\delta_C$ 33.6 via HSQC-DEPT). HMBC correlations observed from H-13 ($\delta_H$ 4.15), H-15 ($\delta_H$ 1.19 and 1.37), and H-17 ($\delta_H$ 1.41) to a quaternary carbon at $\delta_C$ 71.8 allowed the assignment of C-16. The carbon chemical shift of C-16 ($\delta_C$ 71.8) indicated the attachment of a hydroxyl group at C-16 to complete the assignment of ring D and the central core. In addition, the data shows that instead of the commonly found ent-kaurene diterpenoid core in Stevia glycosides, CC-00334 contained ent-atisane diterpeniod core. Furthermore, CC-00334 does not have the commonly found exocyclic double bond at C-16 in the central core. Additional HMBC correlations from H-9 to C-11; H-11 to C-12 and C-16; H-12 to C-9, C-13, and C-14; H-13 to C-11; H-14 to C-13; H-15 to C-8, and C-9 and H-17 to C-12 further confirmed the assignments made above.

Figure 2:
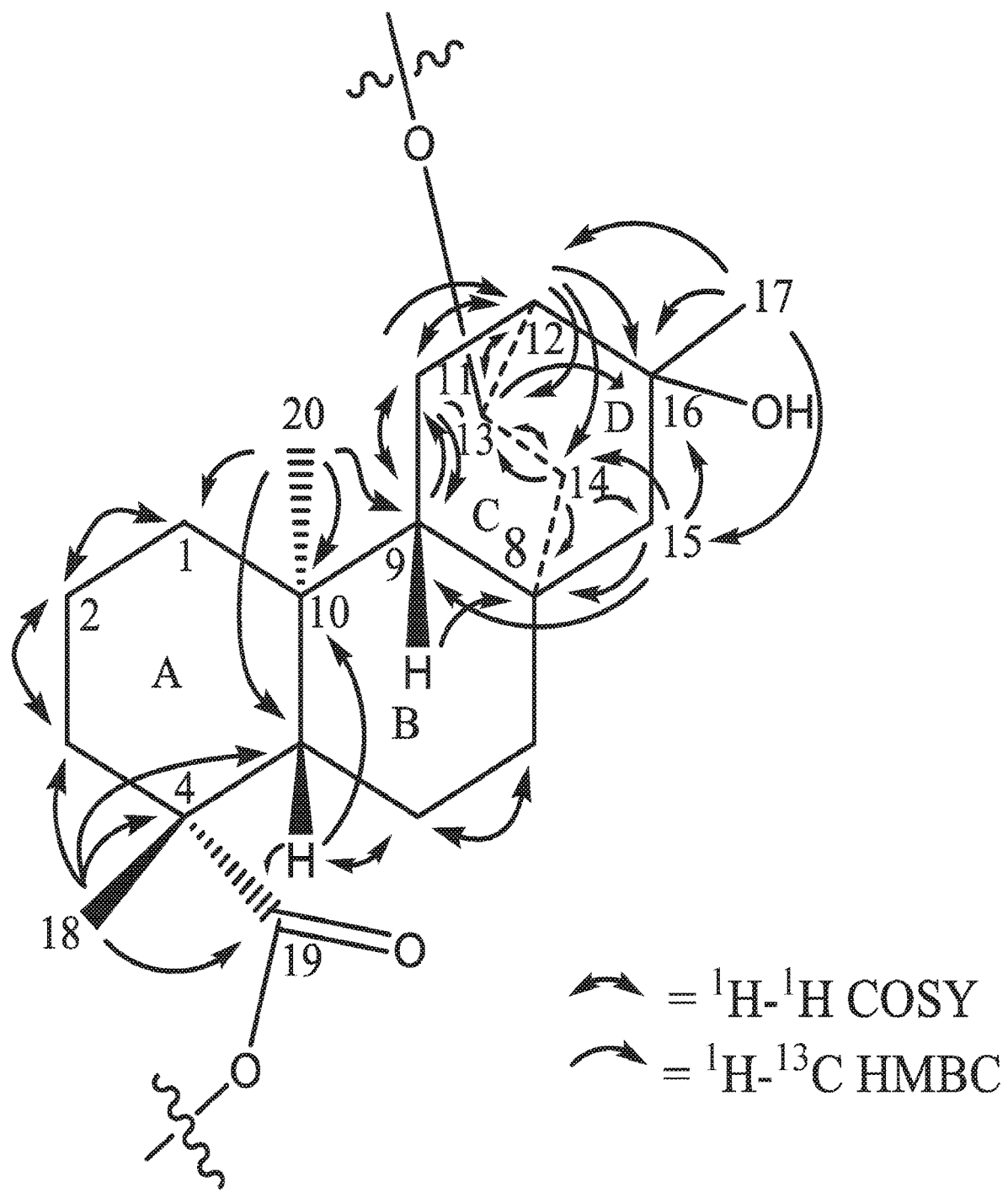
FIG. 2: Shows a summary of key HMBC and COSY correlations used to assign the aglycone region of diterpene glycosides CC-00334 and CC-00341.

Correlations observed in the ROESY spectrum were used to assign the relative stereochemistry of the central diterpene core. In the ROESY spectrum, NOE correlations were observed between H-20 one of the H-14 protons ($\delta_H$ 2.37) indicating that H-14 and H-20 are on the same face of the ring. This assignment was further supported by NOE correlations between H-20 and H-13. Similarly, NOE correlations were observed between H-18 and H-5/H-9 but no NOE correlations were observed with H-13, H-14 and H-20 indicating that H-5, H-9 and H-18 were on the opposite face of the ring compared to H-13, H-14 and H-20. The relative stereochemistry of C-16 hydroxyl and C-17 methyl groups could not be assigned unambiguously. The structure with central core relative stereochemistry is presented in FIG. 2.

Analysis of the $^1$H-$^{13}$C HSQC-DEPT data confirmed the presence of five anomeric protons out of which three were well resolved at $\delta_H$ 5.54 ($\delta_C$ 94.2), 4.64 ($\delta_C$ 104.4) and 4.56 ($\delta_C$ 100.8) and two were overlapped at 4.86 ($\delta_C$ 103.5 or 103.8) in the $^1$H NMR spectrum acquired at 300 K. All five anomeric protons had large couplings (7.8-8.9 Hz) indicating that they had β-configurations. The anomeric proton observed at $\delta_H$ 5.54 showed an HMBC correlation to C-19 which indicated that it corresponded to the anomeric proton of Glc$_I$. Similarly, the anomeric proton observed at $\delta_H$ 4.56 showed an HMBC correlation to C-13 allowing it to be assigned as the anomeric proton of Glc$_{II}$. The reciprocal HMBC correlation from H-13 ($\delta_H$ 4.15) to the anomeric carbon of Glc$_{II}$ ($\delta_C$ 100.8) was also observed.

The Glc$_I$ anomeric proton ($\delta_H$ 5.54) showed a COSY correlation to a proton at $\delta_H$ 3.85 which was assigned as Glc$_I$ H-2 which in turn showed a COSY correlation to a proton at $\delta_H$ 3.67 (Glc$_I$ H-3). This latter proton showed an additional correlation with a proton at $\delta_H$ 3.42 (Glc$_I$ H-4). Due to data overlap the COSY spectrum did not allow assignment of the remaining protons. Therefore, a series of 1D TOCSY experiments were performed using selective irradiation of the Glc$_I$ anomeric proton with several different mixing times. In addition to confirming the assignments for Glc$_I$ H-2 through H-4, the TOCSY data allowed assignment of H-5 ($\delta_H$ 3.37) and H-6 ($\delta_H$ 3.68 and 3.82). The assignment of H-5 was further confirmed by COSY correlations between Glc$_I$ H-5/H-6. The $^{13}$C chemical shifts for Glc$_I$ C-2 ($\delta_C$ 78.7), C-3 ($\delta_C$ 78.9), C-4 ($\delta_C$ 71.1), C-5 ($\delta_C$ 78.6) and C-6 ($\delta_C$ 62.4) were assigned using the HSQC-DEPT data. The HMBC correlations observed from Glc$_I$ H-1 to C-3 and C-5, H-2 to C-1 and C-3, H-3 to C-2 and C-4, H-4 to C-6 and H-6 to C-4 further confirmed the assignments made above to complete the assignment of Glc$_I$. In the $^1$H NMR spectrum a coupling value of 8.0 Hz for Glc$_I$ anomeric proton indicated β-configuration for Glc$_I$.

Of the four remaining unassigned sugar moieties one was assigned as a substituent at C-2 of Glc$_I$ on the basis of HMBC correlations. The anomeric proton observed at $\delta_H$ 4.86 showed an HMBC correlation to Glc$_I$ C-2 and was assigned as the anomeric proton of Glc$_V$. The reciprocal HMBC correlation from Glc$_I$ H-2 to the anomeric carbon of Glc$_V$ was also observed.

Since the anomeric protons observed at $\delta_H$ 4.86, which were also partially obscured by water resonance, corresponded to two glucose units (Glc$_V$ and Glc$_{III}$), assignments for these glucose units were made by combined analysis of COSY, HSQC-DEPT, HMBC and 1D-TOCSY NMR data.

The anomeric protons $\delta_H$ 4.86 showed COSY correlations with the protons at $\delta_H$ 3.21 and $\delta_H$ 3.12 which were assigned as H-2. The proton at $\delta_H$ 3.21 in turn showed a COSY correlation to a proton at $\delta_H$ 3.33 (H-3). Based on comparison with CC-00330 which is very closely related to CC-00334 (CC-00330 differs from CC-00334 only at position 16 in the central core), $\delta_H$ 3.21 was assigned to Glc$_V$ H-2. Due to data overlap the COSY spectrum did not allow assignment of the remaining protons. Therefore, a series of 1D TOCSY experiments were performed using selective irradiation of the anomeric proton with several different mixing times. Since the anomeric protons at $\delta_H$ 4.86 correspond to the anomeric protons of Glc$_V$ and Glc$_{III}$, the TOCSY data showed resonances for the protons of both Glc$_V$ and Glc$_{III}$. While these results did not allow assignment of Glc$_V$ protons, it did show all the protons in the spin-systems of both the sugar units and the proton at $\delta_H$ 3.21 was particularly useful since in $^1$H NMR spectrum, this proton was resolved and thus was utilized for 1D TOCSY experiment with several different mixing times. This data clearly showed protons in the Glc$_V$ spin system. In addition to confirming the assignments for Glc$_V$ H-1 and H-3, the TOCSY data allowed assignment of Glc$_V$ H-4 ($\delta_H$ 3.28), H-5 ($\delta_H$ 3.32) and H-6 ($\delta_H$ 3.68 and 3.89). The additional resonance at $\delta_H$ 4.64 ppm in the TOCSY spectra was due to Glc$_{IV}$ H-1 since Glc$_{IV}$ H-2 at $\delta_H$ 3.26 is very close to the Glc$_V$ H-2 at $\delta_H$ 3.21 and was also was impacted by the TOCSY irradiation pulse and it showed correlation to Glc$_{IV}$ H-1. The assignment of H-5 was further confirmed by COSY correlations between Glc$_V$ H-5/H-6. The $^{13}$C chemical shifts for Glc$_V$ C-2 ($\delta_C$ 75.8), C-3 ($\delta_C$ 78.0-78.4), C-4 ($\delta_C$ 72.1), C-5 ($\delta_C$ 78.0-78.4) and C-6 ($\delta_C$ 63.2) were assigned using the HSQC-DEPT data. The HMBC correlations observed from Glc$_V$ H-1 to C-2 and C-3 and/or C-5, H-2 to C-1 and C-3, H-3 to C-2 and C-4, H-4 to C-6 and H-6 to C-4 further confirmed the assignments made above to complete the assignment of Glc$_V$. In the $^1$H NMR spectrum a coupling value of 8.9 Hz for Glc$_V$ anomeric proton indicated β-configuration for Glc$_V$.

A summary of the $^1$H and $^{13}$C chemical shifts for the glycoside at C-19 are found in Table 8.

TABLE 8

$^1$H and $^{13}$C NMR (500 and 150 MHz, CD$_3$OD), assignments of C-19 glycoside.

| Position | CC-00334 | |
|---|---|---|
| | $^{13}$C | $^1$H |
| Glc$_I$-1 | 94.2 | 5.54 d (8.0) |
| Glc$_I$-2 | 78.7 | 3.85 m |
| Glc$_I$-3 | 78.9 | 3.67 m |
| Glc$_I$-4 | 71.1 | 3.42 m |
| Glc$_I$-5 | 78.6 | 3.37 m |
| Glc$_I$-6 | 62.4 | 3.68 m, 3.82 m |
| Glc$_V$-1 | 103.8 | 4.86† d (8.9) |
| Glc$_V$-2 | 75.8 | 3.21 m |
| Glc$_V$-3 | 78.0-78.4* | 3.33 m |
| Glc$_V$-4 | 72.1 | 3.28 m |
| Glc$_V$-5 | 78.0-78.4* | 3.32 m |
| Glc$_V$-6 | 63.2 | 3.68 m, 3.89 m |

*Six carbon resonances in the range of 78.0-78.4 (77.95, 77.99, 78.22, 78.28, 78.30, and 78.38), hence chemical shifts could not be unequivocally assigned.
†Partially obscured by water resonance.

Assignment of Glc$_{II}$ was carried out in a similar manner. The Glc$_{II}$ anomeric proton ($\delta_H$ 4.56) showed a COSY correlation to a proton at $\delta_H$ 3.69 which was assigned as Glc$_{II}$ H-2 and in turn showed a COSY correlation to a proton at $\delta_H$ 3.73 (Glc$_{II}$ H-3). This latter proton showed an additional correlation with a proton at $\delta_H$ 3.44 (Glc$_{II}$ H-4) which in turn showed COSY correlation to a proton at $\delta_H$ 3.33 (Glc$_{II}$ H-5). Glc$_{II}$ H-5 also showed COSY correlations to the protons at $\delta_H$ 3.70 and 3.87 (Glc$_{II}$ H-6) thus completing the assignment of Glc$_{II}$ spin system. This spin system was further confirmed by a series of 1D TOCSY experiments which were performed using selective irradiation of the Glc$_{II}$ anomeric proton with several different mixing times. The $^{13}$C chemical shifts for Glc$_{II}$ C-2 ($\delta_C$ 80.0), C-3 ($\delta_C$ 87.7), C-4 ($\delta_C$ 70.0), C-5 ($\delta_C$ 77.5), and C-6 ($\delta_C$ 62.5) were assigned using the HSQC-DEPT data. The HMBC correlations observed from Glc$_{II}$ H-1 to C-3 and C-5, H-2 to C-1 and C-3, H-3 to C-2 and C-4, H-4 to C-3 and C-6 and H-6 ($\delta_H$ 3.87) to C-4 further confirmed the assignments made above to complete the assignment of Glc$_{II}$. In the $^1$H NMR spectrum a coupling value of 7.4 Hz for Glc$_{II}$ anomeric proton indicated β-configuration for Glc$_{II}$.

The remaining two unassigned glucose moieties were assigned as substituents at C-2 and C-3 of Glc$_{II}$ on the basis of HMBC correlations. The anomeric proton observed at $\delta_H$ 4.86 showed an HMBC correlation to Glc$_{II}$ C-2 and was assigned as the anomeric proton of Glc$_{III}$. The anomeric proton observed at $\delta_H$ 4.64 showed an HMBC correlation to Glc$_{II}$ C-3 and was assigned as the anomeric proton of Glc$_{IV}$. The reciprocal HMBC correlations from Glc$_{II}$ H-2 to the anomeric carbon of Glc$_{III}$ and from Glc$_{II}$ H-3 to the anomeric carbon of Glc$_{IV}$ were also observed.

Since the anomeric protons observed at $\delta_H$ 4.86 corresponded to two glucose units, Glc$_{III}$ and Glc$_V$, and assignments for Glc$_V$ are already done as discussed above, assignments for Glc$_{III}$ were made by combined analysis of COSY, HSQC-DEPT, HMBC and 1D-TOCSY NMR data and by elimination of assignments already done of Glc$_V$. The anomeric proton of Glc$_{III}$ ($\delta_H$ 4.86) showed a COSY correlation with a proton at $\delta_H$ 3.12 which was assigned as Glc$_{III}$ H-2 and in turn showed a COSY correlation to a proton at $\delta_H$ 3.33 (Glc$_{III}$ H-3). This latter proton showed an additional correlation with a proton at $\delta_H$ 3.16 (Glc$_{III}$ H-4). Due to data overlap the COSY spectrum did not allow assignment of the remaining protons. As discussed above, a series of 1D TOCSY experiments were performed using selective irradiation of the anomeric protons at $\delta_H$ 4.86 with several different mixing times. Since the anomeric protons at $\delta_H$ 4.86 also correspond to the anomeric proton of Glc$_V$, TOCSY data showed resonances for the protons of both sugar units, Glc$_{III}$ and Glc$_V$. Since the proton assignments for Glc$_V$ were made as discussed above, the remaining resonances in the TOCSY spectra corresponded to the protons of Glc$_{III}$. In addition to confirming the assignments for Glc$_{III}$ H-2 through H-4, the TOCSY data allowed assignment of Glc$_{III}$ H-5 ($\delta_H$ 3.29) and H-6 ($\delta_H$ 3.61 and 3.86). The assignments for Glc$_{III}$ protons were further confirmed by 1D TOCSY experiments performed using selective irradiation of the Glc$_{III}$ H-2 at $\delta_H$ 3.12 with several different mixing times. The assignment of H-5 was further confirmed by COSY correlations between Glc$_{III}$ H-5/H-6. The $^{13}$C chemical shifts for Glc$_{III}$ C-2 ($\delta_C$ 76.0), C-3 ($\delta_C$ 78.0-78.4), C-4 ($\delta_C$ 72.2), C-5 ($\delta_C$ 78.0-78.4), and C-6 ($\delta_C$ 63.5) were assigned using the HSQC-DEPT data. HMBC correlations observed from Glc$_{III}$ H-1 to C-3 and/or C-5, H-2 to C-1 and C-3, H-3 to C-2 and C-4, H-4 to C-3 and C-6 and H-6 ($\delta_H$ 3.86) to C-4 further confirmed the assignments made above to complete the assignment of Glc$_{III}$. In the $^1$H NMR spectrum a coupling value of 8.9 Hz for Glc$_{III}$ anomeric proton indicated β-configuration for Glc$_{III}$.

The anomeric proton of Glc$_{IV}$ ($\delta_H$ 4.64) showed a COSY correlation with a proton at $\delta_H$ 3.26 which was assigned as Glc$_{IV}$ H-2. Due to data overlap the COSY spectrum did not allow assignment of the remaining protons. Therefore, a series of 1D TOCSY experiments were performed using selective irradiation of the Glc$_{IV}$ anomeric proton with several different mixing times. In addition to confirming the assignments for Glc$_{IV}$ H-2, the TOCSY data allowed assignment of Glc$_{IV}$ H-3 ($\delta_H$ 3.35), H-4 ($\delta_H$ 3.29) and H-5 ($\delta_H$ 3.34). The protons observed at $\delta_H$ 3.63 and 3.88 in the TOCSY spectrum were assigned as the Glc$_{IV}$ H-6 protons. The assignment of H-5 was further confirmed by COSY correlations between Glc$_{IV}$ H-5/H-6. The $^{13}$C chemical shifts for Glc$_{IV}$ C-2 ($\delta_C$ 75.4), C-3 ($\delta_C$ 78.0-78.4), C-4 ($\delta_C$ 71.5), C-5 ($\delta_C$ 78.0-78.4), and C-6 ($\delta_C$ 62.5) were assigned using the HSQC-DEPT data. The HMBC correlations observed from Glc$_{IV}$ H-1 to C-3 and/or C-5, H-2 to C-1 and C-3, H-3 to C-2 and C-4, H-4 to C-6 and H-6 ($\delta_H$ 3.88) to C-4 further confirmed the assignments made above to complete the assignment of Glc$_{IV}$. In the $^1$H NMR spectrum a coupling value of 7.8 Hz for Glc$_{IV}$ anomeric proton indicated β-configuration for Glc$_{IV}$.

A summary of the $^1$H and $^{13}$C chemical shifts for the glycoside at C-13 are found in Table 9.

TABLE 9

$^1$H and $^{13}$C NMR (500 and 150 MHz, CD$_3$OD), assignments of C-13 glycoside.

| Position | CC-00334 | |
|---|---|---|
| | $^{13}$C | $^1$H |
| Glc$_{II}$-1 | 100.8 | 4.56 d (7.4) |
| Glc$_{II}$-2 | 80.0 | 3.69 m |
| Glc$_{II}$-3 | 87.7 | 3.73 m |
| Glc$_{II}$-4 | 70.0 | 3.44 m |
| Glc$_{II}$-5 | 77.5 | 3.33 m |
| Glc$_{II}$-6 | 62.5 | 3.70 m, 3.87 m |
| Glc$_{III}$-1 | 103.5 | 4.86† d (8.9) |
| Glc$_{III}$-2 | 76.0 | 3.12 m |
| Glc$_{III}$-3 | 78.0-78.4¥ | 3.33 m |
| Glc$_{III}$-4 | 72.2 | 3.16 m |
| Glc$_{III}$-5 | 78.0-78.4¥ | 3.29 m |
| Glc$_{III}$-6 | 63.5 | 3.61 m, 3.86 m |
| Glc$_{IV}$-1 | 104.4 | 4.64 d (7.8) |
| Glc$_{IV}$-2 | 75.4 | 3.26 m |
| Glc$_{IV}$-3 | 78.0-78.4¥ | 3.35 m |
| Glc$_{IV}$-4 | 71.5 | 3.29 m |
| Glc$_{IV}$-5 | 78.0-78.4¥ | 3.34 m |
| Glc$_{IV}$-6 | 62.5 | 3.63 m, 3.88 m |

¥Six carbon resonances in the range of 78.0-78.4 (77.95, 77.99, 78.22, 78.28, 78.30, and 78.38), hence chemical shifts could not be unequivocally assigned.
†Partially obscured by water resonance.

The structure was determined to be (13-[(2-O-β-D-glucopyranosyl-3-O-β-D-glucopyranosyl-β-D-glucopyranosyl)oxy]-16-hydroxy-17-methyl-ent-atis-19-oic acid-[(2-O-β-D-glucopyranosyl-β-D-glucopyranosyl) ester]).

Example 7

Isolation and Characterization of CC-00341

Materials.

The material used for the isolation of CC-00341 was Stevia extract. HPLC Analysis, isolation procedure, were performed as in Example 1 with the deviations described below.

MS and MS/MS.

MS and MS/MS data were generated with a Waters QT of Micro mass spectrometer equipped with an electrospray ionization source. The sample was analyzed by negative ESI. The sample (~0.2 mg) was diluted with 50:50 H$_2$O:ACN to a concentration of 200 μg/mL for HRMS and MS/MS and were introduced via direct infusion.

NMR.

An attempt was made to dissolve 1.7 mg of the sample in 130 μL CD$_3$OD, however the sample did not dissolve readily but upon addition of another 50 μL CD$_3$OD the sample dissolved and NMR data were acquired on a Bruker Avance 500 MHz instrument equipped with a 2.5 mm inverse probe and a 5 mm broad band probe. The HMBC data was acquired at the Rensselaer Polytechnic Institute, Troy, N.Y. using their Bruker Avance 600 MHz instrument equipped with a 5 mm cryo-probe. The $^1$H NMR spectrum was referenced to the CHD$_2$OD resonance at $\delta_H$ 3.30 ppm and $^{13}$C NMR spectrum was referenced to the CD$_3$OD resonance at $\delta_C$ 49.0 ppm.

Results and Discussion

Unless otherwise noted, all solvent ratios are listed as percent by volume (v/v).

Primary Purification.

Approximately 300 g of Stevia extract was processed using the primary preparative HPLC method described above. Collected fractions were analyzed by LC-MS using the analytical method summarized in Table 1.

Secondary Purification.

The collected fractions from primary purification were reprocessed with conditions summarized above, but with 18% MeCN in water as mobile phase A. Fractions were analyzed using the analytical method summarized in Table 2.

Tertiary Purification of CC-00341.

Collected fractions from secondary purification were reprocessed with conditions summarized above.

Final Batch Preparation.

Collected fractions from tertiary purification were concentrated by rotary evaporation for final isolation. The concentrated solution was further dried via lyophilization for 48 h. The final yield of the batch was 2.7 mg.

Mass Spectrometry.

The ESI-TOF mass spectrum acquired by infusing a sample of CC-00341 showed a [M-H]$^-$ ion at m/z 1129.4431. The mass of the [M-H]$^-$ ion was in good agreement with the molecular formula C$_{50}$H$_{82}$O$_{28}$ (calcd for C$_{50}$H$_{81}$O$_{28}$: 1129.4914, error: −2.8 ppm) expected. The MS data confirmed that CC-00341 has a nominal mass of 1130 Daltons with the molecular formula, C$_{50}$H$_{82}$O$_{28}$.

The MS/MS spectrum of CC-00341, selecting the [M-H]$^-$ ion at m/z 1129.0 for fragmentation, indicated loss of one glucose unit at m/z 967.3823 followed by loss of one rhamnose unit at m/z 821.3610 and sequential loss of three sugar units at m/z 659.3145, 497.2600 and 335.2198 indicating the presence of four glucose and one rhamnose units in the structure.

NMR Spectroscopy.

A series of NMR experiments including $^1$H NMR $^{13}$C NMR $^1$H-$^1$H COSY, HSQC-DEPT, HMBC, ROESY and 1D TOCSY were acquired to allow assignment of CC-00341.

The 1D and 2D NMR data indicated the presence of a central diterpene core with five sugar units in the structure. $^1$H NMR and HSQC-DEPT data indicated the presence of three methyl groups instead of two commonly observed in other Stevia glycosides. In the HSQC-DEPT data, only eight methylene units were observed instead of nine methylene units that are commonly observed in the central diterpene core of related Stevia glycosides. Similarly in the HSQC-DEPT data, in addition to two methine units corresponding to C-5 and C-9 positions, two additional methine units at $\delta_H$ 1.88/$\delta_C$ 42.7 and $\delta_H$ 4.11/$\delta_C$ 78.8 were observed and indicated structural changes in the central diterpene core. In addition, the HSQC-DEPT data indicated absence of the exocyclic double bond from the central core which is commonly found in Stevia glycosides.

Complete analysis of 1D and 2D NMR data allowed assignment of the central core and confirmed the structural changes in rings C and D as discussed below. An HMBC correlation from the methyl protons at $\delta_H$ 1.25 to the carbonyl carbon at $\delta_C$ 177.2 allowed assignment of one of the tertiary methyl groups (C-18) as well as C-19 and provided a starting point for the assignment of the rest of the aglycone. Additional HMBC correlations from the methyl protons (H-18) to carbons at $\delta_C$ 38.6, 45.1, and 59.4 allowed assignment of C-3, C-4, and C-5. Analysis of the $^1$H-$^{13}$C HSQC-DEPT data indicated that the carbon at $\delta_C$ 38.6 was a methylene and the carbon at $\delta_C$ 59.4 was a methine which were assigned as C-3 and C-5, respectively. This left the carbon at $\delta_C$ 45.1, which did not show a correlation in the HSQC-DEPT spectrum, to be assigned as the quaternary carbon, C-4. The $^1$H chemical shifts for C-3 ($\delta_H$ 1.05 and 2.28) and C-5 ($\delta_H$ 1.06) were assigned using the HSQC-DEPT data. COSY correlations between the H-3 protons ($\delta_H$ 1.05 and 2.28) and protons at $\delta_H$ 1.37 and 1.89 allowed assignment of the H-2 protons which in turn showed correlations with the protons at $\delta_H$ 0.89 and 1.58 which were assigned to H-1. The $^{13}$C chemical shifts for C-1 and C-2 were then assigned on the basis of HSQC-DEPT correlations and are summarized in Table 7.

TABLE 7

$^1$H and $^{13}$C NMR (500 and 125 MHz, CD$_3$OD), assignments of aglycone.

| Position | CC-00341 | |
|---|---|---|
| | $^{13}$C | $^1$H |
| 1 | 40.7 | 0.89 m |
| | | 1.58 brd |
| | | (13.2) |
| 2 | 20.1 | 1.37 m |
| | | 1.89 m |
| 3 | 38.6 | 1.05 m |
| | | 2.28 m |
| 4 | 45.1 | — |
| 5 | 59.4 | 1.06 m |
| 6 | 21.0 | 1.76 m |
| | | 1.87 m |
| 7 | 40.2 | 1.09 m |
| | | 1.47 m |
| 8 | 35.4 | — |
| 9 | 51.1 | 1.13 m |
| 10 | 39.4 | — |
| 11 | 23.7 | 1.06 m |
| | | 2.07 m |
| 12 | 42.7 | 1.88 brs |
| 13 | 78.8 | 4.11 brt |
| | | (8.4) |
| 14 | 38.3 | 1.06 m |
| | | 2.33 m |
| 15 | 58.6 | 1.18 brd |
| | | (13.3) |
| | | 1.37 m |
| 16 | 71.8 | — |
| 17 | 33.5 | 1.40 s |
| 18 | 29.7 | 1.25 s |

TABLE 7-continued $^1$H and $^{13}$C NMR (500 and 125 MHz, CD$_3$OD), assignments of aglycone.

| Position | CC-00341 | |
|---|---|---|
| | $^{13}$C | $^1$H |
| 19 | 177.2 | — |
| 20 | 13.9 | 0.84 s |

The other tertiary methyl singlet, observed at $\delta_H$ 0.84 ($\delta_C$ 13.9 via HSQC-DEPT), showed HMBC correlations to C-1 and C-5 and was assigned as H-20. The methyl protons showed additional HMBC correlations to a quaternary carbon ($\delta_C$ 39.4) and a methine carbon ($\delta_C$ 51.1) which were assigned as C-10 and C-9, respectively. The $^1$H chemical shift for C-9 ($\delta_H$ 1.13) was assigned using the HSQC-DEPT data. COSY correlations between H-5 ($\delta_H$ 1.06) and the protons at $\delta_H$ 1.76 and 1.87 then allowed assignment of the H-6 protons which in turn showed correlations to protons at $\delta_H$ 1.09 and 1.47 which were assigned to H-7. The $^{13}$C chemical shifts for C-6 ($\delta_C$ 21.0) and C-7 ($\delta_C$ 40.2) were then determined from the HSQC-DEPT data. COSY correlations between H-9 ($\delta_H$ 1.13) and the protons at $\delta_H$ 1.06 and 2.07 allowed assignment of the H-11 protons. The HSQC-DEPT data was then used to assign C-11 ($\delta_C$ 23.7). The H-11 protons at $\delta_H$ 1.06 and 2.07 showed COSY correlation to a methine proton at $\delta_H$ 1.88 ($\delta_C$ 42.7 via HSQC-DEPT) instead of methylene protons in other Stevia glycosides. This data thus indicated that a methine group was present at position 12 instead of a methylene group. The H-12 proton ($\delta_H$ 1.88) also showed COSY correlations to a methine proton at $\delta_H$ 4.11 assigned to H-13 which in turn showed COSY correlations to protons at $\delta_H$ 1.06 and 2.33 (H-14). The HSQC-DEPT data was then used to assign C-13 ($\delta_C$ 78.8) and C-14 ($\delta_C$ 38.3). In this structure, a methine group was present at position 13 instead of a quaternary carbon commonly found in other Stevia glycosides further indicating structural changes in this part of the central core. The carbon chemical shift of C-13 ($\delta_C$ 78.8) indicated a hydroxyl or a substituted hydroxyl at C-13 similar to other Stevia glycosides. The above proton assignments for H-9 to H-14 spin system were further supported by 1D TOCSY experiments performed using selective irradiation of H-13 proton with several different mixing times. HMBC correlations from H-9 ($\delta_H$ 1.13) and H-14 ($\delta_H$ 1.06 and 2.33) to the carbon at $\delta_C$ 35.4 allowed the assignment of C-8 completing the assignment of ring C. H-14 ($\delta_H$ 1.06 and 2.33) also showed HMBC correlations to a carbon at $\delta_C$ 58.6 which was assigned as C-15. The $^1$H chemical shifts at C-15 ($\delta_H$ 1.18 and 1.37) were assigned using the HSQC-DEPT data. The third tertiary methyl singlet, observed at $\delta_H$ 1.40, showed HMBC correlations to the carbons at $\delta_C$ 42.7 (C-12) and $\delta_C$ 58.6 (C-15) thus was assigned to H-17 ($\delta_C$ 33.5 via HSQC-DEPT). HMBC correlations observed from H-13 ($\delta_H$ 4.11), H-15 ($\delta_H$ 1.18 and 1.37), and H-17 ($\delta_H$ 1.40) to a quaternary carbon at $\delta_C$ 71.8 allowed the assignment of C-16. The carbon chemical shift of C-16 ($\delta_C$ 71.8) indicated the attachment of a hydroxyl group at C-16 to complete the assignment of ring D and the central core. In addition, the data shows that instead of the commonly found ent-kaurene diterpenoid core in Stevia glycosides, CC-00341 contained an ent-atisane diterpeniod core. Furthermore, CC-00341 does not have the commonly found exocyclic double bond at C-16 in the central core. Additional HMBC correlations from H-9 to C-11; H-11 to C-12; H-12 to C-9 and C-14;

H-13 to C-11 and C-16; H-14 to C-13; H-15 to C-7, C-8, and C-9 and H-17 to C-12 further confirmed the assignments made above.

Correlations observed in the ROESY spectrum were used to assign the partial relative stereochemistry of the central diterpene core. In the ROESY spectrum, NOE correlations were observed between H-20 one of the H-14 protons ($\delta_H$ 2.33) indicating that H-14 and H-20 are on the same face of the ring. This assignment was further supported by NOE correlations between H-20 and H-13. Due to data overlap, it was not possible to unambiguously assign the NOE correlations for H-18, H-5 and H-9 however no NOE correlations were observed between H-18/H-5/H-9 and H-13/H-14($\delta_H$ 2.33)/H-20 indicating that H-5, H-9 and H-18 were on the opposite face of the ring compared to H-13, H-14 and H-20. The relative stereochemistry of C-16 hydroxyl and C-17 methyl groups could not be assigned. The structure with central core relative stereochemistry is presented in FIG. 2.

Analysis of the $^1$H-$^{13}$C HSQC-DEPT data confirmed the presence of five anomeric protons, of which four were well resolved at $\delta_H$ 5.57 ($\delta_C$ 94.2), 5.28 ($\delta_C$ 101.8), 4.63 ($\delta_C$ 104.4) and 4.52 ($\delta_C$ 101.7) in the $^1$H NMR spectrum acquired at 300 K. One anomeric proton that was partially obscured by water resonance at $\delta_H$ 4.83 at 300K was resolved in the $^1$H NMR spectrum acquired at 302K at $\delta_H$ 4.84 ($\delta_C$ 103.6). Four of the anomeric protons had large couplings (7.9-7.4 Hz) indicating that they had β-configurations and one anomeric proton observed as a broad doublet at $\delta_H$ 5.28 had a small coupling of 1.2 Hz indicating that this had α-configuration. The anomeric proton observed at $\delta_H$ 5.57 showed an HMBC correlation to C-19 which indicated that it corresponded to the anomeric proton of Glc$_I$. Similarly, the anomeric proton observed at $\delta_H$ 4.52 showed an HMBC correlation to C-13 allowing it to be assigned as the anomeric proton of Glc$_{II}$. The reciprocal HMBC correlation from H-13 ($\delta_H$ 4.11) to the anomeric carbon of Glc$_{II}$ ($\delta_C$ 101.7) was also observed.

The Glc$_I$ anomeric proton ($\delta_H$ 5.57) showed a COSY correlation to a proton at $\delta_H$ 3.60 which was assigned as Glc$_I$ H-2. Due to data overlap the COSY spectrum did not allow assignment of the remaining protons. Therefore, a series of 1D TOCSY experiments were performed using selective irradiation of the Glc$_I$ anomeric proton with several different mixing times. In addition to confirming the assignments for Glc$_I$ H-2, the TOCSY data allowed assignment of H-3 ($\delta_H$ 3.56), H-4 ($\delta_H$ 3.42), H-5 ($\delta_H$ 3.36) and H-6 ($\delta_H$ 3.69 and 3.81). The $^{13}$C chemical shifts for Glc$_I$ C-2 ($\delta_C$ 77.9 or 78.0 or 78.1), C-3 ($\delta_C$ 79.1), C-4 ($\delta_C$ 71.4), C-5 ($\delta_C$ 78.2 or 78.3) and C-6 ($\delta_C$ 62.5 or 62.6 or 62.7) were assigned using the HSQC-DEPT data. The HMBC correlations observed from Glc$_I$ H-1 to C-3 and C-5, H-2 to C-1 and C-3, H-3 to C-2 and C-4, H-4 to C-3 and C-6, H-5 to C-4 and H-6 to C-4 and C-5 further confirmed the assignments made above to complete the assignment of Glc$_I$. In the $^1$H NMR spectrum a coupling value of 7.5 Hz for Glc$_I$ anomeric proton indicated β-configuration for Glc$_I$.

Of the five remaining unassigned sugar moieties one was assigned as substituent at C-2 of Glc$_I$ on the basis of HMBC correlations. The anomeric proton observed at $\delta_H$ 5.28 showed an HMBC correlation to Glc$_I$ C-2 and was assigned as the anomeric proton of Rha. The reciprocal HMBC correlation from Glc$_I$ H-2 to the anomeric carbon of Rha ($\delta_C$ 101.8) was also observed.

The anomeric proton of Rha ($\delta_H$ 5.28) showed a COSY correlation to a proton at $\delta_H$ 3.90 which was assigned as Rha H-2. Rha C-2 ($\delta_C$ 72.2) was then assigned using HSQC-DEPT data supporting a rhamnose unit. The Rha H-2 in turn showed a COSY correlation to a proton at $\delta_H$ 3.61 (Rha H-3). Due to data overlap the COSY spectrum did not allow assignment of the remaining protons. Therefore, a series of 1D TOCSY experiments were performed using selective irradiation of the Rha anomeric proton with several different mixing times. In addition to confirming the assignments for Rha H-2 and H-3, the TOCSY data allowed assignment of H-4 ($\delta_H$ 3.37), H-5 ($\delta_H$ 3.75) and H-6 ($\delta_H$ 1.24). The $^{13}$C chemical shifts for Rha C-3 ($\delta_C$ 72.1), C-4 ($\delta_C$ 73.9), C-5 ($\delta_C$ 70.3), and C-6 ($\delta_C$ 18.3) were assigned using the HSQC-DEPT data. The HMBC correlations observed from the Rha H-1 to C-2 and/or C-3 and C-5, H-2 to C-1 and C-3, H-3 to C-2 and C-4, H-4 to C-3 and C-6, and H-6 to C-4 and C-5 further confirmed the assignments made above to complete the assignment of Rha. In the $^1$H NMR spectrum, Rha anomeric proton is observed as a broad doublet having a coupling value of 1.2 Hz which indicated α-configuration for Rha.

A summary of the $^1$H and $^{13}$C chemical shifts for the glycoside at C-19 are found in Table 8.

TABLE 8

$^1$H and $^{13}$C NMR (500 and 125 MHz, CD$_3$OD), assignments of C-19 glycoside.

| | CC-00341 | |
|---|---|---|
| Position | $^{13}$C | $^1$H |
| Glc$_I$-1 | 94.2 | 5.57 d (7.5) |
| Glc$_I$-2 | 77.9 or 78.0 or 78.1 | 3.60 m |
| Glc$_I$-3 | 79.1 | 3.56 m |
| Glc$_I$-4 | 71.4 | 3.42 m |
| Glc$_I$-5 | 78.2 or 78.3 | 3.36 m |
| Glc$_I$-6 | 62.5 or 62.6 or 62.7 | 3.69 m, 3.81 m |
| Rha-1 | 101.8 | 5.28 brd (1.2) |
| Rha-2 | 72.2 | 3.90 m |
| Rha-3 | 72.1 | 3.61 m |
| Rha-4 | 73.9 | 3.37 m |
| Rha-5 | 70.3 | 3.75 m |
| Rha-6 | 18.3 | 1.24 d (6.3) |

Assignment of Glc$_{II}$ was carried out in a similar manner. The Glc$_{II}$ anomeric proton ($\delta_H$ 4.52) showed a COSY correlation to a proton at $\delta_H$ 3.66. Due to data overlap the COSY spectrum did not allow assignment of the remaining protons. Therefore, a series of 1D TOCSY experiments were performed using selective irradiation of the Glc$_{II}$ anomeric proton with several different mixing times. In addition to confirming the assignments for Glc$_{II}$ H-2, the TOCSY data allowed assignment of H-3 ($\delta_H$ 3.70), H-4 ($\delta_H$ 3.41), H-5 ($\delta_H$ 3.30) and H-6 ($\delta_H$ 3.68 and 3.86). The additional resonances observed at $\delta_H$ 3.53, 3.58 and 3.37 were due to impurities. The $^{13}$C chemical shifts for Glc$_{II}$ C-2 ($\delta_C$ 80.3), C-3 ($\delta_C$ 87.6), C-4 ($\delta_C$ 70.1), C-5 ($\delta_C$ 77.5), and C-6 ($\delta_C$ 62.5 or 62.6 or 62.7) were assigned using the HSQC-DEPT data. The HMBC correlations observed from Glc$_{II}$ H-1 to C-3 and C-5, H-2 to C-1 and C-3, H-3 to C-2 and C-4, H-4 to C-3 and C-6 and H-6 ($\delta_H$ 3.68) to C-4 and C-5 further confirmed the assignments made above to complete the assignment of Glc$_{II}$. In the $^1$H NMR spectrum a coupling value of 7.4 Hz for Glc$_{II}$ anomeric proton indicated β-configuration for Glc$_{II}$.

The remaining two unassigned glucose moieties were assigned as substituents at C-2 and C-3 of Glc$_{II}$ on the basis of HMBC correlations. The anomeric proton observed at $\delta_H$ 4.84 showed an HMBC correlation to Glc$_{II}$ C-2 and was assigned as the anomeric proton of Glc$_{III}$. The anomeric proton observed at $\delta_H$ 4.63 showed an HMBC correlation to Glc$_{II}$ C-3 and was assigned as the anomeric proton of Glc$_{IV}$. The reciprocal HMBC correlations from Glc$_{II}$ H-2 to the anomeric carbon of Glc$_{III}$ and from Glc$_{II}$ H-3 to the anomeric carbon of Glc$_{IV}$ were also observed.

The anomeric proton of Glc$_{III}$ ($\delta_H$ 4.84) showed a COSY correlation with a proton at $\delta_H$ 3.12 which was assigned as Glc$_{III}$ H-2 and in turn showed a COSY correlation to a proton at $\delta_H$ 3.32 (Glc$_{III}$ H-3). Due to data overlap the COSY spectrum did not allow assignment of the remaining protons. Therefore, a series of 1D TOCSY experiments were performed using selective irradiation of the Glc$_{III}$ anomeric proton with several different mixing times. In addition to confirming the assignments for Glc$_{III}$ H-2 and H-3, the TOCSY data allowed assignment of Glc$_{III}$ H-4 ($\delta_H$ 3.17), H-5 ($\delta_H$ 3.29) and H-6 ($\delta_H$ 3.62 and 3.84). In the TOCSY spectra, a broad resonance observed at $\delta_H$ 4.83 was due to water. The $^{13}$C chemical shifts for Glc$_{III}$ C-2 ($\delta_C$ 76.0), C-3 ($\delta_C$ 77.9 or 78.0 or 78.1), C-4 ($\delta_C$ 72.1), C-5 ($\delta_C$ 77.9 or 78.0 or 78.1), and C-6 ($\delta_C$ 63.4) were assigned using the HSQC-DEPT data. HMBC correlations observed from Glc$_{III}$ H-1 to C-2 and C-3 and/or C-5, H-2 to C-1 and C-3, H-3 to C-1 and C-4, H-4 to C-3 C-5 and C-6, H-5 to C-6 and H-6 to C-4 further confirmed the assignments made above to complete the assignment of Glc$_{III}$. In the $^1$H NMR spectrum a coupling value of 7.9 Hz for Glc$_{III}$ anomeric proton indicated β-configuration for Glc$_{III}$.

The anomeric proton of Glc$_{IV}$ ($\delta_H$ 4.63) showed a COSY correlation with a proton at $\delta_H$ 3.26 which was assigned as Glc$_{IV}$ H-2. Due to data overlap the COSY spectrum did not allow assignment of the remaining protons. Therefore, a series of 1D TOCSY experiments were performed using selective irradiation of the Glc$_{IV}$ anomeric proton with several different mixing times. In addition to confirming the assignments for Glc$_{IV}$ H-2, the TOCSY data allowed assignment of Glc$_{IV}$ H-3 ($\delta_H$ 3.36), H-4 ($\delta_H$ 3.29) and H-5 ($\delta_H$ ~3.34). The protons observed at $\delta_H$ 3.63 and 3.88 in the TOCSY spectrum were assigned as the Glc$_{IV}$ H-6 protons. The $^{13}$C chemical shifts for Glc$_{IV}$ C-2 ($\delta_C$ 75.3), C-3 ($\delta_C$ 78.2 or 78.3), C-4 ($\delta_C$ 71.5), C-5 ($\delta_C$ 78.2 or 78.3), and C-6 ($\delta_C$ 62.5 or 62.6 or 62.7) were assigned using the HSQC-DEPT data. The HMBC correlations observed from Glc$_{IV}$ H-1 to C-2 and C-3 and/or C-5, H-2 to C-1 and C-3, H-3 to C-2 and C-4, H-4 to C-3, C-5 and C-6 and H-6 ($\delta_H$ 3.88) to C-4 and C-5 further confirmed the assignments made above to complete the assignment of Glc$_{IV}$. In the $^1$H NMR spectrum a coupling value of 7.8 Hz for Glc$_{IV}$ anomeric proton indicated β-configuration for Glc$_{IV}$.

A summary of the $^1$H and $^{13}$C chemical shifts for the glycoside at C-13 are found in Table 9.

TABLE 9

$^1$H and $^{13}$C NMR (500 and 125 MHz, CD$_3$OD), assignments of C-13 glycoside.

| Position | CC-00341 | |
|---|---|---|
| | $^{13}$C | $^1$H |
| Glc$_{II}$-1 | 101.7 | 4.52 d (7.4) |
| Glc$_{II}$-2 | 80.3 | 3.66 m |
| Glc$_{II}$-3 | 87.6 | 3.70 m |
| Glc$_{II}$-4 | 70.1 | 3.41 m |

TABLE 9-continued $^1$H and $^{13}$C NMR (500 and 125 MHz, CD$_3$OD), assignments of C-13 glycoside.

| Position | CC-00341 | |
|---|---|---|
| | $^{13}$C | $^1$H |
| Glc$_{II}$-5 | 77.5 | 3.30 m |
| Glc$_{II}$-6 | 62.5 or 62.6 or 62.7 | 3.68 m, 3.86 m |
| Glc$_{III}$-1 | 103.6 | 4.84 d (7.9) |
| Glc$_{III}$-2 | 76.0 | 3.12 m |
| Glc$_{III}$-3 | 77.9 or 78.0 or 78.1 | 3.32 m |
| Glc$_{III}$-4 | 72.1 | 3.17 m |
| Glc$_{III}$-5 | 77.9 or 78.0 or 78.1 | 3.29 m |
| Glc$_{III}$-6 | 63.4 | 3.62 m, 3.84 m |
| Glc$_{IV}$-1 | 104.4 | 4.63 d (7.8) |
| Glc$_{IV}$-2 | 75.3 | 3.26 m |
| Glc$_{IV}$-3 | 78.2 or 78.3 | 3.36 m |
| Glc$_{IV}$-4 | 71.5 | 3.29 m |
| Glc$_{IV}$-5 | 78.2 or 78.3 | ~3.34 m |
| Glc$_{IV}$-6 | 62.5 or 62.6 or 62.7 | 3.63 m, 3.88 m |

The structure was determined to be (13-[(2-O-β-D-glucopyranosyl-3-O-β-D-glucopyranosyl-β-D-glucopyranosyl)oxy]-16-hydroxy-17-methyl-ent-atis-19-oic acid-[(2-O-α-L-rhamnopyranosyl-β-D-glucopyranosyl) ester]).

Example 8

Isolation and Characterization of CC-00348

Materials.

The material used for the isolation of CC-00348 was Stevia extract. HPLC Analysis, isolation procedure, were performed as in Example 1 with the deviations described below.

MS and MS/MS.

MS and MS/MS data were generated with a Waters QT of Micro mass spectrometer equipped with an electrospray ionization source. The sample was analyzed by negative ESI. The sample (~0.1 mg) was diluted with 50:50 H$_2$O:ACN to a concentration of 200 μg/mL for HRMS and MS/MS and were introduced via direct infusion.

NMR.

An attempt was made to dissolve 0.8 mg of the sample in 150 μL CD$_3$OD, however the sample did not dissolve readily. To this solution, another 50 μL CD$_3$OD was added but the sample was still not completely dissolved. The CD$_3$OD soluble portion of the sample was utilized for NMR analysis. NMR data were acquired on a Bruker Avance 500 MHz instrument equipped with a 2.5 mm inverse probe. The $^{13}$C, HMBC and ROESY data were acquired at the Rensselaer Polytechnic Institute, Troy, N.Y. using their Bruker Avance 600 MHz instrument equipped with a 5 mm cryoprobe. The $^1$H NMR spectrum was referenced to the CHD$_2$OD resonance at $\delta_H$ 3.30 ppm and $^{13}$C NMR spectrum was referenced to the CD$_3$OD resonance at $\delta_C$ 49.0 ppm.

Results and Discussion

Unless otherwise noted, all solvent ratios are listed as percent by volume (v/v).

Primary Purification.

Approximately 300 g of Stevia extract was processed using the primary preparative HPLC method described above. Collected fractions were analyzed by LC-MS using the analytical method summarized in Table 1.

Secondary Purification.

Collected fractions from primary purification were reprocessed with conditions summarized above, but with 18% MeCN in water as mobile phase A. Fractions were analyzed using the analytical method summarized in Table 2.

Tertiary Purification.

Collected fractions from secondary purification were reprocessed with conditions summarized above.

Final Batch Preparation.

Collected fractions from tertiary purification were concentrated by rotary evaporation for final isolation. The concentrated solution was further dried via lyophilization for 48 h. The final yield of the batch was 0.8 mg.

Mass Spectrometry.

The ESI-TOF mass spectrum acquired by infusing a sample showed a [M-H]⁻ ion at m/z 1111.4907. The mass of the [M-H]⁻ ion was in good agreement with the molecular formula $C_{50}H_{80}O_{27}$ (calcd for $C_{50}H_{79}O_{27}$: 1111.4809, error: 1.7 ppm) expected for CC-00348. The MS data confirmed that CC-00348 has a nominal mass of 1112 Daltons with the molecular formula, $C_{50}H_{80}O_{27}$.

The MS/MS spectrum of CC-00348, selecting the [M-H]⁻ ion at m/z 1111.0 for fragmentation, indicated sequential loss of three glucose units at m/z 949.4579, 787.3808 and 625.3123 followed by loss of one rhamnose unit at m/z 479.2650 and loss of one sugar unit at m/z 317.2256 indicating the presence of four glucose and one rhamnose units in the structure. Another fragmentation pathway is evident from the ion at m/z 641.3323 which would correspond to loss of one rhamnose unit from the ion at m/z 787.3808 and subsequent loss of one glucose unit would also give the ion at m/z 479.2650.

NMR Spectroscopy.

A series of NMR experiments including ¹H NMR, ¹³C NMR, ¹H-¹H COSY, HSQC-DEPT, HMBC, ROESY and 1D TOCSY were acquired to allow assignment of CC-00348.

The 1D and 2D NMR data indicated the presence of a central diterpene core with an exocyclic double bond and five sugar units in the structure. In the HSQC-DEPT data, only eight methylene units were observed instead of nine methylene units that are commonly observed in the central diterpene core of related Stevia glycosides. Similarly in the HSQC-DEPT data, in addition to two methine units corresponding to C-5 and C-9 positions, two additional methine units at $\delta_H$ 2.62/$\delta_C$ 39.5 and $\delta_H$ 4.19/$\delta_C$ 74.4 were observed which is relatively rare in this class of compounds and thus indicated structural changes in the central diterpene core.

Complete analysis of 1D and 2D NMR data allowed assignment of the central core and confirmed the structural changes in rings C and D as discussed below. An HMBC correlation from the methyl protons at $\delta_H$ 1.23 to the carbonyl at $\delta_C$ 177.9 allowed assignment of one of the tertiary methyl groups (C-18) as well as C-19 and provided a starting point for the assignment of the rest of the aglycone. Additional HMBC correlations from the methyl protons (H-18) to carbons at $\delta_C$ 39.0, 45.2, and 58.3 allowed assignment of C-3, C-4, and C-5. Analysis of the ¹H-¹³C HSQC-DEPT data indicated that the carbon at $\delta_C$ 39.0 was a methylene and the carbon at $\delta_C$ 58.3 was a methine which were assigned as C-3 and C-5, respectively. This left the carbon at $\delta_C$ 45.2, which did not show a correlation in the HSQC-DEPT spectrum, to be assigned as the quaternary carbon, C-4. The ¹H chemical shifts for C-3 ($\delta_H$ 1.04 and 2.28) and C-5 ($\delta_H$ 1.09) were assigned using the HSQC-DEPT data. COSY correlations between the H-3 protons ($\delta_H$ 1.04 and 2.28) and protons at $\delta_H$ 1.38 and 1.86 allowed assignment of the H-2 protons which in turn showed correlations with the protons at $\delta_H$ 0.89 and 1.57 which were assigned to H-1. The ¹³C chemical shifts for C-1 and C-2 were then assigned on the basis of HSQC-DEPT correlations and are summarized in Table 7.

TABLE 7

¹H and ¹³C NMR (500 and 150 MHz, CD₃OD), assignments of aglycone.

| | CC-00348 | |
|---|---|---|
| Position | ¹³C | ¹H |
| 1 | 40.9 | 0.89 m |
| | | 1.57 m |
| 2 | 19.9 | 1.38 m |
| | | 1.86 m |
| 3 | 39.0 | 1.04 m |
| | | 2.28 m |
| 4 | 45.2 | — |
| 5 | 58.3 | 1.09 m |
| 6 | 21.2 | 1.79 m |
| | | 1.92 m |
| 7 | 40.4 | 1.15 m |
| | | 1.54 m |
| 8 | 35.0 | — |
| 9 | 52.6 | 1.08 m |
| 10 | 39.4 | — |
| 11 | 27.3 | 1.39 m |
| | | 1.63 m |
| 12 | 39.5 | 2.62 brs |
| 13 | 74.4 | 4.19 m |
| 14 | 38.8 | 0.98 m |
| | | 2.47 m |
| 15 | ~48.5¥ | 1.82 m |
| | | 2.24 m |
| 16 | 147.7 | — |
| 17 | 110.1 | 4.82 brs¶ |
| 18 | 29.3 | 1.23 s |
| 19 | 177.9 | — |
| 20 | 13.8 | 0.85 s |

¥Resonance obscured by CD₃OD, assignment based on HSQC-DEPT data.
¶Two protons.

The other tertiary methyl singlet, observed at $\delta_H$ 0.85 ($\delta_C$ 13.8 via HSQC-DEPT), showed HMBC correlations to C-1 and C-5 and was assigned as H-20. The methyl protons showed additional HMBC correlations to a quaternary carbon ($\delta_C$ 39.4) and a methine carbon ($\delta_C$ 52.6) which were assigned as C-10 and C-9, respectively. The ¹H chemical shift for C-9 ($\delta_H$ 1.08) was assigned using the HSQC-DEPT data. COSY correlations between H-5 ($\delta_H$ 1.09) and the protons at $\delta_H$ 1.79 and 1.92 then allowed assignment of the H-6 protons which in turn showed correlations to protons at $\delta_H$ 1.15 and 1.54 which were assigned to H-7. The ¹³C chemical shifts for C-6 ($\delta_C$ 21.2) and C-7 ($\delta_C$ 40.4) were then determined from the HSQC-DEPT data. COSY correlations between H-9 ($\delta_H$ 1.08) and the protons at $\delta_H$ 1.39 and 1.63 allowed assignment of the H-11 protons. The HSQC-DEPT data was then used to assign C-11 ($\delta_C$ 27.3). The H-11 protons at $\delta_H$ 1.39 and 1.63 showed COSY correlation to a methine proton at $\delta_H$ 2.62 ($\delta_C$ 39.5 via HSQC-DEPT) instead of methylene protons in other Stevia glycosides. This data thus indicated that a methine group was present at position 12 instead of a methylene group. The H-12 proton ($\delta_H$ 2.62) also showed COSY correlations to a methine proton at $\delta_H$ 4.19 assigned to H-13 which in turn showed COSY correlations to protons at $\delta_H$ 0.98 and 2.47 (H-14). The HSQC-DEPT data was then used to assign C-13 ($\delta_C$ 74.4) and C-14 ($\delta_C$ 38.8). In this structure, a methine group was present at position 13 instead of a quaternary carbon commonly found in other Stevia glycosides further indicating structural changes in this part of the central core. The carbon chemical shift of C-13 ($\delta_C$ 74.4) indicated a hydroxyl or a substituted hydroxyl at C-13 similar to other Stevia glycosides. The above proton assignments for H-9 to H-14 spin system were further supported by 1D TOCSY experiments performed using selective irradiation of the H-12 and H-13 protons with several different mixing times. HMBC correlations from H-9 ($\delta_H$ 1.08) and H-14 ($\delta_H$ 0.98 and 2.47) to the carbon at $\delta_C$ 35.0 allowed the assignment of C-8 completing the assignment of ring C. The only remaining methylene group in the central core region at $\delta_H$ 1.82 and 2.24 ($\delta_C$ ~48.5 via HSQC-DEPT) was assigned to H-15 and supported by HMBC correlations from H-14 and H-17 to C-15 ($\delta_C$ ~48.5). The HSQC-DEPT data indicated that the exocyclic double bond was present in CC-00348 and was assigned based on the HMBC correlations. Thus, HMBC correlation from H-12 ($\delta_H$ 2.62) and H-15 ($\delta_H$ 2.24) to a carbon at $\delta_C$ 110.1 allowed the assignment of the exocyclic methylene carbon (C-17). The HSQC-DEPT data was then used to assign the protons at C-17 ($\delta_H$ 4.82 [observed as broad singlet integrating for two protons in the $^1$H NMR spectrum]). The HMBC correlations from H-13 ($\delta_H$ 4.19), H-15 ($\delta_H$ 1.82 and 2.24) and H-17 ($\delta_H$ 4.82) to a quaternary carbon at $\delta_C$ 147.7 allowed assignment of C-16 to complete the assignment of ring D and the central core. In addition, the data show that instead of the commonly found ent-kaurene diterpenoid core in Stevia glycosides, CC-00348 contains ent-atisene diterpeniod core (as shown in FIG. 1). Additional HMBC correlations from H-9 to C-11; H-11 to C-12 and C-13; H-12 to C-13 and C-14; H-14 to C-13; H-15 to C-8, C-9 and C-14 and H-17 to C-12 further confirmed the assignments made above.

Correlations observed in the ROESY spectrum and the data comparison with related compounds were used to assign the relative stereochemistry of the central diterpene core. In the ROESY spectrum, NOE correlations were observed between H-20 one of the H-14 protons ($\delta_H$ 2.47) indicating that H-14 and H-20 are on the same face of the ring. This assignment was further supported by NOE correlations between H-20 and H-13. Due to very close chemical shift for H-5 ($\delta_H$ 1.09), H-9 ($\delta_H$ 1.08) and one of the methylene protons of H-3 ($\delta_H$ 1.04), it was not possible to unambiguously assign the relative stereochemistry at H-5, H-9 and H-18; however based on proton and carbon chemical shifts reported for related compounds, the relative stereochemistry for these is proposed as presented herein.

In the $^1$H NMR spectrum acquired at 300K, some of the anomeric protons were obscured by water resonance at 4.83 ppm. Therefore, VT $^1$H NMR experiments were performed. In the $^1$H NMR spectrum acquired at 286K, the protons were sufficiently resolved and thus additional NMR data were acquired at 286K. Analysis of the $^1$H-$^{13}$C HSQC-DEPT data for CC-00348 confirmed the presence of five anomeric protons all of which were well resolved at $\delta_H$ 5.60 ($\delta_C$ 94.1), 5.30 ($\delta_C$ 102.1), 4.94 ($\delta_C$ 103.2), 4.57 ($\delta_C$ 97.9), and 4.46 ($\delta_C$ 104.5) in the $^1$H NMR spectrum acquired at 286K. Four of the anomeric protons had large couplings (8.1-7.7 Hz) indicating that they had β-configurations. One anomeric proton observed as a broad singlet at $\delta_H$ 5.30 was observed as a broad doublet in the 1D-TOCSY spectra with a small coupling of ~1.7 Hz indicating that this had α-configuration. The anomeric proton observed at $\delta_H$ 5.60 showed an HMBC correlation to C-19 which indicated that it corresponded to the anomeric proton of Glc$_I$. Similarly, the anomeric proton observed at $\delta_H$ 4.57 showed an HMBC correlation to C-13 allowing it to be assigned as the anomeric proton of Glc$_{II}$.

The Glc$_I$ anomeric proton ($\delta_H$ 5.60) showed a COSY correlation to a proton at $\delta_H$ 3.91 which was assigned as Glc$_I$ H-2 and in turn showed a COSY correlation to a proton at $\delta_H$ 3.66 (Glc$_I$ H-3). Due to data overlap the COSY spectrum did not allow assignment of the remaining protons. Therefore, a series of 1D TOCSY experiments were performed using selective irradiation of the Glc$_I$ anomeric proton with several different mixing times. In addition to confirming the assignments for Glc$_I$ H-2 and H-3, the TOCSY data allowed assignment of H-4 ($\delta_H$ 3.41), H-5 ($\delta_H$ 3.36) and H-6 ($\delta_H$ 3.69 and 3.82). The $^{13}$C chemical shifts for Glc$_I$ C-2 ($\delta_C$ 78.0), C-3 ($\delta_C$ 79.0), C-4 ($\delta_C$ 71.1), C-5 ($\delta_C$ 78.1-78.6) and C-6 ($\delta_C$ 62.2 or 62.3) were assigned using the HSQC-DEPT data. The HMBC correlations observed from Glc$_I$ H-1 to C-3 and C-5, H-2 to C-1 and C-3, H-3 to C-4, H-4 to C-3 and C-6 and H-6 ($\delta_H$ 3.82) to C-4 and C-5 further confirmed the assignments made above to complete the assignment of Glc$_I$. In the $^1$H NMR spectrum a coupling value of 8.1 Hz for Glc$_I$ anomeric proton indicated β-configuration for Glc$_I$.

Of the four remaining unassigned sugar moieties one was assigned as substituent at C-2 of Glc$_I$ on the basis of HMBC correlations. The anomeric proton observed at $\delta_H$ 4.94 showed an HMBC correlation to Glc$_I$ C-2 and was assigned as the anomeric proton of Glc$_{I'}$. The reciprocal HMBC correlation from Glc$_I$ H-2 to the anomeric carbon of Glc$_{I'}$ was also observed.

The Glc$_{I'}$ anomeric proton ($\delta_H$ 4.94) showed a COSY correlation to a proton at $\delta_H$ 3.17 which was assigned as Glc$_{I'}$ H-2 and in turn showed a COSY correlation to a proton at $\delta_H$ 3.32 (Glc$_{I'}$ H-3). Due to data overlap the COSY spectrum did not allow assignment of the remaining protons. Therefore, a series of 1D TOCSY experiments were performed using selective irradiation of the Glc$_I$ anomeric proton with several different mixing times. In addition to confirming the assignments for Glc$_{I'}$ H-2 and H-3, the TOCSY data allowed assignment of H-4 ($\delta_H$ 3.28), H-5 ($\delta_H$ 3.28) and H-6 ($\delta_H$ 3.69 and 3.90). The additional resonance at $\delta_H$ 4.99 in the TOCSY spectra was due to water. The $^{13}$C chemical shifts for Glc$_{I'}$ C-2 ($\delta_C$ 75.7), C-3 ($\delta_C$ 78.1-78.6), C-4 ($\delta_C$ 72.1), C-5 ($\delta_C$ 78.1-78.6) and C-6 ($\delta_C$ 63.4) were assigned using the HSQC-DEPT data. The HMBC correlations observed from Glc$_{I'}$ H-2 to C-1 and C-3, H-3 to C-2 and C-4, and H-4 to C-5 and C-6 further confirmed the assignments made above to complete the assignment of Glc$_{I'}$. In the $^1$H NMR spectrum a coupling value of 8.0 Hz for Glc$_{I'}$ anomeric proton indicated β-configuration for Glc$_{I'}$.

A summary of the $^1$H and $^{13}$C chemical shifts for the glycoside at C-19 are found in Table 8.

TABLE 8

$^1$H and $^{13}$C NMR (500 and 150 MHz, CD$_3$OD), assignments of C-19 glycoside.

| | CC-00348 | |
|---|---|---|
| Position | $^{13}$C | $^1$H |
| Glc$_I$-1 | 94.1 | 5.60 d (8.1) |
| Glc$_I$-2 | 78.0 | 3.91 m |
| Glc$_I$-3 | 79.0 | 3.66 m |
| Glc$_I$-4 | 71.1 | 3.41 m |
| Glc$_I$-5 | 78.1-78.6§ | 3.36 m |
| Glc$_I$-6 | 62.2 or 62.3 | 3.69 m, 3.82 m |
| Glc$_{I'}$-1 | 103.2 | 4.94 d (8.0) |

TABLE 8-continued

¹H and ¹³C NMR (500 and 150 MHz,
CD₃OD), assignments of C-19 glycoside.

| | CC-00348 | |
|---|---|---|
| Position | ¹³C | ¹H |
| Glc$_V$-2 | 75.7 | 3.17 m |
| Glc$_V$-3 | 78.1-78.6§ | 3.32 m |
| Glc$_V$-4 | 72.1 | 3.28 m |
| Glc$_V$-5 | 78.1-78.6§ | 3.28 m |
| Glc$_V$-6 | 63.4 | 3.69 m, 3.90 m |

§Five carbon resonances in the range of 78.1-78.6 (78.15, 78.26, 78.38 and 78.59 ppm; two carbons overlapped at 78.59 ppm), hence chemical shifts could not be unequivocally assigned.

Assignment of Glc$_{II}$ was carried out in a similar manner. The Glc$_{II}$ anomeric proton ($\delta_H$ 4.57) showed a COSY correlation to a proton at $\delta_H$ 3.50 which was assigned as Glc$_{II}$ H-2 and in turn showed a COSY correlation to a proton at $\delta_H$ 3.69 (Glc$_{II}$ H-3). This latter proton showed an additional correlation with a proton at $\delta_H$ 3.44 (Glc$_{II}$ H-4). Due to data overlap the COSY spectrum did not allow assignment of the remaining protons. Therefore, a series of 1D TOCSY experiments were performed using selective irradiation of the Glc$_{II}$ anomeric proton with several different mixing times. In addition to confirming the assignments for Glc$_{II}$ H-2 through H-4, the TOCSY data allowed assignment of H-5 ($\delta_H$ 3.29) and H-6 ($\delta_H$ 3.72 and 3.87). The ¹³C chemical shifts for Glc$_{II}$ C-2 ($\delta_C$ 77.6), C-3 ($\delta_C$ 88.7), C-4 ($\delta_C$ 69.8), C-5 ($\delta_C$ 77.4), and C-6 ($\delta_C$ 62.2 or 62.3) were assigned using the HSQC-DEPT data. The HMBC correlations observed from Glc$_{II}$ H-1 to C-3 and C-5, H-2 to C-1 and C-3, H-3 to C-2 and C-4, H-4 to C-3 and C-6 and H-6 ($\delta_H$ 3.87) to C-4 and C-5 further confirmed the assignments made above to complete the assignment of Glc$_{II}$. In the ¹H NMR spectrum a coupling value of 7.7 Hz for Glc$_{II}$ anomeric proton indicated β-configuration for Glc$_{II}$.

The remaining two unassigned glucose moieties were assigned as substituents at C-2 and C-3 of Glc$_{II}$ on the basis of HMBC correlations. The anomeric proton observed at $\delta_H$ 5.30 showed an HMBC correlation to Glc$_{II}$ C-2 and was assigned as the anomeric proton of Rha. The anomeric proton observed at $\delta_H$ 4.46 showed an HMBC correlation to Glc$_{II}$ C-3 and was assigned as the anomeric proton of Glc$_{IV}$. The reciprocal HMBC correlations from Glc$_{II}$ H-2 to the anomeric carbon of Rha and from Glc$_{II}$ H-3 to the anomeric carbon of Glc$_{IV}$ were also observed.

The anomeric proton of Rha ($\delta_H$ 5.30) showed a COSY correlation to a proton at $\delta_H$ 3.89 which was assigned as Rha H-2. Rha C-2 ($\delta_C$ 72.2) was then assigned using HSQC-DEPT data supporting a rhamnose unit. Due to data overlap the COSY spectrum did not allow assignment of the remaining protons. Therefore, a series of 1D TOCSY experiments were performed using selective irradiation of the Rhamnose anomeric proton with several different mixing times. In addition to confirming the assignments for Glc$_{II}$ H-2, the TOCSY data allowed assignment of H-3 ($\delta_H$ 3.67), H-4 ($\delta_H$ 3.37), H-5 ($\delta_H$ 4.12) and H-6 ($\delta_H$ 1.22). This assignment was further supported by COSY correlations between H-3/H-4, H-4/H-5 and H-5/H-6. The ¹³C chemical shifts for Rha C-3 ($\delta_C$ 71.7), C-4 ($\delta_C$ 73.9), C-5 ($\delta_C$ 69.6), and C-6 ($\delta_C$ 18.6) were assigned using the HSQC-DEPT data. The HMBC correlations observed from Rha H-1 to C-2, C-3 and C-5, H-2 to C-3 and C-4, H-3 to C-4 to C-5, H-5 to C-3 and C-4, and H-6 to C-4 and C-5 further confirmed the assignments made above to complete the assignment of Rha. In the ¹H NMR spectrum, Rha anomeric proton is observed as a broad singlet, however it is observed as a broad doublet in 1D-TOCSY spectra having a coupling value of ~1.7 Hz which indicated α-configuration for Rha.

The anomeric proton of Glc$_{IV}$ ($\delta_H$ 4.46) showed COSY correlation with a proton at $\delta_H$ 3.23 which was assigned as Glc$_{IV}$ H-2. Due to data overlap the COSY spectrum did not allow assignment of the remaining protons. Therefore, a series of 1D TOCSY experiments were performed using selective irradiation of the Glc$_{IV}$ anomeric proton with several different mixing times. In addition to confirming the assignments for Glc$_{IV}$ H-2, the TOCSY data allowed assignment of Glc$_{IV}$ H-3 ($\delta_H$ 3.35), H-4 ($\delta_H$ 3.27) and H-5 ($\delta_H$ 3.34). The protons observed at $\delta_H$ 3.61 and 3.89 in the TOCSY spectrum were assigned as the Glc$_{IV}$ H-6 protons. The assignment of H-5 was further confirmed by COSY correlations between Glc$_{IV}$ H-5/H-6. The ¹³C chemical shifts for Glc$_{IV}$ C-2 ($\delta_C$ 75.1), C-3 ($\delta_C$ 78.1-78.6), C-4 ($\delta_C$ 71.5), C-5 ($\delta_C$ 78.1-78.6), and C-6 ($\delta_C$ 62.5) were assigned using the HSQC-DEPT data. The HMBC correlations observed from Glc$_{IV}$ H-1 to C-2 and C-3 and/or C-5, H-2 to C-1 and C-3, H-3 to C-2 and C-4, H-4 to C-3 and/or C-5 and C-6 further confirmed the assignments made above to complete the assignment of Glc$_{IV}$. In the ¹H NMR spectrum a coupling value of 7.8 Hz for Glc$_{IV}$ anomeric proton indicated β-configuration for Glc$_{IV}$.

A summary of the ¹H and ¹³C chemical shifts for the glycoside at C-13 are found in Table 9.

TABLE 9

¹H and ¹³C NMR (500 and 150 MHz,
CD₃OD), assignments of C-13 glycoside.

| | CC-00348 | |
|---|---|---|
| Position | ¹³C | ¹H |
| Glc$_{II}$-1 | 97.9 | 4.57 d (7.7) |
| Glc$_{II}$-2 | 77.6 | 3.50 m |
| Glc$_{II}$-3 | 88.7 | 3.69 m |
| Glc$_{II}$-4 | 69.8 | 3.44 m |
| Glc$_{II}$-5 | 77.4 | 3.29 m |
| Glc$_{II}$-6 | 62.2 or 62.3 | 3.72 m, 3.87 m |
| Rha-1 | 102.1 | 5.30 brs¶ |
| Rha-2 | 72.2 | 3.89 m |
| Rha-3 | 71.7 | 3.67 m |
| Rha-4 | 73.9 | 3.37 m |
| Rha-5 | 69.6 | 4.12 m |
| Rha-6 | 18.6 | 1.22€ |
| Glc$_{IV}$-1 | 104.5 | 4.46 d (7.8) |
| Glc$_{IV}$-2 | 75.1 | 3.23 m |
| Glc$_{IV}$-3 | 78.1-78.6§ | 3.35 m |
| Glc$_{IV}$-4 | 71.5 | 3.27 m |
| Glc$_{IV}$-5 | 78.1-78.6§ | 3.34 m |
| Glc$_{IV}$-6 | 62.5 | 3.61 m, 3.89 m |

§Five carbon resonances in the range of 78.1-78.6 (78.15, 78.26, 78.38 and 78.59 ppm; two carbons overlapped at 78.59 ppm), hence chemical shifts could not be unequivocally assigned.
€Partially overlapped with H-18 (1.23 ppm), thus multiplicity could not be determined.
¶Broad doublet (J = ~1.7 Hz) based on 1D-TOCSY data.

The structure was determined to be (13-[(2-O-α-L-rhamnopyranosyl-3-O-β-D-glucopyranosyl-β-D-glucopyranosyl)oxy] ent-atis-16-en-19-oic acid-[(2-O-β-D-glucopyranosyl-β-D-glucopyranosyl) ester]).

Example 9

Isolation and Characterization of CC-00365

The material used for isolation of CC-00365 was Stevia extract.

Primary Purification

Approximately 300 g Stevia extract was processed using the primary preparative HPLC method described in Example 1. Collected fractions were analyzed by HPLC-MS using the anatlytical method summarized in Table 1 of Example 1.

Secondary Purification

Collected fractions from primary purification were reprocessed using the secondary preparative HPLC method described in Example 1. Fractions were analyzed with the analytical method summarized in Table 2 of Example 1. The fraction with retention time at 47 minutes was selected for reprocessing.

Tertiary Purification

The fraction obtained from secondary purification was reprocessed using the tertiary HPLC method described below. The process was performed with a Waters Delta Prep LC Model 2000/4000 system coupled to a UV-Vis detector.

| Column | Waters XBridge Amide (19 × 250 mm, 5 µm) |
|---|---|
| Flow Rate (mL/min) | 20 |
| Detection | UV at 210 nm |
| Mobile Phases | (A) 20% Water in MeCN |
|  | (B) 30% Water in MeCN |
| Sample preparation | Dissolved in minimum volume of MP-A |
| Gradient: | 60-min linear ramp from 100% MP-A to 100% MP-B |

Fractions were analyzed using the analytical method summarized using the method described below.

| Column (Dimensions, mm) | Waters XBridge Amide (4.6 × 150 mm, 3.5 µm) PN186004869, SN 01253516613401 |
|---|---|
| Column Temperature (° C.) | Ambient |
| Sample Temperature (° C.) | Ambient |
| Mobile Phases | (A) Water |
|  | (B) MeCN |
| Detection | CAD and UV at 210 nm |
| Flow Rate (mL/min) | 1 mL/min |

| Gradient | | |
|---|---|---|
| Time (min) | % A | % B |
| 0.0 | 15 | 85 |
| 40.0 | 30 | 70 |
| 40.01-47.0 | 90 | 10 |
| 47.01 | 15 | 85 |

The fraction with a retention time of 30 minutes on the preparative trace was found to be pure enough for NMR analysis. The fraction was filtered through a stainless steel sieve and concentrated in vacuo using a Buchi® Rotary Evaporator, Model R-114. The concentrated solution was dried for 48-72 h using the Kinetics Flexi-Dry Personal Freeze Dryer. The yield was 0.3 mg. The final purity was determined using the analytical method described below to be 66.4% (AUC, CAD) with a retention time of 27.548 min and >99.0% (AUC, UV) with a retention time of 27.482 min.

| Column | Phenomenex Synergi Hydro RP (4.6 × 250 mm, 4 µm) |
|---|---|
| Column Temperature (° C.) | 55 |
| Sample Temperature (° C.) | Ambient |
| Mobile Phases | (A) 0.0284% Ammonium Acetate (NH$_4$OAc) and 0.0116% Acetic Acid (HOAc) in Water |
|  | (B) Acetonitrile (MeCN) |
| Flow Rate (mL/min) | 1.0 |
| Detection | CAD and UV at 210 nm |

| Gradient | | |
|---|---|---|
| Time (min) | % A | % B |
| 0.0 | 85 | 15 |
| 28.5 | 75 | 25 |
| 30.0 | 71 | 29 |
| 36.5 | 70 | 30 |
| 38.5-44.5 | 66 | 34 |
| 46.5-49.0 | 48 | 52 |
| 51.0-57.0 | 30 | 70 |
| 58.0 | 85 | 15 |

MS and MS/MS.

MS and MS/MS data were generated with a Waters QT of Micro mass spectrometer equipped with an electrospray ionization source. The sample (0.1 mg) was analyzed by negative ESI. The sample was diluted with 50:50 H2O:ACN to a concentration of 25 µg/mL for HRMS and MS/MS and were introduced via direct infusion.

The ESI-TOF mass spectrum acquired by infusing a sample of CC-00365 showed a [M-H]$^-$ ion at m/z 1259.4926. The mass of the [M-H]$^-$ ion was in good agreement with the molecular formula $C_{55}H_{88}O_{32}$ (calcd for $C_{55}H_{87}O_{32}$: 1259.5180, error: -2.5 ppm) expected for CC-00365 (FIG. 7). The MS data confirmed that CC-00365 has a nominal mass of 1260 Daltons with the molecular formula, $C_{55}H_{88}O_{32}$. The ion observed at m/z 1387.4056 could be due to an adduct.

The MS/MS spectrum of CC-00365, selecting the [M-H]$^-$ ion at m/z 1259.0 for fragmentation, indicated loss of two glucose units at m/z 1097.4545 and 935.4002 followed by loss of one xylose unit at m/z 803.3441 and sequential loss of three sugar units at m/z 641.2988, 479.2617 and 317.1986. The data thus indicated the presence of five glucose and one xylose units in the structure.

NMR Spectroscopy

Approximately 0.3 mg of the sample was dissolved in 400 µL CD3OD. $^1$H NMR data was acquired initially on a Bruker Avance 400 MHz instrument equipped with a 5 mm probe. For structure elucidation $^1$H, $^{13}$C, COSY, HSQC-DEPT, HMBC and ROESY data were acquired at the Rensselaer Polytechnic Institute, Troy, N.Y. using their Bruker Avance 600 MHz instrument equipped with a 5 mm cryo-probe. The 1D-TOCSY data were acquired on a Bruker Avance 500 MHz instrument equipped with a 5 mm probe. The $^1$H NMR spectrum was referenced to the CHD$_2$OD resonance at δH 3.30 ppm and $^{13}$C NMR spectrum was referenced to the CD$_3$OD resonance at δ C 49.0 ppm.

A series of NMR experiments including $^1$H NMR, $^{13}$C NMR, $^1$H-$^1$H COSY, HSQC-DEPT, HMBC, ROESY, and 1D TOCSY were acquired to allow assignment of CC-00365.

The 1D and 2D NMR data indicated the presence of a central diterpene core with an exocyclic double bond and six sugar units in the structure. In the HSQC-DEPT data, only eight methylene units were observed instead of nine methylene units that are commonly observed in the central diterpene core of related Stevia glycosides. Similarly in the HSQC-DEPT data, in addition to two methine units corresponding to C-5 and C-9 positions, two additional methine units at $δ_H$ 2.49/$δ_C$ 42.1 and $δ_H$ 4.15/$δ_C$ 77.9 were observed which is relatively rare in this class of compounds and thus indicated structural changes in the central diterpene core.

Complete analysis of 1D and 2D NMR data allowed assignment of the central core and confirmed the structural changes in rings C and D as discussed below. An HMBC correlation from the methyl protons at $\delta_H$ 1.20 to the carbonyl at $\delta_C$ 177.8 allowed assignment of one of the tertiary methyl groups (C-18) as well as C-19 and provided a starting point for the assignment of the rest of the aglycone. Additional HMBC correlations from the methyl protons (H-18) to carbons at $\delta_C$ 38.9, 45.2, and 58.5 allowed assignment of C-3, C-4, and C-5. Analysis of the $^1$H-$^{13}$C HSQC-DEPT data indicated that the carbon at $\delta_C$ 38.9 was a methylene and the carbon at $\delta_C$ 58.5 was a methine which were assigned as C-3 and C-5, respectively. This left the carbon at $\delta_C$ 45.2, which did not show a correlation in the HSQC-DEPT spectrum, to be assigned as the quaternary carbon, C-4. The $^1$H chemical shifts for C-3 ($\delta_H$ 1.04 and 2.24) and C-5 ($\delta_H$ 1.07) were assigned using the HSQC-DEPT data. COSY correlations between the H-3 protons ($\delta_H$ 1.04 and 2.24) and protons at $\delta_H$ 1.35 and 1.89 allowed assignment of the H-2 protons which in turn showed correlations with the protons at $\delta_H$ 0.89 and 1.56 which were assigned to H-1. The $^{13}$C chemical shifts for C-1 and C-2 were then assigned on the basis of HSQC-DEPT correlations and are summarized in Table 1.

TABLE 1

$^1$H and $^{13}$C NMR (600 and 150 MHz, CD$_3$OD), assignments of CC-00365 aglycone.

| Position | CC-00365 | |
|---|---|---|
| | $^{13}$C | $^1$H |
| 1 | 40.8 | 0.89 m |
| | | 1.56 m |
| 2 | 19.9 | 1.35 m |
| | | 1.89 m |
| 3 | 38.9 | 1.04 m |
| | | 2.24 brd |
| | | (12.8) |
| 4 | 45.2 | — |
| 5 | 58.5 | 1.07 m |
| 6 | 21.3 | 1.74 brd |
| | | (12.4) |
| | | 1.96 m |
| 7 | 40.4 | 1.15 m |
| | | 1.54 m |
| 8 | 35.2 | — |
| 9 | 52.4 | 1.08 m |
| 10 | 39.4 | — |
| 11 | 27.6 | 1.40 m |
| | | 1.60 m |
| 12 | 42.1 | 2.49 brs |
| 13 | 77.9 | 4.15 m |
| 14 | 38.7 | 1.11 m |
| | | 2.47 m |
| 15 | ~48.9¥ | 1.86 m |
| | | 2.10 brd |
| | | (16.3) |
| 16 | 148.0 | — |
| 17 | 109.5 | 4.67 brs |
| | | ~4.81ϵ |
| 18 | 29.0 | 1.20 s |
| 19 | 177.8 | — |
| 20 | 13.6 | 0.83 s |

¥Resonance obscured by CD$_3$OD, assignment based on HSQC-DEPT data.
ϵResonance obscured by H$_2$O, assignment based on HSQC-DEPT data.

The other tertiary methyl singlet, observed at $\delta_H$ 0.83 ($\delta_C$ 13.6 via HSQC-DEPT), showed HMBC correlations to C-1 and C-5 and was assigned as H-20. The methyl protons showed additional HMBC correlations to a quaternary carbon ($\delta_C$ 39.4) and a methine carbon ($\delta_C$ 52.4) which were assigned as C-10 and C-9, respectively. The $^1$H chemical shift for C-9 ($\delta_H$ 1.08) was assigned using the HSQC-DEPT data. COSY correlations between H-5 ($\delta_H$ 1.07) and the protons at $\delta_H$ 1.74 and 1.96 then allowed assignment of the H-6 protons which in turn showed correlations to protons at $\delta_H$ 1.15 and 1.54 which were assigned to H-7. The $^{13}$C chemical shifts for C-6 ($\delta_C$ 21.3) and C-7 ($\delta_C$ 40.4) were then determined from the HSQC-DEPT data. COSY correlations between H-9 ($\delta_H$ 1.08) and the protons at $\delta_H$ 1.40 and 1.60 allowed assignment of the H-11 protons. The HSQC-DEPT data was then used to assign C-11 ($\delta_C$ 27.6). The H-11 protons at $\delta_H$ 1.40 and 1.60 showed COSY correlation to a methine proton at $\delta_H$ 2.49 ($\delta_C$ 42.1 via HSQC-DEPT) instead of methylene protons in other Stevia glycosides. This data thus indicated that a methine group was present at position 12 instead of a methylene group. The H-12 proton ($\delta_H$ 2.49) also showed COSY correlations to a methine proton at $\delta_H$ 4.15 assigned to H-13 which in turn showed COSY correlations to protons at $\delta_H$ 1.11 and 2.47 (H-14). The HSQC-DEPT data was then used to assign C-13 ($\delta_C$ 77.9) and C-14 ($\delta_C$ 38.7). In this structure, a methine group was present at position 13 instead of a quaternary carbon commonly found in other Stevia glycosides further indicating structural changes in this part of the central core. The carbon chemical shift of C-13 ($\delta_C$ 77.9) indicated a hydroxyl or a substituted hydroxyl at C-13 similar to other Stevia glycosides. The above proton assignments for H-12 to H-14 were further supported by 1D TOCSY experiments performed using selective irradiation of the H-13 proton with several different mixing times. HMBC correlations from H-9 ($\delta_H$ 1.08) and H-14 ($\delta_H$ 1.11 and 2.47) to the carbon at $\delta_C$ 35.2 allowed the assignment of C-8 completing the assignment of ring C. The HSQC-DEPT data indicated that the exocyclic double bond was present in CC-00365 and was assigned based on the HMBC correlations. Thus, HMBC correlation from the protons at $\delta_H$ 4.67 and ~4.81 (obscured by water resonance) to a carbon at $\delta_C$ 42.1 (C-13) allowed the assignment of the exocyclic methylene protons (H-17). The HSQC-DEPT data was then used to assign the carbon at C-17 ($\delta_C$ 109.5). The only remaining methylene group in the central core region at $\delta_H$ 1.86 and 2.10 ($\delta_C$ ~48.9 via HSQC-DEPT) was assigned to H-15 and supported by HMBC correlations from H-9, H-14 and H-17 to C-15 ($\delta_C$ ~48.9). The HMBC correlations from H-11 ($\delta_H$ 1.40), H-13 ($\delta_H$ 4.15) and H-15 ($\delta_H$ 1.86 and 2.10)) to a quaternary carbon at $\delta_C$ 148.0 allowed assignment of C-16 to complete the assignment of ring D and the central core. In addition, the data show that instead of the commonly found ent-kaurene diterpenoid core in Stevia glycosides, CC-00365 contains ent-atisene diterpeniod core. Additional HMBC correlations from H-9 to C-11; H-11 to C-9, and C-12; H-14 to C-13; H-15 to C-8, C-9, and C-14 and H-17 to C-12 further confirmed the assignments made above.

ROESY data was acquired in an attempt to assign the relative stereochemistry of the central diterpene core. Unfortunately, H-5 ($\delta_H$ 1.07) and H-9 ($\delta_H$ 1.08) as well H-12 ($\delta_H$ 2.49) and H-14 ($\delta_H$ 2.47) were partially overlapped, thus the relative stereochemistry of H-5, H-9, H-18, H-14 and H-20 could not be assigned unambiguously. However, since the proton and carbon chemical shifts at positions 5, 9, 14, 18 and 20 of CC-00365 are consistent with the proton and carbon chemical shifts of previously reported ent-atisene compounds from Stevia, the relative stereochemistry in the central core is considered to be the same as that of previously reported ent-atisene Stevia compounds.

Analysis of the $^1$H-$^{13}$C HSQC-DEPT data for CC-00365 confirmed the presence of six anomeric protons of which five were well resolved at $\delta_H$ 5.59 ($\delta_C$ 94.0), 4.94 ($\delta_C$ 104.1), 4.69 ($\delta_C$ 104.3), 4.63 ($\delta_C$ 104.5) and 4.59 ($\delta_C$ 100.5) in the $^1$H NMR spectrum acquired at 300 K. All five anomeric protons had large couplings (8.1-7.7 Hz) indicating that they had β-configurations. The remaining one anomeric proton which was obscured by water resonance at $\delta_H$ 4.82 ($\delta_C$ 103.5) was observed as a doublet with a coupling of ~8.1 Hz in 1D-TOCSY spectrum of Glc$_{III}$ H-2/H-4 (discussed below) indicating that this had also β-configuration. The anomeric proton observed at $\delta_H$ 5.59 showed an HMBC correlation to C-19 which indicated that it corresponded to the anomeric proton of Glc$_I$. Similarly, the anomeric proton observed at $\delta_H$ 4.59 showed an HMBC correlation to C-13 allowing it to be assigned as the anomeric proton of Glc$_{II}$.

The Glc$_I$ anomeric proton ($\delta_H$ 5.59) showed a COSY correlation to a proton at $\delta_H$ 3.80 which was assigned as Glc$_I$ H-2. Due to data overlap the COSY spectrum did not allow assignment of the remaining protons. Therefore, a series of 1D TOCSY experiments were performed using selective irradiation of the Glc$_I$ anomeric proton with several different mixing times. In addition to confirming the assignments for Glc$_I$ H-2, the TOCSY data allowed assignment of H-3 ($\delta_H$ 3.87), H-4 ($\delta_H$ 3.52), H-5 ($\delta_H$ 3.39) and H-6 ($\delta_H$ 3.70 and 3.81). The $^{13}$C chemical shifts for Glc$_I$ C-2 ($\delta_C$ 77.8), C-3 ($\delta_C$ 88.4), C-4 ($\delta_C$ 69.7), C-5 ($\delta_C$ 77.9-78.4) and C-6 ($\delta_C$ 62.3) were assigned using the HSQC-DEPT data. The HMBC correlations observed from Glc$_I$ H-1 to C-5, H-2 to C-1 and C-3, H-3 to C-2 and C-4, H-4 to C-3, C-5 and C-6 and H-6 to C-4 further confirmed the assignments made above to complete the assignment of Glc$_I$. In the $^1$H NMR spectrum a coupling value of 8.1 Hz for Glc$_I$ anomeric proton indicated β-configuration for Glc$_I$.

Of the five remaining unassigned sugar moieties, two were assigned as substituents at C-2 and C-3 of Glc$_I$ on the basis of HMBC correlations. The anomeric proton observed at $\delta_H$ 4.94 showed an HMBC correlation to Glc$_I$ C-2 and was assigned as the anomeric proton of Xyl. The reciprocal HMBC correlation from Glc$_I$ H-2 to the anomeric carbon of Xyl was also observed. Similarly, the anomeric proton observed at $\delta_H$ 4.69 showed an HMBC correlation to Glc$_I$ C-3 and was assigned as the anomeric proton of Glc$_{VI}$. The reciprocal HMBC correlation from Glc$_I$ H-3 to the anomeric carbon of Glc$_{VI}$ was also observed.

The anomeric proton of Xyl ($\delta_H$ 4.94) showed a COSY correlation to a proton at $\delta_H$ 3.11 which was assigned as Xyl H-2. The Xyl H-2 in turn showed a COSY correlation to a proton at $\delta_H$ 3.32 (Xyl H-3). This latter proton showed an additional correlation with a proton at $\delta_H$ 3.50 (Xyl H-4) which in turn showed COSY correlations to the protons at $\delta_H$ 3.21 and 3.82 (Xyl H-5), thus completing $^1$H assignments of Xyl spin system. This spin system was further confirmed by a series of 1D TOCSY experiments which were performed using selective irradiation of the Xyl anomeric proton with several different mixing times. The $^{13}$C chemical shifts for Xyl C-2 ($\delta_C$ 75.7), C-3 ($\delta_C$ 77.9-78.4), C-4 ($\delta_C$ 71.3) and C-5 ($\delta_C$ 67.0) were assigned using the HSQC-DEPT data. The HMBC correlations observed from Xyl H-1 to C-3 and C-5, H-2 to C-1 and C-3, H-3 to C-4, H-4 to C-5, and H-5 to C-3 and C-4 further confirmed the assignments made above to complete the assignment of Xyl. In the $^1$H NMR spectrum a coupling value of 7.9 Hz for Xyl anomeric proton indicated β-configuration for Xyl.

The anomeric proton of Glc$_{VI}$ ($\delta_H$ 4.69) showed a COSY correlation with a proton at $\delta_H$ 3.27 which was assigned as Glc$_{VI}$ H-2. Due to data overlap the COSY spectrum did not allow assignment of the remaining protons. Therefore, a series of 1D TOCSY experiments were performed using selective irradiation of the Glc$_{VI}$ anomeric proton with several different mixing times. In addition to confirming the assignments for Glc$_{VI}$ H-2, the TOCSY data allowed assignment of Glc$_{VI}$ H-3 ($\delta_H$ 3.39), H-4 ($\delta_H$ 3.29), H-5 ($\delta_H$ ~3.37) and H-6 ($\delta_H$ 3.63 and 3.90). The additional resonances at $\delta_H$ 4.67 and ~4.81 ppm in the TOCSY spectra were due to methylene protons at C-17 since H-17 at $\delta_H$ 4.67 is very close to the anomeric proton of Glc$_{VI}$ ($\delta_H$ 4.69), which was also impacted by the TOCSY irradiation pulse. The $^{13}$C chemical shifts for Glc$_{VI}$ C-2 ($\delta_C$ 75.3 or 75.4), C-3 ($\delta_C$ 77.9-78.4), C-4 ($\delta_C$ 71.6), C-5 ($\delta_C$ 77.9-78.4) and C-6 ($\delta_C$ 62.5 or 62.6) were assigned using the HSQC-DEPT data. The HMBC correlations observed from Glc$_{VI}$ H-1 to C-2 and C-3 and/or C-5, H-2 to C-1 and C-3, H-3 to C-2 and C-4, H-4 to C-3 and/or C-5 and C-6 and H-6 ($\delta_H$ 3.90) to C-4 further confirmed the assignments made above to complete the assignment of Glc$_{VI}$. In the $^1$H NMR spectrum a coupling value of 7.9 Hz for Glc$_{VI}$ anomeric proton indicated β-configuration for Glc$_{VI}$.

A summary of the $^1$H and $^{13}$C chemical shifts for the glycoside at C-19 are found in Table 2.

TABLE 2

$^1$H and $^{13}$C NMR (600 and 150 MHz, CD$_3$OD), assignments of CC-00365 C-19 glycoside.

| Position | CC-00365 $^{13}$C | $^1$H |
|---|---|---|
| Glc$_I$-1 | 94.0 | 5.59 d (8.1) |
| Glc$_I$-2 | 77.8 | 3.80 m |
| Glc$_I$-3 | 88.4 | 3.87 m |
| Glc$_I$-4 | 69.7 | 3.52 m |
| Glc$_I$-5 | 77.9-78.4$^\S$ | 3.39 m |
| Glc$_I$-6 | 62.3 | 3.70 m, 3.81 m |
| Xyl-1 | 104.1 | 4.94 d (7.9) |
| Xyl-2 | 75.7 | 3.11 m |
| Xyl-3 | 77.9-78.4$^\S$ | 3.32 m |
| Xyl-4 | 71.3 | 3.50 m |
| Xyl-5 | 67.0 | 3.21 m, 3.82 m |
| Glc$_{VI}$-1 | 104.3 | 4.69 d (7.9) |
| Glc$_{VI}$-2 | 75.3 or 75.4 | 3.27 m |
| Glc$_{VI}$-3 | 77.9-78.4$^\S$ | 3.39 m |
| Glc$_{VI}$-4 | 71.6$^\Psi$ | 3.29 m |
| Glc$_{VI}$-5 | 77.9-78.4$^\S$ | ~3.37 m |
| Glc$_{VI}$-6 | 62.5 or 62.6$^\epsilon$ | 3.63 m, 3.90 m |

$^\S$Eight carbon resonances in the range of 77.9-78.4 ppm (77.93, 78.21, 78.28 and 78.41 ppm; four additional resonances overlapped in this region), hence chemical shifts could not be unequivocally assigned.
$^\Psi$Two carbon resonances observed at 71.6 ppm (71.55 and 71.60 ppm).
$^\epsilon$Three carbon resonances in the range of 62.5-62.6 ppm (62.51, 62.55 and 62.57 ppm), hence chemical shifts could not be unequivocally assigned.

Assignment of Glc$_{II}$ was carried out in a similar manner. The Glc$_{II}$ anomeric proton ($\delta_H$ 4.59) showed a COSY correlation to a proton at $\delta_H$ 3.64 which was assigned as Glc$_{II}$ H-2. Due to data overlap the COSY spectrum did not allow assignment of the remaining protons. Therefore, a series of 1D TOCSY experiments were performed using selective irradiation of the Glc$_{II}$ anomeric proton with several different mixing times. In addition to confirming the assignments for Glc$_{II}$ H-2, the TOCSY data allowed assignment of H-3 ($\delta_H$ 3.76), H-4 ($\delta_H$ 3.39), H-5 ($\delta_H$ 3.36) and H-6 ($\delta_H$ 3.68 and 3.87). The $^{13}$C chemical shifts for Glc$_{II}$ C-2 ($\delta_C$ 80.2), C-3 ($\delta_C$ 87.5), C-4 ($\delta_C$ 70.0), C-5 ($\delta_C$ 77.5), and C-6 ($\delta_C$ 62.5 or 62.6) were assigned using the HSQC-DEPT data. The HMBC correlations observed from Glc$_{II}$ H-1 to C-2, C-3 and C-5, H-2 to C-1 and C-3, H-3 to C-2 and C-4, H-4 to C-2, C-3, C-5 and C-6, H-6 ($\delta_H$ 3.87) to C-4 and H-6 ($\delta_H$ 3.68) to C-5 further confirmed the assignments made above to complete the assignment of $Glc_{II}$. In the $^1H$ NMR spectrum a coupling value of 7.7 Hz for $Glc_{II}$ anomeric proton indicated β-configuration for $Glc_{II}$.

The remaining two unassigned glucose moieties were assigned as substituents at C-2 and C-3 of $Glc_{II}$ on the basis of HMBC correlations. The anomeric proton observed at $\delta_H$ 4.82 showed an HMBC correlation to $Glc_{II}$ C-2 and was assigned as the anomeric proton of $Glc_{III}$. The anomeric proton observed at $\delta_H$ 4.63 showed an HMBC correlation to $Glc_{II}$ C-3 and was assigned as the anomeric proton of $Glc_{IV}$. The reciprocal HMBC correlations from $Glc_{II}$ H-2 to the anomeric carbon of $Glc_{III}$ and from $Glc_{II}$ H-3 to the anomeric carbon of $Glc_{IV}$ were also observed.

As discussed above, the anomeric proton of $Glc_{III}$ ($\delta_H$ 4.82) was obscured by the water resonance. The anomeric proton at $\delta_H$ 4.82 was thus assigned based on HSQC-DEPT data and showed a COSY correlation with a proton at $\delta_H$ 3.18 which was assigned as $Glc_{III}$ H-2. Due to data overlap the COSY spectrum did not allow assignment of the remaining protons. Therefore a series of 1D TOCSY experiments with several different mixing times were performed using $Glc_{III}$ anomeric proton determined to be at $\delta_H$ 4.82 (The O1 value corresponding to $\delta_H$ 4.82 was used for the 1D-TOCSY experiment). In addition to confirming the assignments for $Glc_{III}$ H-2, the TOCSY data allowed assignment of $Glc_{III}$ H-3 ($\delta_H$ 3.32), H-4 ($\delta_H$ 3.18), H-5 ($\delta_H$ 3.28) and H-6 ($\delta_H$ 3.62 and 3.85). The additional resonance at $\delta_H$ 4.67 ppm in the TOCSY spectra is due one of the H-17 protons since $Glc_{III}$ H-1 at $\delta_H$ 4.82 is very close to one of the H-17 protons at $\delta_H$ ~4.81 (obscured by water resonance), hence $\delta_H$ ~4.81 was impacted by the TOCSY irradiation pulse and showed correlation to its germinal pair at $\square_H$ 4.67. Assignments made above for $Glc_{III}$ protons were further confirmed by a series of 1D TOCSY experiments performed by using selective irradiation of the $Glc_{III}$ H-2/H-4 at $\delta_H$ 3.18 with several different mixing times. The $^{13}C$ chemical shifts for C-2 ($\delta_C$ 75.8), C-3 ($\delta_C$ 77.9-78.4), C-4 ($\delta_C$ 72.1), C-5 ($\delta_C$ 77.9-78.4), and C-6 ($\delta_C$ 63.4) were assigned using the HSQC-DEPT data. HMBC correlations observed from $Glc_{III}$ H-1 to C-2 and C-3 and/or C-5, H-2 to C-1 and C-3, H-3 to C-2 and C-4 and H-4 to C-3 and/or C-5 and C-6 further confirmed the assignments made above to complete the assignment of $Glc_{III}$. A coupling value of ~8.1 Hz for $Glc_{III}$ anomeric proton was assigned based on 1D-TOCSY data of $Glc_{III}$ H-2/H-4 which indicated β-configuration for $Glc_{III}$.

The anomeric proton of $Glc_{IV}$ ($\delta_H$ 4.63) showed COSY correlation with a proton at $\delta_H$ 3.25 which was assigned as $Glc_{IV}$ H-2. Due to data overlap the COSY spectrum did not allow assignment of the remaining protons. Therefore, a series of 1D TOCSY experiments were performed using selective irradiation of the $Glc_{IV}$ anomeric proton with several different mixing times. In addition to confirming the assignments for $Glc_{IV}$ H-2 the TOCSY data allowed assignment of $Glc_{IV}$ H-3 ($\delta_H$ 3.37), H-4 ($\delta_H$ 3.28) and H-5 ($\delta_H$ ~3.37). The protons observed at $\delta_H$ 3.63 and 3.88 in the TOCSY spectrum were assigned as the $Glc_{IV}$ H-6 protons. The additional resonances at $\delta_H$ 4.67 and ~4.81 ppm in the TOCSY spectra were due H-17 protons since $Glc_{IV}$ H-1 at $\delta_H$ 4.63 is very close to one of the H-17 protons at $\delta_H$ 4.67 which was also impacted by the TOCSY irradiation pulse and showed correlation to its germinal pair at $\delta_H$ ~4.81. The $^{13}C$ chemical shifts for $Glc_{IV}$ C-2 ($\delta_C$ 75.3 or 75.4), C-3 ($\delta_C$ 77.9-78.4), C-4 ($\delta_C$ 71.6), C-5 ($\delta_C$ 77.9-78.4), and C-6 ($\delta_C$ 62.5 or 62.6) were assigned using the HSQC-DEPT data.

The HMBC correlations observed from $Glc_{IV}$ H-1 to C-2 and C-3 and/or C-5, H-2 to C-1 and C-3, H-3 to C-2 and C-4, H-4 to C-3 and/or C-5 and C-6 and H-6 to C-4 further confirmed the assignments made above to complete the assignment of $Glc_{IV}$. In the $^1H$ NMR spectrum a coupling value of 7.9 Hz for $Glc_{IV}$ anomeric proton indicated β-configuration for $Glc_{IV}$.

A summary of the $^1H$ and $^{13}C$ chemical shifts for the glycoside at C-13 are found in Table 3.

TABLE 3

$^1H$ and $^{13}C$ NMR (600 and 150 MHz, CD$_3$OD), assignments of CC-00365 C-13 glycoside.

| Position | CC-00365 | |
|---|---|---|
| | $^{13}C$ | $^1H$ |
| $Glc_{II}$-1 | 100.5 | 4.59 d (7.7) |
| $Glc_{II}$-2 | 80.2 | 3.64 m |
| $Glc_{II}$-3 | 87.5 | 3.76 t (8.7) |
| $Glc_{II}$-4 | 70.0 | 3.39 m |
| $Glc_{II}$-5 | 77.5 | 3.36 m |
| $Glc_{II}$-6 | 62.5 or 62.6$^\epsilon$ | 3.68 m, 3.87 m |
| $Glc_{III}$-1 | 103.5 | 4.82 d (~8.1)$^\P$ |
| $Glc_{III}$-2 | 75.8 | 3.18 m |
| $Glc_{III}$-3 | 77.9-78.4$^\S$ | 3.32 m |
| $Glc_{III}$-4 | 72.1 | 3.18 m |
| $Glc_{III}$-5 | 77.9-78.4$^\S$ | 3.28 m |
| $Glc_{III}$-6 | 63.4 | 3.62 m, 3.85 m |
| $Glc_{IV}$-1 | 104.5 | 4.63 d (7.9) |
| $Glc_{IV}$-2 | 75.3 or 75.4 | 3.25 m |
| $Glc_{IV}$-3 | 77.9-78.4$^\S$ | 3.37 m |
| $Glc_{IV}$-4 | 71.6$^\Psi$ | 3.28 m |
| $Glc_{IV}$-5 | 77.9-78.4$^\S$ | ~3.37 m |
| $Glc_{IV}$-6 | 62.5 or 62.6$^\epsilon$ | 3.63 m, 3.88 m |

$^\S$Eight carbon resonances in the range of 77.9-78.4 ppm (77.93, 78.21, 78.28 and 78.41 ppm; four additional resonances overlapped in this region), hence chemical shifts could not be unequivocally assigned.
$^\Psi$Two carbon resonances observed at 71.6 ppm (71.55 and 71.60 ppm).
$^\epsilon$Three carbon resonances in the range of 62.5-62.6 ppm (62.51, 62.55 and 62.57 ppm), hence chemical shifts could not be unequivocally assigned.
$^\P$Resonance obscured by H$_2$O, assignment based on HSQC-DEPT data. Coupling constant determined based on 1D-TOCSY data of $Glc_{III}$ H-2/H-4.

The structure was determined to be 13-[((2-O-β-D-glucopyranosyl-3-O-β-D-glucopyranosyl)-β-D-glucopyranosyl)oxy] ent-atis-16-en-19-oic acid-[((2-O-β-D-glucopyranosyl-3-O-β-D-glucopyranosyl)-β-D-glucopyranosyl) ester])

CC-00335
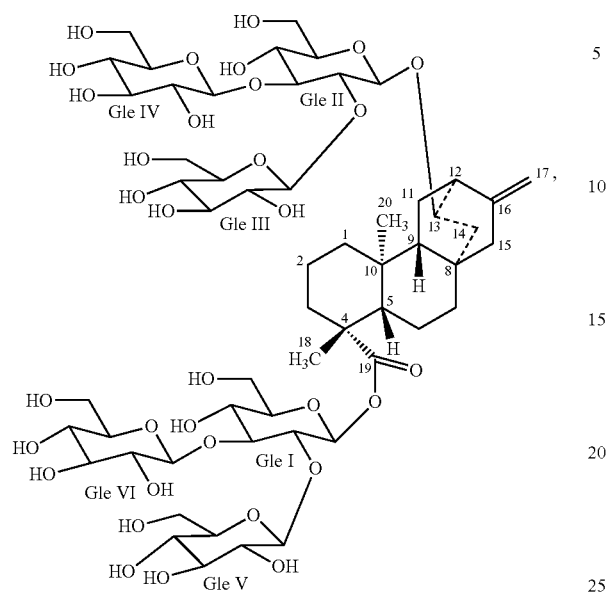
CC-00341
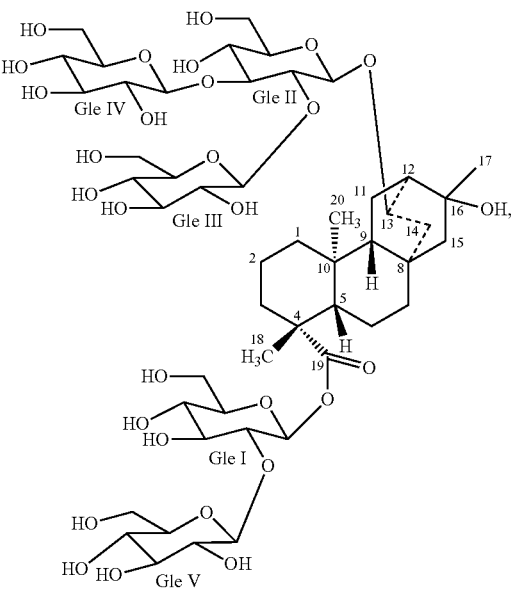
CC-00334
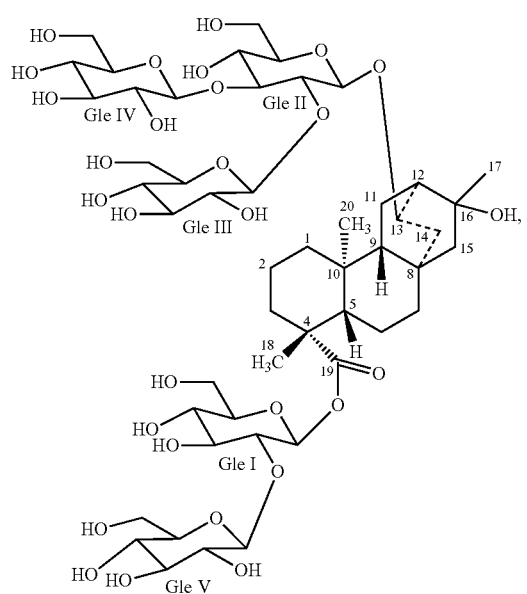
CC-00348
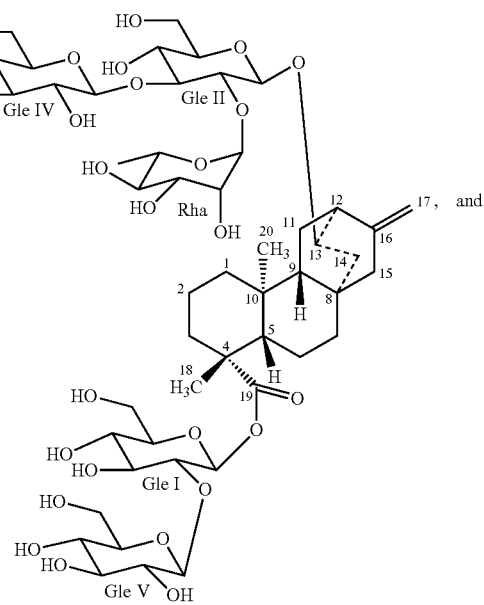
and CC-00365
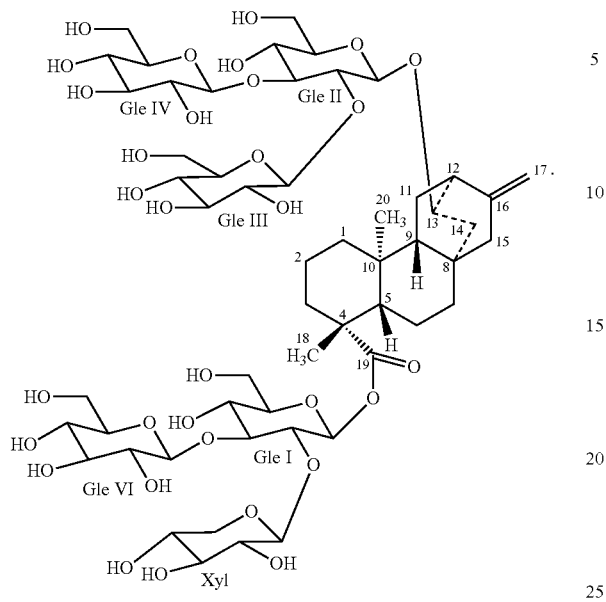

We claim:
1. A diterpene glycoside of Formula I:

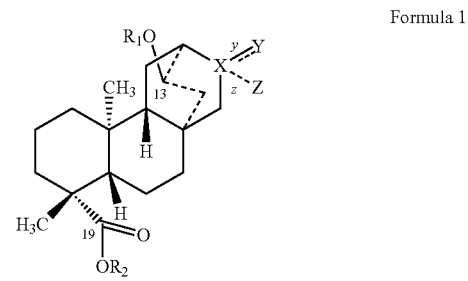

Formula 1 wherein when y is a double bond, X is C, Y is CH$_2$, z is absent and Z is absent;
when y is single bond, z is a single bond, X is C and Y and Z are each independently selected from methyl and hydroxyl; and $R_1$ and $R_2$ are each independently selected from a monosaccharide and an oligosaccharide.

2. The diterpene glycoside of claim 1, wherein each saccharide of the monosaccharide and oligosaccharide is selected from the group consisting of glucose, xylose, rhamnose, fructose, 6-deoxy-glucose and combinations thereof.

3. The diterpene glycoside of claim 1, wherein $R_1$ and $R_2$ are both oligosaccharides.

4. The diterpene glycoside of claim 1, wherein the diterpene glycoside comprises from 4 to 10 saccharides.

5. The diterpene glycoside of claim 1, wherein the diterpene glycoside is selected from the group consisting of:

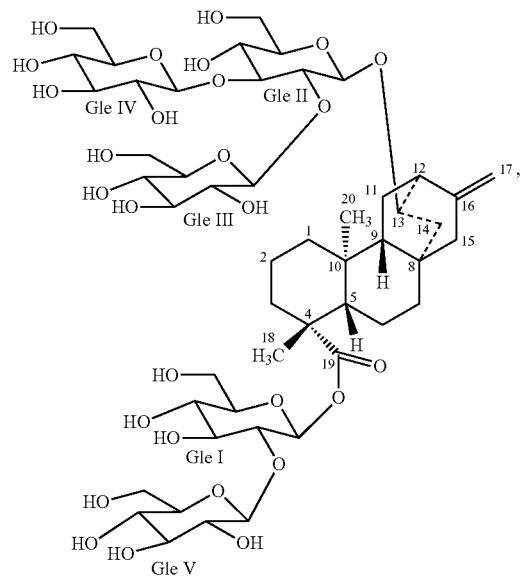

CC-00330

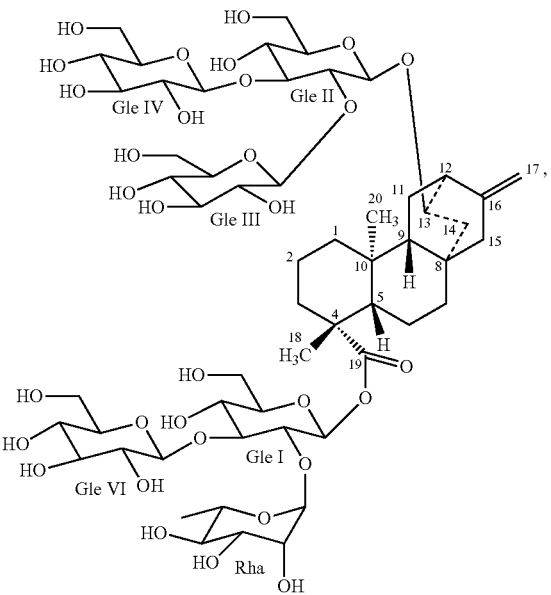

CC-00332

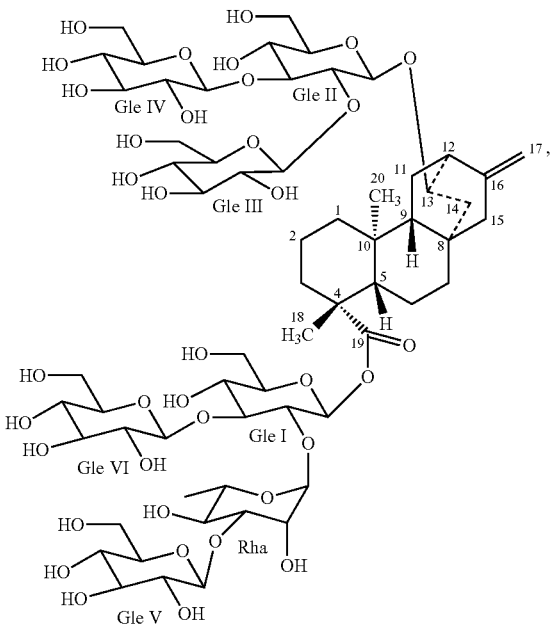

CC-00333

CC-00331

123
-continued
CC-00335
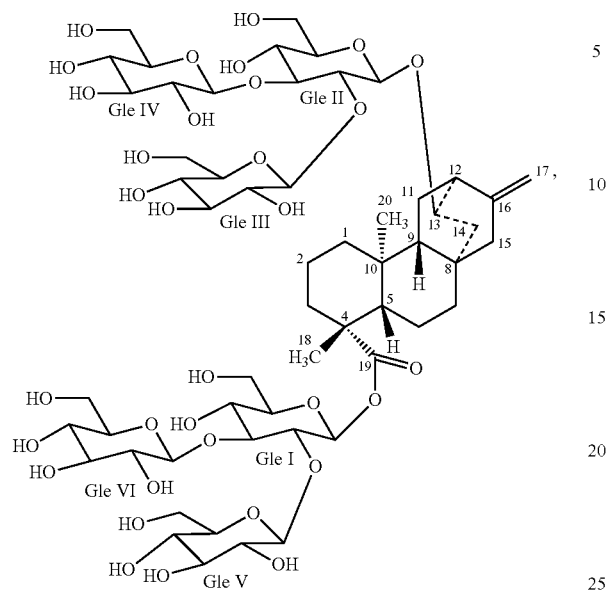
124
-continued
CC-00341
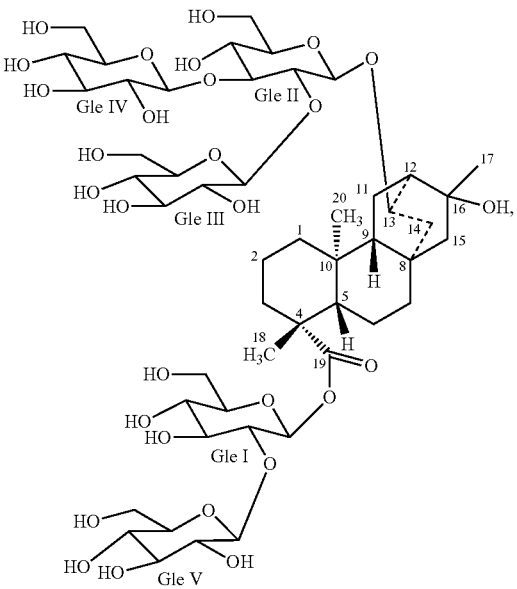
CC-00334
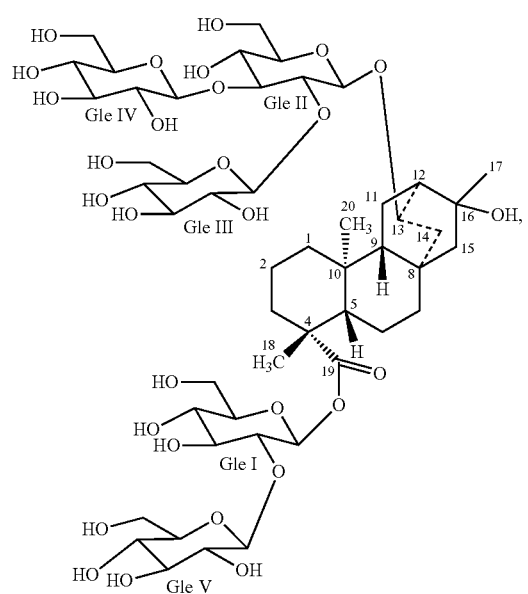
CC-00348
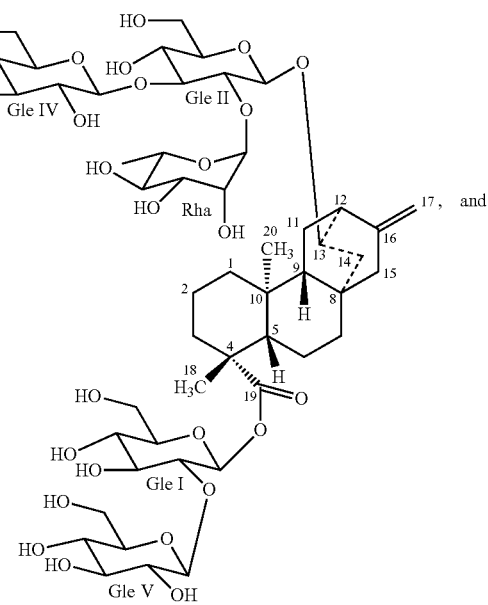
, and -continued

CC-00365

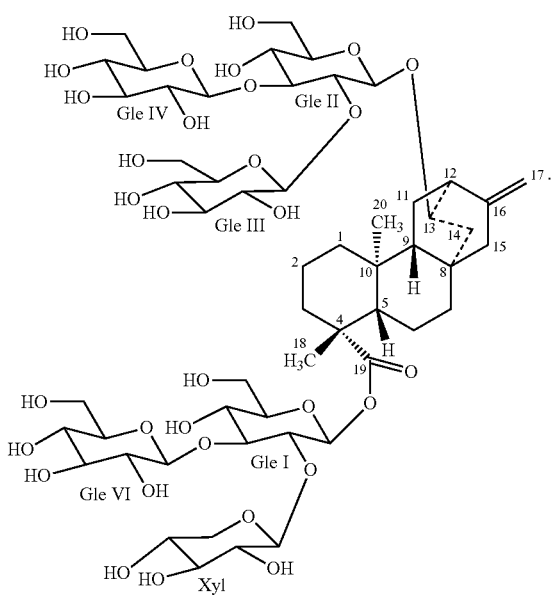

6. The diterpene glycoside of claim 1, wherein the diterpene glycoside is isolated and purified.

7. A composition comprising at least one diterpene glycoside of claim 1.

8. The composition of claim 7, wherein the composition is selected from a sweetener composition, a sweetness enhancing composition and a flavor enhancing composition.

9. The composition of claim 7, wherein the diterpene glycoside is provided as part of a mixture, and wherein the diterpene glycoside is present in the mixture in an amount greater than about 95% by weight on a dry basis.

10. The composition of claim 7, further comprising at least one compound selected from a sweetener, additive and functional ingredient.

11. A consumable comprising at least one diterpene glycoside of claim 1.

12. The consumable of claim 11, wherein the consumable is a beverage or beverage product.

13. A method for enhancing the flavor of a consumable, comprising (i) providing a consumable comprising at least one flavor ingredient and (ii) adding a diterpene glycoside of Formula I to the consumable to provide a consumable with enhanced flavor, wherein the diterpene glycoside of Formula I in present in the consumable with enhanced flavor at a concentration below its flavor recognition threshold, and wherein Formula I is:

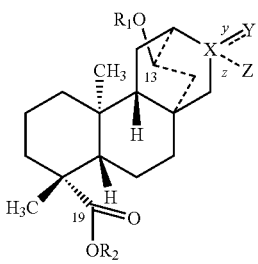

Formula I wherein:
when y is a double bond, X is C, Y is $CH_2$, z is absent and Z is absent;
when y is single bond, z is a single bond, X is C and Y and Z are each independently selected from methyl and hydroxyl; and
$R_1$ and $R_2$ are each independently selected from a monosaccharide and oligosaccharide.

14. A method for enhancing the sweetness of a consumable, comprising (i) providing a consumable comprising at least one sweet ingredient and (ii) adding a diterpene glycoside of Formula I to the consumable to provide a consumable with enhanced sweetness, wherein the diterpene glycoside of Formula I in present in the consumable with enhanced sweetness at a concentration below its flavor recognition threshold, and wherein Formula 1 is:

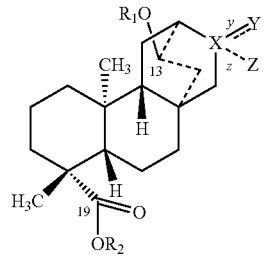

Formula I wherein:
when y is a double bond, X is C, Y is $CH_2$, z is absent and Z is absent;
when y is single bond, z is a single bond, X is C and Y and Z are each independently selected from methyl and hydroxyl; and
$R_1$ and $R_2$ are each independently selected from a monosaccharide and oligosaccharide.

15. The method of claim 13, wherein the consumable is a beverage or beverage product.

16. A method for purifying a diterpene glycoside of Formula I:

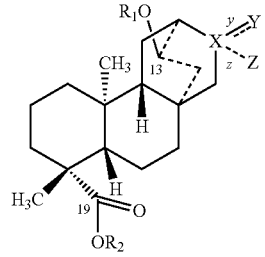

Formula I wherein:
when y is a double bond, X is C, Y is $CH_2$, z is absent and Z is absent;
when y is single bond, z is a single bond, X is C and Y and Z are each independently selected from methyl and hydroxyl; and
$R_1$ and $R_2$ are each independently selected from a monosaccharide and oligosaccharide; comprising:
(i) passing a solution comprising a source material comprising a diterpene glycoside of Formula I through a HPLC column, and (ii) eluting fractions comprising the diterpene glycoside of Formula I to provide a purified diterpene glycoside of Formula 1 having a purity of about 50% or greater.

17. The method of claim 16, wherein the purified diterpene glycoside of Formula I has a purity of about 95% or greater.

18. The method of claim 16, wherein the diterpene glycoside of Formula I is selected from the group consisting of:

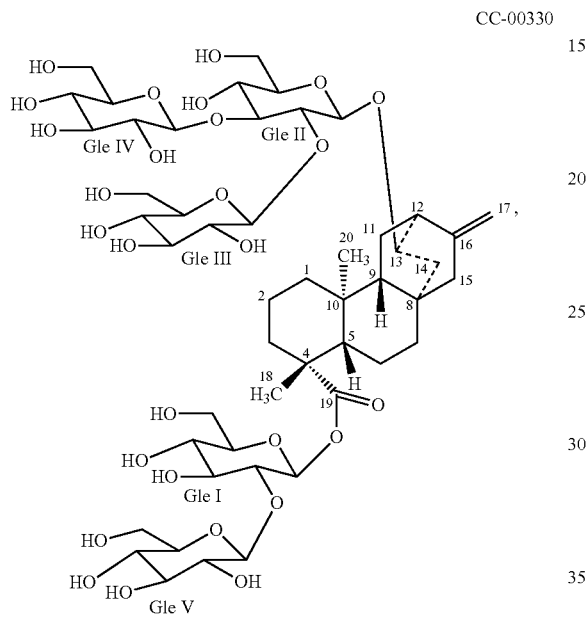

CC-00330

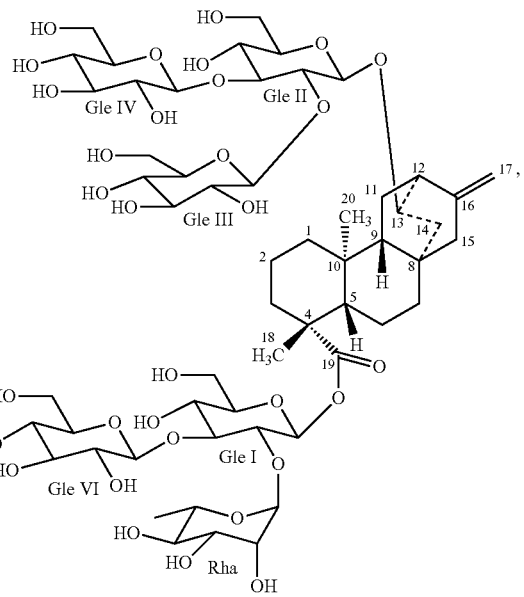

CC-00332

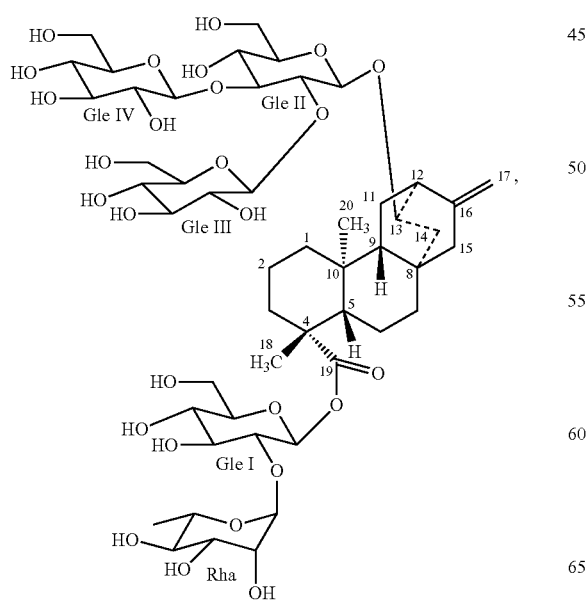

CC-00331

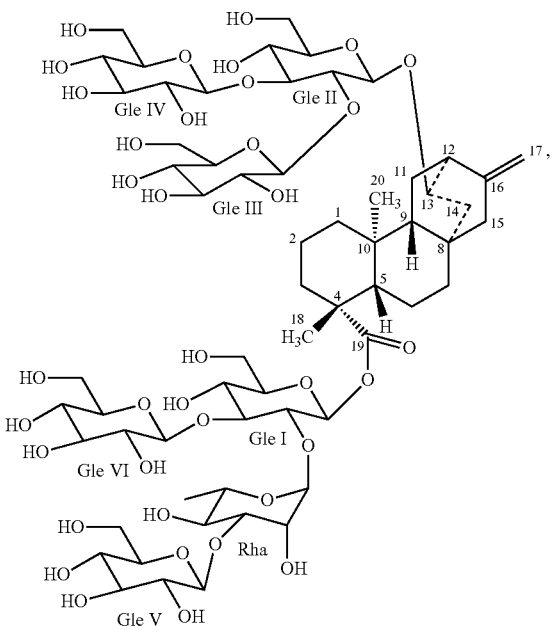

CC-00333